(12) United States Patent
Shim Siew Chen et al.

(10) Patent No.: US 12,018,084 B2
(45) Date of Patent: Jun. 25, 2024

(54) ANTI-CXCR2 ANTIBODIES AND USES THEREOF

(71) Applicant: Cephalon LLC, West Chester, PA (US)

(72) Inventors: Doris Shim Siew Chen, Yagoona (AU); Lynn Dorothy Poulton, Macquarie Park (AU); Adam Clarke, Macquarie Park (AU); David Jose Simon Laine, Macquarie Park (AU); Matthew Pollard, Macquarie Park (AU); Bridget Ann Cooksey, Macquarie Park (AU); Anthony Doyle, Macquarie Park (AU); Jason William Gill, Macquarie Park (AU)

(73) Assignee: Cephalon LLC, West Chester, PA (US)

( * ) Notice: Subject to any disclaimer, the term of this patent is extended or adjusted under 35 U.S.C. 154(b) by 163 days.

(21) Appl. No.: 17/718,622

(22) Filed: Apr. 12, 2022

(65) Prior Publication Data

US 2022/0348671 A1 Nov. 3, 2022

Related U.S. Application Data

(63) Continuation of application No. 16/527,354, filed on Jul. 31, 2019, now Pat. No. 11,332,534.

(60) Provisional application No. 62/713,095, filed on Aug. 1, 2018.

(51) Int. Cl.
| | | |
|---|---|---|
| *A61K 39/395* | (2006.01) | |
| *A61P 11/00* | (2006.01) | |
| *C07K 16/28* | (2006.01) | |
| *G01N 33/53* | (2006.01) | |
| *A61K 39/00* | (2006.01) | |

(52) U.S. Cl.
CPC .......... *C07K 16/2866* (2013.01); *A61P 11/00* (2018.01); *A61K 39/395* (2013.01); *A61K 2039/505* (2013.01); *C07K 2317/21* (2013.01); *C07K 2317/76* (2013.01); *C07K 2317/92* (2013.01); *G01N 33/53* (2013.01)

(58) Field of Classification Search
None
See application file for complete search history.

(56) References Cited

U.S. PATENT DOCUMENTS

| | | |
|---|---|---|
| 5,440,021 A | 8/1995 | Chuntharapai et al. |
| 8,241,630 B2 | 8/2012 | Kao et al. |
| 2009/0191186 A1 | 7/2009 | Bebbington et al. |
| 2012/0183549 A1 | 7/2012 | Bradley et al. |
| 2016/0272714 A1 | 9/2016 | Brown et al. |
| 2017/0114141 A1 | 4/2017 | Amann et al. |
| 2017/0224679 A1 | 8/2017 | Igboko et al. |

FOREIGN PATENT DOCUMENTS

| | | |
|---|---|---|
| JP | 2013-545456 A | 12/2013 |
| JP | 2015-524790 A | 8/2015 |
| RU | 2017106172 A | 8/2018 |
| WO | 88/01649 A1 | 3/1988 |
| WO | 92/01047 A1 | 1/1992 |
| WO | 94/13804 A1 | 6/1994 |
| WO | 98/01649 A1 | 1/1998 |
| WO | 98/44001 A1 | 10/1998 |
| WO | 2008/151081 A1 | 12/2008 |
| WO | 2009/085462 A1 | 7/2009 |
| WO | 2012/062713 A1 | 5/2012 |
| WO | 2013/168108 A2 | 11/2013 |
| WO | 2014/170317 A1 | 10/2014 |
| WO | 2015/169811 A2 | 11/2015 |
| WO | 2018/154391 A1 | 8/2018 |

OTHER PUBLICATIONS

Waterfield et al. The DiscoveRx PathHunter β-arrestin assay; A measure of agonist affinity? ABSTRACT. pA2 Online, vol. 7, No. 4. 2 pages. British Pharmacological Society, BPS Winter Meeting. London, United Kingdom. (Dec. 15, 2009-Dec. 17, 2009). (Year: 2009).*
Petri et al. Neutrophil chemotaxis. Cell and Tissue Research 371:425-436; (2018). (Year: 2018).*
Boshuizen et al: "A combination of in vitro techniques for efficient discovery of functional monoclonal antibodies against human CXC chemokine receptor-2 (CXCR2)", MABS, vol. 6, No. 6, Nov. 1, 2014 (Nov. 1, 2014), pp. 1415-1424, XP55558502.
Chapman, R. W., et al., A novel, orally active CXCR1/2 receptor antagonist, Sch527123, inhibits neutrophil recruitment, mucus production, and goblet cell hyperplasia in animal models of pulmonary inflammation. J Pharmacol Exp Ther, 2007, 322, 486-493.
Citro et al., "CXCR1/2 inhibition blocks and reverses type 1 diabetes in mice." Diabetes, 2015, 64, 1329-1340.
DeSoyza et al., "A randomized, placebo-controlled study of the CXCR2 antagonist AZD5069 in bronchiectasis",, Eur. Respir. J., 2015, 46, 1021-1032.
Division of AIDS (DAIDS) National Institute of Allergy and Infectious Diseases National Institutes of Health US Department of Health and Human Services Table for Grading the Severity of Adult and Pediatric Adverse Events, Version 2.0 Nov. 2014, 33 pages.
French et al., "The role of the IL-8 signaling pathway in the infiltration of granulocytes into the livers of patients with alcoholic hepatitis." Exp Mol Pathol, 2017, 103, 137-140.
Hirose et al., J. Genet. Syndr. Gene Ther. 2013, S3, 9 pages.

(Continued)

*Primary Examiner* — Elizabeth C. Kemmerer
*Assistant Examiner* — Regina M DeBerry
(74) *Attorney, Agent, or Firm* — BakerHostetler

(57) ABSTRACT

Disclosed herein are human antibody molecules that immunospecifically bind to human CXCR2. The disclosed human antibody molecules are potent and selective antagonists of CXCR2 functions and prevent the recruitment of neutrophils into tissues without strongly depleting circulating neutrophil numbers. Pharmaceutical compositions, nucleic acid molecules, vectors, cells, and uses of the disclosed antibodies are also provided.

25 Claims, 23 Drawing Sheets

Specification includes a Sequence Listing.

(56) References Cited

OTHER PUBLICATIONS

Joseph et al., "CXCR2 Inhibition—a novel approach to treating Coronary heart Disease (CICADA): study protocol for a randomized controlled trial." Trials, 2017, 18, 473.
Liu et al., "Neuroinflammation in Alzheimer's disease: chemokines produced by astrocytes and chemokine receptors." Int J Clin Exp Pathol, 2014, 1, 8342-8355.
Liu et al., "The CXCL8-CXCR1/2 pathways in cancer." Cytokine Growth Factor Rev, 2016, 31, 61-71.
Mahler, D. A., et al., Efficacy and safety of a monoclonal antibody recognizing interleukin-8 in COPD: a pilot study. Chest, 2004, 126, 926-934.
Miller B. et al., Late Breaking Abstract—"Danirixin (GSK1325756) improves respiratory symptoms and health status in mild to moderate COPD—results of a 1 year first time in patient study", European Respiratory Journal, 2017, 50.
Miller et al., "The pharmacokinetics and pharmacodynamics of danirixin (GSK1325756)—a selective CXCR2 Antagonist—in healthy adult subjects", BMC Pharmacol. Toxicol, 2015, 16(18), 12 pages.
Moser, B., CXCR5, the defining marker for follicular B helper T (TFH) cells. Frontiers in Immunology, 296(6), 3 pages, Jun. 8, 2015 (Year: 2015).
Moss et al., "Safety and early treatment effects of the CXCR2 antagonist SB-656933 in patients with cystic fibrosis" J Cyst Fibros, 2013, 12, 241-248.
Munoz, L., et al. Dynamic regulation of CXCR1 and CXCR2 homo-and heterodimers. The Journal of Immunology, 183, pp. 7337-7346, Nov. 4, 2009 (Year: 2009).
Nair et al., "Safety and efficacy of a CXCR2 antagonist in patients with severe asthma and sputum neutrophils: a randomized, placebo-controlled clinical trial." Clin Exp Allergy, 2012, 42, 1097-1103.
Pierson et al., "The contribution of neutrophils to CNS autoimmunity." Clin Immunol, 2018, 189, 23-28.
Qiao et al., "CXCR2 Expression on neutrophils is upregulated during the relapsing phase of ocular Behcet disease" Curr Eye Res. 2005; 30: 195-203.
Rabia, L., etal. Understanding and overcoming trade-offs between antibody affinity, specificity, stability and solubility. Biochemical Engineering Journal, 137, pp. 365-374, Jun. 5, 2018 (Year: 2018).
Reutershan, J., et al., Critical role of endothelial CXCR2 in LPS-induced neutrophil migration into the lung. J Clin Invest, 2006, 116, 695-702.
Saunders, "Conceptual Approaches to Modulating Antibody Effector Functions and Circulation Half-Life", Front. Immunol., 2019, 10, 1296, 20 pages.
Silva et al., "CXCL1/CXCR2 signaling in pathological pain: Role in peripheral and central sensitization." Neurobiol Dis, 2017, 105, 109-116.
Stadtmann and Zarbock, "CXCR2: From Bench to Bedside", Front Immunol, 2012, 3, 263, 12 pages.
Steele et al., "CXCR2 inhibition suppresses acute and chronic pancreatic inflammation." J. Pathol, 2015, 237, 85-97.
Study NCT02469298 described on ClinicalTrials.gov entitled, "Saftey, Tolerability and Clinical Effect of Danirixin in Adults With Influenza".
Todd et al., Pulm. Pharmacol. Ther, The effects of a CXCR1/CXCR2 antagonist on neutrophil migration in mild atopic asthmatic subjects Dec. 2016, 41, 34-39.
Tomassen et al., "Inflammatory endotypes of chronic rhinosinusitis based on cluster analysis of biomarkers." J Allergy Clin Immunol, 2016, 137, 1449-1456 e4.
Veenstra and Ransohoff, "Chemokine receptor CXCR2: physiology regulator and neuroinflammation controller?" J Neuroimmunol, 2012, 246, 1-9.
Ye et al., "Lipocalin-2 mediates non-alcoholic steatohepatitis by promoting neutrophil-macrophage crosstalk via the induction of CXCR2." J Hepatol, 2016, 65, 988-997.
Young, A., et al., The Effect of the CXCR1/2 Antagonist SCH257123 in a Mouse Model of Severe Asthma. Experimental Biology 2016 Meeting, 2016 San Diego, USA: The FASEB Journal, 1202.10.
Andrew, "Genetic Analysis of Protein Stability and Function", Annu. Rev. Genet., 1989, vol. 23, pp. 289-310.
Chen et al., "Enhancement and destruction of antibody function by somatic mutation: Unequal occurrence is controlled by V gene combinatorial associations", The EMBO Journal, 1995, vol. 14, No. 12, pp. 2784-2794.
Derksen et al., "Illegitimate WNT signaling promotes proliferation of multiple myeloma cells", Proceedings of the National Academy of Sciences, 2004, vol. 101, No. 16, pp. 6122-6127.
Dirks, "Brain Tumor Stem Cells: Bringing Order to the Chaos of Brain Cancer", Journal of Clinical Oncology, 2008, vol. 26, No. 17, pp. 2916-2924.
Knappik et al., "Fully Synthetic Human Combinatorial Antibody Libraries (HuCAL) Based on Modular Consensus Frameworks and CDRs Randomized with Trinucleotides", J. Mol. Biol., 2000, 296, 57-68.
Lazaar et al., "SB-656933, a novel CXCR2 selective antagonist, inhibits ex vivo neutrophil activation and ozone-induced airway inflammation in humans", Br. J. Clin. Pharmacol., 2011, 72, 282-293.
Lopez-Lozaro M., "The migration ability of stem cells can explain the existence of cancer of unknown primary site. Rethinking metastasis", Oncoscience, May 2015, vol. 2, No. 5, pp. 467-475.
Nicholls et al., "Pharmacological Characterization of AZD5069, a Slowly Reversible CXC Chemokine Receptor 2 Antagonist", J. Pharmacol. Exp. Ther., 2015, 353, 340-350.
Rudikoff et al., "Single amino acid substitution altering antigen-binding specificity", PNAS, USA, 1982, vol. 79, No. 6, pp. 1979-1983.
Shi et al., "De Novo Selection of High-Affinity Antibodies from Synthetic Fab Libraries Displayed on Phage as pIX Fusion Proteins", J. Mol. Biol., 2010, 397, 385-396.
Wu and Kabat, "An Analysis of the sequences of the variable regions of Bence Jones proteins and myeloma light chains and their implications for Anti-body complementarity", J. Exp. Med., 1970, 132, 211-250.

* cited by examiner

FIG. 5A cont.

```
                                   27B
                             27A 27C 30             40                50
             9 11         20  |  |  |                |                 |
             | ||          |  |  |  |                                  
BKO-4A8 VL   QSALTQPPSASGSPGQSVTISC IGTSSDVGGYNYVS WYQQHPDKAPKLMIY EVNKRPSGVP
4A8 VL var b ......................  ..............  ......G........  ...S......
4A8 VL var c ......................  ..............  ......G........  ...S......

Consensus VL                         IGTSSDVGGYNYVS       D            EVNKRPS
                                                          G                  S
                                         CDR1                             CDR2
```

FIG. 5B

FIG. 12A
FIG. 12B
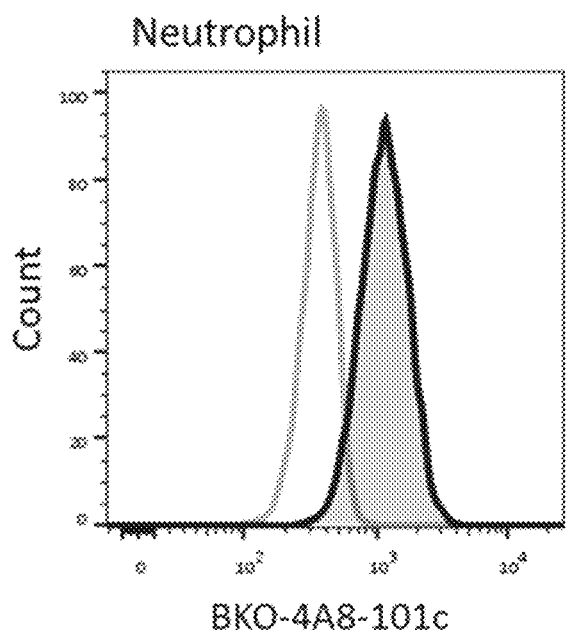
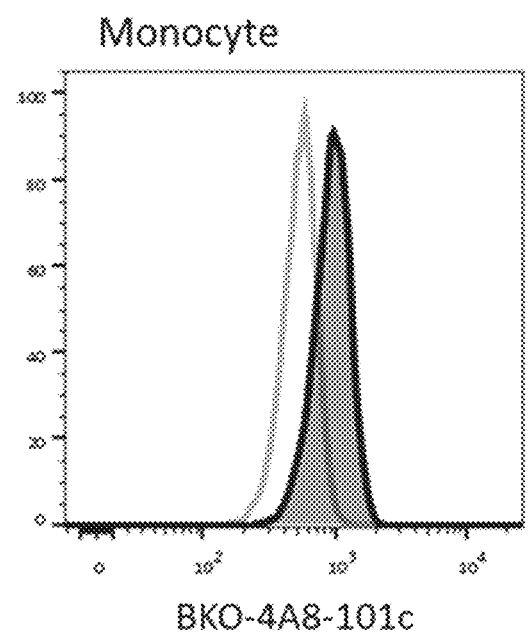

ANTI-CXCR2 ANTIBODIES AND USES THEREOF

CROSS REFERENCE TO RELATED APPLICATIONS

This application is a continuation of U.S. application Ser. No. 16/527,354, filed on Jul. 31, 2019, which claims the benefit of the filing date of U.S. Provisional Application No. 62/713,095, filed Aug. 1, 2018, the disclosure of each of which are hereby incorporated by reference in their entirety.

SEQUENCE LISTING

The instant application contains a Sequence Listing which has been submitted electronically in ASCII format and is hereby incorporated by reference in its entirety. The ASCII copy, created on Apr. 12, 2022, is named 102085_006007_SL and is 273 KB in size.

TECHNICAL FIELD

The instant application is directed to human antibody molecules that immunospecifically bind to human CXCR2.

BACKGROUND

Neutrophils are the most abundant leukocytes in the blood. They are important effector cells of innate immunity, with a primary role in the clearance of extracellular pathogens. However, if neutrophil recruitment to tissue is inadequately controlled, chronic infiltration and activation of neutrophils may result in the persistent release of inflammatory mediators and proteinases which cause overt tissue damage.

The migration and activation of neutrophils is moderated through the interaction of CXC chemokine receptor 1 (CXCR1) and CXC chemokine receptor 2 (CXCR2) on the plasma membrane of the neutrophil with ELR+ CXC chemokines (CXCL1, 2, 3, 5, 6, 7, and 8). CXCR2 acts as a high affinity receptor for all ELR+ CXC chemokines and plays a key role in the mobilization and recruitment of neutrophils and monocytes from the blood to tissue. The chemokines CXCL6, 7, and 8 also interact with CXCR1, which modulates respiratory burst activity and protease release from neutrophils, and which is critical for immunity to bacteria and fungi.

Increased neutrophil counts in sputum have been associated with phenotypes associated with increased asthma severity, corticosteroid insensitivity, and chronic airflow obstruction. Airway neutrophilia is increased during acute asthma exacerbations. Airway neutrophilia is also a feature of all clinical phenotypes of chronic obstructive pulmonary disease (COPD) including COPD with a predominance of emphysema, COPD with frequent exacerbations, and COPD with evidence of high eosinophil activity. The degree of airway neutrophilia also correlates with severity of disease and rate of physiological decline. Neutrophil proteinases, especially neutrophil elastase, are implicated in all pathological features of COPD. Proteinases released by neutrophils are also associated with the development of emphysema, contribute to destruction of the extracellular matrix, and are associated with mucus hypersecretion. These associations suggest that neutrophil infiltration into the airways may have a crucial role in the pathophysiological processes underlying severe asthma and COPD.

CXCL1, CXCL5, and CXCL8 are CXCR2-binding chemokines which are implicated in neutrophil recruitment. CXCL1, CXCL5, and CXCL8 are upregulated in chronic airway inflammation and elevated in sputum or in bronchial biopsy material from subjects with severe neutrophilic asthma or COPD. Antagonizing the chemokine activation of CXCR2 offers a potential therapeutic strategy by reducing neutrophil recruitment into tissues and neutrophil mediated pathologies associated with these inflammatory diseases.

Chemokine receptors, however, have proven to be difficult targets to antagonise selectively. Despite difficulties in developing compounds with a desirable target specificity and antagonist activity, several small-molecule CXCR2 antagonists have proven effective in animal models of inflammation. Human clinical trials of small molecule CXCR2 antagonists in subjects with neutrophilic asthma or COPD have not demonstrated broad efficacy, even though studies of inhaled ozone- and lipopolysaccharide-induced sputum neutrophilia in otherwise normal human subjects demonstrated marked efficacy. Only a modest improvement in baseline lung function ($FEV_1$) was observed in COPD patients who were current smokers when compared with ex-smokers. To date, all published clinical trials have used small molecule CXCR2 antagonists. The most studied is danirixin (GSK1325756), a reversible and selective CXCR2 antagonist ($IC_{50}$ for CXCL8 binding =12.5 nM), which has also shown to block CD11b upregulation on neutrophils. (See, e.g. Miller et al., *BMC Pharmacol Toxicol* 2015; 16: 18). Danirixin failed to meet primary end points in a Phase IIb trial for COPD. Other CXCR2 selective molecules include SB-566933 (Lazaar et al., *Br. J. Clin. Pharmacol.* 2011; 72: 282-293) and AZD5069, which is CXCR2 selective (>150-fold less potent at CXCR1 and CCR2b receptors) and has no effect on C5a, LTB4 or fMLP induced CD11b expression) (Nicolls et al., *J Pharmacol Exp. Ther.* 2015; 353: 340-350). Molecules which inhibit both CXCR2 and CXCR1 include navarixin (SCH 527123, MK-7123; Todd et al., *Pulm Pharmacol Ther.* 2016 December; 41: 34-39), and ladarixin (DF2156A; Hirose et al., *J Genet Syndr Gene Ther* 2013, S3). These molecules are being investigated for multiple indications, including COPD, asthma and other inflammatory lung conditions, cancer, and more.

In some studies, the use of small molecule CXCR2 antagonists resulted in a marked undesirable reduction in circulating neutrophils (neutropenia), which potentially limits the tolerable dose of such agents. Neutropenia may be a result of the antagonist not being completely specific to CXCR2, and/or if the antagonist was active across all CXCR2-binding ligands. CXCL8 and related CXC chemokines, for example, have a significant role in mobilizing mature granulocytes into peripheral blood, and consequently strong antagonism of these ligands on CXCR2 may prevent the normal migration of neutrophils to the blood. Conversely, preferential antagonism of the downstream pathway involving calcium flux signalling following ligand binding to CXCR2 may antagonize undesirable levels of migration of neutrophils into the lungs, whilst retaining the desirable ability of neutrophils to be mobilized into the blood.

SUMMARY

Disclosed herein are human antibody molecules that immunospecifically bind to human CXCR2. The disclosed human antibody molecules are more selective antagonists of CXCR2 than currently described small molecule CXCR2 antagonists, more potent antagonists of CXCL1 and CXCL5 activation of CXCR2 than currently described antibody antagonists of CXCR2, and antagonize the recruitment of neutrophils into tissues without strongly depleting circulating neutrophil numbers. The human antibody molecules comprise the heavy chain CDR1, CDR2, and CDR3 of SEQ ID NO: 167 and the light chain CDR1, CDR2, and CDR3 of SEQ ID NO: 168 or the heavy chain CDR1, CDR2, and CDR3 of SEQ ID NO: 226 and the light chain CDR1, CDR2, and CDR3 of SEQ ID NO: 227, and inhibit activation of human CXCR2 by human CXCL1 or human CXCL5. In certain embodiments the disclosed human antibody molecules are able to inhibit activation of CXCR2 by CXCL1 or CXCL5 in a subject without inducing severe, sustained neutropenia.

Pharmaceutical compositions comprising the human antibody molecules are also provided.

Also disclosed are nucleic acid molecules encoding the human antibody molecules, vectors comprising the nucleic acid molecules, and cells transformed to express the human antibody molecules.

Methods of preventing or treating neutrophilia in a peripheral tissue of a subject, such as airway neutrophilia, are also disclosed herein. Also disclosed herein are methods of reducing monocytes in a peripheral tissue of a subject. Also disclosed are methods of reducing eosinophilia in a peripheral tissue of a subject.

Also disclosed herein are methods of reducing acute airway inflammation, methods of preventing or reducing chronic airway inflammation for example in bronchiectasis, methods of reducing tumor burden, methods of arresting or slowing the growth of a cancer, methods of reducing chronic pain, methods of preventing or reducing neuroinflammation such as in multiple sclerosis, methods of reducing inflammation in the liver, methods of reducing inflammation in the pancreas or methods of reducing the symptoms of type I diabetes. The methods comprise administering to the subject a therapeutically- or prophylactically-effective amount of any of the disclosed human antibody molecules or any of the disclosed pharmaceutical compositions to treat or prevent the disclosed condition in the subject.

Also provided are the disclosed human antibody molecules or pharmaceutical compositions for use in the prevention or treatment of airway neutrophilia or acute lung inflammation. Also provided is the use of the human antibodies molecules or pharmaceutical compositions in the manufacture of a medicament for the prevention or treatment of airway neutrophilia or acute lung inflammation.

BRIEF DESCRIPTION OF THE DRAWINGS

The summary, as well as the following detailed description, is further understood when read in conjunction with the appended drawings. For the purpose of illustrating the disclosed human antibody molecules, methods, and uses, there are shown in the drawings exemplary embodiments of the human antibody molecules, methods, and uses; however, the human antibody molecules, methods, and uses are not limited to the specific embodiments disclosed. In the drawings:

FIG. 4A=variable heavy chain sequences (BKO-4A8 SEQ ID NO:17; consensus sequence SEQ ID NO:167); FIG. 4B=variable light chain sequences (BKO-4A8 SEQ ID NO:18; consensus sequence SEQ ID NO:168). The positioning of the CDRs within these sequences is according to Kabat. Accordingly, the 53rd amino acid residue in the alignment in FIG. 4A is numbered 52a according to Kabat (although the G52aD variant has a G to D change at the 53rd residue, the residue is named 52a). Similarly, in FIG. 4B, the 96th amino acid residue is named 95a. FIG. 4A discloses SEQ ID NOs: 17, 53-75, and 167 and the CDR1, CDR2, and CDR3 sequences of SEQ ID NOs: 169-171, respectively, in order of appearance. FIG. 4B discloses SEQ ID NOs: 18, 76-97, and 168 and the CDR1, CDR2, and CDR3 sequences of SEQ ID NOs: 172-174, respectively, in order of appearance.

FIG. 5A=variable heavy chain sequences (BKO-4A8 SEQ ID NO:17; consensus sequence SEQ ID NO:226); FIG. 5B=variable light chain sequences (BKO-4A8 SEQ ID NO:18; consensus sequence SEQ ID NO:227). FIG. 5A discloses SEQ ID NOs: 17, 98-108, 163-165, and 226 and the CDR1, CDR2, and CDR3 sequences of SEQ ID NOs: 228-230, respectively, in order of appearance. FIG. 5B discloses SEQ ID NOs: 18, 109-110, and 227 and the CDR1, CDR2, and CDR3 sequences of SEQ ID NOs: 201 and 231-232, respectively, in order of appearance.

FIG. 12A and FIG. 12B illustrate an exemplary binding profile of BKO-4A8-101c (shaded histogram) to phenotypically defined human peripheral blood hematopoietic cells assessed by flow cytometry (N=8), incorporating isotype controls (human-IgG unshaded histogram). Expression was high on neutrophils (FIG. 12A), while monocytes (FIG. 12B) expressed intermediate levels of CXCR2.

(FIG. 14A) Peripheral blood neutrophil counts were not impacted by three repeat administrations of BKO-4A8-101c given at two weekly intervals on Day 0, 14 and 28. Group median and range shown, N=4. (FIG. 14B)

DETAILED DESCRIPTION OF ILLUSTRATIVE EMBODIMENTS

Figure 1A:
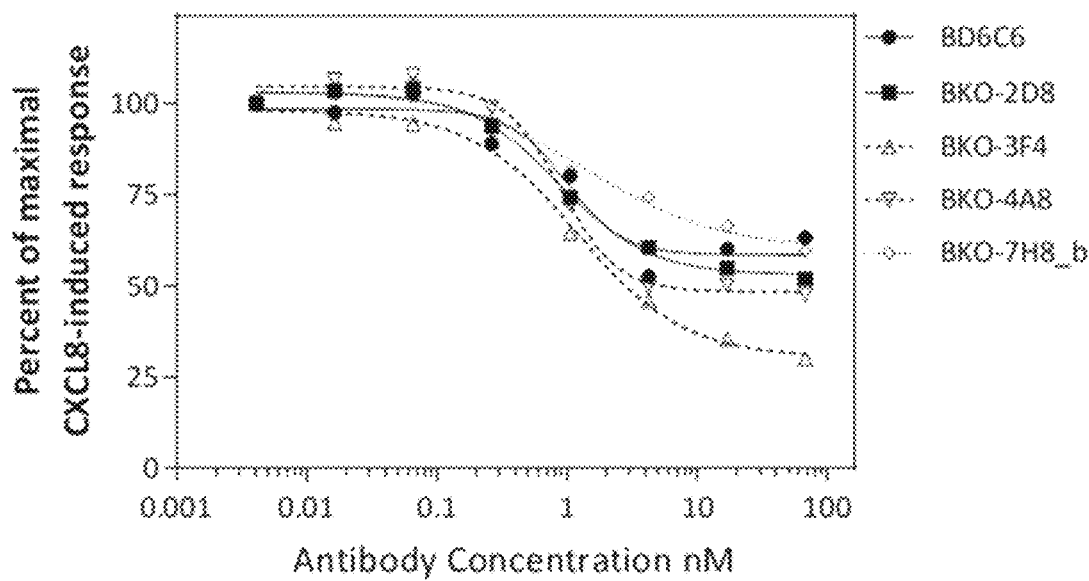
FIG. 1A and FIG. 1B illustrate the results of an exemplary dose response inhibition study of CXCL8-induced activation of CXCR2 by exemplary disclosed anti-CXCR2 antibodies as measured in the Tango™ cell based assay.

The disclosed human antibody molecules, methods, and uses may be understood more readily by reference to the following detailed description taken in connection with the accompanying figures, which form a part of this disclosure. It is to be understood that the disclosed human antibody molecules, methods, and uses are not limited to the specific human antibody molecules, methods, and uses described and/or shown herein, and that the terminology used herein is for the purpose of describing particular embodiments by way of example only and is not intended to be limiting of the claimed human antibody molecules, methods, and uses.

Unless specifically stated otherwise, any description as to a possible mechanism or mode of action or reason for improvement is meant to be illustrative only, and the disclosed human antibody molecules, methods, and uses are not to be constrained by the correctness or incorrectness of any such suggested mechanism or mode of action or reason for improvement.

Throughout this text, the descriptions refer to human antibody molecules and methods of using said human antibody molecules. Where the disclosure describes or claims a feature or embodiment associated with a human antibody molecule, such a feature or embodiment is equally applicable to the methods of using said human antibody molecule. Likewise, where the disclosure describes or claims a feature or embodiment associated with a method of using a human antibody molecule, such a feature or embodiment is equally applicable to the human antibody molecule.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

It is to be appreciated that certain features of the disclosed human antibody molecules, methods, and uses which are, for clarity, described herein in the context of separate embodiments, may also be provided in combination in a single embodiment. Conversely, various features of the disclosed human antibody molecules, methods, and uses that are, for brevity, described in the context of a single embodiment, may also be provided separately or in any subcombination.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, the singular forms "a," "an," and "the" include the plural.

The term "about" when used in reference to numerical ranges, cutoffs, or specific values is used to indicate that the recited values may vary by up to as much as 10% from the listed value. As many of the numerical values used herein are experimentally determined, it should be understood by those skilled in the art that such determinations can, and often times will, vary among different experiments. The values used herein should not be considered unduly limiting by virtue of this inherent variation. Thus, the term "about" is used to encompass variations of ±10% or less, variations of ±5% or less, variations of ±1% or less, variations of ±0.5% or less, or variations of ±0.1% or less from the specified value. When values are expressed by use of the antecedent "about" it will be understood that the particular value forms another embodiment.

Reference to a particular numerical value includes at least that particular value, unless the context clearly dictates otherwise.

The term "comprising" is intended to include examples encompassed by the terms "consisting essentially of" and "consisting of"; similarly, the term "consisting essentially of" is intended to include examples encompassed by the term "consisting of."

As used herein, "wherein the antibody molecule inhibits CXCL1-induced activation of CXCR2 or CXCL5-induced activation of CXCR2" and like phrases refers to the ability of the disclosed human antibody molecules to reduce CXCL1-induced or CXCL5-induced CXCR2 activation as determined in a β-arrestin recruitment in a Tango™ cell based assay by about 80%, about 85%, about 90%, about 92%, about 95%, about 97%, or about 100% compared to the level of CXCL1- and/or CXCL5-induced CXCR2 activation in the absence of the disclosed human antibody molecules and with an $IC_{50}$ of from 0.08 to 0.5 nM at a concentration of from 1.5-3.4 nM for CXCL1 and from 47.7 to 150 nM for CXCL5.

As used herein, "treating" and like terms refers to at least one of reducing the severity and/or frequency of symptoms, eliminating symptoms, ameliorating or eliminating the underlying cause of the symptoms, reducing the frequency or likelihood of symptoms and/or their underlying cause, and/or improving or remediating damage caused, directly or indirectly, by the described conditions or disorders. Treating may also include prolonging survival as compared to the expected survival of a subject not receiving the disclosed human antibody molecules or pharmaceutical compositions comprising the same.

As used herein, "preventing" and like terms refers to prophylactic or maintenance measures. Subjects for receipt of such prophylactic or maintenance measures include those who are at risk of having the described conditions or disorders due to, for example, genetic predisposition or environmental factors, or those who were previously treated for having the described conditions or disorders and are receiving therapeutically effective doses of the disclosed human antibody molecules or pharmaceutical compositions as a maintenance medication (e.g. to maintain low levels of lung neutrophils).

As used herein, "administering to the subject" and similar terms indicate a procedure by which the disclosed human antibody molecules or pharmaceutical compositions comprising the same are injected into/provided to a patient such that target cells, tissues, or segments of the body of the subject are contacted with the disclosed human antibody molecules.

The phrase "therapeutically effective amount" refers to an amount of the disclosed human antibody molecules or pharmaceutical compositions comprising the same, as described herein, effective to achieve a particular biological or therapeutic or prophylactic result such as, but not limited to, biological or therapeutic results disclosed, described, or exemplified herein. The therapeutically effective amount may vary according to factors such as the disease state, age, sex, and weight of the individual, and the ability of the composition to cause a desired response in a subject. Exemplary indicators of a therapeutically effect amount include, for example, improved well-being of the subject, a reduction in neutrophilia in one or more peripheral tissues, such as a reduction in airway neutrophilia, a reduction in the numbers of monocytes in one or more peripheral tissues, a reduction of acute airway inflammation, a reduction of chronic airway inflammation for example in bronchiectasis, a reduction of a tumor burden, arrested or slowed growth of a cancer, a reduction in chronic pain, a reduction in neuroinflammation such as in multiple sclerosis, a reduction in inflammation in the liver, a reduction of inflammation in the pancreas, or a decrease in the symptoms of type I diabetes.

As used herein, "pharmaceutically acceptable carrier" or "pharmaceutical acceptable excipient" includes any material which, when combined with an active ingredient (such as the disclosed human antibody molecules), allows the ingredient to retain biological activity and is non-reactive with the subject's immune system. Examples include, but are not limited to, any of the standard pharmaceutical carriers such as a phosphate buffered saline solution, water, and various types of wetting agents (such as polysorbate 20, polysorbate 80, and salts of tris(hydoxymethyl)aminomethane ("Tris"), such as the hydrochloride, acetate, maleate and lactate salts. Also may be added as stabilizing agents are amino acids (such as histidine, glutamine, glutamate, glycine, arginine), sugars (such as sucrose, glucose, trehalose), chelators (e.g. ETDA), and antioxidants (e.g. reduced cysteine). Preferred diluents for aerosol or parenteral administration are phosphate buffered saline or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000). In particular embodiments the pharmaceutical composition is a composition for parenteral delivery.

The term "subject" as used herein is intended to mean monkeys, such as cynomolgus macaques, and humans, and most preferably humans. "Subject" and "patient" are used interchangeably herein.

The term "antibody" and like terms is meant in a broad sense and includes immunoglobulin molecules including, monoclonal antibodies, antibody fragments, bispecific or multispecific antibodies, dimeric, tetrameric or multimeric antibodies, and single chain antibodies. Immunoglobulins can be assigned to five major classes, namely IgA, IgD, IgE, IgG, and IgM, depending on the heavy chain constant domain amino acid sequence. IgA and IgG are further sub-classified as the isotypes IgA1, IgA2, IgG1, IgG2, IgG3, and IgG4. Antibody light chains of any vertebrate species can be assigned to one of two clearly distinct types, namely kappa (κ) and lambda (λ), based on the amino acid sequences of their constant domains.

"Antibody fragment" refers to a portion of an immunoglobulin molecule that retains the specific antigen binding properties of the parental full length antibody (i.e. antigen-binding fragment thereof). Exemplary antibody fragments comprise heavy chain complementarity determining regions (HCDR) 1, 2, and 3 and light chain complementarity determining regions (LCDR) 1, 2, and 3. Other exemplary antibody fragments comprise a heavy chain variable region (VH) and a light chain variable region (VL). Antibody fragments include without limitation: an Fab fragment, a monovalent fragment consisting of the VL, VH, constant light (CL), and constant heavy 1 (CH1) domains; an F(ab)$_2$ fragment, a bivalent fragment comprising two Fab fragments linked by a disulfide bridge at the hinge region; and an Fv fragment consisting of the VL and VH domains of a single arm of an antibody. VH and VL domains can be engineered and linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Int'l Pat. Pub. Nos. WO1998/044001, WO1988/001649, WO1994/013804, and WO1992/001047. These antibody fragments are obtained using techniques well known to those of skill in the art, and the fragments are screened for utility in the same manner as are full length antibodies.

Each antibody heavy chain or light chain variable region consists of four "framework" regions (FRs) which alternate with three "Complementarity Determining Regions" (CDRs), in the sequence FR1, CDR1, FR2, CDR2, FR3, CDR3, FR4 (from amino to carboxy termini). The three CDRs in the VH are identified as HCDR1, HCDR2, HCDR3, and the three CDRs in the VL are identified as LCDR1, LCDR2, LCDR3 respectively. The location and size of the CDRs are defined based on rules which identify regions of sequence variability within the immunoglobulin variable regions (Wu and Kabat J Exp Med 132:211-50, 1970; Kabat et al. Sequences of Proteins of Immunological Interest, 5th Ed. Public Health Service, National Institutes of Health, Bethesda, Md., 1991). Amino acid residues within a variable region may be numbered according the scheme of Kabat (ibid.) "Frameworks" or "framework regions" are the remaining sequences of a variable region other than those defined to be CDRs.

"Human antibody" refers to an antibody having heavy and light chain variable regions in which both the framework and the antigen binding sites are derived from sequences of human origin. If the antibody contains a constant region, the constant region also is derived from sequences of human origin. A human antibody comprises heavy or light chain variable regions that are "derived from" sequences of human origin if the variable regions of the antibody are obtained from a system that uses human germline immunoglobulin or rearranged human immunoglobulin genes. Such systems include human immunoglobulin gene libraries displayed on phage, and transgenic non-human animals such as mice or rats carrying human immunoglobulin loci. "Human antibody" may contain amino acid differences when compared to the human germline or rearranged immunoglobulin sequences due to, for example, naturally occurring somatic mutations or intentional introduction of substitutions in the framework or antigen binding sites. Typically, a "human antibody" is at least about 80%, 81%, 82%, 83%, 84%, 85%, 86%, 87%, 88%, 89%, 90%, 91%, 92%, 93%, 94%, 95%, 96%, 97%, 98%, 99%, or 100% identical in amino acid sequence to an amino acid sequence encoded by a human germline or rearranged immunoglobulin gene. In some cases, a "human antibody" may contain consensus framework sequences derived from human framework sequence analyses, for example as described in Knappik et al., *J Mol Biol* 296:57-86, 2000, or synthetic HCDR3 incorporated into human immunoglobulin gene libraries displayed on phage, as described in, for example, Shi et al., *J Mol Biol* 397:385-96, 2010 and Int'l Pat. Pub. No. WO2009/085462.

Human antibodies, while derived from human immunoglobulin sequences, may be generated using systems such as phage display incorporating synthetic CDRs and/or synthetic frameworks, and/or can be subjected to in vitro mutagenesis to improve antibody properties in the variable regions or the constant regions or both, resulting in antibodies that do not naturally exist within the human antibody germline repertoire in vivo.

"Monoclonal antibody" refers to a population of antibody molecules of a substantially single molecular composition. A monoclonal antibody composition displays a single binding specificity and affinity for a particular epitope, or in a case of a bispecific monoclonal antibody, a dual binding specificity to two distinct epitopes. Monoclonal antibody therefore refers to an antibody population with single amino acid composition in each heavy and each light chain, except for possible well known alterations such as removal of C-terminal lysine from the antibody heavy chain, and processing variations in which there is incomplete cleavage of the N-terminal leader sequence that is produced in the cell and ordinarily cleaved upon secretion. For example, U.S. Pat. No. 8,241,630 describes a commercial antibody in which 5-15% of the antibody population retain the leader sequence. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Epitope" refers to a portion of an antigen to which an antibody specifically binds. Epitopes usually consist of chemically active (such as polar, non-polar, or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Variant" refers to a polypeptide or a polynucleotide that differs from a reference polypeptide or a reference polynucleotide by one or more modifications for example, substitutions, insertions, or deletions.

The phrase "immunospecifically binds" refers to the ability of the disclosed human antibody molecules to preferentially bind to its target (CXCR2 in the case of "anti-CXCR2 antibody) without preferentially binding other molecules of the CXCR family in a sample containing a mixed population of molecules. Human antibody molecules that immunospecifically bind CXCR2 are substantially free of other antibodies having different antigenic specificities (e.g., an anti-CXCR2 antibody is substantially free of antibodies that specifically bind antigens other than CXCR2). Antibody molecules that immunospecifically bind human CXCR2, however, can have cross-reactivity to other antigens, such as orthologs of human CXCR2, including *Macaca fascicularis* (cynomolgus monkey) CXCR2. The antibody molecules disclosed herein are able to immunospecifically bind both naturally produced human CXCR2 and to human CXCR2 which is recombinantly produced in mammalian or prokaryotic cells.

As used herein, "severe, sustained neutropenia" refers to an absolute peripheral blood neutrophil count (ANC) less than $0.4 \times 10^9$ cells/L for greater than 2 weeks. Severe, sustained neutropenia can be graded as follows:
  Grade 1 indicates a mild event ($0.8-1.0 \times 10^9$ cells/L)
  Grade 2 indicates a moderate event ($0.6-0.8 \times 10^9$ cells/L)
  Grade 3 indicates a severe event ($0.4-0.6 \times 10^9$ cells/L)
  Grade 4 indicates a potentially life threatening event (less than $0.4 \times 10^9$ cells/L) (See Division of AIDS (DAIDS) National Institute of Allergy and Infectious Diseases National Institutes of Health US Department of Health and Human Services Table for Grading the Severity of Adult and Pediatric Adverse Events, Version 2.0 November 2014).

The following abbreviations are used herein: variable heavy chain (VH); variable light chain (VL); complementarity-determining region (CDR); heavy chain CDR (HCDR); light chain CDR (LCDR); CXC chemokine receptor 2 (CXCR2); and chemokine ligand 1, 2, 3, 5, 6, 7, and 8 (CXCL1, 2, 3, 5, 6, 7, and 8).

The disclosed antibody molecules can comprise one or more substitutions, deletions, or insertions, in the framework and/or constant regions. In some embodiments, an IgG4 antibody molecule can comprise a S228P substitution. S228 (residue numbering according to EU index) is located in the hinge region of the IgG4 antibody molecule. Substitution of the serine ("S") to a proline ("P") serves to stabilize the hinge of the IgG4 and prevent Fab arm exchange in vitro and in vivo. In some embodiments, the antibody molecules can comprise one or more modifications which increase the in vivo half-life of the antibody molecules. For instance in certain embodiments the antibody can comprise a M252Y substitution, a S254T substitution, and a T256E substitution (collectively referred to as the "YTE" substitution). M252, S254, and T256 (residue numbering according to EU index) are located in in the CH2 domain of the heavy chain. Substitution of these residues to tyrosine ("Y"), threonine ("T"), and glutamate ("E"), respectively, protects the antibody molecules from lysosomal degradation, thereby enhancing the serum half-life of the antibody molecules. In some embodiments, the antibody molecules can comprise a deletion of the heavy chain C-terminal lysine residue. Deletion of the heavy chain C-terminal lysine residue reduces heterogeneity of the antibody molecules when produced by mammalian cells. In some embodiments, the antibody molecules can comprise a combination of substitutions, deletions, or insertions. For example, in some aspects, the disclosed antibody molecules can comprise a S228P substitution and a deletion of a heavy chain C-terminal lysine residue. Antibody constant regions of different classes are known to be involved in modulating antibody effector functions such as antibody-dependent cellular cytotoxicity (ADCC), complement-dependent cytotoxicity (CDC), and antibody dependent phagocytosis (ADP). In some embodiments the disclosed antibody molecules may comprise one or more substitutions, deletions, or insertions in the constant regions which modulate one or more antibody effector functions, such as reducing or ablating one or more effector functions. Other alterations that affect antibody effector functions and circulation half-life are known. See, e.g. Saunders KO "Conceptual Approaches to Modulating Antibody Effector Functions and Circulation Half-Life" *Front. Immunol.* (2019) 10:1296.

Human Antibody Molecules

Disclosed herein are human antibody molecules that immunospecifically bind to human CXCR2. The human antibody molecules can comprise the heavy chain CDR1, CDR2, and CDR3 of SEQ ID NO: 167 and the light chain CDR1, CDR2, and CDR3 of SEQ ID NO: 168 and inhibit activation of CXCR2 by CXCL1 or CXCL5. As provided in Table 19 and FIGS. 4A and 4B, SEQ ID NOS: 167 and 168 represent a consensus heavy chain variable region and light chain variable region, respectively (SEQ ID NO: 167="consensus VH" and SEQ ID NO: 168="consensus VL"), of the disclosed human antibody molecules. Consensus CDR sequences are provided as SEQ ID NOs: 169, 170, 171, 172, 173, and 174. The numbering in the names of the disclosed CDR sequences, unless otherwise noted, is according to Kabat. In some embodiments, the human antibody molecules can comprise:

the heavy chain CDR1 comprising the amino acid sequence of $SX_1X_2X_3S$ wherein: $X_1$ is S, Q, H, L, W, or Y; $X_2$ is T or A; and $X_3$ is M, Q, D, H, or W as provided in SEQ ID NO: 169;

the heavy chain CDR2 comprising the amino acid sequence of $AX_4SX_5X_6X_7RX_8TYYADSVKG$ wherein: $X_4$ is I or H; $X_5$ is G or D; $X_6$ is R, S, or Q; $X_7$ is G or D; and $X_8$ is N or S as provided in SEQ ID NO: 170;

the heavy chain CDR3 comprising the amino acid sequence of $QX_{10}X_{11}X_{12}$ wherein: $X_{10}$ is M, A, Q, or K; $X_{11}$ is G or D; and $X_{12}$ is Y, S, or K as provided in SEQ ID NO: 171;

the light chain CDR1 comprising the amino acid sequence of IGTSSDVGGYNYVS as provided in SEQ ID NO: 172;

the light chain CDR2 comprising the amino acid sequence of $X_{13}VX_{14}X_{15}X_{16}PS$ wherein: $X_{13}$ is E or D; $X_{14}$ is N, D, or S; $X_{15}$ is K, A, D, or H; and $X_{16}$ is R or Q as provided in SEQ ID NO: 173; and the light chain CDR3 comprising the amino acid sequence of $SSX_{17}AGX_{18}NX_{19}FGX_{20}$ wherein: $X_{17}$ is Y or A; $X_{18}$ is N, A, S, K, L, W, or Y; $X_{19}$ is N, Q, D, H, K, L, or Y; and $X_{20}$ is V, A, or K as provided in SEQ ID NO: 174.

The human antibody molecules can comprise the heavy chain CDR1, CDR2, and CDR3 of SEQ ID NO: 226 and the light chain CDR1, CDR2, and CDR3 of SEQ ID NO: 227. As provided in Table 19 and FIGS. 5A and 5B, SEQ ID NO: 226 and 227 represent a consensus heavy chain variable region and light chain variable region, respectively (SEQ ID NO: 226="consensus VH" and SEQ ID NO: 227="consensus VL"), of the disclosed human antibody molecules. Consensus CDR sequences are provided as SEQ ID NOs: 228, 229, 230, 201, 231, and 232. In some embodiments, the human antibody molecules can comprise:

the heavy chain CDR1 comprising the amino acid sequence of $SSTX_{21}S$ wherein $X_{21}$ is M or Q as provided in SEQ ID NO: 228;

the heavy chain CDR2 comprising the amino acid sequence of $AISGX_{23}GX_{24}X_{25}TYYADSVKG$ wherein: $X_{23}$ is R or S; $X_{24}$ is R or G; and $X_{25}$ is N or S as provided in SEQ ID NO: 229;

the heavy chain CDR3 comprising the amino acid sequence of $QX_{28}GY$ wherein: $X_{28}$ is M, K, or A as provided in SEQ ID NO: 230;

the light chain CDR1 comprising the amino acid sequence of IGTSSDVGGYNYVS as provided in SEQ ID NO: 201;

the light chain CDR2 comprising the amino acid sequence of $EVX_{30}KRPS$ wherein: $X_{30}$ is N or S as provided in SEQ ID NO: 231; and the light chain CDR3 comprising the amino acid sequence of $SSYAGX_{31}NNFGV$ wherein: $X_{31}$ is N or S as provided in SEQ ID NO: 232.

The disclosed human antibody molecules can comprise a combination of the heavy chain and light chain CDRs provided in Table 1. In some embodiments, for example, the human antibody molecule can comprise a heavy chain CDR1 comprising the amino acid sequence of any one of SEQ ID NOs: 175-185, a heavy chain CDR2 comprising the amino acid sequence of any one of SEQ ID NOs: 186-192, a heavy chain CDR3 comprising the amino acid sequence of any one of SEQ ID NOs: 194-200, a light chain CDR1 comprising the amino acid sequence of SEQ ID NO: 201, a light chain CDR2 comprising the amino acid sequence of any one of SEQ ID NOs: 202-209, and a light chain CDR3 comprising the amino acid sequence of any one of SEQ ID NOs: 210-225.

TABLE 1

| Heavy chain and light chain CDR sequences | | | |
|---|---|---|---|
| Antibody chain with substitution(s) identified by Kabat position SEQ ID NO: | CDR1 | CDR2 | CDR3 |
| HC Variable Regions | | | |
| 4A8 VH S32Q SEQ ID NO: 53 | SEQ ID NO: 176 | SEQ ID NO: 186 | SEQ ID NO: 194 |
| 4A8 VH S32H SEQ ID NO: 54 | SEQ ID NO: 177 | SEQ ID NO: 186 | SEQ ID NO: 194 |
| 4A8 VH S32L SEQ ID NO: 55 | SEQ ID NO: 178 | SEQ ID NO: 186 | SEQ ID NO: 194 |
| 4A8 VH S32W SEQ ID NO: 56 | SEQ ID NO: 179 | SEQ ID NO: 186 | SEQ ID NO: 194 |
| 4A8 VH S32Y SEQ ID NO: 57 | SEQ ID NO: 180 | SEQ ID NO: 186 | SEQ ID NO: 194 |
| 4A8 VH T33A SEQ ID NO: 58 | SEQ ID NO: 181 | SEQ ID NO: 186 | SEQ ID NO: 194 |
| 4A8 VH M34Q SEQ ID NO: 59 | SEQ ID NO: 182 | SEQ ID NO: 186 | SEQ ID NO: 194 |
| 4A8 VH M34D SEQ ID NO: 60 | SEQ ID NO: 183 | SEQ ID NO: 186 | SEQ ID NO: 194 |
| 4A8 VH M34H SEQ ID NO: 61 | SEQ ID NO: 184 | SEQ ID NO: 186 | SEQ ID NO: 194 |
| 4A8 VH M34W SEQ ID NO: 62 | SEQ ID NO: 185 | SEQ ID NO: 186 | SEQ ID NO: 194 |
| 4A8 VH I51H SEQ ID NO: 63 | SEQ ID NO: 175 | SEQ ID NO: 187 | SEQ ID NO: 194 |
| 4A8 VH G52aD SEQ ID NO: 64 | SEQ ID NO: 175 | SEQ ID NO: 188 | SEQ ID NO: 194 |
| 4A8 VH R53S SEQ ID NO: 65 | SEQ ID NO: 175 | SEQ ID NO: 189 | SEQ ID NO: 194 |
| 4A8 VH R53Q SEQ ID NO: 66 | SEQ ID NO: 175 | SEQ ID NO: 190 | SEQ ID NO: 194 |
| 4A8 VH G54D SEQ ID NO: 67 | SEQ ID NO: 175 | SEQ ID NO: 191 | SEQ ID NO: 194 |
| 4A8 VH N56S SEQ ID NO: 68 | SEQ ID NO: 175 | SEQ ID NO: 192 | SEQ ID NO: 194 |
| 4A8 VH M96A SEQ ID NO: 70 | SEQ ID NO: 175 | SEQ ID NO: 186 | SEQ ID NO: 195 |
| 4A8 VH M96Q SEQ ID NO: 71 | SEQ ID NO: 175 | SEQ ID NO: 186 | SEQ ID NO: 196 |
| 4A8 VH M96K SEQ ID NO: 72 | SEQ ID NO: 175 | SEQ ID NO: 186 | SEQ ID NO: 197 |
| 4A8 VH G101D SEQ ID NO: 73 | SEQ ID NO: 175 | SEQ ID NO: 186 | SEQ ID NO: 198 |
| 4A8 VH Y102S SEQ ID NO: 74 | SEQ ID NO: 175 | SEQ ID NO: 186 | SEQ ID NO: 199 |
| 4A8 VH Y102K SEQ ID NO: 75 | SEQ ID NO: 175 | SEQ ID NO: 186 | SEQ ID NO: 200 |
| 4A8 VH M34Q, N56S (SEQ ID NO: 98) | SEQ ID NO: 182 | SEQ ID NO: 192 | SEQ ID NO: 194 |
| 4A8 VH M34Q, A40P, N56S (SEQ ID NO: 99) | SEQ ID NO: 182 | SEQ ID NO: 192 | SEQ ID NO: 194 |
| 4A8 VH M34Q, A40P, N56S, R75K (SEQ ID NO: 100) | SEQ ID NO: 182 | SEQ ID NO: 192 | SEQ ID NO: 194 |
| 4A8 VH M34Q, A40P, N56S, M96K (SEQ ID NO: 101) | SEQ ID NO: 182 | SEQ ID NO: 192 | SEQ ID NO: 197 |
| 4A8 VH M34Q, A40P, N56S, R75K, M96K (SEQ ID NO: 102) | SEQ ID NO: 182 | SEQ ID NO: 192 | SEQ ID NO: 197 |
| 4A8 VH M34Q, A40P, N56S, R75K, I94K, M96K (SEQ ID NO: 103) | SEQ ID NO: 182 | SEQ ID NO: 192 | SEQ ID NO: 197 |
| 4A8 VH M34Q, A40P, N56S, I94K, M96K (SEQ ID NO: 104) | SEQ ID NO: 182 | SEQ ID NO: 192 | SEQ ID NO: 197 |
| 4A8 VH M34Q, N56S, M96K (SEQ ID NO: 105) | SEQ ID NO: 182 | SEQ ID NO: 192 | SEQ ID NO: 197 |
| 4A8 VH M34Q, N56S, R75K, M96K (SEQ ID NO: 106) | SEQ ID NO: 182 | SEQ ID NO: 192 | SEQ ID NO: 197 |
| 4A8 VH I94K, M96K | SEQ ID NO: 175 | SEQ ID NO: 186 | SEQ ID NO: 197 |

TABLE 1-continued

Heavy chain and light chain CDR sequences

| Antibody chain with substitution(s) identified by Kabat position SEQ ID NO: | CDR1 | CDR2 | CDR3 |
|---|---|---|---|
| (SEQ ID NO: 107) 4A8 VH M34Q, A40P, N56S, R75K, M96A (SEQ ID NO: 108) | SEQ ID NO: 182 | SEQ ID NO: 192 | SEQ ID NO: 195 |
| LC Variable Regions | | | |
| 4A8 VL E50D SEQ ID NO: 76 | SEQ ID NO: 201 | SEQ ID NO: 203 | SEQ ID NO: 210 |
| 4A8 VL N52D SEQ ID NO: 77 | SEQ ID NO: 201 | SEQ ID NO: 204 | SEQ ID NO: 210 |
| 4A8 VL N52S SEQ ID NO: 78 | SEQ ID NO: 201 | SEQ ID NO: 205 | SEQ ID NO: 210 |
| 4A8 VL K53A SEQ ID NO: 79 | SEQ ID NO: 201 | SEQ ID NO: 206 | SEQ ID NO: 210 |
| 4A8 VL K53D SEQ ID NO: 80 | SEQ ID NO: 201 | SEQ ID NO: 207 | SEQ ID NO: 210 |
| 4A8 VL K53H SEQ ID NO: 81 | SEQ ID NO: 201 | SEQ ID NO: 208 | SEQ ID NO: 210 |
| 4A8 VL R54Q SEQ ID NO: 82 | SEQ ID NO: 201 | SEQ ID NO: 209 | SEQ ID NO: 210 |
| 4A8 VL Y91A SEQ ID NO: 83 | SEQ ID NO: 201 | SEQ ID NO: 202 | SEQ ID NO: 211 |
| 4A8 VL N94A SEQ ID NO: 84 | SEQ ID NO: 201 | SEQ ID NO: 202 | SEQ ID NO: 212 |
| 4A8 VL N94S SEQ ID NO: 85 | SEQ ID NO: 201 | SEQ ID NO: 202 | SEQ ID NO: 213 |
| 4A8 VL N94K SEQ ID NO: 86 | SEQ ID NO: 201 | SEQ ID NO: 202 | SEQ ID NO: 214 |
| 4A8 VL N94L SEQ ID NO: 87 | SEQ ID NO: 201 | SEQ ID NO: 202 | SEQ ID NO: 215 |
| 4A8 VL N94W SEQ ID NO: 88 | SEQ ID NO: 201 | SEQ ID NO: 202 | SEQ ID NO: 216 |
| 4A8 VL N94Y SEQ ID NO: 89 | SEQ ID NO: 201 | SEQ ID NO: 202 | SEQ ID NO: 217 |
| 4A8 VL N95aQ SEQ ID NO: 90 | SEQ ID NO: 201 | SEQ ID NO: 202 | SEQ ID NO: 218 |
| 4A8 VL N95aD SEQ ID NO: 91 | SEQ ID NO: 201 | SEQ ID NO: 202 | SEQ ID NO: 219 |
| 4A8 VL N95aH SEQ ID NO: 92 | SEQ ID NO: 201 | SEQ ID NO: 202 | SEQ ID NO: 220 |
| 4A8 VL N95aK SEQ ID NO: 93 | SEQ ID NO: 201 | SEQ ID NO: 202 | SEQ ID NO: 221 |
| 4A8 VL N95aL SEQ ID NO: 94 | SEQ ID NO: 201 | SEQ ID NO: 202 | SEQ ID NO: 222 |
| 4A8 VL N95aY SEQ ID NO: 95 | SEQ ID NO: 201 | SEQ ID NO: 202 | SEQ ID NO: 223 |
| 4A8 VL V97A SEQ ID NO: 96 | SEQ ID NO: 201 | SEQ ID NO: 202 | SEQ ID NO: 224 |
| 4A8 VL V97K SEQ ID NO: 97 | SEQ ID NO: 201 | SEQ ID NO: 202 | SEQ ID NO: 225 |
| 4A8 VL N52S, N94S (SEQ ID NO: 109) | SEQ ID NO: 201 | SEQ ID NO: 205 | SEQ ID NO: 213 |
| 4A8 VL D41G, N52S, N94S (SEQ ID NO: 110) | SEQ ID NO: 201 | SEQ ID NO: 205 | SEQ ID NO: 213 |

Residue positions of substitutions defined according to Kabat.

In some aspects, the human antibody molecule can comprise:
a heavy chain CDR1, CDR2, and CDR3 of:
SEQ ID NO: 176, SEQ ID NO: 186, and SEQ ID NO: 194, respectively;
SEQ ID NO: 177, SEQ ID NO: 186, and SEQ ID NO: 194, respectively;
SEQ ID NO: 178, SEQ ID NO: 186, and SEQ ID NO: 194, respectively;
SEQ ID NO: 179, SEQ ID NO: 186, and SEQ ID NO: 194, respectively;
SEQ ID NO: 180, SEQ ID NO: 186, and SEQ ID NO: 194, respectively;
SEQ ID NO: 181, SEQ ID NO: 186, and SEQ ID NO: 194, respectively;
SEQ ID NO: 182, SEQ ID NO: 186, and SEQ ID NO: 194, respectively;
SEQ ID NO: 183, SEQ ID NO: 186, and SEQ ID NO: 194, respectively;
SEQ ID NO: 184, SEQ ID NO: 186, and SEQ ID NO: 194, respectively;
SEQ ID NO: 185, SEQ ID NO: 186, and SEQ ID NO: 194, respectively;
SEQ ID NO: 175, SEQ ID NO: 187, and SEQ ID NO: 194, respectively;

SEQ ID NO: 175, SEQ ID NO: 188, and SEQ ID NO: 194, respectively;

SEQ ID NO: 175, SEQ ID NO: 189, and SEQ ID NO: 194, respectively;

SEQ ID NO: 175, SEQ ID NO: 190, and SEQ ID NO: 194, respectively;

SEQ ID NO: 175, SEQ ID NO: 191, and SEQ ID NO: 194, respectively;

SEQ ID NO: 175, SEQ ID NO: 192, and SEQ ID NO: 194, respectively;

SEQ ID NO: 175, SEQ ID NO: 186, and SEQ ID NO: 195, respectively;

SEQ ID NO: 175, SEQ ID NO: 186, and SEQ ID NO: 196, respectively;

SEQ ID NO: 175, SEQ ID NO: 186, and SEQ ID NO: 197, respectively;

SEQ ID NO: 175, SEQ ID NO: 186, and SEQ ID NO: 198, respectively;

SEQ ID NO: 175, SEQ ID NO: 186, and SEQ ID NO: 199, respectively; or

SEQ ID NO: 175, SEQ ID NO: 186, and SEQ ID NO: 200, respectively; and a light chain CDR1, CDR2, and CDR3 of SEQ ID NO: 201, SEQ ID NO: 202, and SEQ ID NO: 210, respectively.

In some aspects, the human antibody molecule can comprise:

a heavy chain CDR1, CDR2, and CDR3 of SEQ ID NO: 175, SEQ ID NO: 186, and SEQ ID NO: 194, respectively, and a light chain CDR1, CDR2, and CDR3 of:

SEQ ID NO: 201, SEQ ID NO: 203, and SEQ ID NO: 210, respectively;

SEQ ID NO: 201, SEQ ID NO: 204, and SEQ ID NO: 210, respectively;

SEQ ID NO: 201, SEQ ID NO: 205, and SEQ ID NO: 210, respectively;

SEQ ID NO: 201, SEQ ID NO: 206, and SEQ ID NO: 210, respectively;

SEQ ID NO: 201, SEQ ID NO: 207, and SEQ ID NO: 210, respectively;

SEQ ID NO: 201, SEQ ID NO: 208, and SEQ ID NO: 210, respectively;

SEQ ID NO: 201, SEQ ID NO: 209, and SEQ ID NO: 210, respectively;

SEQ ID NO: 201, SEQ ID NO: 202, and SEQ ID NO: 211, respectively;

SEQ ID NO: 201, SEQ ID NO: 202, and SEQ ID NO: 212, respectively;

SEQ ID NO: 201, SEQ ID NO: 202, and SEQ ID NO: 213, respectively;

SEQ ID NO: 201, SEQ ID NO: 202, and SEQ ID NO: 214, respectively;

SEQ ID NO: 201, SEQ ID NO: 202, and SEQ ID NO: 215, respectively;

SEQ ID NO: 201, SEQ ID NO: 202, and SEQ ID NO: 216, respectively;

SEQ ID NO: 201, SEQ ID NO: 202, and SEQ ID NO: 217, respectively;

SEQ ID NO: 201, SEQ ID NO: 202, and SEQ ID NO: 218, respectively;

SEQ ID NO: 201, SEQ ID NO: 202, and SEQ ID NO: 219, respectively;

SEQ ID NO: 201, SEQ ID NO: 202, and SEQ ID NO: 220, respectively;

SEQ ID NO: 201, SEQ ID NO: 202, and SEQ ID NO: 221, respectively;

SEQ ID NO: 201, SEQ ID NO: 202, and SEQ ID NO: 222, respectively;

SEQ ID NO: 201, SEQ ID NO: 202, and SEQ ID NO: 223, respectively;

SEQ ID NO: 201, SEQ ID NO: 202, and SEQ ID NO: 224, respectively; or

SEQ ID NO: 201, SEQ ID NO: 202, and SEQ ID NO: 225, respectively.

In some aspects, the human antibody molecule can comprise:

a heavy chain CDR1, CDR2, and CDR3 of:

SEQ ID NO: 182, SEQ ID NO: 192, and SEQ ID NO: 194, respectively;

SEQ ID NO: 182, SEQ ID NO: 192, and SEQ ID NO: 197, respectively;

SEQ ID NO: 175, SEQ ID NO: 186, and SEQ ID NO: 197, respectively; or

SEQ ID NO: 182, SEQ ID NO: 192, and SEQ ID NO: 195, respectively; and a light chain CDR1, CDR2, and CDR3 of SEQ ID NO: 201, SEQ ID NO: 205, and SEQ ID NO: 213, respectively.

The human antibody molecules can comprise the heavy chain CDR1 comprising the amino acid sequence of SEQ ID NO: 182, the heavy chain CDR2 comprising the amino acid sequence of SEQ ID NO: 192, the heavy chain CDR3 comprising the amino acid sequence of SEQ ID NO: 195, the light chain CDR1 comprising the amino acid sequence of SEQ ID NO: 201, the light chain CDR2 comprising the amino acid sequence of SEQ ID NO: 205, and the light chain CDR3 comprising the amino acid sequence of SEQ ID NO: 213.

Figure 4A:
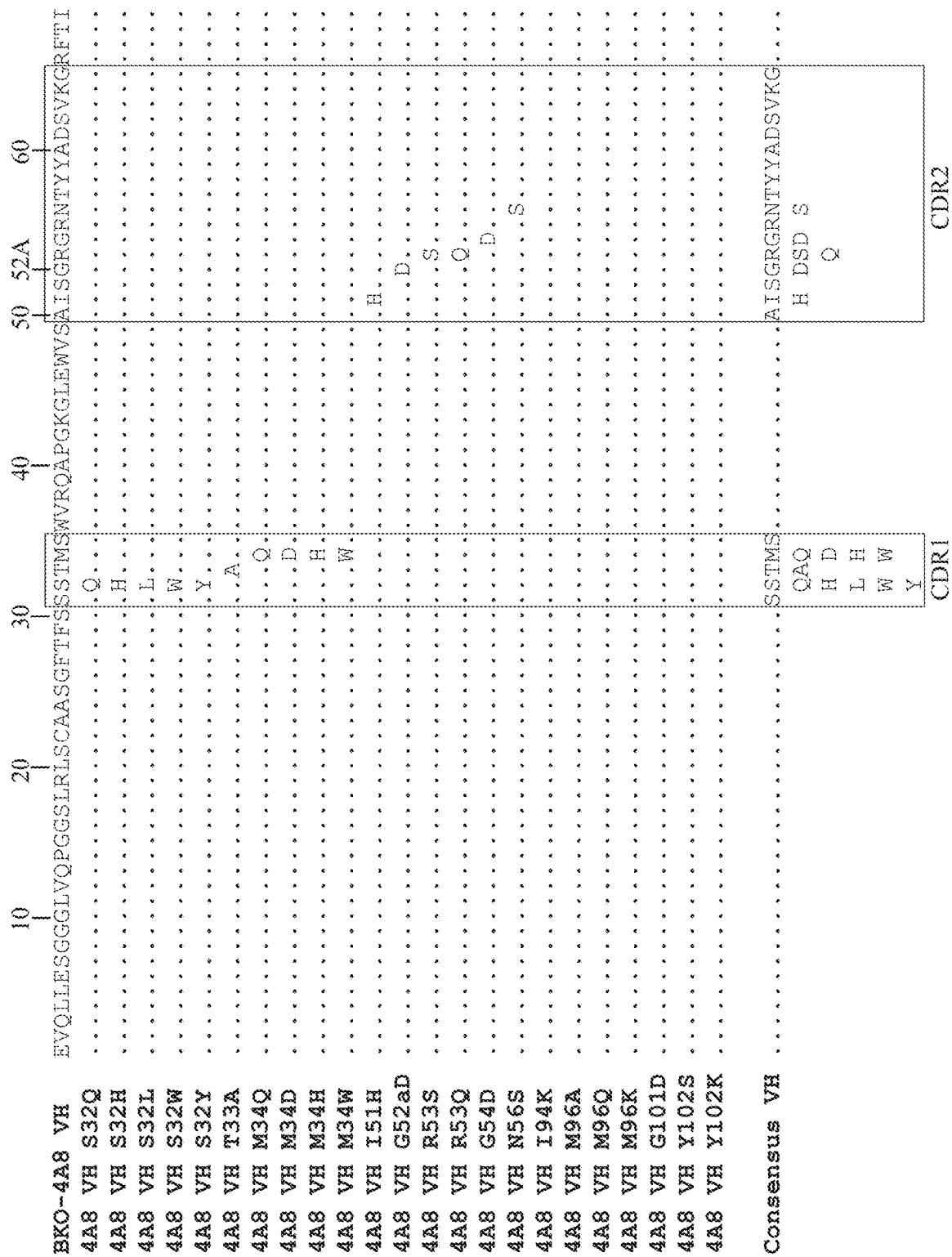
FIG. 4A and FIG. 4B illustrate an amino acid sequence alignment of exemplary BKO-4A8 variants with similar potency to parental BKO-4A8, and provides a consensus sequence.
Figure 4A:
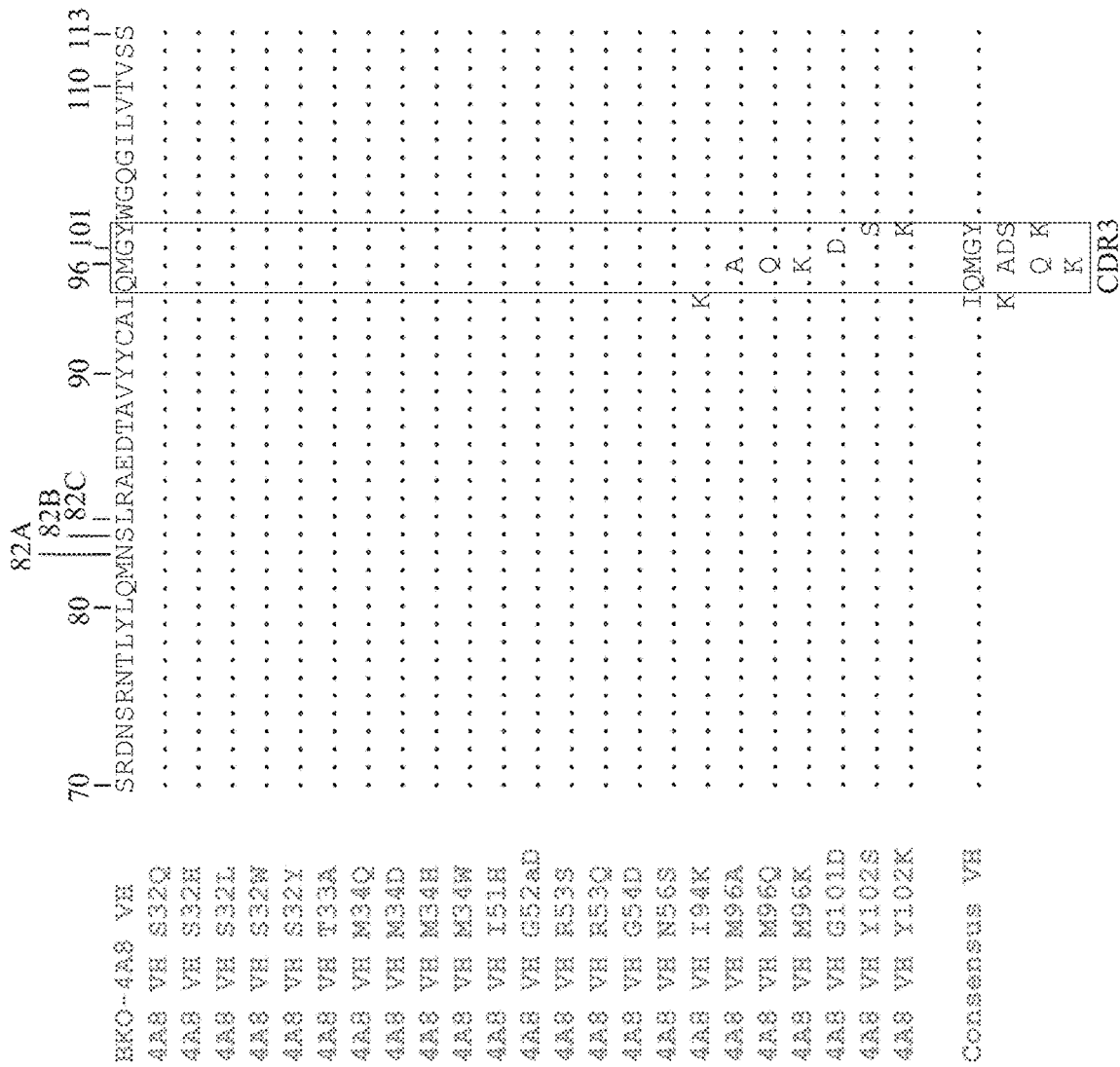
Figure 4B:
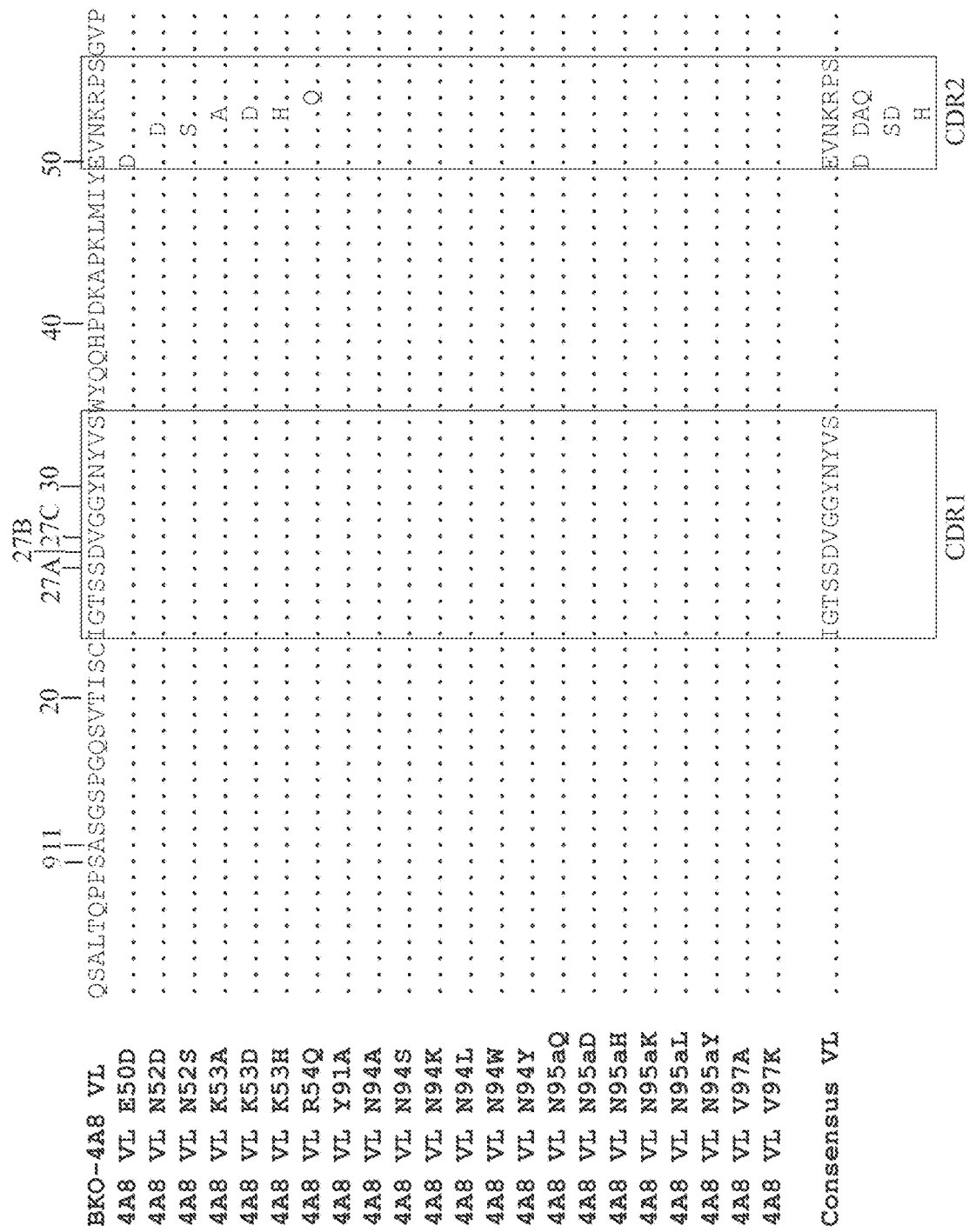
Figure 4B:
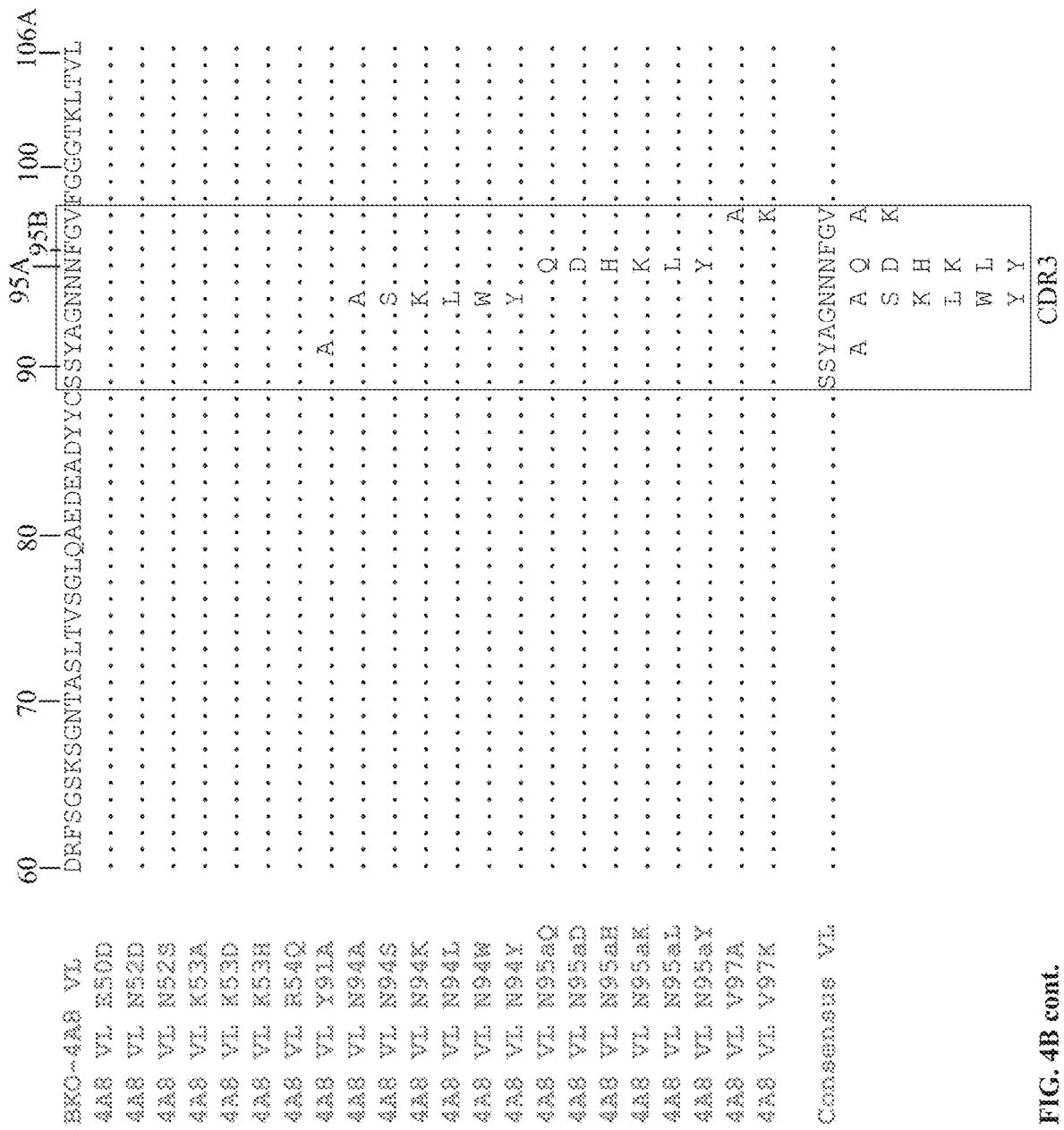

As provided in Table 19 and FIGS. 4A and 4B, SEQ ID NO: 167 and 168 represent a consensus heavy chain variable region and light chain variable region, respectively (SEQ ID NO: 167="consensus VH" and SEQ ID NO: 168="consensus VL"), of the disclosed human antibody molecules. Thus, the disclosed human antibody molecules can comprise the heavy chain variable region comprising the amino acid sequence of EVQLLESGGGLVQPGGSLRLSCAASGFTFSS<u>X$_1$X$_2$X$_3$</u>SWVRQAPGKGLEWV SA<u>X$_4$SX$_5$X$_6$X$_7$RX$_8$</u>TYYADSVKGRFTISRDNSRNTLYLQMNSLRAEDTAVYY CAX<u>QX$_{10}$X$_{11}$X$_{12}$</u>WQGILVTVSS wherein: $X_1$ is S, Q, H, L, W, or Y; $X_2$ is T or A; $X_3$ is M, Q, D, H, or W; $X_4$ is I or H; $X_5$ is G or D; $X_6$ is R, S, or Q; $X_7$ is G or D; $X_8$ is N or S; $X_9$ is I or K; $X_{10}$ is M, A, Q, or K; $X_{11}$ is G or D; and $X_{12}$ is Y, S, or K as provided in SEQ ID NO: 167 and the light chain variable region comprising the amino acid sequence of QSALTQPPSASGSPGQSVTISC<u>IGTSSDVGGYNYVS</u>WYQQHPDKAPKLMI Y<u>X$_{13}$VX$_{14}$X$_{15}$X$_{16}$P</u>SGVPDRFSGSKSGNTASLTVSGLQAEDEADYYC<u>SSX$_{17}$</u>

<u>AGX$_{18}$NX$_{19}$FGX$_{20}$</u>FGGGTKLTVL wherein: $X_{13}$ is E or D; $X_{14}$ is N, D, or S; $X_{15}$ is K, A, D, or H; $X_{16}$ is R or Q; $X_{17}$ is Y or A; $X_{18}$ is N, A, S, K, L, W, or Y; $X_{19}$ is N, Q, D, H, K, L, or Y; and $X_{20}$ is V, A, or K as provided in SEQ ID NO: 168. The underlined residues represent the consensus CDRs as disclosed above.

The human antibody molecules can comprise the heavy chain variable region comprising the amino acid sequence of EVQLLESGGGLVQPGGSLRLSCAASGFTFS<u>SSTX$_{21}$</u>SWVRQX$_{22}$PGKGLEWV <u>SAISGX$_{23}$GX$_{24}$X$_{25}$TYYADSVKG</u>RFTISRDNSX$_{26}$NTLYLQMNSLRAEDTAV YYCAX$_{27}$<u>QX$_{28}$GYWGQG</u>ILVTVSS wherein: X$_{21}$ is M or Q; X$_{22}$ is A or P; X$_{23}$ is R or S; X$_{24}$ is R or G; X$_{25}$ is N or S; X$_{26}$ is R or K; X$_{27}$ is I or K; and X$_{28}$ is M, K, or A as provided in SEQ ID NO: 226 and the light chain variable region comprising the amino acid sequence of QSALTQPPSASGSPGQSVTIS<u>CIGTSSDVGGYNYVS</u>WYQQHPX$_{29}$KAPKLM IYEVX$_{30}$KRPSGVPDRFSGSKSGNTASLTVSGLQAEDEADYYC<u>SSYAGX$_{31}$N</u>

<u>NFGV</u>FGGGTKLTVL wherein: X$_{29}$ is D or G; X$_{30}$ is N or S; and X$_{31}$ is N or S as provided in SEQ ID NO: 227. The underlined residues represent the consensus CDRs as disclosed above.

The human antibody molecules can comprise:
a) the heavy chain variable region comprising the amino acid sequence of SEQ ID NO: 98 and the light chain variable region comprising the amino acid sequence of SEQ ID NO: 109 or 110;
b) the heavy chain variable region comprising the amino acid sequence of SEQ ID NO: 99 and the light chain variable region comprising the amino acid sequence of SEQ ID NO: 109 or 110;
c) the heavy chain variable region comprising the amino acid sequence of SEQ ID NO: 100 and the light chain variable region comprising the amino acid sequence of SEQ ID NO: 109 or 110;
d) the heavy chain variable region comprising the amino acid sequence of SEQ ID NO: 101 and the light chain variable region comprising the amino acid sequence of SEQ ID NO: 109 or 110;
e) the heavy chain variable region comprising the amino acid sequence of SEQ ID NO: 102 and the light chain variable region comprising the amino acid sequence of SEQ ID NO: 109 or 110;
f) the heavy chain variable region comprising the amino acid sequence of SEQ ID NO: 103 and the light chain variable region comprising the amino acid sequence of SEQ ID NO: 109 or 110
g) the heavy chain variable region comprising the amino acid sequence of SEQ ID NO: 104 and the light chain variable region comprising the amino acid sequence of SEQ ID NO: 109 or 110;
h) the heavy chain variable region comprising the amino acid sequence of SEQ ID NO: 105 and the light chain variable region comprising the amino acid sequence of SEQ ID NO: 109 or 110;
i) the heavy chain variable region comprising the amino acid sequence of SEQ ID NO: 106 and the light chain variable region comprising the amino acid sequence of SEQ ID NO: 109 or 110;
j) the heavy chain variable region comprising the amino acid sequence of SEQ ID NO: 107 and the light chain variable region comprising the amino acid sequence of SEQ ID NO: 109 or 110
k) the heavy chain variable region comprising the amino acid sequence of SEQ ID NO: 108 and the light chain variable region comprising the amino acid sequence of SEQ ID NO: 109 or 110;
l) the heavy chain variable region comprising the amino acid sequence of SEQ ID NO: 162 and the light chain variable region comprising the amino acid sequence of SEQ ID NO: 109 or 110;
m) the heavy chain variable region comprising the amino acid sequence of SEQ ID NO: 163 and the light chain variable region comprising the amino acid sequence of SEQ ID NO: 109 or 110;
n) the heavy chain variable region comprising the amino acid sequence of SEQ ID NO: 164 and the light chain variable region comprising the amino acid sequence of SEQ ID NO: 109 or 110;
o) the heavy chain variable region comprising the amino acid sequence of SEQ ID NO: 165 and the light chain variable region comprising the amino acid sequence of SEQ ID NO: 109 or 110; or
p) the heavy chain variable region comprising the amino acid sequence of SEQ ID NO: 166 and the light chain variable region comprising the amino acid sequence of SEQ ID NO: 109 or 110.

In some embodiments, the human antibody molecules comprise:
a) the heavy chain variable region comprising the amino acid sequence of SEQ ID NO: 108 and the light chain variable region comprising the amino acid sequence of SEQ ID NO: 110;
b) the heavy chain variable region comprising the amino acid sequence of SEQ ID NO: 162 and the light chain variable region comprising the amino acid sequence of SEQ ID NO: 110;
c) the heavy chain variable region comprising the amino acid sequence of SEQ ID NO: 163 and the light chain variable region comprising the amino acid sequence of SEQ ID NO: 110;
d) the heavy chain variable region comprising the amino acid sequence of SEQ ID NO: 164 and the light chain variable region comprising the amino acid sequence of SEQ ID NO: 110;
e) the heavy chain variable region comprising the amino acid sequence of SEQ ID NO: 165 and the light chain variable region comprising the amino acid sequence of SEQ ID NO: 110; or
f) the heavy chain variable region comprising the amino acid sequence of SEQ ID NO: 166 and the light chain variable region comprising the amino acid sequence of SEQ ID NO: 110.

The human antibody molecules can comprise the heavy chain variable region comprising the amino acid sequence of SEQ ID NO: 108 and the light chain variable region comprising the amino acid sequence of SEQ ID NO: 110.

The disclosed human antibody molecules can comprise a human IgG1, IgG2, or IgG4 heavy chain constant region. In some embodiments, the human antibody molecule comprises a human IgG1 heavy chain constant region. Suitable human IgG1 heavy chain constant regions include, for example, the amino acid sequence of SEQ ID NO: 122 or 124. In some aspects, the human IgG1 heavy chain constant region comprises the amino acid sequence of SEQ ID NO: 122. In some aspects, the human IgG1 heavy chain constant region comprises the amino acid sequence of SEQ ID NO: 124. In some embodiments, the human antibody molecule comprises a human IgG2 heavy chain constant region. In some aspects, the human IgG2 heavy chain constant region comprises the amino acid sequence of SEQ ID NO: 120. In some embodiments, the human antibody molecule comprises a human IgG4 heavy chain constant region. Suitable human IgG4 heavy chain constant regions include, for example, the amino acid sequence of SEQ ID NO: 116 or 118. In some embodiments, the human IgG4 heavy chain constant region comprises the amino acid sequence of SEQ ID NO: 116. In some aspects, the human IgG4 heavy chain constant region comprises the amino acid sequence of SEQ ID NO: 118. In some embodiments the human IgG4 heavy chain constant region comprises an S228P substitution. In some embodiments the human IgG4 heavy chain constant region comprises M252Y, S254T and T256E substitutions. In some embodiments, the IgG4 constant region comprises deletion of the carboxyl-terminal lysine residue relative to the wild type IgG4.

The human antibody molecules can comprise a human lambda (λ) light chain constant region or a human kappa (κ) light chain constant region. In some embodiments, the human antibody molecule comprises a human lambda II (λ$_2$) light chain constant region.

The human antibody molecules can comprise a human IgG1 heavy chain constant region and a human lambda II light chain constant region. The human antibody molecules can comprise a human IgG2 heavy chain constant region and a human lambda II light chain constant region. The human antibody molecules can comprise a human IgG4 heavy chain constant region and a human lambda II light chain constant region.

The human antibody molecules can be a full-length antibody or an antigen-binding fragment thereof. Suitable antigen-binding fragments include, for example, an Fab fragment, an F(ab)$_2$ fragment, or a single chain antibody.

The disclosed human antibody molecules selectively antagonize human CXCR2, thereby inhibiting CXCL1- or CXCL5-induced activation of CXCR2. The disclosed human antibody molecules may also partially inhibit CXCL8-induced activation of CXCR2. The disclosed human antibody molecules may also exhibit one or more of the following properties:
  a) inhibit CXCL1-induced calcium flux in an HTS002C-CHEMISCREEN™ human CXCR2 chemokine receptor calcium-optimized cell line with an IC$_{50}$ of 0.8 to 2.4 at a CXCL1 concentration of from 1.5 to 3.4 nM;
  b) not substantially inhibit CXCL8-induced calcium flux in an HTS002C-CHEMISCREEN™ human CXCR2 chemokine receptor calcium-optimized cell line;
  c) inhibit CXCL1 or CXCL5-induced β-arrestin recruitment in a Tango™ cell based assay with an IC$_{50}$ of from 0.08 to 0.5 nM at a concentration of from 1.5-3.4 nM for CXCL1 and from 47.7 to 150 nM for CXCL5; or
  d) reduce airway neutrophilia in a subject with airway neutrophilia without causing severe, sustained neutropenia.

Pharmaceutical compositions comprising any of the herein disclosed human antibody molecules are also provided. In some embodiments, the pharmaceutical compositions can comprise any of the herein disclosed human antibody molecules in combination with a pharmaceutically acceptable carrier.

Also provided are nucleic acid molecules encoding any of the herein disclosed human antibody molecules. Exemplary polynucleotides which encode a human antibody or fragment thereof as described herein are provided as SEQ ID NOS: 233-247. Exemplary polynucleotides which encode human antibody heavy chain constant regions are provided as SEQ ID NOS:248-256.

Vectors comprising the herein disclosed nucleic acid molecules are also disclosed.

Further provided are cells transformed to express any of the herein disclosed human antibody molecules.

Methods of Treatment and Uses

CXCR2 antagonists have been the subject of studies, including clinical trials, for a range of conditions which involve pathologies associated with neutrophilic and/or monocytic inflammation and certain cancers which express CXCR2 or in which there is an element of neutrophil suppression of an anti-cancer response. Small molecule antagonists of CXCR2 have, for example, been developed for:
  (a) COPD (see, for example, Miller, B. et al., (2017). Late Breaking Abstract—"Danirixin (GSK1325756) improves respiratory symptoms and health status in mild to moderate COPD—results of a 1 year first time in patient study." *European Respiratory Journal*, 50);
  (b) influenza (see, for example, study NCT02469298 described on ClinicalTrials.gov entitled "Safety, Tolerability and Clinical Effect of Danirixin in Adults With Influenza");
  (c) bronchiectasis (see, for example, De Soyza et al., (2015) "A randomised, placebo-controlled study of the CXCR2 antagonist AZD5069 in bronchiectasis." *Eur Respir J*, 46, 1021-32);
  (d) cystic fibrosis (see, for example, Moss et al., (2013). "Safety and early treatment effects of the CXCR2 antagonist SB-656933 in patients with cystic fibrosis." *J Cyst Fibros*, 12, 241-8);
  (e) severe asthma (see, for example, Nair et al., (2012) "Safety and efficacy of a CXCR2 antagonist in patients with severe asthma and sputum neutrophils: a randomized, placebo-controlled clinical trial." *Clin Exp Allergy*, 42, 1097-103); and
  (f) prostate cancer (see, for example, study number NCT03177187 described on ClinicalTrials.gov entitled "Combination Study of AZD5069 and Enzalutamide").

Additionally, there is evidence that antagonism of CXCR2 may be beneficial in chronic upper airway diseases such as chronic rhinosinusitis (see, for example, Tomassen et al., (2016) "Inflammatory endotypes of chronic rhinosinusitis based on cluster analysis of biomarkers." *J Allergy Clin Immunol*, 137, 1449-1456 e4); in vascular diseases including ischemia-reperfusion injury (Stadtmann and Zarbock, (2012), "CXCR2: From Bench to Bedside." *Front Immunol*, 3, 263) and coronary artery disease (see, for example, Joseph et al., (2017) "CXCR2 Inhibition—a novel approach to treating Coronary heart Disease (CICADA): study protocol for a randomised controlled trial." Trials, 18, 473); in chronic pain (see, for example, Silva et al., (2017) "CXCL1/CXCR2 signaling in pathological pain: Role in peripheral and central sensitization." *Neurobiol Dis*, 105, 109-116); in neuroinflammatory conditions (see, for example, Veenstra and Ransohoff, (2012) "Chemokine receptor CXCR2: physiology regulator and neuroinflammation controller?" *J Neuroimmunol*, 246, 1-9) including multiple sclerosis (see, for example, Pierson et al., (2018) "The contribution of neutrophils to CNS autoimmunity." *Clin Immunol*, 189, 23-28) and Alzheimer's disease (see, for example, Liu et al., (2014) "Neuroinflammation in Alzheimer's disease: chemokines produced by astrocytes and chemokine receptors." *Int J Clin Exp Pathol*, 7, 8342-55); in alcoholic and non-alcoholic steatohepatitis (see, for example, French et al., (2017) "The role of the IL-8 signaling pathway in the infiltration of granulocytes into the livers of patients with alcoholic hepatitis." *Exp Mol Pathol*, 103, 137-140 and Ye et al., (2016) "Lipocalin-2 mediates non-alcoholic steatohepatitis by promoting neutrophil-macrophage crosstalk via the induction of CXCR2." *J Hepatol*, 65, 988-997); in pancreatitis (see, for example, Steele et al., (2015) "CXCR2 inhibition suppresses acute and chronic pancreatic inflammation." *J Pathol*, 237, 85-97); in diabetes (see, for example, Citro et al., (2015) "CXCR1/2 inhibition blocks and reverses type 1 diabetes in mice." *Diabetes*, 64, 1329-40); and in multiple types of cancer (see, for example, Liu et al., (2016) "The CXCL8-CXCR1/2 pathways in cancer." *Cytokine Growth Factor Rev,* 31, 61-71). Behcet's disease is characterized by neutrophil activation and has also been linked to CXCR2 (Qiao et al., "CXCR2 Expression on neutrophils is upregulated during the relapsing phase of ocular Behcet disease" *Curr Eye Res.* 2005; 30: 195-203).

The methods comprise administering to the subject a therapeutically effective amount of any of the herein disclosed human antibody molecules or the herein disclosed pharmaceutical compositions to treat or prevent the inflammation condition described herein. In some embodiments, the human antibody molecules or pharmaceutical compositions comprising the same are administered in a therapeutically effective amount to treat airway neutrophilia, as determined for example by sputum neutrophil counts, or acute lung inflammation. In such embodiments, the subjects receiving the human antibody molecules or pharmaceutical compositions comprising the same have airway neutrophilia or acute lung inflammation. In some embodiments, the human antibody molecules or pharmaceutical compositions comprising the same are administered in a therapeutically effective amount to prevent airway neutrophilia or acute lung inflammation. In such embodiments, the subjects receiving the human antibody molecules or pharmaceutical compositions comprising the same are at risk of having airway neutrophilia or acute lung inflammation due to, for example, genetic predisposition or environmental factors, or were previously treated for having airway neutrophilia or acute lung inflammation and are receiving, or are set to receive, therapeutically effective doses of the disclosed human antibody molecules or pharmaceutical compositions as a maintenance medication (e.g. to maintain low levels of lung neutrophils).

Also provided is the disclosed human antibody molecules or the disclosed pharmaceutical compositions for use in the prevention or treatment of airway neutrophilia or acute lung inflammation, as is the use of any of the disclosed human antibody molecules or any of the disclosed pharmaceutical compositions in the manufacture of a medicament for the prevention or treatment of neutrophilia in a peripheral tissue, airway neutrophilia or acute or chronic lung inflammation.

The airway neutrophilia, acute lung inflammation, or both can be chronic obstructive pulmonary disease, severe neutrophilic asthma, or both.

In at least one experimental model, the antibodies described herein have been observed to inhibit the migration of eosinophils into lung in response to inflammatory stimuli. Accordingly, the antibodies are useful for treating inflammatory diseases characterized by eosinophilia, such as eosinophilic asthma, allergic rhinitis, skin conditions, fungal and parasitic infections, autoimmune diseases (such as inflammatory bowel diseases, neuromyelitis optica, bullous pemphigoid, autoimmune myocarditis, primary biliary cirrhosis, eosinophilic granulomatosis with polyangiitis (Churg-Strauss syndrome), some cancers, and bone marrow disorders.

Without being bound by theory, the ability of the present CXCR2 antibodies to block eosinophilic migration into the lungs is surprising because eosinophils lack the CXCR2 receptor. For inflammatory cells to migrate into a site, they must first cross through the lining of the blood vessels, which are made up of endothelial cells, which are known to express CXCR2. Accordingly, the antibodies are further able to inhibit cell migration through effects on the endothelial cells.

The ability to affect endothelial cells also indicates that the present antibodies may be able to affect angiogenesis and metastasis, which is important in cancer. Accordingly, provided herein is a method for the treatment of cancer.

EXAMPLES

The following examples are provided to further describe some of the embodiments disclosed herein. The examples are intended to illustrate, not to limit, the disclosed embodiments.

General Methods

Generation of Plasmids for Antibody Production

Variable region amino acid sequences were backtranslated into DNA sequences prior to synthesis of the resulting DNA de novo. Synthesized heavy chain variable region genes were subcloned into an expression vector containing a polynucleotide sequence encoding a human IgG4 constant region comprising the core hinge stabilizing substitution S228P (SEQ ID NO: 118). Synthesized lambda light chain variable region genes were subcloned into an expression vector containing a polynucleotide sequence encoding the human lambda light chain constant region amino acid sequence (SEQ ID NO: 134). Synthesized kappa light chain variable region genes were subcloned into an expression vector containing a polynucleotide sequence encoding the human kappa light chain constant region amino acid sequence (SEQ ID NO: 135).

Transient Expression of Antibodies Using the Expi293F™ System

Antibodies were produced by co-transfecting antibody heavy and light plasmids into Expi293™ cells (Life Technologies). For each 20 mL transfection, $3.6 \times 10^7$ cells were required in 20 mL of Expi293™ Expression Medium. Transfections were carried out using ExpiFectamine™ 293 Reagent according to manufacturer's instructions.

Antibodies were harvested by centrifugation (3000×g for 20 minutes) between 72 hours and 84 hours post-transfection. Unless indicated otherwise, all antibodies were produced as human IgG4 incorporating the hinge stabilizing substitution S228P.

Purification and Buffer Exchange of Antibodies

Antibodies were purified from harvested material from transient transfections using protein A resin (MabSelece™ SuRe™, GE Healthcare) according to manufacturer's instructions.

Following elution, antibodies were buffer exchanged from citric acid into Sorensen's PBS, pH 5.8 (59.5 mM $KH_2PO_4$, 7.3 mM $Na_2HPO_4 \cdot 2H_2O$, 150 mM NaCl) using PD-10 desalting columns (52-1308-00 BB, GE Healthcare) containing 8.3 mL of Sephadex™ G-25 Resin.

Transient Transfection of CXCR Family Members into Expi293F™ Cells

Expi293F™ cells (Life Technologies) were transiently transfected, using the commercially available mammalian expression vector pTT5 (Durocher, 2002) containing a polynucleotide encoding either: human CXCR1 (SEQ ID NO: 133); human CXCR2 (SEQ ID NO: 125); human CXCR3 (SEQ ID NO: 128); human CXCR4 (SEQ ID NO: 129); human CXCR5 (SEQ ID NO: 130); human CXCR6 (SEQ ID NO: 131); human CXCR7 (SEQ ID NO: 132); or cynomolgus monkey CXCR2 (SEQ ID NO: 127).

For each 10 mL transfection, lipid-DNA complexes were prepared by diluting 10 µg of plasmid DNA in Opti-MEM™ I Reduced Serum Medium (Cat. no. 31985-062) to a total volume of 1.0 mL. 54 µL of ExpiFectamine™ 293 Reagent was diluted in Opti-MEM™ I medium to a total volume of 1.0 mL. Transfections were carried out according to manufacturer's instructions. The cells were incubated in a 37° C. incubator with a humidified atmosphere of 8% $CO_2$ in air on an orbital shaker rotating at 200 rpm. Approximately 18-24 hours post-transfection, the cell viability was evaluated and transfected cells harvested for use.

Flow Cytometry Binding Assays Using Transiently Transfected Expi293F™ Cells

Harvested cells were resuspended in FACS buffer (1×PBS+0.5% (w/v) bovine serum albumin (BSA)+2 mM EDTA pH 7.2). Approximately $2 \times 10^5$ cells were added per well in a 96-well round-bottomed plate. Cells were pelleted by centrifugation at 400 g for 5 mins at 4° C. and supernatants discarded. 25 µL of each test antibody or control antibody was added to the cells and incubated for 30 minutes at 4° C. Cells were washed twice in 100 µL FACS buffer followed by centrifugation at 400 g for 5 mins at 4° C.

For detection, 50 µL of secondary antibody (Table 2) was added to relevant samples. Commercially available antibodies that bound to transfected CXCR family members were used as positive controls to ensure that the cells were expressing the receptors. Cells were washed twice in 200 µL of FACS buffer followed by centrifugation at 400 g for 5 mins at 4° C. Before sample acquisition, cells were resuspended in 100 µL of FACS buffer. Samples were acquired using the high throughput sampler on a FACSCanto™ II cytometer (Beckton-Dickinson).

TABLE 2

Reagents used for flow cytometry analysis

| Reagents | Catalogue Number | Manufacturer Supplier | Recommended final dilutions |
|---|---|---|---|
| Anti-human CXCR1-FITC | FAB330F | R&D Systems | 1 in 10 |
| Anti-human CXCR2-FITC | 551126 | BD Biosciences | 1 in 5 |
| Anti-human CXCR3-FITC | 558047 | BD Biosciences | 1 in 10 |
| Anti-human CXCR4-FITC | 561735 | BD Biosciences | 1 in 10 |
| Anti-human CXCR5-FITC | 558112 | BD Biosciences | 1 in 10 |
| Anti-human CXCR6-PE | 356004 | BioLegend | 1 in 20 |
| Anti-human CXCR7-PE | 331104 | Bio Legend | 1 in 20 |
| Human IgG4, kappa (isotype control) | I4639-1MG | Sigma-Aldrich | 10 µg/mL |
| Anti-human IgG Fc specific-FITC | F9512-2ML | Sigma-Aldrich | 1 in 200 |
| Anti-Human Ig light chain λ Antibody - APC | 316610 | BioLegend | 1 in 20 |
| Anti-human CXCR2-APC | 320710 | BioLegend | 1 in 20 |
| Anti-human CXCR2-Alexa Fluor™ 647 | FAB331R-100 | R&D Systems | 1 in 20 |
| Anti-human CXCR2 | 555932 | BD Biosciences | |
| Anti-human CXCR2 | MAB331 | R&D Systems | |
| 7AAD | 559925 | BD Biosciences | 1 in 50 |

Human CXCR2 Cell-based Potency Assay

Tango™ CXCR2 cell-based assay: The commercially available reporter cell line Tango™ CXCR2-bla U2OS was used to assess the ability of antibodies to inhibit CXCR2 activation by CXCL8 and CXCL1 (ThermoFisher Scientific, Australia). Cells were thawed, propagated, cultured and frozen according to the manufacturer's directions.

Preparation of Tango™ CXCR2-bla U2OS cells for use in cell-based assays: The manufacturer's protocol was altered to make use of 96-well plates instead of 384-well plates. Briefly, dividing cells were harvested one day prior to use. Cells were harvested and resuspended in assay medium (100% FreeStyle™ Expression Medium; Life Technologies; Cat #12338-018) at a viable cell density of 312,500 cells/mL. 128 µL of cell suspension was added per well in 96-well black-walled, clear bottom tissue culture-treated plates. Cells were incubated for 16-20 hrs at 37° C. in an atmosphere of 5% $CO_2$ prior to use in assays.

Tango™ assay procedure: Assays were set up and run as described in the manufacturer's protocol. The agonists used in both agonist and antagonist potency assays are provided in Table 3. For antagonist assays, agonists were used at concentrations in the $EC_{50}$-$EC_{80}$ range. Assays were read using a FlexStation® 3 (Molecular Devices) fluorescence plate reader configured with the parameters given in Table 4. The blue/green emission ratio for each well was calculated by dividing the blue emission values by the green emission values. All inhibition curves were fitted using a four-parameter dose-response using GraphPad Prism™ (Version 7.01).

TABLE 3

Agonists used in cell based potency assays

| Human Agonist | Manufacturer | Catalogue Number | Tango™ Assay $EC_{50}$ (nM) | | Calcium Flux Assay $EC_{50}$ (nM) | |
|---|---|---|---|---|---|---|
| | | | Mean | Range | Mean | Range |
| CXCL1 | Miltenyi Biotec | 130-108-974 | 2.3 | 1.5-3.4 | 2.62 | 0.7-6.7 |
| CXCL2 | R&D Systems | 276-GB | 33.3 | 15-45.7 | 37.02 | insufficient data |

TABLE 3-continued

Agonists used in cell based potency assays

| Human Agonist | Manufacturer | Catalogue Number | Tango™ Assay $EC_{50}$ (nM) | | Calcium Flux Assay $EC_{50}$ (nM) | |
|---|---|---|---|---|---|---|
| | | | Mean | Range | Mean | Range |
| CXCL3 | R&D Systems | 277-GG | 11.9 | 6.0-22.7 | 12.25 | 10-18 |
| CXCL5 | R&D Systems | 254-XB | 97.7 | 47.7-150 | 39.17 | 10.3-20.5 |
| CXCL6 | R&D Systems | 333-GC | 9.4 | 5.6-12.4 | 28.94 | 26.8-32.4 |
| CXCL7 | R&D Systems | 393-NP | 39.6 | 15.3-77.2 | 7.14 | 5.3-9 |

TABLE 3-continued

Agonists used in cell based potency assays

| Human Agonist | Manufacturer | Catalogue Number | Tango™ Assay EC$_{50}$ (nM) | | Calcium Flux Assay EC$_{50}$ (nM) | |
|---|---|---|---|---|---|---|
| | | | Mean | Range | Mean | Range |
| CXCL8 | Miltenyi Biotec | 130-108-979 | 2.2 | 1.6-4.0 | 3.2 | 0.9-6.5 |

TABLE 4

Flexstation ® 3 fluorescence plate reader settings

| | Scan 1 (Blue) | Scan 2 (Green) |
|---|---|---|
| Excitation Filter | 409/20 nm | 409/20 nm |
| Emission Filter | 460/40 nm | 530/30 nm |

Peripheral Blood Preparations

Whole human buffy coat, PBMC enriched fractions prepared from human peripheral blood buffy coat or cynomolgus monkey whole blood was used for analysis of antibody binding activity by flow cytometry. Briefly, blood was untreated or diluted 1:1 in sterile filtered room temperature phosphate-buffered saline (PBS). 30 mL samples were layered over 15 mL Lymphoprep™ (Stem Cell Technologies, cat #07851). Peripheral blood mononuclear cells (PBMC) were enriched by room temperature centrifugation at 700 g for 30 minutes with no braking. The PBMC layer was isolated and cells washed in PBS containing 2 mM EDTA with low speed centrifugation at 200 g, to remove platelet contamination. Whole blood or PBMC enriched cell fractions were resuspended in red blood cell lysing solution (BioLegend, 420301). Viable cell counts were determined and cells resuspended at $1\times10^7$ cells per mL in FACS buffer (1×PBS+0.5% (w/v) BSA+2 mM EDTA pH 7.2).

Flow cytometry binding assays using whole blood or PBMC enriched preparations: Binding assays to detect CXCR2 on blood neutrophil populations using test antibodies were performed essentially as described for assays using transiently transfected Expi293F™ cells. Binding of antibodies to human CXCR2 on the surface of the neutrophils was measured using anti-CXCR2 antibody directly conjugated to the fluorophore allophycocyanin (APC). Matched isotype control antibodies were included for comparison. Cells were incubated with lineage specific antibodies and 2 µg/ml of APC conjugated anti-CXCR2 antibody or isotype control prepared in ice cold 3% BSA/PBS for a minimum of 30 minutes at 4° C. The commercial anti-CXCR2 antibody (clone 48331 (R&D Systems FAB331A)) was used as a positive control. Neutrophil populations were identified by characteristic granularity and size, and positive binding of commercially available antibodies against CD10 (Biolegend, clone H110a, catalogue number 312204). Cells were washed and fixed (BioLegend Fixation buffer, 420801) prior to analysis. The level of fluorescence on the cell surface was measured by flow cytometry. Using this method, test anti-CXCR2 antibodies were detected binding neutrophils from both human and cynomolgus monkey.

Generation of Human CXCR2 Transgenic Mice hCXCR2 knock-in mice were generated by use of homologous recombination in embryonic stem (ES) cells to insert the human CXCR2 into exon 1 of the mouse CXCR2 gene. The single coding exon of human CXCR2 was inserted into a vector with 5' and 3' arms homologous to the genomic location of the mouse coding exon of CXCR2, giving rise to a gene structure that coded for human CXCR2 but retained the mouse non-coding and regulatory elements. This vector was electroporated into C57B1/6 mouse ES cells which were incorporated into C57B1/6 mouse blastocysts and transplanted into pseudopregnant female mice. Pups were backcrossed to the parental C57B1/6 strain and offspring screened by southern blot for germline transmission of the human CXCR2 gene. Mice heterozygous for human CXCR2 were intercrossed to give a homozygous human CXCR2 line and phenotype was confirmed by analysis of binding of anti-mouse and anti-human CXCR2 antibodies by flow cytometry.

Comparator Antibody and Small Molecule CXCR2 Antagonists

Antagonist 1 is antibody HY29GL as described in Int'l Pub. No. WO2015/169811 A2 (VH and VL of sequences 20 and 29 from that reference). Antagonist 2 is antibody CX1_5 as described in Int'l Pub. No. WO2014/170317 A1 (VH and VL of sequences 115 and 114 from that reference). Antagonist 3 is anti-CXCR2 antibody clone 48311 (R&D systems, Catalogue number MAB331-500). Antagonist 4 is anti-CXCR2 antibody clone 6C6 (BD Biosciences, Catalogue number 555932). Antagonist 5 is the small molecule CXCR2 antagonist Danirixin. Antagonist 6 is the small molecule CXCR2 antagonist SCH 527123.

Example 1—Generation of Anti-CXCR2 Antibodies

Generation of Anti-CXCR2 Antibodies with Human Variable Regions

Transgenic rats engineered to express antibodies with human variable regions (as disclosed in Int'l Pub. No. WO2008/151081) were used to raise antibodies against human CXCR2. Briefly, animals were subjected to weekly genetic immunization using a plasmid which encoded the amino acid sequence of human CXCR2 (SEQ ID NO: 125) until antibody titres against human CXCR2 were obtained, as measured by flow cytometry using CXCR2 positive transiently transfected HEK-293 cells.

Production and Expansion of Hybridomas Expressing Anti-CXCR2 Antibodies

To generate hybridomas which produced monoclonal antibodies to human CXCR2, splenocytes and/or lymph node cells from animals with the highest anti-CXCR2 titres were isolated and fused to mouse myeloma cells (ATCC, CRL-1580). Cells were plated at approximately $1\times10^5$ cells/mL in flat bottom microtiter plates, followed by a two week incubation in selective medium (10% FCS and 1×HAT (Sigma)). Hybridomas were expanded by serial passage through four media changes in 96-well plates (96-well stages 1 to 4), then, where required, expanded into T25 and T75 flasks. During the hybridoma expansion process, supernatants were monitored for CXCR2 binding activity by cell-based ELISA (cELISA) on cells transiently transfected to express human CXCR2 or murine CXCR2 (SEQ ID NOs: 125 or 126, respectively). Bound antibodies were detected using a goat anti-rat IgG-HRP (Southern Biotech, #3030-05) secondary antibody.

A panel of hybridomas was generated using lymph nodes and spleen cells from the transgenic rats engineered to express human variable region sequences. A cellular ELISA (cELISA) was used to detect human CXCR2 binding activity in supernatants taken during the expansion process for the hybridomas (Table 5). Hybridomas that retained expression of antibodies that bound CXCR2 after several passages were selected for DNA sequencing.

TABLE 5

Binding of Hybridoma Supernatants to Human CXCR2 or Mouse CXCR2 Transfected Cells as Determined by cELISA

| | cELISA using hybridoma supernatant from rats with human variable regions | |
|---|---|---|
| CLONE | Human CXCR2 % Positive* | Murine CXCR2 % Positive* |
| BKO-1A1 | 38% | 6% |
| BKO-1B10 | 75% | 4% |
| BKO-1C1 | 3% | 5% |
| BKO-1C6 | 88% | 5% |
| BKO-1D1 | 67% | 7% |
| BKO-1D5 | 46% | 6% |
| BKO-1D9 | 85% | 5% |
| BKO-1E3 | 3% | 6% |
| BKO-1H3 | 41% | 3% |
| BKO-2A3 | 3% | 3% |
| BKO-2B10 | 79% | 5% |
| BKO-2C2 | 77% | 5% |
| BKO-2D1 | 28% | 4% |
| BKO-2D8 | 100% | 7% |
| BKO-2E4 | 80% | 7% |
| BKO-2F6 | 11% | 3% |
| BKO-2G4 | 83% | 4% |
| BKO-2G7 | 75% | 3% |
| BKO-2G10 | 139% | 4% |
| BKO-2H4 | 2% | 3% |
| BKO-2H7 | 23% | 5% |
| BKO-3A9 | 2% | 4% |
| BKO-3C3 | 8% | 10% |
| BKO-3D3 | 3% | 6% |
| BKO-3D6 | 2% | 3% |
| BKO-3E3 | 107% | 3% |
| BKO-3F4 | 86% | 42% |
| BKO-3F5 | 5% | 5% |
| BKO-3F6 | 6% | 5% |
| BKO-3G11 | 61% | 7% |
| BKO-3H11 | 24% | 5% |
| BKO-4A4 | 32% | 7% |
| BKO-4A5 | 2% | 7% |
| BKO-4A8 | 110% | 5% |
| BKO-4A10 | 11% | 5% |
| BKO-4B2 | 107% | 6% |
| BKO-4B7 | 2% | 3% |
| BKO-4B11 | 103% | 7% |
| BKO-4C1 | 97% | 6% |
| BKO-4E8 | 53% | 7% |
| BKO-4F10 | 118% | 7% |
| BKO-4F11 | 77% | 8% |
| BKO-4G3 | 2% | 2% |
| BKO-4G4 | 93% | 3% |
| BKO-4H5 | 81% | 4% |
| BKO-4H6 | 108% | 4% |
| BKO-4H11 | 4% | 6% |
| BKO-5A5 | 66% | 5% |
| BKO-5B8 | 53% | 5% |
| BKO-5C4 | 101% | 5% |
| BKO-5E8 | 109% | 8% |
| BKO-5F9 | 2% | 4% |
| BKO-5F10 | 119% | 4% |
| BKO-5G6 | 103% | 4% |
| BKO-5G11 | 101% | 22% |
| BKO-5H1 | 4% | 7% |
| BKO-5H4 | 5% | 8% |
| BKO-6A1 | 60% | 6% |
| BKO-6A2 | 4% | 7% |
| BKO-6A3 | 8% | 7% |
| BKO-6B8 | 53% | 4% |
| BKO-6C2 | 3% | 6% |
| BKO-6C4 | 39% | 5% |
| BKO-6D10 | 2% | 4% |
| BKO-6E4 | 79% | 3% |
| BKO-6F3 | 44% | 6% |
| BKO-6G1 | 101% | 4% |

TABLE 5-continued

Binding of Hybridoma Supernatants to Human CXCR2 or Mouse CXCR2 Transfected Cells as Determined by cELISA

| | cELISA using hybridoma supernatant from rats with human variable regions | |
|---|---|---|
| CLONE | Human CXCR2 % Positive* | Murine CXCR2 % Positive* |
| BKO-6H1 | 52% | 5% |
| BKO-7A3 | 21% | 8% |
| BKO-7A9 | 2% | 4% |
| BKO-7B1 | 15% | 5% |
| BKO-7B2 | 84% | 4% |
| BKO-7C11 | 73% | 4% |
| BKO-7D8 | 67% | 6% |
| BKO-7D9 | 5% | 7% |
| BKO-7E4 | 4% | 6% |
| BKO-7E7 | 94% | 12% |
| BKO-7F3 | 95% | 7% |
| BKO-7F11 | 2% | 3% |
| BKO-7G1 | 21% | 3% |
| BKO-7G2 | 2% | 8% |
| BKO-7G10 | 104% | 26% |
| BKO-7H7 | 3% | 7% |
| BKO-7H8 | 105% | 7% |
| BKO-7H11 | 4% | 9% |
| BKO-8B6 | 95% | 6% |
| BKO-8C2 | 5% | 8% |
| BKO-8C4 | 124% | 6% |
| BKO-8D2 | 11% | 7% |
| BKO-8D4 | 38% | 7% |
| BKO-8F3 | 56% | 3% |
| BKO-8G3 | 114% | 6% |
| BKO-8H8 | 104% | 7% |
| BKO-8H10 | 81% | 8% |
| BKO-9A8 | 124% | 8% |
| BKO-9C3 | 56% | 7% |
| BKO-9C4 | 2% | 3% |
| BKO-9E7 | 2% | 3% |
| BKO-9G1 | 66% | 4% |
| BKO-9G6 | 34% | 8% |
| BKO-9H5 | 4% | 7% |
| BKO-10A2 | 25% | 5% |
| BKO-10B4 | 109% | 6% |
| BKO-10D1 | 2% | 6% |
| BKO-10D8 | 30% | 10% |
| BKO-10F3 | 7% | 4% |
| BKO-10G10 | 89% | 4% |
| BKO-10H6 | 6% | 6% |
| Positive control | 100% | 100% |
| Negative control | 4% | 8% |

*Fluorescence units relative to positive control (100%)

Sequencing of Antibodies Produced by Hybridoma Cells

Antibody variable domains were isolated by reverse transcription polymerase chain reaction (RT-PCR) using RNA produced from the non-clonal hybridoma cell pellets as a template. RNA was isolated from the plates of hybridomas using a GENELUTE™ 96 well total RNA purification kit (Sigma #RTN9602, RTN9604) according to the manufacturer's protocol. For standard RT-PCR, RNA was reverse transcribed into cDNA using an oligo (dT) primer and an AccuScript PfuUltra® II RT-PCR kit (Agilent #600184). cDNA synthesis reactions were assembled according the manufacturer's protocol and cDNA synthesis carried out at 42° C. for 30 minutes. For use in 5'-Rapid Amplification of CDNA Ends (5'-RACE) PCR, RNA was reverse transcribed into cDNA using a SMARTer® RACE kit (Takara) according to the manufacturer's directions to give 5'-RACE ready cDNA.

Amplification of human antibody variable regions from the panel of hybridomas was performed by PCR using either PfuUltraII (Agilent) or Q5 high fidelity DNA polymerases (NEB) according to the manufacturer's directions. The hybridoma panel heavy chains were amplified using primer pairs specific to the rodent heavy chain constant region DNA sequence and the DNA sequences of the human heavy chain leader sequences. The hybridoma panel lambda light chain variable regions were similarly amplified using primer pairs specific to the human lambda constant region DNA sequence and the DNA sequences of the human lambda chain leader sequences.

The concentration of the resulting purified DNA was assessed using a Nanodrop spectrophotometer. Sanger sequencing of the PCR fragments was performed using oligos designed to bind internally in the heavy or light chain amplicons. The resulting DNA sequences were conceptually translated into amino acid sequences for further analysis prior to their use in full length antibody chain generation. Antibodies with unique amino acid sequences were selected for conversion to full-length human antibodies.

Recombinant Monoclonal Antibodies with Binding to Human CXCR2

Hybridomas selected from those which secreted antibody that bound CXCR2 (as described in Table 5) were sequenced to identify variable region DNA and amino acids using RT-PCR as described above. These antibody variable regions were then generated by gene synthesis and subcloned into mammalian expression vectors as described in General Methods. Antibodies were produced by co-expression of heavy and light chain plasmids in Expi293F™ cells and purified by protein A column chromatography as described in General Methods. Where several heavy and/or light chains were identified from the same hybridoma cells, each heavy chain was paired with each light chain and the resulting antibodies given suffix a, b, c, etc. Purified antibodies were desalted into Sorensen's PBS pH 5.8 and tested by flow cytometry for binding to Expi293F™ cells transfected with human CXCR2 or human CXCR1 and mock transfected Expi293F™ cells. 26 antibodies that bound human CXCR2 but not human CXCR1 or mock transfected Expi293F™ cells were identified from the hybridoma panel for further characterization. These antibody sequences are given in Table 6.

TABLE 6

Sequences of Antibodies with a Human Variable Region That Bound Human CXCR2 but Not Closely Related Human CXCR1 or Mock-Transfected Expi293F ™ Cells

| Antibody Name | VH (SEQ ID NO) | VL (SEQ ID NO) |
| --- | --- | --- |
| BKO-1A1 | BKO_1A1_VH (SEQ ID NO: 1) | BKO_1A1_VL (SEQ ID NO: 2) |
| BKO-1B10 | BKO_1B10_VH (SEQ ID NO: 3) | BKO_1B10_VL (SEQ ID NO: 4) |
| BKO-1D1 | BKO_1D1_VH (SEQ ID NO: 5) | BKO_1D1_VL (SEQ ID NO: 6) |
| BKO-1H3 | BKO_1H3_VH (SEQ ID NO: 7) | BKO_1H3_VL (SEQ ID NO: 8) |
| BKO-2D8 | BKO_2D8_VH (SEQ ID NO: 9) | BKO_2D8_VL (SEQ ID NO: 10) |
| BKO-3A9_b | BKO_3A9_VH (SEQ ID NO: 11) | BKO_3A9_L3_E03_VL (SEQ ID NO: 12) |
| BKO-3D6 | BKO_3D6_VH (SEQ ID NO: 13) | BKO_3D6_L6_G06_VL (BKO_5H4_VL) (SEQ ID NO: 14) |
| BKO-3F4 | BKO_3F4_VH (SEQ ID NO: 15) | BKO_3F4_L11_A11_VL (SEQ ID NO: 16) |
| BKO-4A8 | BKO_4A8_VH (SEQ ID NO: 17) | BKO_4A8_VL (SEQ ID NO: 18) |
| BKO-4F10 | BKO_4F10_VH (SEQ ID NO: 19) | BKO_4F10_VL (SEQ ID NO: 20) |
| BKO-5E8 | BKO_5E8_H5_C05_VH (SEQ ID NO: 21) | BKO_5E8_L3_C03_VL (SEQ ID NO: 22) |
| BKO-5G11 | BKO_5G11_VH (SEQ ID NO: 23) | BKO_5G11_VL (SEQ ID NO: 24) |
| BKO-5G6_c | BKO_5G6_VH (SEQ ID NO: 25) | BKO_5G6_L12_E12_VL (SEQ ID NO: 26) |
| BKO-6A1_b | BKO_6A1_H4_A04_VH (SEQ ID NO: 27) | BKO_6A1_E10_VL (SEQ ID NO: 28) |
| BKO-6A2_a | BKO_6A2_H1_B01_VH (SEQ ID NO: 29) | BKO_6A2_L6_A06_VL (SEQ ID NO: 30) |
| BKO_7C11 | BKO_7C11_H6_B06_VH (SEQ ID NO: 31) | BKO_7C11_G01_VL (SEQ ID NO: 32) |
| BKO-7G10_a | BKO_7G10_H1_B01_VH (SEQ ID NO: 33) | BKO_7G10_L6_E06_VL (SEQ ID NO: 34) |
| BKO-7H8_b | BKO_7H8_H3_C03_VH (SEQ ID NO: 35) | BKO_7H8_L10_F10_VL (SEQ ID NO: 36) |
| BKO-8B6 | BKO_8B6_VH (SEQ ID NO: 37) | BKO_8B6_VL (SEQ ID NO: 38) |
| BKO-8C4 | BKO_8C4_VH (SEQ ID NO: 39) | BKO_8C4_VL (SEQ ID NO: 40) |
| BKO-8G3_b | BKO_8G3_H4_D04_VH (SEQ ID NO: 41) | BKO_8G3_L1_G01_VL (SEQ ID NO: 42) |
| BKO-8H10 | BKO_8H10_VH (SEQ ID NO: 43) | BKO_8H10_VL (SEQ ID NO: 44) |
| BKO-8H8_b | BKO_8H8_H5_E05_VH (SEQ ID NO: 45) | BKO_8H8_L7_H08_VL (SEQ ID NO: 46) |

TABLE 6-continued

Sequences of Antibodies with a Human Variable Region
That Bound Human CXCR2 but Not Closely Related Human
CXCR1 or Mock-Transfected Expi293F ™ Cells

| Antibody Name | VH (SEQ ID NO) | VL (SEQ ID NO) |
|---|---|---|
| BKO-9A8 | BKO_9A8_H3_F03_VH (SEQ ID NO: 47) | BKO_9A8_L1_H02_VL (SEQ ID NO: 48) |
| BKO-9C3_a | BKO_9C3_H8_G08_VH (SEQ ID NO: 49) | BKO_9C3_L1_F01_VL (SEQ ID NO: 50) |
| BKO-10G10 | BKO_10G10_VH (SEQ ID NO: 51) | BKO_10G10_VL (SEQ ID NO: 52) |

Example 2—Functional Characterization of Anti-CXCR2 Hits

Binding to Cynomolgus Monkey CXCR2

All recombinant antibodies that bound human CXCR2 but not human CXCR1 or mock-transfected Expi293™ cells were tested for binding to cynomolgus CXCR2 (SEQ ID NO: 127) using Expi293F™ cells transiently transfected with a plasmid encoding cynomolgus CXCR2 protein as described herein. Antibodies with detectable levels of cynomolgus CXCR2 binding were characterized further.

Binding to Other Human CXCR Family Members

Human and cynomolgus monkey CXCR2 cross-reactive antibodies were tested by flow cytometry for binding to other human CXCR family members—CXCR3, CXCR4, CXCR5, CXCR6 and CXCR7 using Expi293F™ cells transiently transfected with a plasmid encoding either human CXCR3 (SEQ ID NO: 128), CXCR4 (SEQ ID NO: 129), CXCR5 (SEQ ID NO: 130), CXCR6 (SEQ ID NO: 131) or CXCR7 (SEQ ID NO: 132). Antibodies that were not selective for CXCR2 were discounted from further analysis.

Inhibition of CXCL8-mediated Activation of Human CXCR2

Figure 1B:
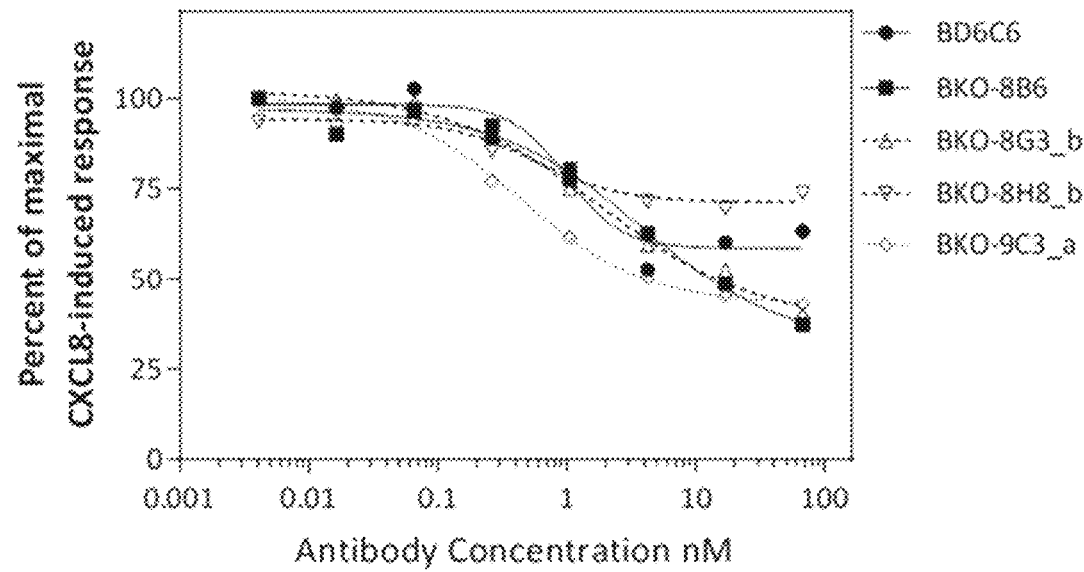

Antibodies were tested in a Tango™ CXCR2 cell-based assay using human CXCL8 as an agonist as described in General Methods. Eight antibodies inhibited CXCL8-induced activation of CXCR2, as shown in FIGS. 1A and 1B. A commercially available anti-CXCR2 antibody 6C6 (BD Biosciences; "BD6C6") was used as a positive control in these assays.

Figure 2:
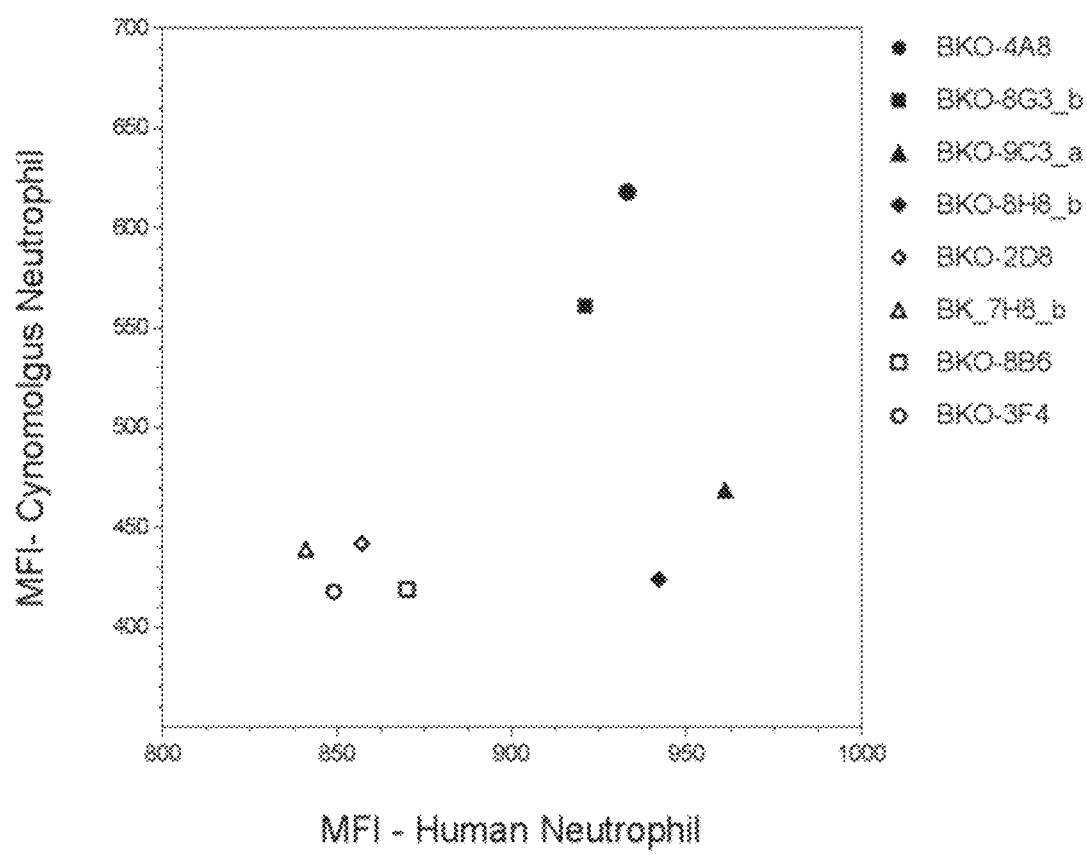
FIG. 2 illustrates a dot plot showing binding activity of exemplary disclosed anti-CXCR2 antibodies to native human CXCR2 expressed by human neutrophils and native cynomolgus CXCR2 expressed by cynomolgus neutrophils. Antibody binding activity was quantified as average mean fluorescence intensity (MFI) values obtained from 4 to 8 independent samples.

Binding of Antibodies to Human CXCR2 Expressed by Human PBMCs and Cynomolgus CXCR2 Expressed by Cynomolgus PBMCs The eight antibodies that inhibited CXCL8-mediated activation of CXCR2 were tested for binding to native CXCR2 expressed on human and cynomolgus PBMCs. Two antibodies, BKO-4A8 and BKO-8G3_b, demonstrated high binding activity to both human and cynomolgus CXCR2 while a third, BKO-9C3_a, exhibited substantial levels of binding to human CXCR2 and above average levels of binding to cynomolgus CXCR2, as shown in FIG. 2.

Inhibition of CXCL1-mediated Activation of Human CXCR2

Figure 3:
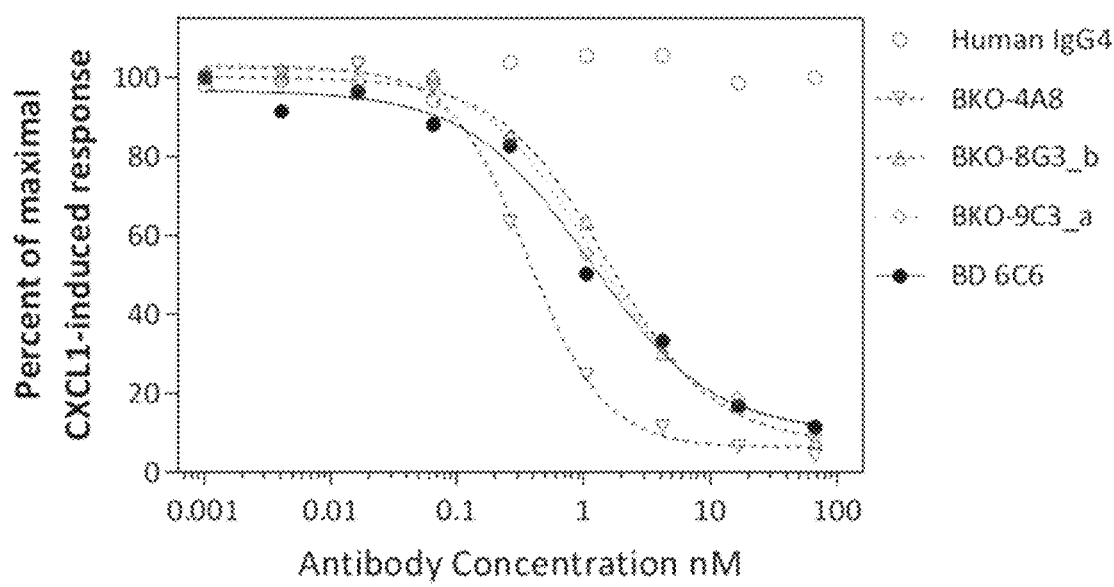
FIG. 3 illustrates the results of an exemplary dose response study of the inhibition of CXCL1-mediated activation of CXCR2 by selected anti-CXCR2 antibodies, as measured in the Tango™ cell based assay.

Antibodies BKO-4A8, BKO-8G3_b, and BKO-9C3_a were tested in a Tango™ CXCR2 cell-based assay using CXCL1 as an agonist as described in General Methods. Antibody BKO-4A8 was consistently the most potent of the antibodies tested in this format. Typical inhibition of CXCL1 activation of CXCR2 curves for these antibodies are shown below FIG. 3.

Example 3—Amino Acid Sequence Optimization of anti-CXCR2 Antibody BKO-4A8

Heavy and light chain variable region variants of the anti-CXCR2 antibody BKO-4A8 were constructed in an attempt to optimize the sequence of this molecule for stability and manufacturability.

Variants of antibody BKO-4A8, each comprising a single amino acid substitution, were produced as described below. A summary of these variants is provided in Table 7.

TABLE 7

Variants of BKO-4A8

| Antibody Chain | Substitution | Variable region Sequence ID NO: |
|---|---|---|
| Heavy CDR1 | S32Q | 53 |
| | S32D | 136 |
| | S32H | 54 |
| | S32L | 55 |
| | S32W | 56 |
| | S32Y | 57 |
| | T33A | 58 |
| | M34Q | 59 |
| | M34D | 60 |
| | M34H | 61 |
| | M34W | 62 |
| | S35Q | 137 |
| | S35D | 138 |
| | S35K | 139 |
| Heavy CDR2 | A50S | 140 |
| | I51H | 63 |
| | G52aD | 64 |
| | R53S | 65 |
| | R53Q | 66 |
| | G54D | 67 |
| | R55Q | 141 |
| | R55D | 142 |
| | R55H | 143 |
| | N56S | 68 |
| Heavy CDR3 | I94K | 69 |
| | M96A | 70 |
| | M96S | 144 |
| | M96Q | 71 |
| | M96D | 145 |
| | M96H | 146 |
| | M96K | 72 |
| | M96L | 147 |
| | M96W | 148 |
| | M96Y | 149 |
| | G101D | 73 |
| | Y102S | 74 |
| | Y102Q | 150 |
| | Y102D | 151 |
| | Y102K | 75 |
| Light CDR2 | E50D | 76 |
| | V51D | 152 |
| | V51Y | 153 |
| | N52D | 77 |

TABLE 7-continued

Variants of BKO-4A8

| Antibody Chain | Substitution | Variable region Sequence ID NO: |
|---|---|---|
| Light CDR3 | N52S | 78 |
| | K53A | 79 |
| | K53D | 80 |
| | K53H | 81 |
| | R54Q | 82 |
| | R54D | 154 |
| | Y91A | 83 |
| | Y91S | 155 |
| | Y91H | 156 |
| | N94A | 84 |
| | N94S | 85 |
| | N94H | 157 |
| | N94K | 86 |
| | N94L | 87 |
| | N94W | 88 |
| | N94Y | 89 |
| | N95aS | 158 |
| | N95aQ | 90 |
| | N95aD | 91 |
| | N95aH | 92 |
| | N95aK | 93 |
| | N95aL | 94 |
| | N95aW | 159 |
| | N95aY | 95 |
| | V97A | 96 |
| | V97S | 160 |
| | V97D | 161 |
| | V97K | 97 |

Generation of Plasmids Encoding Antibody Variants by Site Directed Mutagenesis

Plasmids encoding antibody chains requiring single amino acid changes were prepared by mutagenic primer-directed replication of the plasmid strands using a high fidelity DNA polymerase. This process used supercoiled double-stranded plasmid DNA as the template and two complementary synthetic oligonucleotide primers both containing the desired mutation. The oligonucleotide primers, each complementary to opposite strands of the plasmid, were extended during the PCR cycling without primer displacement, resulting in copies of the mutated plasmid containing staggered nicks. Following PCR cycling, the PCR reaction was treated using the restriction enzyme DpnI. DpnI preferentially cuts the original vector DNA, leaving the newly synthesized strands intact.

To generate variants incorporating multiple amino acid substitutions that required mutagenic oligonucleotide primers of over forty bases in length, either the above process was repeated to introduce the changes sequentially or the genes were synthesized de novo by assembly of synthetic oligonucleotides. All construct DNA sequences were confirmed by Sanger DNA sequencing prior to use.

Generation of Plasmids Encoding Antibody Variants by Polynucleotide Synthesis

Variable region amino acid sequences were backtranslated into DNA sequences using GeneOptimizer® technology prior to synthesis of the resulting DNA de novo by assembly of synthetic oligonucleotides (GeneArt, Germany). Polynucleotides encoding synthesized heavy chain variable regions paired with human IgG4 constant region comprising the core hinge stabilizing substitution S228P (SEQ ID NO: 118) were subcloned into an expression vector. Polynucleotides encoding synthesized lambda light chain variable region genes were subcloned into an expression vector encoding a human lambda light chain constant region (SEQ ID NO: 134).

Binding of BKO-4A8 Variants to CXCR2

Each variant heavy chain was co-expressed with the parental light chain and vice versa. The resulting antibodies were purified and tested in CXCR2 binding assays relative to parental antibody BKO-4A8 as described herein. Antibody variants that had similar levels of binding to parental BKO-4A8 are shown in Table 8.

TABLE 8

BKO-4A8 point variants with similar CXCR2 binding to parental BKO-4A8

| Antibody Chain | Substitution | Variable region Sequence ID NO: | Fold change in binding relative to BKO-4A8 |
|---|---|---|---|
| Heavy CDR1 | S32Q | 53 | 1.71 |
| | S32H | 54 | 0.86 |
| | S32L | 55 | 1.33 |
| | S32W | 56 | 0.83 |
| | S32Y | 57 | 1.33 |
| | T33A | 58 | 1.30 |
| | M34Q | 59 | 1.00 |
| | M34D | 60 | 1.60 |
| | M34H | 61 | 0.80 |
| | M34W | 62 | 1.17 |
| Heavy CDR2 | I51H | 63 | 1.80 |
| | G52aD | 64 | 1.18 |
| | R53S | 65 | 1.00 |
| | R53Q | 66 | 0.64 |
| | G54D | 67 | 1.00 |
| | N56S | 68 | 1.0 |
| Heavy CDR3 | I94K[#] | 69 | 0.7 |
| | M96A | 70 | 1.5 |
| | M96Q | 71 | 1.5 |
| | M96K | 72 | 1.0 |
| | G101D | 73 | 1.0 |
| | Y102S | 74 | 1.5 |
| | Y102K | 75 | 1.3 |
| Light CDR2 | E50D | 76 | 2.0 |
| | N52D | 77 | 1.7 |
| | N52S | 78 | 1.0 |
| | K53A | 79 | 1.4 |
| | K53D | 80 | 1.4 |
| | K53H | 81 | 1.4 |
| | R54Q | 82 | 1.6 |
| Light CDR3 | Y91A | 83 | 1.7 |
| | N94A | 84 | 1.0 |
| | N94S | 85 | 1.0 |
| | N94K | 86 | 1.33 |
| | N94L | 87 | 0.88 |
| | N94W | 88 | 0.63 |
| | N94Y | 89 | 0.50 |
| | N95aQ | 90 | 1.0 |
| | N95aD | 91 | 2.3 |
| | N95aH | 92 | 1.3 |
| | N95aK | 93 | 1.0 |
| | N95aL | 94 | 1.7 |
| | N95aY | 95 | 1.7 |
| | V97A | 96 | 1.7 |
| | V97K | 97 | 1.0 |

[#]is a framework residue which flanks Heavy CDR3

An alignment of the variable heavy chain sequences and variable light chain sequences of the above antibody variants are shown in FIG. 4A and FIG. 4B, respectively. The consensus variable heavy chain ("consensus VH"; SEQ ID NO: 167) and consensus variable light chain ("consensus VL"; SEQ ID NO: 168) are also provided in those figures.

BKO-4A8 Point Variants with Similar Potency to BKO-4A8 in Inhibiting CXCL1 or CXCL8 Activation of CXCR2

Sixteen antibody variants showing similar levels of CXCR2 binding to parental BKO-4A8 were tested in potency assays using CXCL1 or CXCL8 as an agonist as described in the General Methods. Twelve antibodies had similar potency to parental BKO-4A8 as shown in Table 9.

Amino acid sequence alignments of these variants relative to the parental heavy and light chain sequences are provided in FIGS. 4A and 4B.

TABLE 9

BKO-4A8 Point Variants with Similar Potency to BKO-4A8 in Inhibiting CXCL1- or CXCL8-mediated Activation of CXCR2

| Antibody Chain | Substitution | Variable region SEQ ID NO: | Tango Assay $IC_{50}$ (nM) CXCL1 | CXCL8 |
|---|---|---|---|---|
| BKO-4A8 | — | 17 | 0.177 | 0.112 |
| Heavy CDR1 | M34Q | 59 | 0.242 | 0.0776 |
|  | M34H | 61 | 0.186 | 0.107 |
| Heavy CDR2 | N56S | 68 | 0.158 | 0.129 |
| Heavy CDR3 | I94K[#] | 69 | 0.078 | 0.071 |
|  | M96A | 70 | 0.140 | 0.126 |
|  | M96Q | 71 | 0.330 | 0.140 |
|  | M96K | 72 | 0.135 | 0.091 |
| Light CDR2 | N52S | 78 | 0.214 | 0.126 |
| Light CDR3 | N94S | 85 | 0.149 | 0.169 |
|  | N94K | 86 | 0.123 | 0.113 |
|  | N94Y | 89 | 0.164 | 0.105 |
|  | N95aQ | 90 | 0.213 | 0.084 |

[#]is a framework residue which flanks Heavy CDR3

Combinatorial Variants of BKO-4A8

Three non-germline framework amino acids were substituted back to those seen in the closest human germline sequence—heavy chain R75K and I94K and light chain D41G. The substitution A40P was also introduced in framework 2 of the heavy chain.

Figure 5A:
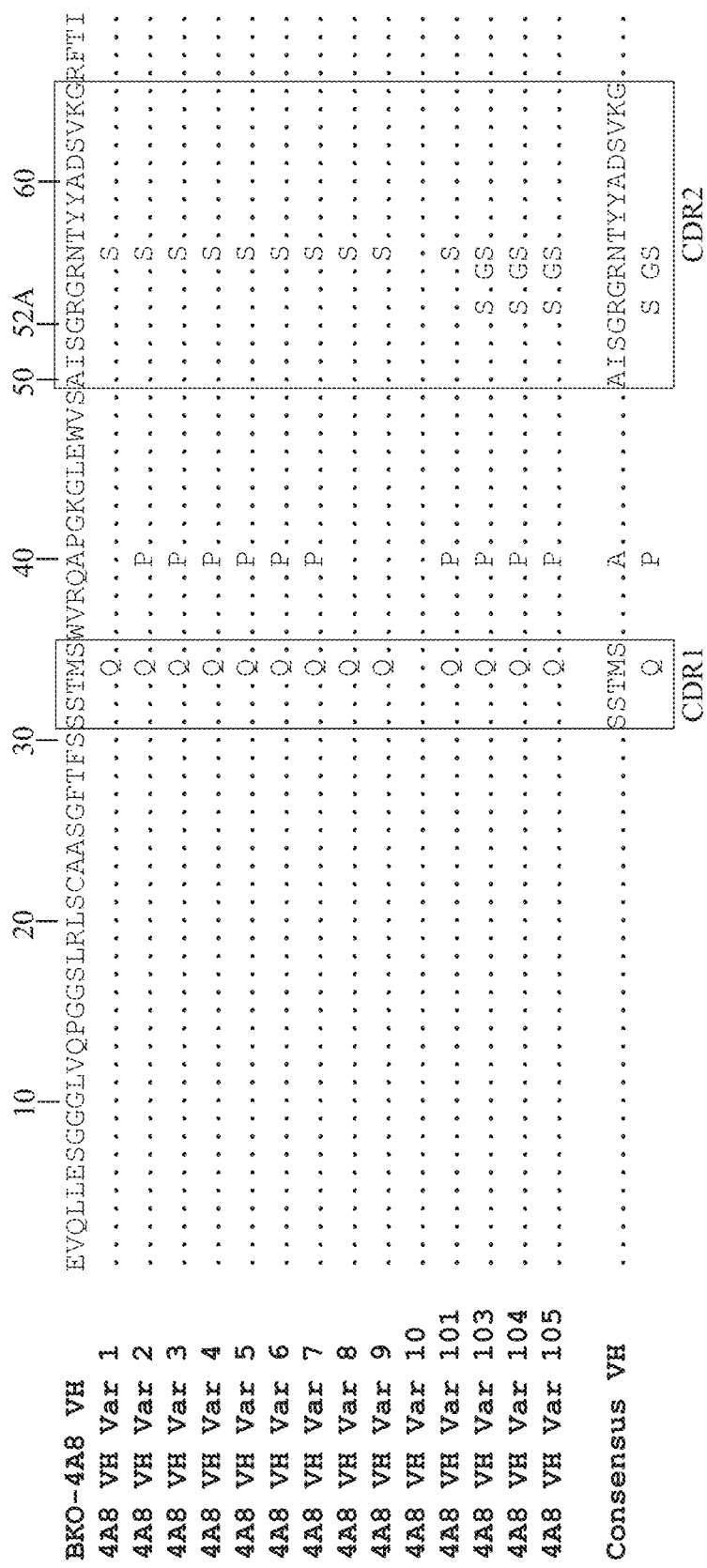
FIG. 5A and FIG. 5B illustrate an amino acid sequence alignment of exemplary combinatorial BKO-4A8 variants (abbreviated "Var") with parental BKO-4A8, and provides a consensus sequence based on these variants.
Figure 5B:
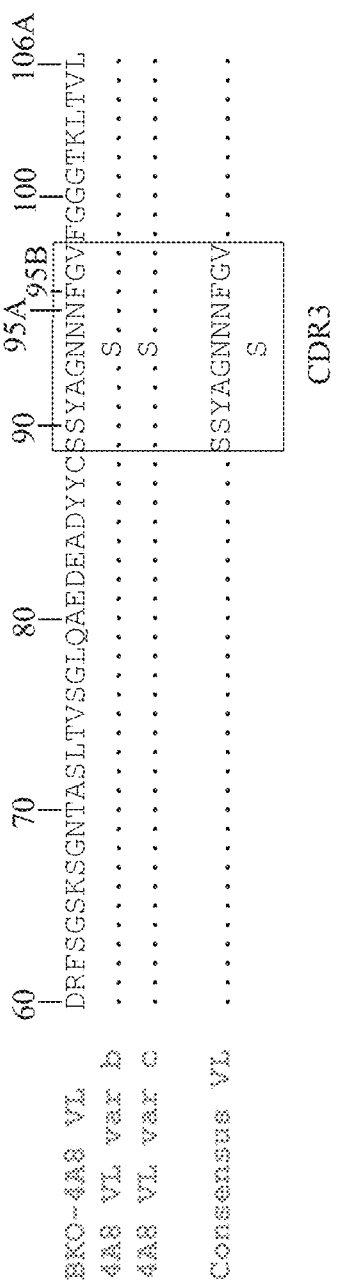

A panel of combinatorial variants comprising two or more amino acid substitutions was designed to examine whether it was possible to further optimize these sequences. Table 10 describes a total of two light chain variants and eleven heavy chain variants which were produced. Amino acid sequence alignments with the parental BKO-4A8 variable heavy chain and variable light chain are illustrated in FIGS. 5A and 5B, respectively. The consensus variable heavy chain ("consensus VH"; SEQ ID NO: 226) and consensus variable light chain ("consensus VL"; SEQ ID NO: 227) are also provided in those figures.

TABLE 10

Combinatorial Variants of BKO-4A8

| Chain | Variant: | Substitutions (vs BKO-4A8) (Relative to parental HC variable region of SEQ ID NO: 17 or parental LC variable region of SEQ ID NO: 18) |
|---|---|---|
| Heavy | 1 | M34Q, N56S (SEQ ID NO: 98) |
|  | 2 | M34Q, A40P, N56S (SEQ ID NO: 99) |
|  | 3 | M34Q, A40P, N56S, R75K (SEQ ID NO: 100) |
|  | 4 | M34Q, A40P, N56S, M96K (SEQ ID NO: 101) |
|  | 5 | M34Q, A40P, N56S, R75K, M96K (SEQ ID NO: 102) |
|  | 6 | M34Q, A40P, N56S, R75K, I94K, M96K (SEQ ID NO: 103) |
|  | 7 | M34Q, A40P, N56S, I94K, M96K (SEQ ID NO: 104) |
|  | 8 | M34Q, N56S, M96K (SEQ ID NO: 105) |
|  | 9 | M34Q, N56S, R75K, M96K (SEQ ID NO: 106) |
|  | 10 | I94K, M96K (SEQ ID NO: 107) |
|  | 101 | M34Q, A40P, N56S, R75K, M96A (SEQ ID NO: 108) |
| Light | b | N52S, N94S (SEQ ID NO: 109) |
|  | c | D41G, N52S, N94S (SEQ ID NO: 110) |

Each heavy chain was co-expressed with each light chain to produce a sequence optimized antibody variant. Antibodies were purified and tested for CXCR2 binding activity as described in General Methods. Most of the combinatorial antibody variants retained similar CXCR2 binding activity to parental antibody BKO-4A8, as shown in Table 11.

TABLE 11

Summary of CXCR2 binding data $EC_{50}$ values using combinatorial variants

| Antibody Name | VH change(s) | VL change(s) | CXCR2 binding $EC_{50}$ (nM) | Fold Improvement over 4A8 WT |
|---|---|---|---|---|
| 1b | M34Q, N56S (SEQ ID NO: 98) | N52S, N94S (SEQ ID NO: 109) | 0.3 | 1.33 |
| 1c |  | D41G, N52S, N94S (SEQ ID NO: 110) | 0.3 | 1.33 |
| 4A8 control for VH1 | N/A | N/A | 0.4 | N/A |
| 2b | M34Q, A40P, N56S (SEQ ID NO: 99) | N52S, N94S (SEQ ID NO: 109) | 0.4 | 1.25 |
| 2c |  | D41G, N52S, N94S (SEQ ID NO: 110) | 0.3 | 1.67 |
| 4A8 control for VH2 | N/A | N/A | 0.5 | N/A |
| 3b | M34Q, A40P, N56S, R75K (SEQ ID NO: 100) | N52S, N94S (SEQ ID NO: 109) | 0.1 | 4 |
| 3c |  | D41G, N52S, N94S (SEQ ID NO: 110) | 0.2 | 2 |
| 4A8 control for VH3 | N/A | N/A | 0.4 | N/A |
| 4b | M34Q, A40P, N56S, M96K | N52S, N94S (SEQ ID NO: 109) | 0.4 | 1.25 |

TABLE 11-continued

Summary of CXCR2 binding data EC$_{50}$ values using combinatorial variants

| Antibody Name | VH change(s) | VL change(s) | CXCR2 binding EC$_{50}$ (nM) | Fold Improvement over 4A8 WT |
|---|---|---|---|---|
| 4c | (SEQ ID NO: 101) | D41G, N52S, N94S (SEQ ID NO: 110) | 0.4 | 1.25 |
| 4A8 control for VH4 | N/A | N/A | 0.5 | N/A |
| 5b | M34Q, A40P, N56S, R75K, M96K | N52S, N94S (SEQ ID NO: 109) | 0.4 | 1.25 |
| 5c | (SEQ ID NO: 102) | D41G, N52S, N94S (SEQ ID NO: 110) | 0.4 | 1.25 |
| 4A8 control for VH5 | N/A | N/A | 0.5 | N/A |
| 6b | M34Q, A40P, N56S, R75K, I94K, M96K | N52S, N94S (SEQ ID NO: 109) | 0.4 | 1.00 |
| 6c | (SEQ ID NO: 103) | D41G, N52S, N94S (SEQ ID NO: 110) | 0.9 | 0.44 |
| 4A8 control for VH6 | N/A | N/A | 0.4 | N/A |
| 7b | M34Q, A40P, N56S, I94K, M96K | N52S, N94S (SEQ ID NO: 109) | 0.8 | 0.63 |
| 7c | (SEQ ID NO: 104) | D41G, N52S, N94S (SEQ ID NO: 110) | 1 | 0.50 |
| 4A8 control for VH7 | N/A | N/A | 0.5 | N/A |
| 8b | M34Q, N56S, M96K (SEQ ID NO: 105) | N52S, N94S (SEQ ID NO: 109) | N/A | N/A |
| 8c | | D41G, N52S, N94S (SEQ ID NO: 110) | N/A | N/A |
| 4A8 control for VH8 | N/A | N/A | 0.6 | N/A |
| 9b | M34Q, N56S, R75K, M96K | N52S, N94S (SEQ ID NO: 109) | 0.3 | 3.00 |
| 9c | (SEQ ID NO: 106) | D41G, N52S, N94S (SEQ ID NO: 110) | 6.4 | 0.14 |
| 4A8 control for VH9 | N/A | N/A | 0.9 | N/A |
| 10b | I94K, M96K (SEQ ID NO: 107) | N52S, N94S (SEQ ID NO: 109) | 0.3 | 1.67 |
| 10c | | D41G, N52S, N94S (SEQ ID NO: 110) | 0.5 | 1.00 |
| 4A8 control for VH10 | N/A | N/A | 0.5 | N/A |

A further six heavy chain combinational variants comprising four or more amino acid substitutions were produced as provided in Table 12. Amino acid sequence alignments with the parental BKO-4A8 heavy chain are illustrated in FIG. 5A. Each heavy chain was co-expressed with light chain c (SEQ ID NO:110) to produce an antibody variant. Antibodies were purified and tested for CXCR2 binding activity as described in General Methods. CXCR2 binding activity was reduced in antibody 102c and antibody 106c.

TABLE 12

Summary of CXCR2 binding data EC$_{50}$ values using combinatorial variants

| Antibody Name | VH change(s) | CXCR2 binding EC$_{50}$ (nM) | Max binding (MFI) | Max binding (MFI Percent of 4A8 WT) |
|---|---|---|---|---|
| 101c | M34Q, A40P, N56S, R75K, M96A (SEQ ID NO: 108) | 3.05 | 55048 | 89% |
| 102c | M34Q, A40P, N56S, R75K, M96E (SEQ ID NO: 162) | 8.70 | 32980 | 53% |
| 103c | M34Q, A40P, R53S, R55G, N56S, R75K (SEQ ID NO: 163) | 5.15 | 44445 | 72% |
| 4A8 Control for 101c-103c | N/A | 1.58 | 62074 | N/A |
| 104c | M34Q, A40P, R53S, R55G, N56S, R75K, M96K (SEQ ID NO: 164) | 6.45 | 45097 | 54% |
| 105c | M34Q, A40P, R53S, R55G, N56S, R75K, M96A (SEQ ID NO: 165) | 5.73 | 42741 | 52% |
| 106c | M34Q, A40P, R53S, R55G, N56S, R75K, M96E (SEQ ID NO: 166) | >100 | 11633 | N/A |

TABLE 12-continued

Summary of CXCR2 binding data $EC_{50}$ values using combinatorial variants

| Antibody Name | VH change(s) | CXCR2 binding $EC_{50}$ (nM) | Max binding (MFI) | Max binding (MFI Percent of 4A8 WT) |
|---|---|---|---|---|
| 4A8 Control for 104c-106c | N/A | 3.82 | 82797 | N/A |

Antibodies were tested in potency assays using CXCL1 or CXCL8 as an agonist as described in the General Methods. Combinatorial antibody variants 103c, 104c, and 105c demonstrated reduced potency when compared to the parental antibody, while variant 101c demonstrated improved potency compared to the parental antibody as shown in Table 13 and FIGS. 6A and 6B.

TABLE 13

Summary of CXCR2 potency data $EC_{50}$ values using combinatorial variants

| Antibody Name | VH change(s) (VH SEQ ID NO) | CXCL8 $IC_{50}$ (nM) | CXCL1 $IC_{50}$ (nM) | CXCL8 Fold Improvement over 4A8 WT | CXCL1 Fold Improvement over 4A8 WT |
|---|---|---|---|---|---|
| 101c | M34Q, A40P, N56S, R75K, M96A (SEQ ID NO: 108) | 0.28 | 0.63 | 2.39 | 1.49 |
| 103c | M34Q, A40P, R53S, R55G, N56S, R75K (SEQ ID NO: 163) | 1.25 | 2.40 | 0.53 | 2.55 |
| 104c | M34Q, A40P, R53S, R55G, N56S, R75K, M96K (SEQ ID NO: 164) | 0.75 | 2.17 | 0.88 | 0.43 |
| 105c | M34Q, A40P, R53S, R55G, N56S, R75K, M96A (SEQ ID NO: 165) | 1.85 | 4.00 | 0.36 | 0.24 |
| 4A8 Control | N/A | 0.66 | 94 | N/A | N/A |

Figure 6A:
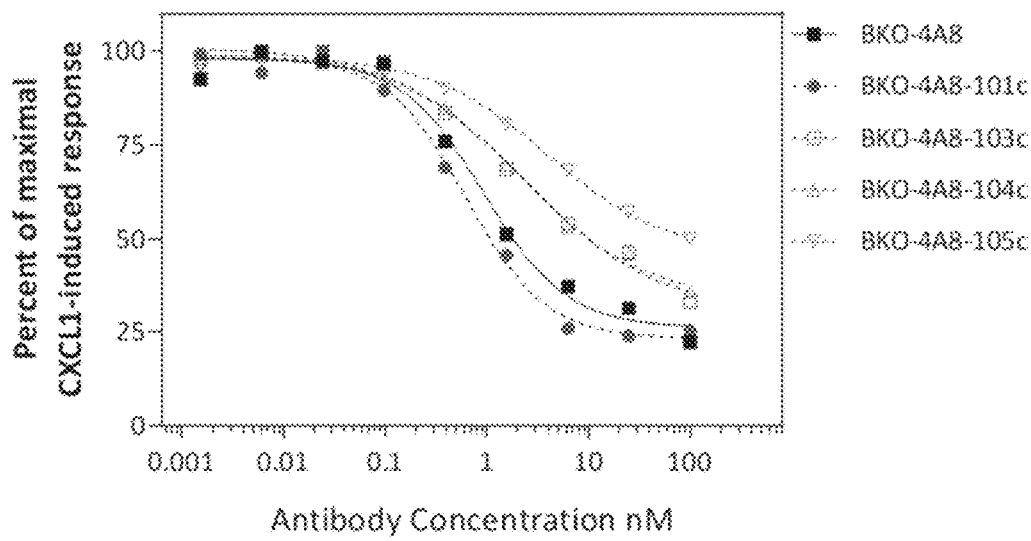
FIG. 6A and FIG. 6B illustrate the results of a dose response inhibition study of (FIG. 6A) CXCL1- and (FIG. 6B) CXCL8-mediated activation of CXCR2 by select anti-CXCR2 antibodies BKO-4A8 and the optimized antibodies BKO-4A8-101c, BKO-4A8-103c, BKO-4A8-104c and BKO-4A8-105c as measured in the Tango™ cell based assay.
Figure 6B:
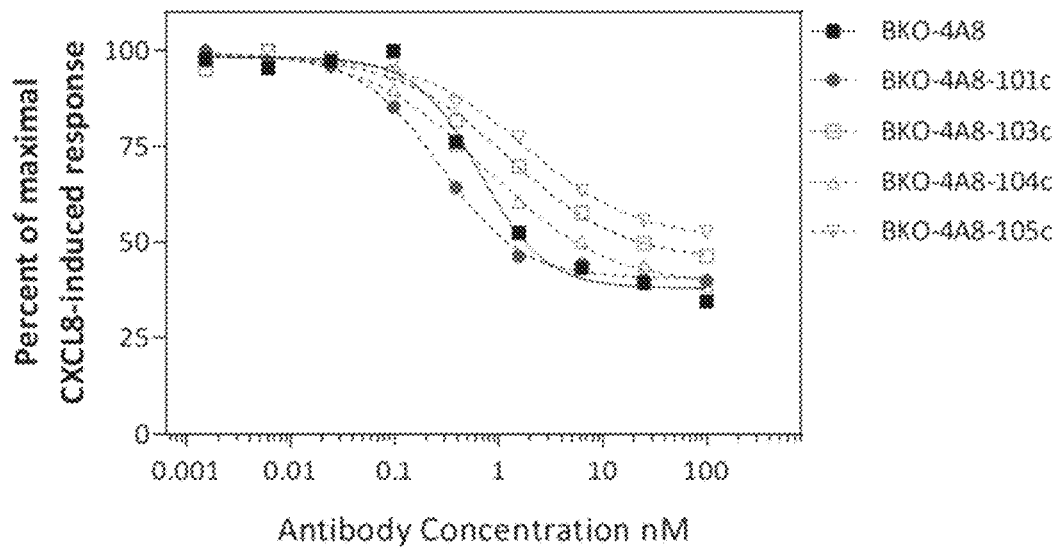

Antibody 101c comprising heavy chain variable region "101" and light chain variable region "c" was selected for evaluation in cell-based potency assays due to its favorable observed properties. Antibody 101c was renamed BKO-4A8-101c. BKO-4A8-101c comprised five heavy- and three light-chain optimizing substitutions. The comparison of BKO-4A8 with BKO-4A8-101c in cell-based potency assays measuring their ability to inhibit CXCL1 or CXCL8 mediated activation of CXCR2 suggested the sequence changes to optimize BKO-4A8-101c also increased its potency relative to parental BKO-4A8, as illustrated in FIGS. 6A and 6B.

Example 5—Characterization of Anti-CXCR2 Antagonist Activity

Figure 7:
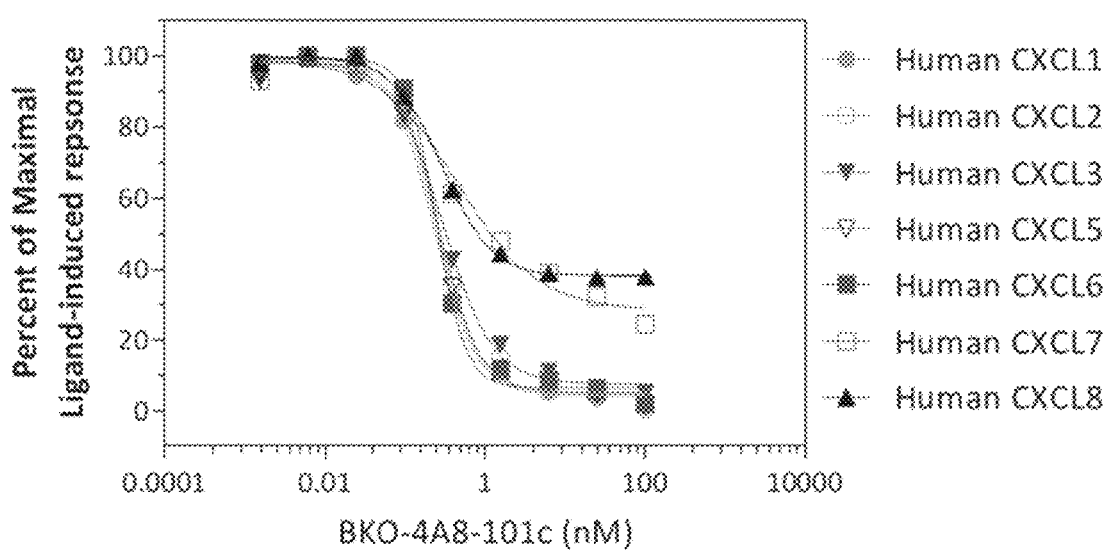
FIG. 7 illustrates the results of a dose response inhibition study of ELR+ CXC chemokine-mediated activation of CXCR2 by the disclosed anti-CXCR2 antibody BKO-4A8-101c as measured in the Tango™ cell based assay.

Characterization of BKO-4A8-101c Inhibition of Ligand Mediated β-arrestin Recruitment The Human CXCR2 Tango™ cell line was used to assess the ability of antibody BKO-4A8-101c to inhibit β-arrestin recruitment to agonist-activated CXCR2. All human ELR+ chemokine CXCR2 ligands were tested in antagonist dose response assays using calculated $EC_{50}$ values of agonist. BKO-4A8-101c was able to inhibit CXCR2-mediated β-arrestin signaling induced by all ELR+ CXCL chemokines, with comparable $IC_{50}$ values obtained for all agonists tested (Table 14). BKO-4A8-101c completely inhibited human CXCR2 activation by human CXCL1, 2, 3, 5, and 6 in a dose-dependent manner, but only partially inhibited CXCL7 and CXCL8 over the same dose range. Representative data from four independent experiments is shown in FIG. 7.

Without wishing to be bound by any proposed mechanism of action, it is proposed that the selective antagonist activity observed provides a therapeutic window to enable substantially complete inhibition of CXCL1- and CXCL5-mediated migration of neutrophils from the circulation into tissue without substantially affecting the migration of neutrophils mediated by CXCL8 from the bone marrow to the circulation. Partial inhibition of CXCL8-mediated β-arrestin in the reporter assay demonstrates that the β-arrestin-mediated receptor internalization pathway is functional.

TABLE 14

BKO-4A8-101c CXCR2 antagonist activity in a ligand-mediated β-arrestin reporter assay (n = 7-13)

| | $IC_{50}$ nM | | Maximal Inhibition % |
|---|---|---|---|
| Hu Ligands | Mean | Range | Mean |
| Hu CXCL1 | 0.27 | 0.08-0.42 | 98 |
| Hu CXCL2 | 0.36 | 0.23-0.44 | 100 |
| Hu CXCL3 | 0.39 | 0.30-0.46 | 96 |
| Hu CXCL5 | 0.30 | 0.11-0.47 | 98 |
| Hu CXCL6 | 0.28 | 0.16-0.38 | 98 |
| Hu CXCL7 | 0.44 | 0.29-0.62 | 76 |
| Hu CXCL8 | 0.34 | 0.18-0.66 | 78 |

Characterization of BKO-4A8-101c Inhibition of Ligand-mediated Calcium Flux

One of the signaling pathways downstream of CXCR2 activation that has a role in cell chemotaxis is characterized by calcium mobilization (flux). The ability of BKO-4A8-101c to inhibit human CXCR2 ligand-induced calcium flux was tested in the commercially available HTS002C-CHE-MISCREEN™ human CXCR2 chemokine receptor calcium-optimized cell line. All human ELR+ chemokine CXCR2 ligands were tested in antagonist dose response assays using calculated agonist $EC_{50}$ values.

Figure 8:
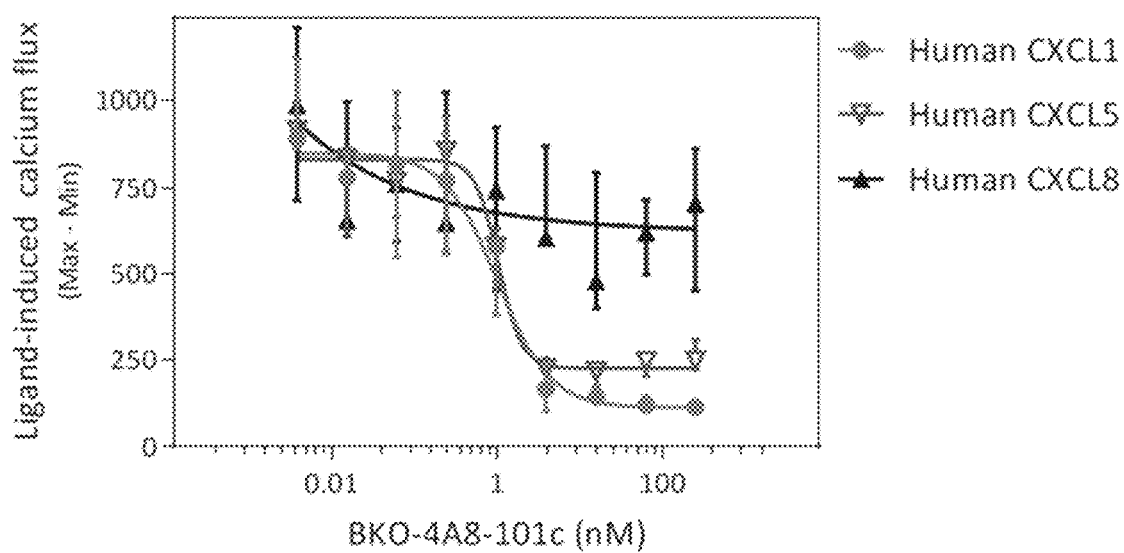
FIG. 8 illustrates the results of a dose response inhibition study of CXCL1-, CXCL5- and CXCL8-mediated activation of CXCR2 by the disclosed anti-CXCR2 antibody BKO-4A8-101c as measured in a calcium flux assay.

BKO-4A8-101c strongly inhibited calcium flux induced by human CXCL1, 2, 3, 5, and 6 in a dose-dependent manner, but only weakly inhibited CXCL7 and marginally inhibited CXCL8 over the same dose range, as shown in Table 15. Representative data is shown for CXCL1, CXCL5, and CXCL8 (FIG. 8).

The neutrophil chemotactic response is known to be mediated via CXCR2-activated calcium mobilization. Without wishing to be limited to any proposed mode of action, the selective antagonist activity provided by antibodies disclosed herein potentially provides a therapeutic window to enable substantially complete inhibition of the CXCL1- and CXCL5-mediated migration of neutrophils into lungs without substantially impacting CXCL8-mediated migration of neutrophils from bone marrow into the circulation. This may allow for blockade of neutrophil-mediated pathology at sites of chronic inflammation without necessarily impairing baseline neutrophil-mediated antimicrobial functions.

TABLE 15

Summary of mean $IC_{50}$ values of BKO-4A8-101c for human ELR+ chemokines on human CXCR2 in a calcium flux assay (N = 4-9)

| | $IC_{50}$ nM | | Maximal Inhibition % |
|---|---|---|---|
| Hu Ligands | Mean | Range | Mean |
| Hu CXCL1 | 1.55 | 0.84-2.31 | 91 |
| Hu CXCL2 | 1.62 | 0.75-2.30 | 88 |
| Hu CXCL3 | 0.63 | 0.25-1.15 | 52 |
| Hu CXCL5 | 1.03 | N.A.[a] | 81 |
| Hu CXCL6 | 1.71 | 1.57-2.00 | 81 |
| Hu CXCL7 | 2.14 | 0.47-5.5 | 43 |
| Hu CXCL8 | N.D.[b] | — | 9 |

[a]Insufficient data.
[b]N.D. No inhibition or data that did not fit a four point dose response curve fit analysis.

Figure 9:
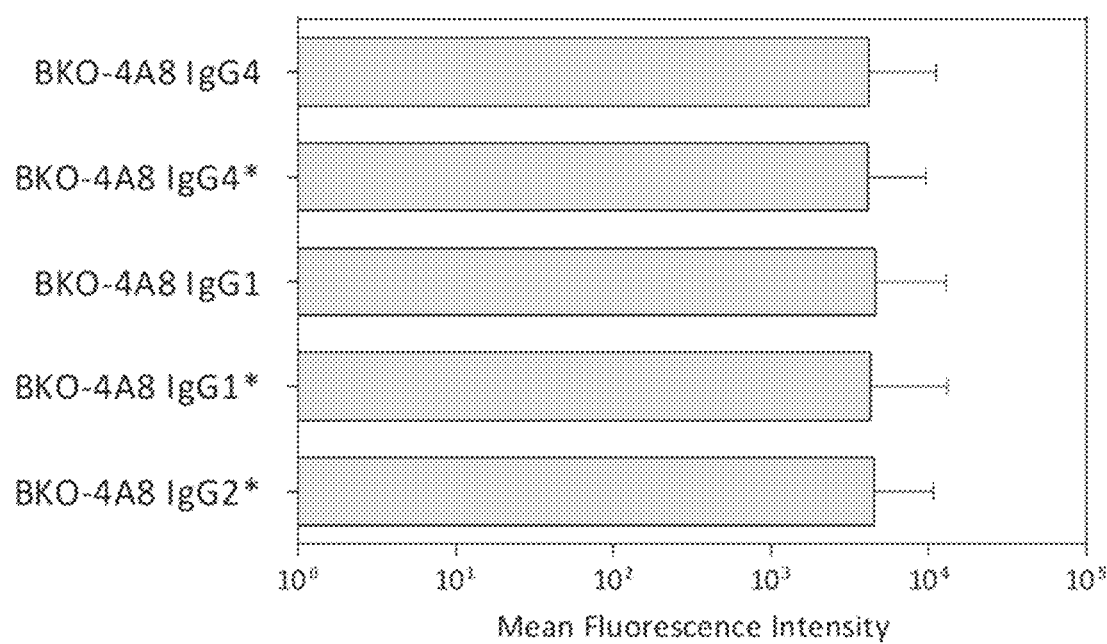
FIG. 9 illustrates human CXCR2 binding activity of the disclosed anti-CXCR2 antibody BKO-4A8 formatted onto different human IgG constant regions, as determined by flow cytometry analysis.

Example 6—In Vitro Binding and Functional Activity of Anti-CXCR2 Antibodies is Independent of Fc Region Variable regions from the BKO-4A8 heavy chain were formatted onto different human IgG constant regions as provided in the Table 16. The ability of purified antibodies to bind to human CXCR2 was routinely assessed on Expi293F™ cells transiently transfected to express human CXCR2 (SEQ ID NO: 125). Binding of BKO-4A8 and variants thereof was detected by incubation of fluorochrome-conjugate anti-human IgG light chain lambda antibody. The binding activity of antibodies tested, quantified as mean fluorescent intensity, was independent of the antibody Fc region as illustrated in FIG. 9.

TABLE 16

Heavy chain variants of BKO-4A8

| BKO-4A8 heavy chain variant | Heavy Chain SEQ ID NO |
|---|---|
| BKO-4A8 IgG4* | 115 |
| BKO-4A8 IgG4 | 117 |
| BKO-4A8 IgG2* | 119 |
| BKO-4A8 IgG1* | 121 |
| BKO-4A8 IgG1 | 123 |

*refers to a modified Fc

Figure 10:
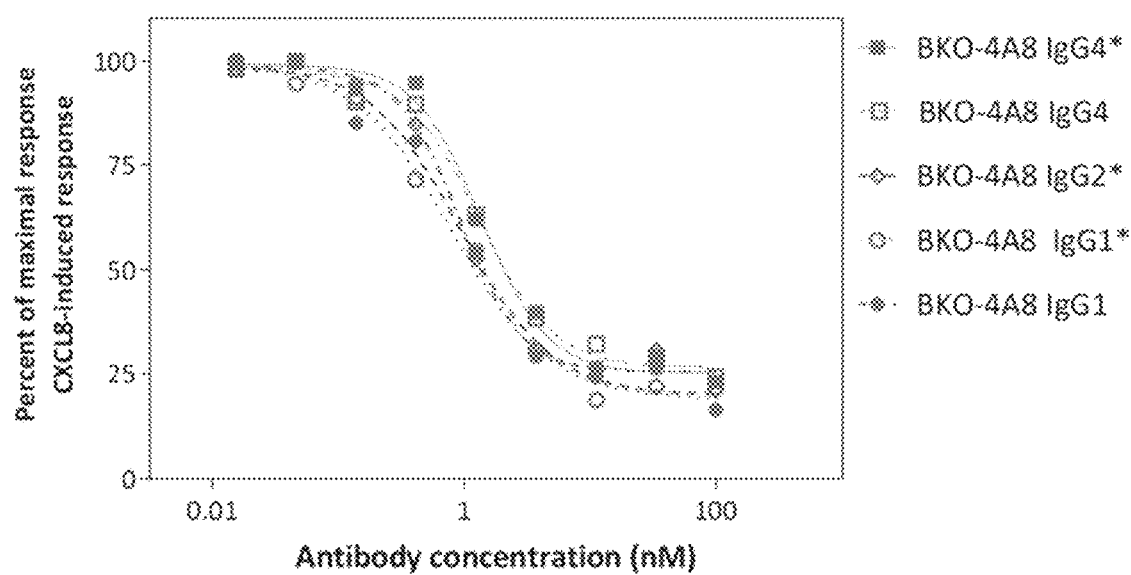
FIG. 10 illustrates the results of a dose response inhibition study of CXCL8-mediated activation of the disclosed anti-CXCR2 antibody BKO-4A8 formatted onto different human IgG constant regions, as measured in the Tango™ cell based assay.

The commercially available reporter cell line Tango™ CXCR2-bla U2OS (ThermoFisher Scientific) was used to assess the ability of the anti-CXCR2 antibodies to inhibit β-arrestin recruitment to agonist-activated CXCR2. Agonists were provided at their assay $EC_{50}$ concentration for antagonist assays. The dose response curves demonstrated that functional activity of BKO-4A8 was not impacted by the sequence modification in the Fc region, with comparable antagonist activity evident for all antibodies evaluated, as illustrated in FIG. 10.

Example 7—Specificity of Anti-CXCR2 Antibody BKO-4A8-101c

Figure 11:
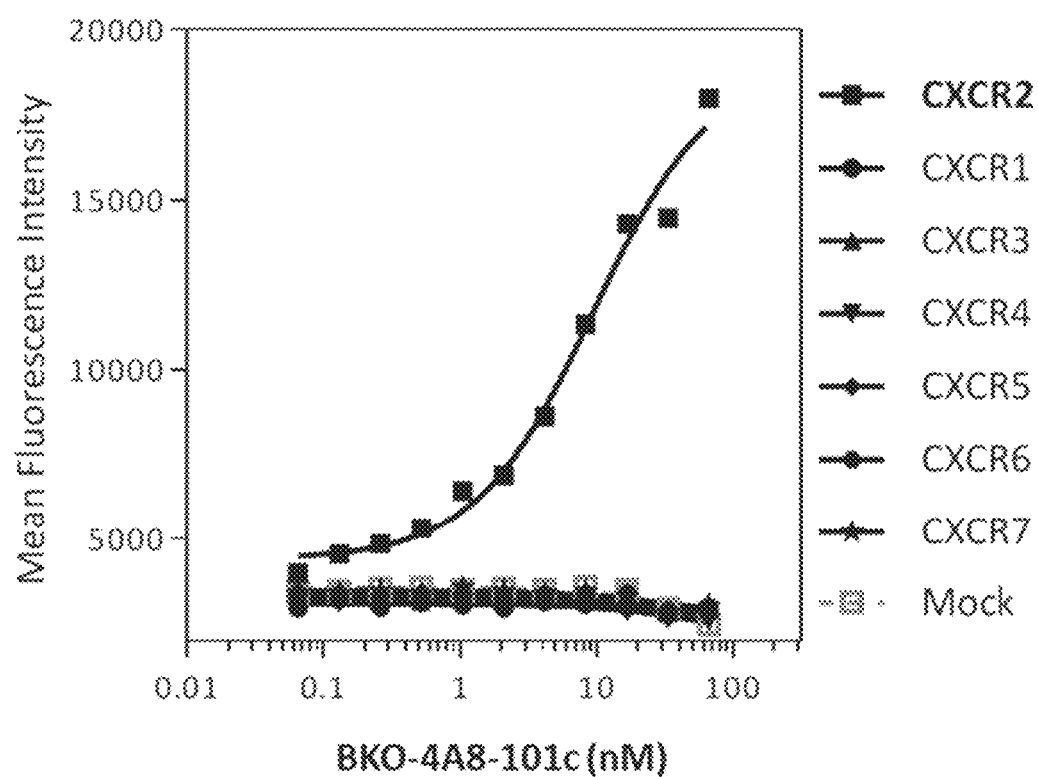
FIG. 11 illustrates results from binding studies of the anti-CXCR2 antibody BKO-4A8-101c with a variety of human CXCR family members. The results demonstrated that BKO-4A8-101c only bound to CXCR2 amongst the human CXCR family members.

The specificity of the anti-CXCR2 antibody BKO-4A8-101c was tested by assessing binding activity on Expi293F™ cells transiently transfected to express closely related human CXCR family members as illustrated in FIG. 11. Sequences of the tested human CXCR family members are provided in Table 19. Binding of BKO-4A8-101c was detected by incubation of fluorochrome-conjugate anti-human IgG antibody. The anti-CXCR2 antibody BKO-4A8-101c was found to strongly and exclusively bind human CXCR2.

Example 8—Flow Cytometry Binding Assays Using Primary Blood Cells

To further characterize the anti-CXCR2 antibody BKO-4A8-101c, the ability to bind CXCR2 on neutrophils was tested on anticoagulated human blood. Binding was measured using BKO-4A8-101c directly conjugated to fluorophore APC. Matched isotype control antibodies conjugated to APC were included for comparison. Cells were incubated with lineage-specific antibodies and 2 μg/mL of APC conjugated anti-CXCR2 antibody or isotype control. The level of fluorescence on the cell surface was measured by flow cytometry. Cellular debris and non-viable cells were excluded based on light scatter characteristics and incorporation of Zombie Violet fixable viability dye (BioLegend, 423113). Hematopoietic cell subsets were identified based on CD45 expression together with characteristic size (forward scatter, FSC) and granularity (side scatter, SSC) in association with expression of phenotypic markers as follows: T lymphocytes=CD3; B lymphocytes=CD20; Monocytes=CD14; and natural killer lymphocytes=CD56 (or CD3-CD20-CD16+ lymphocytes). Granulocytes were identified according to size and granularity and the absence of binding of lineage specific markers: CD3, CD19, CD20, CD56, and CD14. Neutrophils were further distinguished by high levels of expression of CD16 and CD177, while eosinophils were identified based on Siglec-8 expression. Using this method BKO-4A8-101c bound neutrophils (FIG. 12A) and monocytes (FIG. 12B) from human blood. A commercial anti-CXCR2 antibody (BioLegend 5E8/CXCR2) was used as a positive control in the experiment.

Example 9—The Ability of Purified Antibodies to Inhibit Agonist-induced CXCR2-mediated Functional Response Relative to Comparator Antibodies and Small Molecules Characterization of BKO-4A8-101c Inhibition of Ligand Mediated β-arrestin Recruitment Relative to Comparator Reagents The ability of BKO-4A8-101c to block ligand-activated CXCR2 signaling was compared with comparator antibodies and small molecules (see General Methods) in the Tango™ CXCR2 β-arrestin recruitment assay (Thermo), using the human ligands CXCL1, CXCL5, and CXCL8 at calculated $EC_{50}$ values.

BKO-4A8-101c inhibited CXCR2-mediated β-arrestin functional activity elicited by a panel of known CXCR2 ligands, with comparable $IC_{50}$ values for different ligands. The antibody demonstrated ligand selective inhibition of CXCR2-dependent β-arrestin recruitment with complete inhibition of CXCL1- and CXCL5 and partial inhibition of CXCL8-induced β-arrestin recruitment (range 70-80%) as shown in Table 17.

The potency of BKO-4A8-101c inhibition of CXCL1 and CXCL5-mediated β-arrestin signaling was similar or higher than that observed for other comparator antibodies and small molecules. Based on $IC_{50}$ values, BKO-4A8-101c was shown to be 2- to 39-fold more potent in inhibiting CXCL1- or CXCL5-ligand mediated β-arrestin activation than comparator CXCR2 antagonist antibodies or small molecules, but only an incomplete inhibitor of CXCL8-induced activation of CXCR2. Incomplete inhibition of CXCL8-mediated β-arrestin reporter activity demonstrates that the β-arrestin-mediated receptor internalization pathway is functional.

TABLE 17

Summary of mean $IC_{50}$ Values of CXCR2 antagonists for human ELR+ chemokines on human CXCR2 in a β-arrestin recruitment assay

| Compound | CXCL1 | | CXCL5 | | CXCL8 | |
|---|---|---|---|---|---|---|
| | $IC_{50}$ (nM) | Maximal Inhibition % | $IC_{50}$ (nM) | Maximal Inhibition % | $IC_{50}$ (nM) | Maximal Inhibition % |
| BKO-4A8-101c | 0.38 | 97 | 0.34 | 98 | 0.34 | 78 |
| Antagonist 1 | 1.20 | 98 | 0.80 | 98 | 0.58 | 97 |
| Antagonist 2 | 1.14 | 93 | 0.56 | 96 | 0.82 | 74 |
| Antagonist 3 | 14.80 | 85 | 8.12 | 96 | N.D.[a] | 82 |
| Antagonist 4 | 1.47 | 96 | 0.75 | 99 | 1.01 | 94 |
| Antagonist 5 | 2.77 | 99 | 1.75 | 99 | 1.23 | 99 |
| Antagonist 6 | 0.71 | 99 | 0.29 | 97 | 1.22 | 98 |

[a]N.D. No inhibition or data that did not fit a four point dose response curve fit analysis.

Characterization of BKO-4A8-101c Inhibition of Calcium Mobilization

The ability of antagonists to inhibit CXCR2 activation of calcium mobilization induced by CXCL1 and CXCL8 was assessed in the commercially available HTS002C-CHEMIS-CREEN™ human CXCR2 chemokine receptor calcium-optimized stable cell line (Eurofins Pharma Discovery Services). CXC ligands were provided at their assay $EC_{50}$ concentration (see Table 3) for antagonist assays. The Fluo-4 NW calcium assay kit (Life Technologies) was used according to manufacturer's protocol for in-cell measurement of calcium mobilization, which was read using a FLIPR Tetra high-throughput cellular screening system (Molecular Devices). The peak response minus the basal response from each well was used to determine inhibition dose response curves fitting a four-parameter logistic equation and $IC_{50}$ values.

The ability of BKO-4A8-101c to block ligand-induced calcium flux was compared with comparator antibodies and small molecules (Table 18) using the human ligands CXCL1 and CXCL8 at calculated $EC_{50}$ values. The $IC_{50}$ values from at least 3 independent replicates are shown in Table 18. BKO-4A8-101c was an equivalent or more potent CXCL1 antagonist than comparator antibodies and small molecules and strongly inhibited calcium flux induced by human CXCL1. In contrast, BKO-4A8-101c and other comparator antibodies did not substantially inhibit calcium flux induced by CXCL8, while the comparator small molecule CXCR2 antagonists proved to be able to completely inhibit CXCL8 induced calcium flux in this assay. The neutrophil chemotactic response mediated via CXCR2 is dependent on calcium mobilization. Without wishing to be bound by any proposed mechanism of action, the selective antagonist activity observed with BKO-4A8-101c provides a therapeutic window to enable substantially complete inhibition of CXCL1- and CXCL5-mediated migration of neutrophils into tissue, without substantially impacting CXCL8-mediated migration from the bone marrow. This ligand selectivity may also affect the chemokine gradients that drive neutrophil chemotactic responses.

TABLE 18

Summary of $IC_{50}$ values of human CXCR2 antagonists for human ELR+ chemokines on human CXCR2 in a calcium flux assay

| Compound | CXCL1 | | CXCL8 | |
|---|---|---|---|---|
| | $IC_{50}$ (nM) | Maximal Inhibition % | $IC_{50}$ (nM) | Maximal Inhibition % |
| BKO-4A8-101c | 1.47 | 93 | N.D.[a] | 9 |
| Antagonist 1 | N.D.[a] | 28 | N.D.[a] | 8 |
| Antagonist 2 | 1.02 | 79 | N.D.[a] | 3 |
| Antagonist 3 | 30.74 | 37 | N.D.[a] | 18 |
| Antagonist 4 | 1.29 | 93 | N.D.[a] | 1 |
| Antagonist 5 | 48.94 | 95 | 115.12 | 97 |
| Antagonist 6 | 8.46 | 96 | 16.09 | 98 |

[a]N.D. No inhibition or data that did not fit a four point dose response curve fit analysis.

Example 10—Anti-CXCR2-mediated Inhibition of Lung Neutrophilia in a Mouse Model of Severe Asthma Sensitized mice challenged with intranasal house dust mite extract (HDM) develop an inflammatory profile with mixed pulmonary eosinophilia and neutrophilia associated with goblet cell hyperplasia. A severe asthma model has previously been reported using the small molecule CXCR2 antagonist SCH527123 at 10 and 30 mg/kg doses (as discussed in YOUNG, A., et al., The Effect of the CXCR1/2 Antagonist SCH257123 in a Mouse Model of Severe Asthma. Experimental Biology 2016 Meeting, 2016 San Diego, USA: The FASEB Journal, 1202.10) known to work in mouse models of neutrophilic inflammation (as discussed in CHAPMAN, R. W., et al., A novel, orally active CXCR1/2 receptor antagonist, Sch527123, inhibits neutrophil recruitment, mucus production, and goblet cell hyperplasia in animal models of pulmonary inflammation. *J Pharmacol Exp Ther*, (2007) 322, 486-93). Pre-treatment with 10 and 30 mg/kg SCH527123 only inhibited neutrophil cell numbers by a maximum of 30% in the BAL, which was not significantly different when compared to the house dust mite (HDM)-vehicle treated group (as discussed in Young et al., supra).

The anti-CXCR2 antibody BKO-4A8-mIgG1 (SEQ ID NOs: 113 and 114) was generated by formatting the variable heavy and light chains of BKO-4A8 onto an effector function-reduced mouse IgG1 constant region. Female hCXCR2 knock-in mice were subjected to sensitization with 50 μg HDM in complete Freund's adjuvant (CFA) administered by subcutaneous injection on day 0 and intranasal challenge with 50 mg HDM without CFA on day 14. Animals were treated with vehicle or BKO-4A8-mIgG1 (10 mg/kg) via intraperitoneal injection on days 5 and 12. Inflammatory responses were characterized at endpoint on day 16 by total and differential cell counts in bronchoalveolar lavage (BAL) fluid of the right lung. The left lung was fixed in 10% formalin for histopathology and mucus production assessment.

Figure 13A:
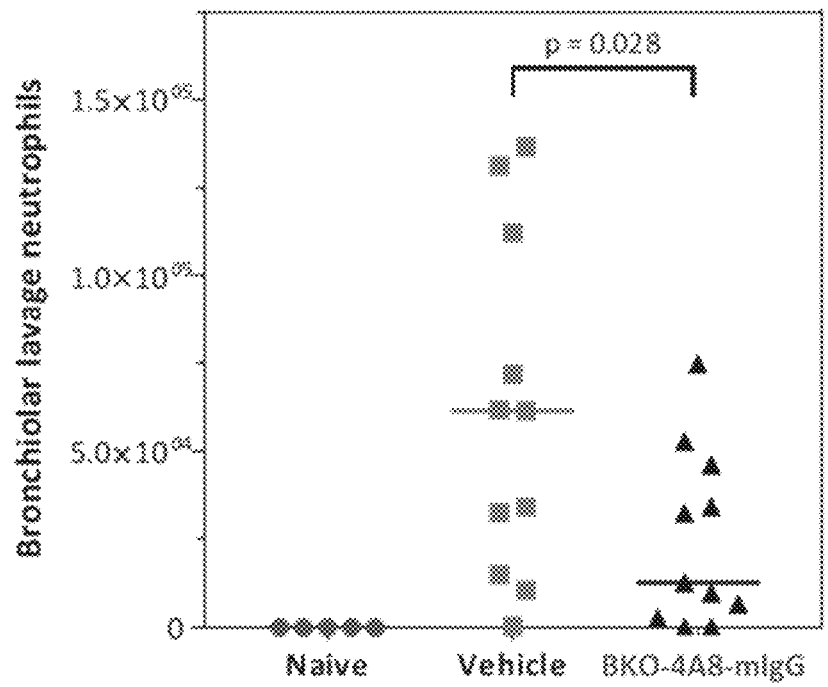
FIG. 13A, FIG. 13B, and FIG. 13C illustrate the results of a subcutaneous sensitization and intranasal challenge (on Day 14) using House Dust Mite (HDM) antigen, which induced features of acute allergic (asthma-like) inflammation in the lungs of human-CXCR2 transgenic mice. Specifically, following challenge mice demonstrated a moderate to marked multifocal pulmonary inflammation with eosinophils, and mild to moderate bronchiolar goblet cell hyperplasia compared to control (naïve) mice that had little to no inflammation. Treatment with BKO-4A8-mIgG resulted in a reduction in the severity of pathology including significant reductions in lung neutrophil (FIG. 13A) and lung eosinophil counts (FIG. 13B) and mucus density score (FIG. 13C) compared to vehicle.
Figure 13B:
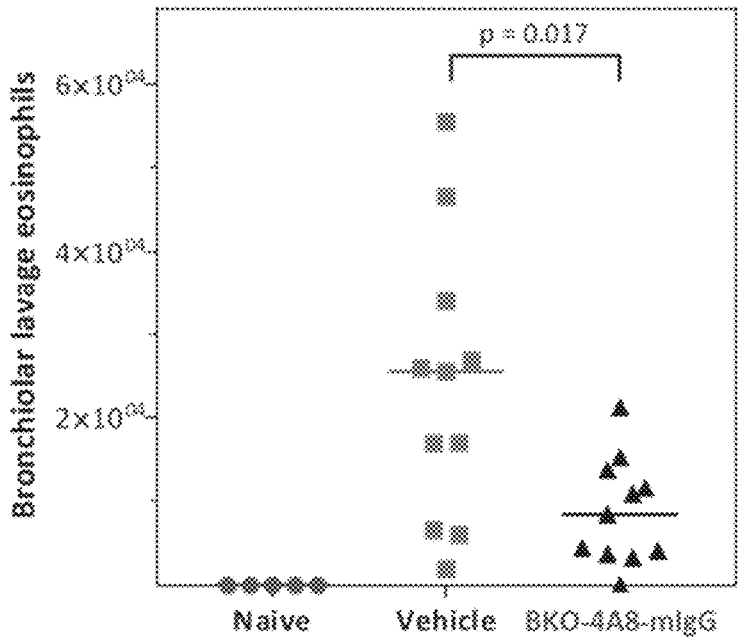
Figure 13C:
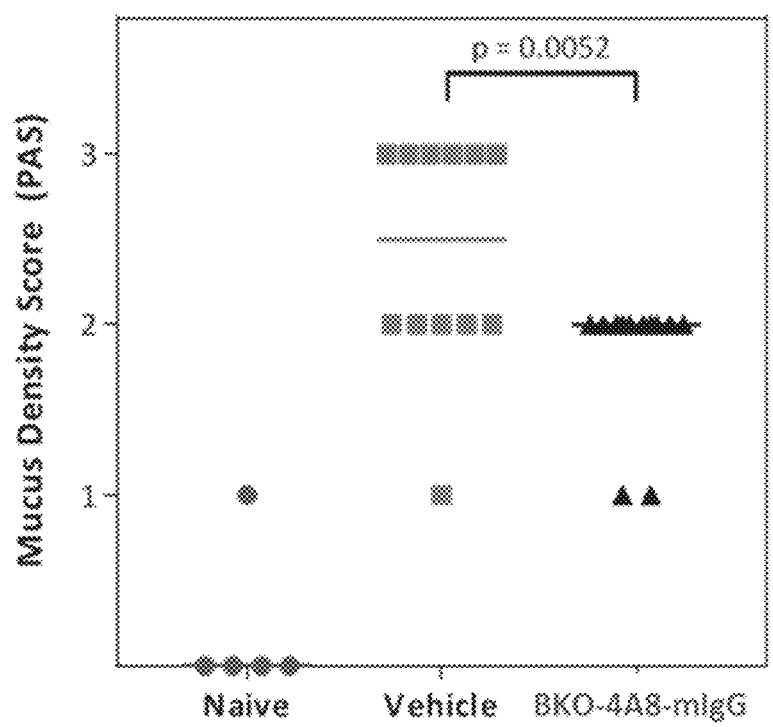

Anti-CXCR2 antibody BKO-4A8-mIgG1 treatment prior to HDM challenge resulted in a reduction in disease severity, including a significant (>60%) reduction in BAL eosinophil (p=0.017) and neutrophil (p=0.028) counts and reduced goblet cell hyperplasia (p=0.0052), when compared to the vehicle treated control group, as shown in FIGS. 13A, 13B, and 13C. Statistical evaluation was performed using a Mann-Whitney nonparametric unpaired t test with outliers identified using Grubbs' test (Alpha=0.01) to discern statistically significant differences between the vehicle and treatment groups. All statistical analyses were performed using GraphPad Prism™ 7.01.

The reduction in BAL eosinophil numbers in this model is surprising. The ability of BKO-4A8-mIgG1 to suppress eosinophilic migration supports its utility in treating diseases of eosinophilia, such as eosinophilic asthma, in addition to neutrophilic conditions.

Example 11—LPS Induced Acute Lung Inflammation in Cynomolgus Monkey

Biologics naïve (i.e. not previously administered exogenous biologics) male cynomolgus monkeys were randomized into groups receiving vehicle or the anti-CXCR2 antibody BKO-4A8-101c administered by intravenous administration at a dose of 1 mg/kg on days 0, 14, and 28. One hour post-treatment of test antibodies on day 0, animals were exposed to aerosolized bacterial lipopolysaccharide (LPS) by inhalation of 20 μg/L for 5 mins (total dose 20 μg/kg). This is a well-established model of acute lung inflammation. Inflammatory responses were characterized at 24 hours after LPS exposure by total and differential cell counts of bronchoalveolar lavage fluid of the left lung and compared to matched counts from naïve animals at pre-treatment day 14. Blood was collected at various time points for differential cell count and serum collected for pharmacokinetic analysis.

Figure 14A:
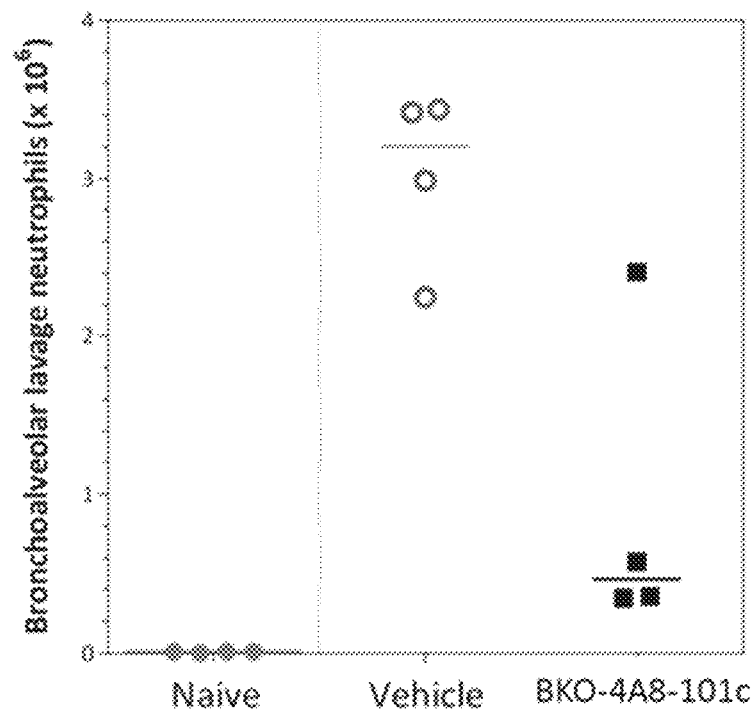
FIG. 14A and FIG. 14B illustrate results of anti-CXCR2 activity of the antibody BKO-4A8-101c in a cynomolgus monkey model of acute lung inflammation. Aerosol inhalation of lipopolysaccharide (LPS) (on Day 0) successfully induced features of acute neutrophilic inflammation in the lungs of cynomolgus monkeys. Treatment with anti-CXCR2 antibody BKO-4A8-101c (1 mg/kg) 1 hour prior to challenge with LPS on day 0 resulted in a significant reduction in bronco-alveolar lavage neutrophil counts 24 hours after LPS challenge.
Figure 14B:
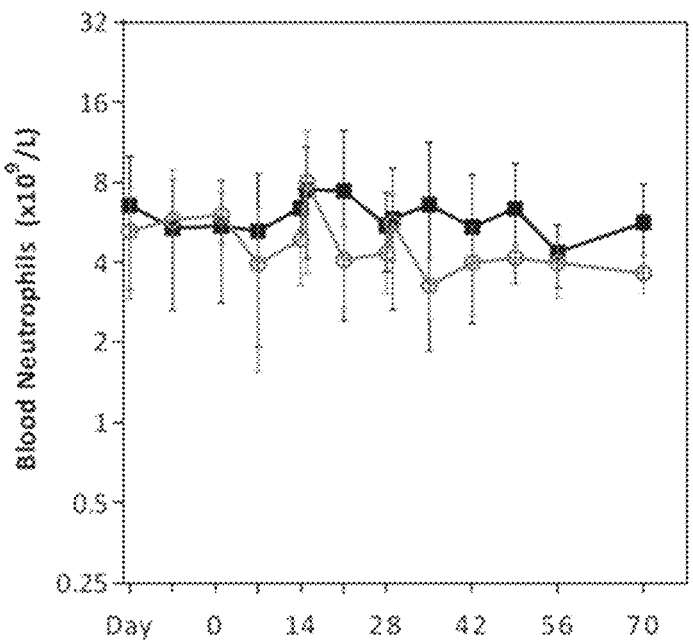

A single aerosol LPS treatment induced an influx of neutrophils into the lung in vehicle treated animals. Pre-treatment with 1 mg/kg of the anti-CXCR2 antibody BKO-4A8-101c markedly inhibited LPS-induced pulmonary neutrophilia in cynomolgus monkeys, as illustrated in FIG. 14A. Treatment was well tolerated with no loss in body weight. Treatment with BKO-4A8-101c did not induce measurable changes in blood neutrophil counts following repeat antibody dosing, as illustrated in FIG. 14B.

CXCR2 signaling is involved in neutrophil movement both out of the bone marrow and into peripheral tissues in response to chemokines produced by tissue-resident cells following stress, injury, or infection. CXCR2 binds multiple chemokines implicated in neutrophil recruitment and chronic inflammation, including CXCL1, CXCL5, and CXCL8. These chemokines are also elevated in patients with severe neutrophilic asthma and COPD. BKO-4A8-101c was shown herein to be a potent and specific antagonist of CXCR2-mediated signaling. Without wishing to be limited by any proposed mechanism of action, based on its in vitro profile, and its potency in the cynomolgus monkey, the anti-inflammatory activity of BKO-4A8-101c appears to be mediated via antagonism of CXCL1 and CXCL5-mediated CXCR2 signaling. These data support the concept that the CXCR2 receptor is the predominant chemokine receptor controlling neutrophil migration into the lungs under inflammatory conditions, and are consistent with the lack of marked efficacy of a humanized neutralizing anti-CXCL8 antibody administered to COPD patients (as discussed in MAHLER, D. A., et al., Efficacy and safety of a monoclonal antibody recognizing interleukin-8 in COPD: a pilot study. Chest, (2004) 126, 926-34), an approach that would only partially inhibit the CXCR1/CXCR2 inflammatory axis. A component of the anti-inflammatory activity of BKO-4A8-101c may be mediated via endothelial and epithelial cells, because CXCR2 expression on these cell types has also been implicated in neutrophil recruitment and lung injury (as discussed in REUTERSHAN, J., et al., Critical role of endothelial CXCR2 in LPS-induced neutrophil migration into the lung. *J Clin Invest*, (2006) 116, 695-702). The demonstrated in-vivo efficacy of BKO-4A8-101c in inhibiting lung neutrophil migration in response to LPS challenge without affecting circulating neutrophil numbers or any other measured safety parameters may be a consequence of its exquisite specificity and selective antagonist activity.

Example 12—Anti-CXCR2 Antibody Efficiently Occupies the CXCR2 Receptor and Selectively Suppresses CXCR2-mediated Neutrophil Responses Receptor occupancy assays measure binding of a specific molecule or drug to a receptor expressed on a specific cell. This is a quantitative assay that can be used to evaluate receptor binding and other pharmacodynamic characteristics.

Receptor occupancy was examined in a human CXCR2 expressing cell line and human neutrophils enriched from whole blood. At least 85% of the CXCR2 receptors were occupied at 2 μg/mL of antibody. This amount was sufficient to suppress CXCL1-induced calcium flux by more than 85% in HTS002C-CHEMISCREEN™ human CXCR2 chemokine receptor calcium-optimized cells (results not shown).

While 2 μg/mL of antibody was sufficient to effectively antagonize CXCR2-mediated-signaling, it did not interfere with neutrophil functions. End-target chemoattractants C5a and fMLF bind to C5a receptor (CD88) and FPR1, respectively. Both of these agents induce chemotaxis and the expression of CD11b, a widely accepted marker of neutrophil activation in response to infection and inflammation. CXCR2 antibody did not suppress neutrophil CD11b upregulation or chemotaxis in response to C5a and fMLF (results not shown).

Figure 15A:
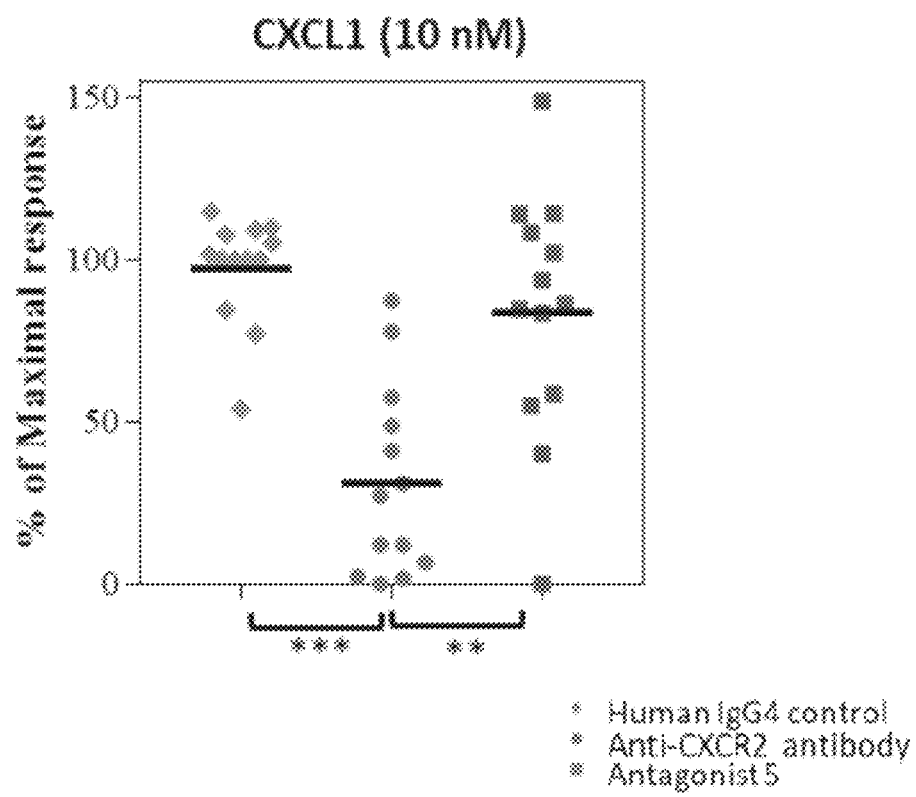
FIG. 15A, FIG. 15B, and FIG. 15C show selective inhibition of chemokine-induced upregulation of CD11b on enriched human neutrophils. Anti-CXCR2 antibody significantly inhibited the response to CXCL1 (p=0.0002) (FIG. 15A) and CXCL5 (p=0.0001) (FIG. 15B). Anti-CXCR2 antibody was significantly more inhibitory than the small-molecule antagonist 5 in the same assays (p<0.0058) (FIG. 15A-B). CXCL8-mediated CD11b upregulation was reduced by a CXCR1 antagonist (data not shown), but not by anti-CXCR2 antibody or antagonist 5 (FIG. 15C).
Figure 15B:
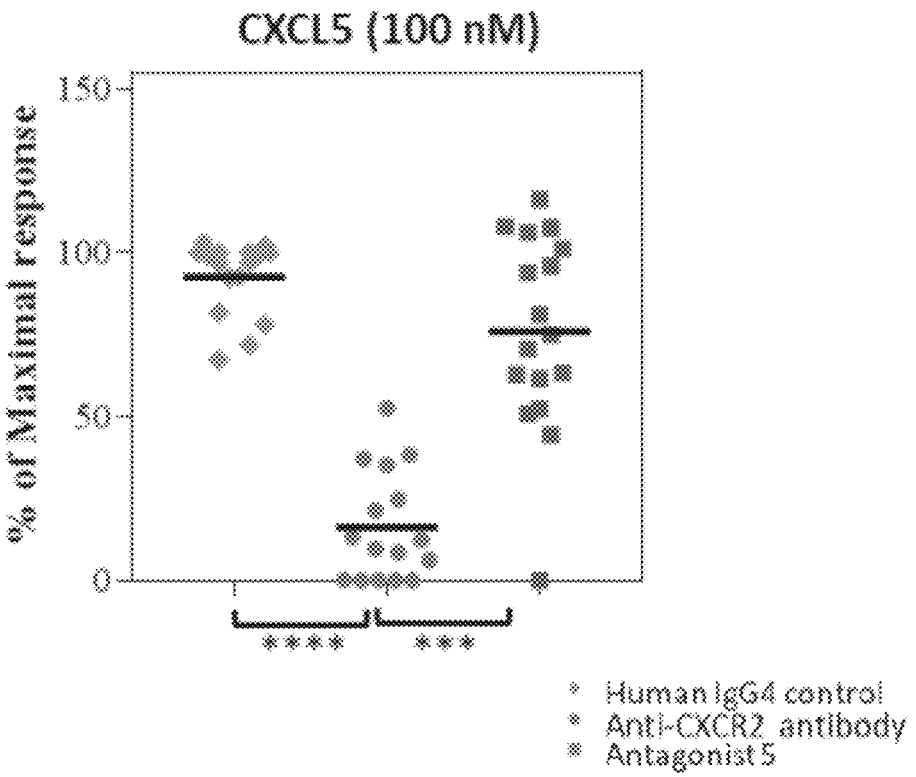

10 μg/ml (70 nM) CXCR2 antibody potently and specifically antagonized CXCR2-mediated responses to CXCL1 (p<0.0002, FIG. 15A) and CXCL5 (p<0.0001, FIG. 15B) in human neutrophils isolated (to 95%) from whole blood. 70 nM CXCR2 antibody demonstrated greater potency in this assay than the small molecule Antagonist 5 (danirixin) used at 1400 nM. This compares with previous reports that Agonist 5 inhibited CXCL1-induced ex vivo neutrophil surface expression of CD11b with an $IC_{50}$ of 69 ng/mL [156 nM], and $IC_{90}$ of 620 ng/mL (range 158-1080 ng/ml) [1400 nM, (range 356-2443 nM)] (Miller et al. "The pharmacokinetics and pharmacodynamics of danirixin (GSK1325756)—a selective CXCR2 antagonist—in healthy adult subjects" *BMC Pharmacology and Toxicology* 2015; 16).

Figure 15C:
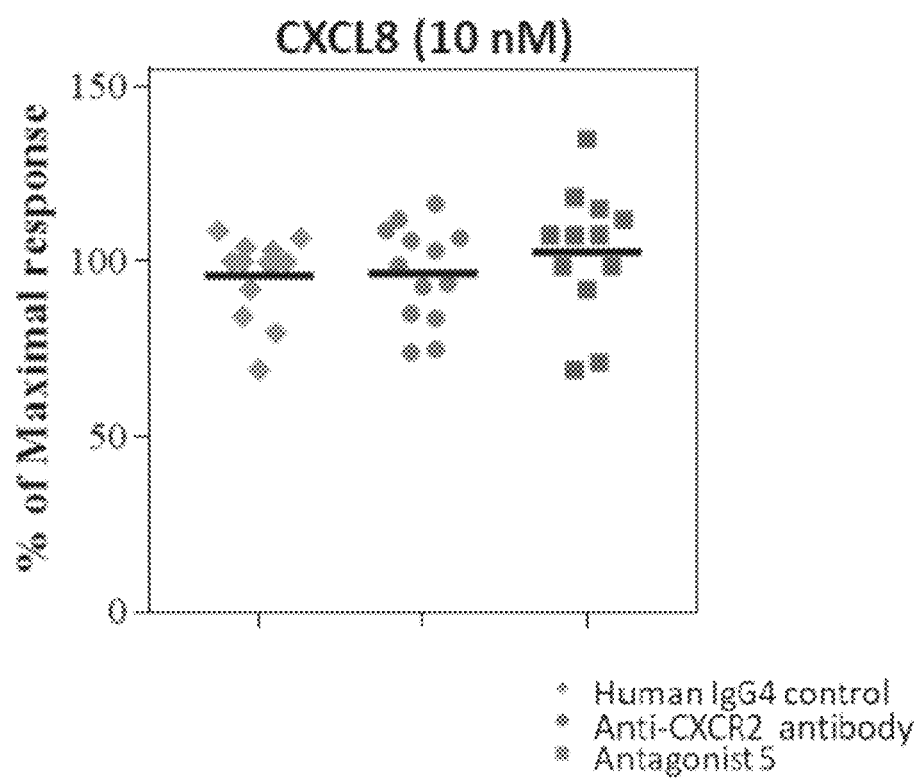

Neither CXCR2 nor Antagonist 5 significantly impacted the neutrophil response to CXCL8 in this assay (FIG. 15C). CXCL8 binds to both CXCR1 and CXCR2.

These data demonstrate that CXCR2 antibody is a potent and selective inhibitor of CXCR2 on human neutrophils.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

TABLE 19

Sequences

| Sequence Identifier | Sequence | Sequence Identifier | Sequence |
|---|---|---|---|
| BKO-1A1 | | | |
| SEQ ID NO: 1 (BKO_1A1_VH) | QLQLQESGPGLVKPSETLSLTCTVSGGSIRTSS YYWGWIRQPPGKGLEYIGSIYYSGTTYYNPS LKSRVTMSVDTSKNQFSLKMSSVTAADSAV YYCARHGRVREVPPFDYWGQGTLVTVSS | SEQ ID NO: 2 (BKO_A1_VL) | SSELTQDPAVSVALGQTVRITCQGDSLRYY YASWYQQKPGQAPVLVIYDENSRPSGIPDR 1 FSGSSSGNTASLSITGTQAEDEADYYCNSR DTSGNHWAFGGGTKLTVL |
| BKO-1B10 | | | |
| SEQ ID NO: 3 (BKO_1B10_VH) | QLQLQESGPGLVKPSETLSLTCTVSGGSIRTSS YYWGWIRQPPGKGLEYIGSIYYSGTTYYNPS LKSRVTMSVDTSKNQFSLKLSSVTAADTAVY YCARHGRVREVPPFDYWGQGTLVTVSS | SEQ ID NO: 4 (BKO_1B10_VL) | SSELTQDPAVSVALGQTVRITCQGDSLRYY YASWYQQKPGQAPVLVIYDENSRPSGIPDR FSGSSSSGNTASLRITGTQAEDEADYYCNSR DTSGNHWAFGGGTKLTVL |
| BKO-1D1 | | | |
| SEQ ID NO: 5 (BKO_1D1_VH) | EVQLLESGGGLVQPGGSLRLSCAASKLTFKN SAMSWVRQAPGKGLEWVSAITGSSGGRTYYA DSVKGRFTISRDNSKNTLYLQMNSLRAEDTA IYYCAIQMGYWGQGILVTVSS | SEQ ID NO: 6 (BKO_1D1_VL) | QSALTQPPSASGSPGQSVTISCTGTSSDVGG YNYVSWYQQHPGKAPKLMIYEVNKRPSGV PARFSGSKSGNTASLTVSGLQAEDEADYYC SSYAGSNNFGVFGGGTKLTVL |
| BKO-1H3 | | | |
| SEQ ID NO: 7 (BKO_1H3_VH) | EVQLLESGGGLVQPGGSLRLSCAASGFTLSRS STSWVRQTPGKGLEWVSAISGSSGGRTYYADS VKGRFTISRDNSKNTLYLQMNSLRAEDTAVY YCAIQLGYWGQGILVTVSS | SEQ ID NO: 8 (BKO_1H3_VL) | QSALTQPASVSGSPGQSITISCTGTSSDVGG YNYVSWYQQHPGKAPKLMIYDVSNRPSGV SNRFSGSKSGNTASLTISGLQAEDEADYYC SSYTSSSTWVFGGGTKLTVL |
| BKO-2D8 | | | |
| SEQ ID NO: 9 (BKO_2D8_VH) | EVQLLESGGGLVQPGGSLRLSCAASGYTFTSS TMSWVRQAPGKGLEWVTAISGRGGRTYYAD SVKGRFTISRDNSKNTLYLQMNSLRAEDTAV YYCAIQLGNWGQGILVTVSS | SEQ ID NO: 10 (BKO_2D8_VL) | QSALTQPPSASGSPGQSVTISCTGTSSDIGG YNYVSWYQQHPGKAPKLVIYEVNMRPSGV PARFSGSKSGNTASLTVSGLQAEDEADYYC SSYAGNDNFGVFGGGTKLSVL |
| BKO-3A9_b | | | |
| SEQ ID NO: 11 (BKO_3A9_VH) | QVQVQQSGPGLVKPSQTLSLTCAISGDSVSSN SAAWNWIRQSPSRGLEWLGRTYYRSKWYND YAVSLKRRITIRPDTSRNHFSLHLSSVTPEDTA VYYCVRAYCGGGSCLDYWGQGTLVTVSS | SEQ ID NO: 12 (BKO_3A9_L3_E03_VL) | QSALTQPASASGSPGQSITISCTGTSSDVGN YNYVSWYQQHPGKVPKLMIYEGSKRPSGIS NRFSGSKSGNTASLTISGLQPEDEADYFCCS YAGSNTLVFGGGTKLTVL |
| BKO-3D6 | | | |
| SEQ ID NO: 13 (BKO_3D6_VH) | EVQLVESGGDLVQPGRSLRLSCAASGFTFDD YAMHWVRQAPGKGLKWVSGITWNSGNKRY ADSVKGRFTISRDNAKNSLYLQMNSLRAEDT ALYYCAKDMKGSGTYFPAFDYWGQGTLVT VSS | SEQ ID NO: 14 (BKO_3D6_L6_G0 6_VL (BKO_5H4_VL)) | SYELTQPPSVSVSPGQTASITCSGDKLGDKY ACWYQQKPGQSPVLVIYQDSKRPSGIPERF SGSNSGNTATLTISGTQAMDEADYYCQAW DSSTVVFGGGTKLTVL |
| BKO-3F4 | | | |
| SEQ ID NO: 15 (BKO_3F4_VH) | EVQLLESGGGLVQPGGSLRLSCAASGLTFSSY AMSWVRQAPGKGLEWVSAISGSGGKIYYAD SVKGRFTISRDNSKNTLYLQMNSLRAEDTAV YYCAIQVGYWGQGTLVTVSS | SEQ ID NO: 16 (BKO_3F4_L11_A 11_VL) | QSALTQPPSASGSPGQSVTMSCTGTSSDVG GYNYVTWYQQHPGKAPKLMIYEVSKRPSG VPARFSGSKSGNTASLTVSGLQAEDEADYY CSSYAGPNNFGVFGGGTKLTVL |

TABLE 19-continued

Sequences

| Sequence Identifier | Sequence | Sequence Identifier | Sequence |
|---|---|---|---|
| BKO-4A8 | | | |
| SEQ ID NO: 17 (BKO_4A8_VH) | EVQLLESGGGLVQPGGSLRLSCAASGFTFSSSTMSWVRQAPGKGLEWVSAISGRGRNTYYADSVKGRFTISRDNSRNTLYLQMNSLRAEDTAVYYCAIQMGYWGQGILVTVSS | SEQ ID NO: 18 (BKO_4A8_VL) | QSALTQPPSASGSPGQSVTISCIGTSSDVGGYNYVSWYQQHPDKAPKLMIYEVNKRPSGVPDRFSGSKSGNTASLTVSGLQAEDEADYYCSSYAGNNNFGVFGGGTKLTVL |
| BKO-4F10 | | | |
| SEQ ID NO: 19 (BKO_4F10_VH) | QVQLVQSGAEVKKPGASVKVSCKASGYTFTGYYIHWVRQAPGQGLEWMGRFNPNNGGTNYAQRFQGRVTMTRDTSISTAYMELSRLSDDTAVYYCARGPTIRLWFDNWFDSWGQGTLVTVSS | SEQ ID NO: 20 (BKO_4F10_VL) | QSALTQPASVSGSPGQSITISCTGTSSDVGGYNYVSWYQQHPGKAPKLMIYDVSNRPSGISNRFSGSKSGNTASLTISGLQAEDEADYYCSSYTSSSTWVFGGGTKLTVL |
| BKO-5E8 | | | |
| SEQ ID NO: 21 (BKO_5E8_H5_C0 5_VH) | EVQLLESGGGLVQPGGSLRLSCAASGFTFSSYAMSWVRQAPGRGLEWVSAIRGSGAGTYYADSMKGRFTISRDTSKDTLYLLMNSLRAEDTAVYYCSKLEAVSGTGKYFQHWGQGTLVTVSS | SEQ ID NO: 22 (BKO_5E8_L3_C0 3_VL) | SYELTQPPSVSVSPGQTANITCSGDTLGDKFACWYQQKPGQSPVLVIYQDTKRPSGIPERFSGSKSGITATLTISGTQAMDEADFYCQAWNSRGVVFGGGTRLTVL |
| BKO-5G11 | | | |
| SEQ ID NO: 23 (BKO_5G11_VH) | EVQLLESGGGLVQPGGSLRLSCAVSGFTFSNYAMTWVRQAPGKGLEWVSAISGRGSRTYYADSVKGRFTISRDTSKNTLYLQMNSLRAEDTAVYYCAKMDYWGQGTLVTVSS | SEQ ID NO: 24 (BKO_5G11_VL) | QSALTQPPSASGSPGQSVTISCTGTSSDVGGYNYVSWYQQHPGKAPKLMIFEVSKRPSGVPDRFSGSKSGNTASLTVSGLQAEDEADYYCSSYAGSNNFGVFGGGTKLTVL |
| BKO-5G6_c | | | |
| SEQ ID NO: 25 (BKO_5G6_VH) | QVQLVQSGAEVTKPGASVKVSCKASGYTFTGYYIHWVRQAPGQGLEWMGRFNPNNGGTNYAQRFQGRVTMTRDTSISTAYMELSRLSDDTAVYYCARGPTIRLWFDNWFDSWGQGTLVTVSS | SEQ ID NO: 26 (BKO_5G6_L12_E 12_VL) | QSALTQPASVSGSPGQSITISCTGTSSDVGGYNYVSWYQQHPGKAPKLMIYDVSNRPSGISNRFSGSKSGNTASLTISGLQAEDEADYYCSSYTSSSTWVFGGGTTLTVL |
| BKO-6A1_b | | | |
| SEQ ID NO: 27 (BKO_6A1_H4_A 04_VH) | QVQLKQWGAGLLKPSETLSLTCAVYGGSFGYYWTWIRQPPGKGLEWIGEINHSGSTNYNPSLKSRVTMSVDTSKNQFSLKLRSVTAADTAVYYCARGEVRGLITLYWYFDVWGRGSLVTVSS | SEQ ID NO: 28 (BKO_6A1_E10_V L) | SSELTQDPAVSVALGQTVRITCQGDSLRSYYASWYQQKPGQAPVLVIYGKNNRPSGIPDRFSGSSSGNTASLTITGAQAEDEADYYCNSRDSSGNHVVFGGGTKLTVL |
| BKO-6A2_a | | | |
| SEQ ID NO: 29 (BKO_6A2_H1_B 01_VH) | QVQLVESGGGVVQPGRSLRLSCAASGFTFSTYDIHWVRQAPGKGLEWVAVIWYDGSNKYYADSVKGRFTISRDNSKNTLYLQMNSLRAEDTAVYYCARDEGYNYGYGGYWGQGTLVTVSS | SEQ ID NO: 30 (BKO_6A2_L6_A0 6_VL) | SYELTQPPSVSVSPGQTASITCSGDKLGDKYACWYQQKPGQSPVLVIYDSKRPSGIPERFSGSNSGNTATLTISGTQAMDEADYYCQAWDSSTVVFGGGTKLTVL |
| BKO-7C11 | | | |
| SEQ ID NO: 31 (BKO_7C11_H6_B 06_VH) | QVQLQQWGAGLLKPSETLSLTCAVYGGSFGYYWSWIRQPPGKGLEWIGEINHSRNTNYNPSLKSRVTISVDTSKNQFSLKLSSVTAADTAVYYCARGEVRGVFTLYWYFDVWGRGTLVTVSS | SEQ ID NO: 32 (BKO_7C11_G01_ VL) | SSELTQGPAVSVALGQTVRITCQGNSLRFYYASWYQQRPGQAPILVIYDKNNRPSGIPDRFSGSSSGNTASLTITGAQAEDEADYYCNSRDSSGYYMIFGGGTKLTVL |
| BKO-7G10_a | | | |
| SEQ ID NO: 33 | EVQLLESGGGLVQPGGSLRLSCAVSGFTFSNYAMTWVRQAPGKGLEWVSAISGRGSRTYYA | SEQ ID NO: 34 | QSALTQPPSASGSPGQSVTISCTGTSSDVGGYNYVSWYQQHPGKAPKLMIFEVSKRPSGV |

TABLE 19-continued

Sequences

| Sequence Identifier | Sequence | Sequence Identifier | Sequence |
|---|---|---|---|
| (BKO_7G10_H1_B01_VH) | DSVKGRFTISRDTSKNTLYLQMNSLRAEDTAVYYCAKMDYWGQGTLVTVSS | (BKO_7G10_L6_E06_VL) | PDRFSGSKSGNTASLTVSGLQAEDEADYYCSSYAGSNNFGVFGGGTKLTVL |

BKO-7H8_b

| SEQ ID NO: 35 (BKO_7H8_H3_C03_VH) | EVQLLESGGGLVQPGGSLRLSCAASGYTFTSSTMSWVRQAPGKGLEWVTAISGRGGRTYYADSVKGRFTISRDNSKNTLYLQMNSLRAEDTAVYYCAIQLGNWGQGILVTVSS | SEQ ID NO: 36 (BKO_7H8_L10_F10_VL) | QSALTQPPSASGSPGQSVTISCTGTSSDIGGYNYVSWYQQHPGKAPKLVIYEVNMRPSGVPARFSGSKSGNTASLTVSGLQAEDEADYYCSSYAGNDNFGVFGGGTKLSVL |

BKO-8B6

| SEQ ID NO: 37 (BKO_8B6_VH) | EVQLLESGGGLVQPGGSLRLSCAASGFTFSSNAMSWVRQAPGKGLEWVSAISNSGRSTYYADSVKGRFTISRDSSKNTLYLLMNSLRAEDSAVYYCAIKLGYWGQGSLVTVSS | SEQ ID NO: 38 (BKO_8B6_VL) | QSALTQPPSASGSPGQSVTISCTGTSSDVGGYNYVSWYQQHPGKAPKLMMYEVSKRPSGVPDRFSGSKSGNTASLTVSGLQAEDEADYYCSSYAGSDNFGVFGGGTRLTVL |

BKO-8C4

| SEQ ID NO: 39 (BKO_8C4_VH) | QLQLQESGPGLVKPSETLSLTCTVSGGSIRTSSYYWGWIRQPPGKGLEYIGSIYYSGTTYYNPSLKSRVTMSVDTSKNQFSLKLSSVTAADTAVYYCARHGRVREVPPFDYWGQGTLVTVSS | SEQ ID NO: 40 (BKO_8C4_VL) | SSELTQDPAVSVALGQTVRITCQGDSLRYYYASWYQQKPGQAPVLVIYDENSRPSGIPDRFSGSSSGNTASLRITGTQAEDEADYYCNSRDTSGNHWAFGGGTKLTVL |

BKO-8G3_b

| SEQ ID NO: 41 (BKO_8G3_H4_D04_VH) | EVQLLESGGGLVQPGGSLRLSCAASGFTFSSYAMSWVRQAPGKGLEWVSAITGSGGTYYADSVKGRFTISRDKSKNTLYLQMNSLRAEDTAVYYCAIRLGYWGQGSLVTVSS | SEQ ID NO: 42 (BKO_8G3_L1_G01_VL) | QSALTQPPSASGSPGQSVTISCTGTSSDVGGYNYVSWYQQHPGKVPKLVIYEVSKRPSGVPDRFSGSKSGNTASLTVSGLQAEDEADYYCSSYAGSNNFGVFGGGTKLTVL |

BKO-8H10

| SEQ ID NO: 43 (BKO_8H10_VH) | QVQLVQSGAEVKKPGASVKVSCKASGYTFTGYYIHWVRQAPGQGLEWMGRIKPDSGGTNYAQKFQGRVTMTRDTSITTAYMELSRLRSDDTAVYYCARGGSGWDYWGQGTLVTVSS | SEQ ID NO: 44 (BKO_8H10_VL) | QSALTQPPSASGSPGQSVTISFTGTSRDVGDYNYVSWYQQHPGKAPKLMIYEVNKRPSGVPDRFSGSKSGNTASLTVSGLQAEDEADYYCSSYAGSNTYVFGTGTKVTVL |

BKO-8H8_b

| SEQ ID NO: 45 (BKO_8H8_H5_E05_VH) | EVQLLESGGGLVQPGGSLRLSCAASGLTVSSYAMSWVRQAPGKGLEWVSAISGSGGKIYYADSVKGRFTISRDNSKNTLYLQMNSLSAEDTAVYYCAIQVGYWGQGTLVTVSS | SEQ ID NO: 46 (BKO_8H8_L7_H08_VL) | QSALTQPPSASGSPGQSVTMSCTGTSSDVGGYNYVTWYQQHPGKAPKLVIYEVSKRPSGVPVRFSGSKSGNTASLTVSGLQAEDEADYYCSSYAGPNNFGIFGGGTKLTVL |

BKO-9A8

| SEQ ID NO: 47 (BKO_9A8_H3_F03_VH) | EVQLLESGGGLVQTGGSLRLSCAASGFTFSSNTMSWVRQAPGKGLEWVSAISGSGGRTYYVDSVKGRFTISRDNSKNTLYLQMHSLRAEDTAVYYCAIQLGSWGQGILVTVSS | SEQ ID NO: 48 (BKO_9A8_L1_H02_VL) | QSALTQPPSASGSPGQSVTISCTGTSSDVGAYNYVSWYQQHPGKAPKLMIYEVTKRPSGVPDRFSGSKSGNTASLTVSGLQAEDEADYYCSSYAGNNNFGVFGGGTKLTVL |

BKO-9C3_a

| SEQ ID NO: 49 (BKO_9C3_H8_G08_VH) | EVQVLESGGGLVQPGGSLRLSCAASGFTFRSYAMSWVRQAPGKGLEWVSAISGSGGSTYYADSVKGRFTISRDKSKNTLYLQMNSLRAEDTAVYYCAIQLGYWGQGTLVTVSS | SEQ ID NO: 50 (BKO_9C3_L1_F01_VL) | QSALTQPPSASGSPGQSVIISCTGTSSDVGGYNYVSWYQQHPGKVPKLMIYEVSKRPSGVPDRFSGSKSGNTASLTVSGLQAEDEADYYCTSYAGSNNFGVFGGGTKLTVL |

TABLE 19-continued

Sequences

| Sequence Identifier | Sequence | Sequence Identifier | Sequence |
|---|---|---|---|
| BKO-10G10 | | | |
| SEQ ID NO: 51 (BKO_10G10_VH) | QLQLQESGPGLVKPSETLSLTCTVSGGSIRRSSYYWGWIRQPPGKGLEWIGSFYNSGNTYYKPSLKSRVAISVDTPKNQFSLKLSSVTAADTAVYYCARGYSSGGFDPWGQGTLVTVSS | SEQ ID NO: 52 (BKO_10G10_VL) | QSALTQPASVSGSPGQSITISCTGTSSDVGGYNYVSWCQQHPGKAPKIMIFDVSNRPSGVSNRFSGSKSGNTASLTISGLQAEDEADYYCSSYTSSSTWVFGGGTRLTVL |
| BKO-4A8 single aa variants | | | |
| SEQ ID NO: 53 (4A8 VH S32Q) | EVQLLESGGGLVQPGGSLRLSCAASGFTFSSQTMSWVRQAPGKGLEWVSAISGRGRNTYYADSVKGRFTISRDNSRNTLYLQMNSLRAEDTAVYYCAIQMGYWGQGILVTVSS | SEQ ID NO: 54 (4A8 VH S32H) | EVQLLESGGGLVQPGGSLRLSCAASGFTFSSHTMSWVRQAPGKGLEWVSAISGRGRNTYYADSVKGRFTISRDNSRNTLYLQMNSLRAEDTAVYYCAIQMGYWGQGILVTVSS |
| SEQ ID NO: 55 (4A8 VH S32L) | EVQLLESGGGLVQPGGSLRLSCAASGFTFSSLTMSWVRQAPGKGLEWVSAISGRGRNTYYADSVKGRFTISRDNSRNTLYLQMNSLRAEDTAVYYCAIQMGYWGQGILVTVSS | SEQ ID NO: 56 (4A8 VH S32W) | EVQLLESGGGLVQPGGSLRLSCAASGFTFSSWTMSWVRQAPGKGLEWVSAISGRGRNTYYADSVKGRFTISRDNSRNTLYLQMNSLRAEDTAVYYCAIQMGYWGQGILVTVSS |
| SEQ ID NO: 57 (4A8 VH S32Y) | EVQLLESGGGLVQPGGSLRLSCAASGFTFSSYTMSWVRQAPGKGLEWVSAISGRGRNTYYADSVKGRFTISRDNSRNTLYLQMNSLRAEDTAVYYCAIQMGYWGQGILVTVSS | SEQ ID NO: 58 (4A8 VH T33A) | EVQLLESGGGLVQPGGSLRLSCAASGFTFSSAMSWVRQAPGKGLEWVSAISGRGRNTYYADSVKGRFTISRDNSRNTLYLQMNSLRAEDTAVYYCAIQMGYWGQGILVTVSS |
| SEQ ID NO: 59 (4A8 VH M34Q) | EVQLLESGGGLVQPGGSLRLSCAASGFTFSSTQSWVRQAPGKGLEWVSAISGRGRNTYYADSVKGRFTISRDNSRNTLYLQMNSLRAEDTAVYYCAIQMGYWGQGILVTVSS | SEQ ID NO: 60 (4A8 VH M34D) | EVQLLESGGGLVQPGGSLRLSCAASGFTFSSTDSWVRQAPGKGLEWVSAISGRGRNTYYADSVKGRFTISRDNSRNTLYLQMNSLRAEDTAVYYCAIQMGYWGQGILVTVSS |
| SEQ ID NO: 61 (4A8 VH M34H) | EVQLLESGGGLVQPGGSLRLSCAASGFTFSSTHSWVRQAPGKGLEWVSAISGRGRNTYYADSVKGRFTISRDNSRNTLYLQMNSLRAEDTAVYYCAIQMGYWGQGILVTVSS | SEQ ID NO: 62 (4A8 VH M34W) | EVQLLESGGGLVQPGGSLRLSCAASGFTFSSTWSWVRQAPGKGLEWVSAISGRGRNTYYADSVKGRFTISRDNSRNTLYLQMNSLRAEDTAVYYCAIQMGYWGQGILVTVSS |
| SEQ ID NO: 63 (4A8 VH I51H) | EVQLLESGGGLVQPGGSLRLSCAASGFTFSSTMSWVRQAPGKGLEWVSAHSGRGRNTYYADSVKGRFTISRDNSRNTLYLQMNSLRAEDTAVYYCAIQMGYWGQGILVTVSS | SEQ ID NO: 64 (4A8 VH G52aD) | EVQLLESGGGLVQPGGSLRLSCAASGFTFSSTMSWVRQAPGKGLEWVSAISDRGRNTYYADSVKGRFTISRDNSRNTLYLQMNSLRAEDTAVYYCAIQMGYWGQGILVTVSS |
| SEQ ID NO: 65 (4A8 VH R53S) | EVQLLESGGGLVQPGGSLRLSCAASGFTFSSTMSWVRQAPGKGLEWVSAISGSGRNTYYADSVKGRFTISRDNSRNTLYLQMNSLRAEDTAVYYCAIQMGYWGQGILVTVSS | SEQ ID NO: 66 (4A8 VH R53Q) | EVQLLESGGGLVQPGGSLRLSCAASGFTFSSTMSWVRQAPGKGLEWVSAISGQGRNTYYADSVKGRFTISRDNSRNTLYLQMNSLRAEDTAVYYCAIQMGYWGQGILVTVSS |
| SEQ ID NO: 67 (4A8 VH G54D) | EVQLLESGGGLVQPGGSLRLSCAASGFTFSSTMSWVRQAPGKGLEWVSAISGRDRNTYYADSVKGRFTISRDNSRNTLYLQMNSLRAEDTAVYYCAIQMGYWGQGILVTVSS | SEQ ID NO: 68 (4A8 VH N56S) | EVQLLESGGGLVQPGGSLRLSCAASGFTFSSTMSWVRQAPGKGLEWVSAISGRGRSTYYADSVKGRFTISRDNSRNTLYLQMNSLRAEDTAVYYCAIQMGYWGQGILVTVSS |
| SEQ ID NO: 69 (4A8 VH I94K) | EVQLLESGGGLVQPGGSLRLSCAASGFTFSSTMSWVRQAPGKGLEWVSAISGRGRNTYYADSVKGRFTISRDNSRNTLYLQMNSLRAEDTAVYYCAKQMGYWGQGILVTVSS | SEQ ID NO: 70 (4A8 VH M96A) | EVQLLESGGGLVQPGGSLRLSCAASGFTFSSTMSWVRQAPGKGLEWVSAISGRGRNTYYADSVKGRFTISRDNSRNTLYLQMNSLRAEDTAVYYCAIQAGYWGQGILVTVSS |
| SEQ ID NO: 71 (4A8 VH M96Q) | EVQLLESGGGLVQPGGSLRLSCAASGFTFSSTMSWVRQAPGKGLEWVSAISGRGRNTYYADSVKGRFTISRDNSRNTLYLQMNSLRAEDTAVYYCAIQQGYWGQGILVTVSS | SEQ ID NO: 72 (4A8 VH M96K) | EVQLLESGGGLVQPGGSLRLSCAASGFTFSSTMSWVRQAPGKGLEWVSAISGRGRNTYYADSVKGRFTISRDNSRNTLYLQMNSLRAEDTAVYYCAIQKGYWGQGILVTVSS |
| SEQ ID NO: 73 (4A8 | EVQLLESGGGLVQPGGSLRLSCAASGFTFSSTMSWVRQAPGKGLEWVSAISGRGRNTYYADSVKGRFTISRDNSRNTLYLQMNSLRAEDTAV | SEQ ID NO: 74 (4A8 | EVQLLESGGGLVQPGGSLRLSCAASGFTFSSTMSWVRQAPGKGLEWVSAISGRGRNTYYADSVKGRFTISRDNSRNTLYLQMNSLRAE |

TABLE 19-continued

Sequences

| Sequence Identifier | Sequence | Sequence Identifier | Sequence |
|---|---|---|---|
| VH G101D) | YYCAIQMDYWGQGILVTVSS | VH Y102S) | DTAVYYCAIQMGSWGQGILVTVSS |
| SEQ ID NO: 75 (4A8 VH Y102K) | EVQLLESGGGLVQPGGSLRLSCAASGFTFSSS TMSWVRQAPGKGLEWVSAISGRGRNTYYAD SVKGRFTISRDNSRNTLYLQMNSLRAEDTAV YYCAIQMGKWGQGILVTVSS | SEQ ID NO: 76 (4A8 VL E50D) | QSALTQPPSASGSPGQSVTISCIGTSSDVGG YNYVSWYQQHPDKAPKLMIYDVNKRPSG VPDRFSGSKSGNTASLTVSGLQAEDEADYY CSSYAGNNNFGVFGGGTKLTVL |
| SEQ ID NO: 77 (4A8 VL N52D) | QSALTQPPSASGSPGQSVTISCIGTSSDVGGY NYVSWYQQHPDKAPKLMIYEVDKRPSGVPD RFSGSKSGNTASLTVSGLQAEDEADYYCSSY AGNNNFGVFGGGTKLTVL | SEQ ID NO: 78 (4A8 VL N52S) | QSALTQPPSASGSPGQSVTISCIGTSSDVGG YNYVSWYQQHPDKAPKLMIYEVSKRPSGV PDRFSGSKSGNTASLTVSGLQAEDEADYYC SSYAGNNNFGVFGGGTKLTVL |
| SEQ ID NO: 79 (4A8 VL K53A) | QSALTQPPSASGSPGQSVTISCIGTSSDVGGY NYVSWYQQHPDKAPKLMIYEVNARPSGVPD RFSGSKSGNTASLTVSGLQAEDEADYYCSSY AGNNNFGVFGGGTKLTVL | SEQ ID NO: 80 (4A8 VL K53D) | QSALTQPPSASGSPGQSVTISCIGTSSDVGG YNYVSWYQQHPDKAPKLMIYEVNDRPSGV PDRFSGSKSGNTASLTVSGLQAEDEADYYC SSYAGNNNFGVFGGGTKLTVL |
| SEQ ID NO: 81 (4A8 VL K53H) | QSALTQPPSASGSPGQSVTISCIGTSSDVGGY NYVSWYQQHPDKAPKLMIYEVNHRPSGVPD RFSGSKSGNTASLTVSGLQAEDEADYYCSSY AGNNNFGVFGGGTKLTVL | SEQ ID NO: 82 (4A8 VL R54Q) | QSALTQPPSASGSPGQSVTISCIGTSSDVGG YNYVSWYQQHPDKAPKLMIYEVNKQPSG VPDRFSGSKSGNTASLTVSGLQAEDEADYY CSSYAGNNNFGVFGGGTKLTVL |
| SEQ ID NO: 83 (4A8 VL Y91A) | QSALTQPPSASGSPGQSVTISCIGTSSDVGGY NYVSWYQQHPDKAPKLMIYEVNKRPSGVPD RFSGSKSGNTASLTVSGLQAEDEADYYCSSA AGNNNFGVFGGGTKLTVL | SEQ ID NO: 84 (4A8 VL N94A) | QSALTQPPSASGSPGQSVTISCIGTSSDVGG YNYVSWYQQHPDKAPKLMIYEVNKRPSGV PDRFSGSKSGNTASLTVSGLQAEDEADYYC SSYAGANNFGVFGGGTKLTVL |
| SEQ ID NO: 85 (4A8 VL N94S) | QSALTQPPSASGSPGQSVTISCIGTSSDVGGY NYVSWYQQHPDKAPKLMIYEVNKRPSGVPD RFSGSKSGNTASLTVSGLQAEDEADYYCSSY AGSNNFGVFGGGTKLTVL | SEQ ID NO: 86 (4A8 VL N94K) | QSALTQPPSASGSPGQSVTISCIGTSSDVGG YNYVSWYQQHPDKAPKLMIYEVNKRPSGV PDRFSGSKSGNTASLTVSGLQAEDEADYYC SSYAGKNNFGVFGGGTKLTVL |
| SEQ ID NO: 87 (4A8 VL N94L) | QSALTQPPSASGSPGQSVTISCIGTSSDVGGY NYVSWYQQHPDKAPKLMIYEVNKRPSGVPD RFSGSKSGNTASLTVSGLQAEDEADYYCSSY AGLNNFGVFGGGTKLTVL | SEQ ID NO: 88 (4A8 VL N94W) | QSALTQPPSASGSPGQSVTISCIGTSSDVGG YNYVSWYQQHPDKAPKLMIYEVNKRPSGV PDRFSGSKSGNTASLTVSGLQAEDEADYYC SSYAGWNNFGVFGGGTKLTVL |
| SEQ ID NO: 89 (4A8 VL N94Y) | QSALTQPPSASGSPGQSVTISCIGTSSDVGGY NYVSWYQQHPDKAPKLMIYEVNKRPSGVPD RFSGSKSGNTASLTVSGLQAEDEADYYCSSY AGYNNFGVFGGGTKLTVL | SEQ ID NO: 90 (4A8 VL N95aQ) | QSALTQPPSASGSPGQSVTISCIGTSSDVGG YNYVSWYQQHPDKAPKLMIYEVNKRPSGV PDRFSGSKSGNTASLTVSGLQAEDEADYYC SSYAGNNQFGVFGGGTKLTVL |
| SEQ ID NO: 91 (4A8 VL N95aD) | QSALTQPPSASGSPGQSVTISCIGTSSDVGGY NYVSWYQQHPDKAPKLMIYEVNKRPSGVPD RFSGSKSGNTASLTVSGLQAEDEADYYCSSY AGNNDFGVFGGGTKLTVL | SEQ ID NO: 92 (4A8 VL N95aH) | QSALTQPPSASGSPGQSVTISCIGTSSDVGG YNYVSWYQQHPDKAPKLMIYEVNKRPSGV PDRFSGSKSGNTASLTVSGLQAEDEADYYC SSYAGNNHFGVFGGGTKLTVL |
| SEQ ID NO: 93 (4A8 VL N95aK) | QSALTQPPSASGSPGQSVTISCIGTSSDVGGY NYVSWYQQHPDKAPKLMIYEVNKRPSGVPD RFSGSKSGNTASLTVSGLQAEDEADYYCSSY AGNNKFGVFGGGTKLTVL | SEQ ID NO: 94 (4A8 VL N95aL) | QSALTQPPSASGSPGQSVTISCIGTSSDVGG YNYVSWYQQHPDKAPKLMIYEVNKRPSGV PDRFSGSKSGNTASLTVSGLQAEDEADYYC SSYAGNNLFGVFGGGTKLTVL |
| SEQ ID NO: 95 (4A8 VL N95aY) | QSALTQPPSASGSPGQSVTISCIGTSSDVGGY NYVSWYQQHPDKAPKLMIYEVNKRPSGVPD RFSGSKSGNTASLTVSGLQAEDEADYYCSSY AGNNYFGVFGGGTKLTVL | SEQ ID NO: 96 (4A8 VL V97A) | QSALTQPPSASGSPGQSVTISCIGTSSDVGG YNYVSWYQQHPDKAPKLMIYEVNKRPSGV PDRFSGSKSGNTASLTVSGLQAEDEADYYC SSYAGNNNFGAFGGGTKLTVL |
| SEQ ID NO: 97 (4A8 VL V97K) | QSALTQPPSASGSPGQSVTISCIGTSSDVGGY NYVSWYQQHPDKAPKLMIYEVNKRPSGVPD RFSGSKSGNTASLTVSGLQAEDEADYYCSSY AGNNNFGKFGGGTKLTVL | | |

TABLE 19-continued

Sequences

BKO-4A8 combinatorial variants

| Sequence Identifier | Sequence | Sequence Identifier | Sequence |
|---|---|---|---|
| SEQ ID NO: 98 (4A8 VH Variant 1 (M34Q_N56S)) | EVQLLESGGGLVQPGGSLRLSCAASGFTFSSS TQSWVRQAPGKGLEWVSAISGRGRSTYYAD SVKGRFTISRDNSRNTLYLQMNSLRAEDTAV YYCAIQMGYWGQGILVTVSS | SEQ ID NO: 99 (4A8 VH Variant 2 (M34Q_A40P_N56S)) | EVQLLESGGGLVQPGGSLRLSCAASGFTFS SSTQSWVRQPPGKGLEWVSAISGRGRSTYY ADSVKGRFTISRDNSRNTLYLQMNSLRAED TAVYYCAIQMGYWGQGILVTVSS |
| SEQ ID NO: 100 (4A8 VH Variant 3 (M34Q_A40P_N56S_R75K)) | EVQLLESGGGLVQPGGSLRLSCAASGFTFSSS TQSWVRQPPGKGLEWVSAISGRGRSTYYADS VKGRFTISRDNSKNTLYLQMNSLRAEDTAVY YCAIQMGYWGQGILVTVSS | SEQ ID NO: 101 (4A8 VH Variant 4 (M34Q_A40P_N56S_M96K)) | EVQLLESGGGLVQPGGSLRLSCAASGFTFS SSTQSWVRQPPGKGLEWVSAISGRGRSTYY ADSVKGRFTISRDNSRNTLYLQMNSLRAED TAVYYCAIQKGYWGQGILVTVSS |
| SEQ ID NO: 102 (4A8 VH Variant 5 (M34Q_A40P_N56S_R75K_M96K)) | EVQLLESGGGLVQPGGSLRLSCAASGFTFSSS TQSWVRQPPGKGLEWVSAISGRGRSTYYADS VKGRFTISRDNSKNTLYLQMNSLRAEDTAVY YCAIQKGYWGQGILVTVSS | SEQ ID NO: 103 (4A8 VH Variant 6 (M34Q_A40P_N56S_R75K_I94K_M96K)) | EVQLLESGGGLVQPGGSLRLSCAASGFTFS SSTQSWVRQPPGKGLEWVSAISGRGRSTYY ADSVKGRFTISRDNSKNTLYLQMNSLRAED TAVYYCAKQKGYWGQGILVTVSS |
| SEQ ID NO: 104 (4A8 VH Variant 7 (M34Q_A40P_N56S_I94K_M96K)) | EVQLLESGGGLVQPGGSLRLSCAASGFTFSSS TQSWVRQPPGKGLEWVSAISGRGRSTYYADS VKGRFTISRDNSRNTLYLQMNSLRAEDTAVY YCAKQKGYWGQGILVTVSS | SEQ ID NO: 105 (4A8 VH Variant 8 (M34Q_N56S_M96K)) | EVQLLESGGGLVQPGGSLRLSCAASGFTFS SSTQSWVRQAPGKGLEWVSAISGRGRSTY YADSVKGRFTISRDNSRNTLYLQMNSLRAE DTAVYYCAIQKGYWGQGILVTVSS |
| SEQ ID NO: 106 (4A8 VH Variant 9 (M34Q_N56S_R75K_M96K)) | EVQLLESGGGLVQPGGSLRLSCAASGFTFSSS TQSWVRQAPGKGLEWVSAISGRGRSTYYAD SVKGRFTISRDNSKNTLYLQMNSLRAEDTAV YYCAIQKGYWGQGILVTVSS | SEQ ID NO: 107 (4A8 VH Variant 10 I94K_M96K) | EVQLLESGGGLVQPGGSLRLSCAASGFTFS SSTMSWVRQAPGKGLEWVSAISGRGRNTY YADSVKGRFTISRDNSRNTLYLQMNSLRAE DTAVYYCAKQKGYWGQGILVTVSS |
| SEQ ID NO: 108 (4A8 VH Variant 101 M34Q_A40P_N56S_R75K_M96A) | EVQLLESGGGLVQPGGSLRLSCAASGFTFSSS TQSWVRQPPGKGLEWVSAISGRGRSTYYADS VKGRFTISRDNSKNTLYLQMNSLRAEDTAVY YCAIQAGYWGQGILVTVSS | SEQ ID NO: 109 (4A8 VL variant b N52S_N94S) | QSALTQPPSASGSPGQSVTISCIGTSSDVGG YNYVSWYQQHPDKAPKLMIYEVSKRPSGV PDRFSGSKSGNTASLTVSGLQAEDEADYYC SSYAGSNNFGVFGGGTKLTVL |
| SEQ ID NO: 110 (4A8 VL variant c D41G_N52S_N94S) | QSALTQPPSASGSPGQSVTISCIGTSSDVGGY NYVSWYQQHPGKAPKLMIYEVSKRPSGVPD RFSGSKSGNTASLTVSGLQAEDEADYYCSSY AGSNNFGVFGGGTKLTVL | SEQ ID NO: 111 (4A8 VH M34Q_A40P_N56S_R75K_M96A) | GAAGTTCAGCTGCTTGAATCTGGCGGAG GACTGGTTCAGCCTGGCGGATCTCTGAGA CTGTCTTGTGCCGCCAGCGGCTTCACCTT TAGCAGCAGCACACAGAGCTGGGTCCGA CAGCCTCCTGGCAAAGGACTGGAATGGG TGTCCGCCATCTCTGGCAGAGGCAGAAG CACCTACTACGCCGACTCTGTGAAGGGCA GATTCACCATCAGCCGGGACAACAGCAA |

TABLE 19-continued

Sequences

| Sequence Identifier | Sequence | Sequence Identifier | Sequence |
|---|---|---|---|
| | | | GAACACCCTGTACCTGCAGATGAACAGC CTGAGAGCCGAGGACACCGCCGTGTACT ATTGTGCCATCCAGGCCGGCTATTGGGGC CAGGGAATACTCGTGACAGTGTCCTCA |
| SEQ ID NO: 112 (4A8 VL D41G_ N52S_ N94S) | CAGTCTGCTCTGACACAGCCTCCTAGCGCC TCTGGCTCTCCTGGCCAGAGCGTGACCATC AGCTGTATCGGCACCAGCAGCGACGTGGG CGGCTACAACTACGTGTCCTGGTATCAGCA GCACCCCGgTAAGGCCCCCAAGCTGATGAT CTACGAAGTGTCCAAGCGGCCCAGCGGCGT GCCCGATAGATTCAGCGGCAGCAAGAGCG GCAACACCGCCAGCCTCACAGTGTCTGGAC TGCAGGCCGAGGACGAGGCCGACTACTAC TGTAGCAGCTACGCCGGCAgCAACAACTTC GGCGTGTTCGGCGGAGGCACCAAGCTGAC AGTCCTA | | |

BKO-4A8-mIgG1

| SEQ ID NO: 113 (BKO-4A8-mIgG1 VH) | EVQLLESGGGLVQPGGSLRLSCAASGFTFSSS TMSWVRQAPGKGLEWVSAISGRGRNTYYAD SVKGRFTISRDNSRNTLYLQMNSLRAEDTAV YYCAIQMGYWGQGILVTVSSAKTTPPSVYPL APGSAAQTNSMVTLGCLVKGYFPEPVTVTW NSGSLSSGVHTFPAVLQSDLYTLSSSVTVPSS PRPSETVTCNVAHPASSTKVDKKIVPRDCGC KPCICTVPEVSSVFIFPPKPKDVLTITLTPKVTC VVVAISKDDPEVQFSWFVDDVEVHTAQTQP REEQFNSTFRSVSELPIMHQDWLNGKEFKCR VNSAAFPAPIEKTISKTKGRPKAPQVYTIPPPK EQMAKDKVSLTCMITDFFPEDITVEWQWNG QPAENYKNTQPIMNTNGSYFVYSKLNVQKS NWEAGNTFTCSVLHEGLHNHHTEKSLSHSPG | SEQ ID NO: 114 (BKO-4A8-mIgG1 VL) | QSALTQPPSASGSPGQSVTISCIGTSSDVGG YNYVSWYQQHPDKAPKLMIYEVNKRPSGV PDRFSGSKSGNTASLTVSGLQAEDEADYYC SSYAGNNNFGVFGGGTKLTVLGQPKSSPSV TLFPPSSEELETNKATLVCTITDFYPGVVTV DWKVDGTPVTQGMETTQPSKQSNNKYMA SSYLTLTARAWERHSSYSCQVTHEGHTVE KSLSRADCS |

BKO-4A8 heavy chain variant

| SEQ ID NO: 115 (BKO-4A8 IgG4*) | EVQLLESGGGLVQPGGSLRLSCAASGFTFSSS TMSWVRQAPGKGLEWVSAISGRGRNTYYAD SVKGRFTISRDNSRNTLYLQMNSLRAEDTAV YYCAIQMGYWGQGILVTVSSASTKGPSVFPL APCSRSTSESTAALGCLVKDYFPEPVTVSWN SGALTSGVHTFPAVLQSSGLYSLSSVVTVPSS SLGTKTYTCNVDHKPSNTKVDKRVESKYGPP CPPCPAPEFLGGPSVFLFPPKPKDTLYITREPE VTCVVVDVSQEDPEVQFNWYVDGVEVHNA KTKPREEQFNSTYRVVSVLTVLHQDWLNGK EYKCKVSNKGLPSSIEKTISKAKGQPREPQVY TLPPSQEEMTKNQVSLTCLVKGFYPSDIAVE WESNGQPENNYKTTPPVLDSDGSFFLYSRLT VDKSRWQEGNVFSCSVMHEALHNHYTQKSL SLSLG | SEQ ID NO: 116 (IgG4*) | ASTKGPSVFPLAPCSRSTSESTAALGCLVKD YFPEPVTVSWNSGALTSGVHTFPAVLQSSG LYSLSSVVTVPSSSLGTKTYTCNVDHKPSN TKVDKRVESKYGPPCPPCPAPEFLGGPSVFL FPPKPKDTLYITREPEVTCVVVDVSQEDPEV QFNWYVDGVEVHNAKTKPREEQFNSTYRV VSVLTVLHQDWLNGKEYKCKVSNKGLPSS IEKTISKAKGQPREPQVYTLPPSQEEMTKNQ VSLTCLVKGFYPSDIAVEWESNGQPENNYK TTPPVLDSDGSFFLYSRLTVDKSRWQEGNV FSCSVMHEALHNHYTQKSLSLSLG |
| SEQ ID NO: 117 (BKO-4A8 IgG4) | EVQLLESGGGLVQPGGSLRLSCAASGFTFSSS TMSWVRQAPGKGLEWVSAISGRGRNTYYAD SVKGRFTISRDNSRNTLYLQMNSLRAEDTAV YYCAIQMGYWGQGILVTVSSASTKGPSVFPL APCSRSTSESTAALGCLVKDYFPEPVTVSWN SGALTSGVHTFPAVLQSSGLYSLSSVVTVPSS SLGTKTYTCNVDHKPSNTKVDKRVESKYGPP CPPCPAPEFLGGPSVFLFPPKPKDTLMISRTPE VTCVVVDVSQEDPEVQFNWYVDGVEVHNA KTKPREEQFNSTYRVVSVLTVLHQDWLNGK EYKCKVSNKGLPSSIEKTISKAKGQPREPQVY TLPPSQEEMTKNQVSLTCLVKGFYPSDIAVE WESNGQPENNYKTTPPVLDSDGSFFLYSRLT VDKSRWQEGNVFSCSVMHEALHNHYTQKSL SLSLG | SEQ ID NO: 118 (IgG4) | ASTKGPSVFPLAPCSRSTSESTAALGCLVKD YFPEPVTVSWNSGALTSGVHTFPAVLQSSG LYSLSSVVTVPSSSLGTKTYTCNVDHKPSN TKVDKRVESKYGPPCPPCPAPEFLGGPSVFL FPPKPKDTLMISRTPEVTCVVVDVSQEDPE VQFNWYVDGVEVHNAKTKPREEQFNSTYR VVSVLTVLHQDWLNGKEYKCKVSNKGLPS SIEKTISKAKGQPREPQVYTLPPSQEEMTKN QVSLTCLVKGFYPSDIAVEWESNGQPENNY KTTPPVLDSDGSFFLYSRLTVDKSRWQEGN VFSCSVMHEALHNHYTQKSLSLSLG |
| SEQ ID NO: 119 (BKO-4A8 IgG2*) | EVQLLESGGGLVQPGGSLRLSCAASGFTFSSS TMSWVRQAPGKGLEWVSAISGRGRNTYYAD SVKGRFTISRDNSRNTLYLQMNSLRAEDTAV YYCAIQMGYWGQGILVTVSSASTKGPSVFPL APCSRSTSESTAALGCLVKDYFPEPVTVSWN | SEQ ID NO: 120 (IgG2*) | ASTKGPSVFPLAPCSRSTSESTAALGCLVKD YFPEPVTVSWNSGALTSGVHTFPAVLQSSG LYSLSSVVTVPSSNFGTQTYTCNVDHKPSN TKVDKTVERKCCVECPPCPAPPVAGPSVFL FPPKPKDTLMISRTPEVTCVVVDVSHEDPE |

TABLE 19-continued

Sequences

| Sequence Identifier | Sequence | Sequence Identifier | Sequence |
|---|---|---|---|
| | SGALTSGVHTFPAVLQSSGLYSLSSVVTVPSS NFGTQTYTCNVDHKPSNTKVDKTVERKCCV ECPPCPAPPVAGPSVFLFPPKPKDTLMISRTPE VTCVVVDVSHEDPEVQFNWYVDGVEVHNA KTKPREEQFNSTFRVVSLTVVHQDWLNGK EYKCKVSNKGLPSSIEKTISKTKGQPREPQVY TLPPSREEMTKNQVSLTCLVKGFYPSDIAVE WESNGQPENNYKTTPPMLDSDGSFFLYSKLT VDKSRWQQGNVFSCSVMHEALHNHYTQKSL SLSPG | | VQFNWYVDGVEVHNAKTKPREEQFNSTFR VVSVLTVVHQDWLNGKEYKCKVSNKGLP SSIEKTISKTKGQPREPQVYTLPPSREEMTK NQVSLTCLVKGFYPSDIAVEWESNGQPENN YKTTPPMLDSDGSFFLYSKLTVDKSRWQQ GNVFSCSVMHEALHNHYTQKSLSLSPG |
| SEQ ID NO: 121 (BKO-4A8 IgG1*) | EVQLLESGGGLVQPGGSLRLSCAASGFTFSSS TMSWVRQAPGKGLEWVSAISGRGRNTYYAD SVKGRFTISRDNSRNTLYLQMNSLRAEDTAV YYCAIQMGYWGQGILVTVSSASTKGPSVFPL APSSKSTSGGTAALGCLVKDYFPEPVTVSWN SGALTSGVHTFPAVLQSSGLYSLSSVVTVPSS SLGTQTYICNVNHKPSNTKVDKKVEPKSCDK THTCPPCPAPELAGAPSVFLFPPKPKDTLMISR TPEVTCVVVDVSHEDPEVKFNWYVDGVEVH NAKTKPREEQYNSTYRVVSVLTVLHQDWLN GKEYKCKVSNKALPAPIEKTISKAKGQPREPQ VYTLPPSRDELTKNQVSLTCLVKGFYPSDIAV EWESNGQPENNYKTTPPVLDSDGSFFLYSKL TVDKSRWQQGNVFSCSVMHEALHNHYTQKS LSLSPG | SEQ ID NO: 122 (IgG1*) | ASTKGPSVFPLAPSSKSTSGGTAALGCLVK DYFPEPVTVSWNSGALTSGVHTFPAVLQSS GLYSLSSVVTVPSSSLGTQTYICNVNHKPSN TKVDKKVEPKSCDKTHTCPPCPAPELAGAP SVFLFPPKPKDTLMISRTPEVTCVVVDVSHE DPEVKFNWYVDGVEVHNAKTKPREEQYN STYRVVSVLTVLHQDWLNGKEYKCKVSN KALPAPIEKTISKAKGQPREPQVYTLPPSRD ELTKNQVSLTCLVKGFYPSDIAVEWESNGQ PENNYKTTPPVLDSDGSFFLYSKLTVDKSR WQQGNVFSCSVMHEALHNHYTQKSLSLSP G |
| SEQ ID NO: 123 (BKO-4A8 IgG1) | EVQLLESGGGLVQPGGSLRLSCAASGFTFSSS TMSWVRQAPGKGLEWVSAISGRGRNTYYAD SVKGRFTISRDNSRNTLYLQMNSLRAEDTAV YYCAIQMGYWGQGILVTVSSASTKGPSVFPL APSSKSTSGGTAALGCLVKDYFPEPVTVSWN SGALTSGVHTFPAVLQSSGLYSLSSVVTVPSS SLGTQTYICNVNHKPSNTKVDKKVEPKSCDK THTCPPCPAPELLGGPSVFLFPPKPKDTLMISR TPEVTCVVVDVSHEDPEVKFNWYVDGVEVH NAKTKPREEQYNSTYRVVSVLTVLHQDWLN GKEYKCKVSNKALPAPIEKTISKAKGQPREPQ VYTLPPSRDELTKNQVSLTCLVKGFYPSDIAV EWESNGQPENNYKTTPPVLDSDGSFFLYSKL TVDKSRWQQGNVFSCSVMHEALHNHYTQKS LSLSPG | SEQ ID NO: 124 (IgG1) | ASTKGPSVFPLAPSSKSTSGGTAALGCLVK DYFPEPVTVSWNSGALTSGVHTFPAVLQSS GLYSLSSVVTVPSSSLGTQTYICNVNHKPSN TKVDKKVEPKSCDKTHTCPPCPAPELLGGP SVFLFPPKPKDTLMISRTPEVTCVVVDVSHE DPEVKFNWYVDGVEVHNAKTKPREEQYN STYRVVSVLTVLHQDWLNGKEYKCKVSN KALPAPIEKTISKAKGQPREPQVYTLPPSRD ELTKNQVSLTCLVKGFYPSDIAVEWESNGQ PENNYKTTPPVLDSDGSFFLYSKLTVDKSR WQQGNVFSCSVMHEALHNHYTQKSLSLSP G |
| CXCR Sequences | | | |
| SEQ ID NO: 125 (Human CXCR2) | MEDFNMESDSFEDFWKGEDLSNYSYSSTLPP FLLDAAPCEPESLEINKYFVVIIYALVFLLSLL GNSLVMLVILYSRVGRSVTDVYLLNLALADL LFALTLPIWAASKVNGWIFGTFLCKVVSLLK EVNFYSGILLLACISVDRYLAIVHATRTLTQK RYLVKFICLSIWGLSLLLALPVLLFRRTVYSS NVSPACYEDMGNNTANWRMLLRILPQSFGFI VPLLIMLFCYGFTLRTLFKAHMGQKHRAMR VIFAVVLIFLLCWLPYNLVLLADTLMRTQVIQ ETCERRNHIDRALDATEILGILHSCLNPLIYAF IGQKFRHGLLKILAIHGLISKDSLPKDSRPSFV GSSSGHTSTTL | SEQ ID NO: 126 (Mouse CXCR2) | MGEFKVDKFNIEDFFSGDLDIFNYSSGMPSI LPDAVPCHSENLEINSYAVVVIYVLVTLLSL VGNSLVMLVILYNRSTCSVTDVYLLNLAIA DLFFALTLPVWAASKVNGWTFGSTLCKIFS YVKEVTFYSSVLLLACISMDRYLAIVHATS TLIQKRHLVKFVCIAMWLLSVILALPILILR NPVKVNLSTLVCYEDVGNNTSRLRVVLRIL PQTFGFLVPLLIMLFCYGFTLRTLFKAHMG QKHRAMRVIFAVVLVFLLCWLPYNLVLFT DTLMRTKLIKETCERRDDIDKALNATEILGF LHSCLNPIIYAFIGQKFRHGLLKIMATYGLV SKEFLAKEGRPSFVSSSSANTSTTL |
| SEQ ID NO: 127 (cynomolgus CXCR2) | MQSFNFEDFWENEDFSNYSYSSDLPPSLPDV APCRPESLEINKYFVVIIYALVFLLSLLGNSLV MLVILHSRVGRSITDVYLLNLAMADLLFALT LPIWAAAKVNGWIFGTFLCKVVSLLKEVNFY SGILLLACISVDRYLAIVHATRTLTQKRYLVK FVCLSIWSLSLLLALPVLLFRRTVYLTYISPVC YEDMGNNTAKWRMVLRILPQTFGFILPLLIM LFCYGFTLRTLFKAHMGQKHRAMRVIFAVV LIFLLCWLPYHLVLLADTLMRTRLINETCQRR NNIDQALDATEILGILHSCLNPLIYAFIGQKFR HGLLKILATHGLISKDSLPKDSRPSFVGSSSGH TSTTL | SEQ ID NO: 128 (human CXCR3) | MVLEVSDHQVLNDAEVAALLENFSSSYDY GENESDSCCTSPPCPQDFSLNFDRAFLPALY SLLFLLGLLGNGVAAVLLSRRTALSSTDT FLLHLAVADTLLVLTLPLWAVDAAVQWVF GSGLCKVAGALFNINFYAGALLLACISFDR YLNIVHATQLYRRGPPARVTLTCLAVWGL CLLFALPDFIFLSAHHDERLNATHCQYNFP QVGRTALRVLQLVAGFLLPLLVMAYCYAH ILAVLLVSRGQRRLRAMRLVVVVVAFAL CWTPYHLVVLVDILMDLGALARNCGRESR VDVAKSVTSGLGYMHCCLNPLLYAFVGVK FRERMWMLLLRLGCPNQRGLQRQPSSSRR DSSWSETSEASYSGL |
| SEQ ID NO: 129 | MEGISIYTSDNYTEEMGSGDYDSMKEPCFRE ENANFNKIFLPTIYSIIFLTGIVGNGLVILVMG | SEQ ID NO: 130 | MNYPLTLEMDLENLEDLFWELDRLDNYND TSLVENHLCPATEGPLMASFKAVFVPVAYS |

TABLE 19-continued

Sequences

| Sequence Identifier | Sequence | Sequence Identifier | Sequence |
|---|---|---|---|
| (human CXCR4) | YQKKLRSMTDKYRLHLSVADLLFVITLPFWA VDAVANWYFGNFLCKAVHVIYTVNLYSSVLI LAFISLDRYLAIVHATNSQRPRKLLAEKVVY VGVWIPALLLTIPDFIFANVSEADDRYICDRF YPNDLWVVVFQFQHIMVGLILPGIVILSCYCII ISKLSHSKGHQKRKALKTTVILILAFFACWLP YYIGISIDSFILLEIIKQGCEFENTVHKWISITEA LAFFHCCLNPILYAFLGAKFKTSAQHALTSVS RGSSLKILSKGKRGGHSSVSTESESSSFHSS | (human CXCR5) | LIFLLGVIGNVLVLVILERHRQTRSSTETFLF HLAVADLLLVFILPFAVAEGSVGWVLGTFL CKTVIALHKVNFYCSSLLLACIAVDRYLAIV HAVHAYRHRRLLSIHITCGTIWLVGFLLALP EILFAKVSQGHHNNSLPRCTFSQENQAETH AWFTSRFLYHVAGFLLPMLVMGWCYVGV VHRLRQAQRRPQRQKAVRVAILVTSIFFLC WSPYHIVIFLDTLARLKAVDNTCKLNGSLP VAITMCEFLGLAHCCLNPMLYTFAGVKFRS DLSRLLTKLGCTGPASLCQLFPSWRRSSLSE SENATSLTTF |
| SEQ ID NO: 131 (human CXCR6) | MAEHDYHEDYGFSSFNDSSQEEHQDFLQFSK VFLPCMYLVVFVCGLVGNSLVLVISIFYHKL QSLTDVFLVNLPLADLVFVCTLPFWAYAGIH EWVFGQVMCKSLLGIYTINFYTSMLILTCITV DRFIVVVKATKAYNQQAKRMTWGKVTSLLI WVISLLVSLPQIIYGNVFNLDKLICGYHDEAIS TVVLATQMTLGFFLPLLTMIVCYSVIIKTLLH AGGFQKHRSLKIIFLVMAVFLLTQMPFNLMK FIRSTHWEYYAMTSFHYTIMVTEAIAYLRAC LNPVLYAFVSLKFRKNFWKLVKDIGCLPYLG VSHQWKSSEDNSKTFSASHNVEATSMFQL | SEQ ID NO: 132 (human CXCR7) | MDLHLFDYSEPGNFSDISWPCNSSDCIVVD TVMCPNMPNKSVLLYTLSFIYIFIFVIGMIA NSVVVWVNIQAKTTGYDTHCYILNLAIADL WVVLTIPVWVVSLVQHNQWPMGELTCKV THLIFSINLFGSIFFLTCMSVDRYLSITYFTNT PSSRKKMVRRVVCILVWLLAFCVSLPDTYY LKTVTSASNNETYCRSFYPEHSIKEWLIGM ELVSVVLGFAVPFSIIAVFYFLLARAISASSD QEKHSSRKIIFSYVVVFLVCWLPYHVAVLL DIFSILHYIPFTCRLEHALFTALHVTQCLSLV HCCVNPVLYSFINRNYRYELMKAFIFKYSA KTGLTKLIDASRVSETEYSALEQSTK |
| SEQ ID NO: 133 (Human CXCR1) | MSNITDPQMWDFDDLNFTGMPPADEDYSPC MLETETLNKYVVIIAYALVFLLSLLGNSLVM LVILYSRVGRSVTDVYLLNLALADLLFALTLP IWAASKVNGWIFGTFLCKVVSLLKEVNFYSG ILLLACISVDRYLAIVHATRTLTQKRHLVKFV CLGCWGLSMNLSLPFFLFRQAYHPNNSSPVC YEVLGNDTAKWRMVLRILPHTFGFIVPLFVM LFCYGFTLRTLFKAHMGQKHRAMRVIFAVV LIFLLCWLPYNLVLLADTLMRTQVIQESCERR NNIGRALDATEILGFLHSCLNPIIYAFIGQNFR HGFLKILAMHGLVSKEFLARHRVTSYTSSSV NVSSNL | | |

Light chain constant regions

| Sequence Identifier | Sequence | Sequence Identifier | Sequence |
|---|---|---|---|
| SEQ ID NO: 134 (Human Lambda light chain constant region) | GQPKAAPSVTLFPPSSEELQANKATLVCLISD FYPGAVTVAWKADSSPVKAGVETTTPSKQS NNKYAASSYLSLTPEQWKSHRSYSCQVTHEG STVEKTVAPTECS | SEQ ID NO: 135 (Human Kappa light chain constant region) | RTVAAPSVFIFPPSDEQLKSGTASVVCLLNN FYPREAKVQWKVDNALQSGNSQESVTEQD SKDSTYSLSSTLTLSKADYEKHKVYACEVT HQGLSSPVTKSFNRGEC |

Additional BK0-4A8 single aa variants

| Sequence Identifier | Sequence | Sequence Identifier | Sequence |
|---|---|---|---|
| SEQ ID NO: 136 (4A8 VH S32D) | EVQLLESGGGLVQPGGSLRLSCAASGFTFSSD TMSWVRQAPGKGLEWVSAISGRGRNTYYAD SVKGRFTISRDNSRNTLYLQMNSLRAEDTAV YYCAIQMGYWGQGILVTVSS | SEQ ID NO: 137 (4A8 VH S35Q) | EVQLLESGGGLVQPGGSLRLSCAASGFTFS SSTMQWVRQAPGKGLEWVSAISGRGRNTY YADSVKGRFTISRDNSRNTLYLQMNSLRAE DTAVYYCAIQMGYWGQGILVTVSS |
| SEQ ID NO: 138 (4A8 VH S35D) | EVQLLESGGGLVQPGGSLRLSCAASGFTFSSS TMDWVRQAPGKGLEWVSAISGRGRNTYYA DSVKGRFTISRDNSRNTLYLQMNSLRAEDTA VYYCAIQMGYWGQGILVTVSS | SEQ ID NO: 139 (4A8 VH S35K) | EVQLLESGGGLVQPGGSLRLSCAASGFTFS SSTMKWVRQAPGKGLEWVSAISGRGRNTY YADSVKGRFTISRDNSRNTLYLQMNSLRAE DTAVYYCAIQMGYWGQGILVTVSS |
| SEQ ID NO: 140 (4A8 VH A50S) | EVQLLESGGGLVQPGGSLRLSCAASGFTFSSS TMSWVRQAPGKGLEWVSSISGRGRNTYYAD SVKGRFTISRDNSRNTLYLQMNSLRAEDTAV YYCAIQMGYWGQGILVTVSS | SEQ ID NO: 141 (4A8 VH R55Q) | EVQLLESGGGLVQPGGSLRLSCAASGFTFS SSTMSWVRQAPGKGLEWVSAISGRGQNTY YADSVKGRFTISRDNSRNTLYLQMNSLRAE DTAVYYCAIQMGYWGQGILVTVSS |
| SEQ ID NO: 142 (4A8 VH R55D) | EVQLLESGGGLVQPGGSLRLSCAASGFTFSSS TMSWVRQAPGKGLEWVSAISGRGDNTYYAD SVKGRFTISRDNSRNTLYLQMNSLRAEDTAV YYCAIQMGYWGQGILVTVSS | SEQ ID NO: 143 (4A8 VH R55H) | EVQLLESGGGLVQPGGSLRLSCAASGFTFS SSTMSWVRQAPGKGLEWVSAISGRGHNTY YADSVKGRFTISRDNSRNTLYLQMNSLRAE DTAVYYCAIQMGYWGQGILVTVSS |
| SEQ ID NO: 144 | EVQLLESGGGLVQPGGSLRLSCAASGFTFSSS TMSWVRQAPGKGLEWVSAISGRGRNTYYAD | SEQ ID NO: 145 | EVQLLESGGGLVQPGGSLRLSCAASGFTFS SSTMSWVRQAPGKGLEWVSAISGRGRNTY |

TABLE 19-continued

Sequences

| Sequence Identifier | Sequence | Sequence Identifier | Sequence |
|---|---|---|---|
| (4A8 VH M96S) | SVKGRFTISRDNSRNTLYLQMNSLRAEDTAV YYCAIQSGYWGQGILVTVSS | (4A8 VH M96D) | YADSVKGRFTISRDNSRNTLYLQMNSLRAE DTAVYYCAIQDGYWGQGILVTVSS |
| SEQ ID NO: 146 (4A8 VH M96H) | EVQLLESGGGLVQPGGSLRLSCAASGFTFSSS TMSWVRQAPGKGLEWVSAISGRGRNTYYAD SVKGRFTISRDNSRNTLYLQMNSLRAEDTAV YYCAIQHGYWGQGILVTVSS | SEQ ID NO: 147 (4A8 VH M96L) | EVQLLESGGGLVQPGGSLRLSCAASGFTFS SSTMSWVRQAPGKGLEWVSAISGRGRNTY YADSVKGRFTISRDNSRNTLYLQMNSLRAE DTAVYYCAIQLGYWGQGILVTVSS |
| SEQ ID NO: 148 (4A8 VH M96W) | EVQLLESGGGLVQPGGSLRLSCAASGFTFSSS TMSWVRQAPGKGLEWVSAISGRGRNTYYAD SVKGRFTISRDNSRNTLYLQMNSLRAEDTAV YYCAIQWGYWGQGILVTVSS | SEQ ID NO: 149 (4A8 VH M96Y) | EVQLLESGGGLVQPGGSLRLSCAASGFTFS SSTMSWVRQAPGKGLEWVSAISGRGRNTY YADSVKGRFTISRDNSRNTLYLQMNSLRAE DTAVYYCAIQYGYWGQGILVTVSS |
| SEQ ID NO: 150 (4A8 VH Y102Q) | EVQLLESGGGLVQPGGSLRLSCAASGFTFSSS TMSWVRQAPGKGLEWVSAISGRGRNTYYAD SVKGRFTISRDNSRNTLYLQMNSLRAEDTAV YYCAIQMGWGQGILVTVSS | SEQ ID NO: 151 (4A8 VH Y102D) | EVQLLESGGGLVQPGGSLRLSCAASGFTFS SSTMSWVRQAPGKGLEWVSAISGRGRNTY YADSVKGRFTISRDNSRNTLYLQMNSLRAE DTAVYYCAIQMGDWGQGILVTVSS |
| SEQ ID NO: 152 (4A8 VL V51D) | QSALTQPPSASGSPGQSVTISCIGTSSDVGGY NYVSWYQQHPDKAPKLMIYEDNKRPSGVPD RFSGSKSGNTASLTVSGLQAEDEADYYCSSY AGNNNFGVFGGGTKLTVL | SEQ ID NO: 153 (4A8 VL V51Y) | QSALTQPPSASGSPGQSVTISCIGTSSDVGG YNYVSWYQQHPDKAPKLMIYEYNKRPSGV PDRFSGSKSGNTASLTVSGLQAEDEADYYC SSYAGNNNFGVFGGGTKLTVL |
| SEQ ID NO: 154 (4A8 VL R54D) | QSALTQPPSASGSPGQSVTISCIGTSSDVGGY NYVSWYQQHPDKAPKLMIYEVNKDPSGVPD RFSGSKSGNTASLTVSGLQAEDEADYYCSSY AGNNNFGVFGGGTKLTVL | SEQ ID NO: 155 (4A8 VL Y91S) | QSALTQPPSASGSPGQSVTISCIGTSSDVGG YNYVSWYQQHPDKAPKLMIYEVNKRPSGV PDRFSGSKSGNTASLTVSGLQAEDEADYYC SSSAGNNNFGVFGGGTKLTVL |
| SEQ ID NO: 156 (4A8 VL Y91H) | QSALTQPPSASGSPGQSVTISCIGTSSDVGGY NYVSWYQQHPDKAPKLMIYEVNKRPSGVPD RFSGSKSGNTASLTVSGLQAEDEADYYCSSH AGNNNFGVFGGGTKLTVL | SEQ ID NO: 157 (4A8 VL N94H) | QSALTQPPSASGSPGQSVTISCIGTSSDVGG YNYVSWYQQHPDKAPKLMIYEVNKRPSGV PDRFSGSKSGNTASLTVSGLQAEDEADYYC SSYAGHNNFGVFGGGTKLTVL |
| SEQ ID NO: 158 (4A8 VL N95aS) | QSALTQPPSASGSPGQSVTISCIGTSSDVGGY NYVSWYQQHPDKAPKLMIYEVNKRPSGVPD RFSGSKSGNTASLTVSGLQAEDEADYYCSSY AGNNSFGVFGGGTKLTVL | SEQ ID NO: 159 (4A8 VL N95aW) | QSALTQPPSASGSPGQSVTISCIGTSSDVGG YNYVSWYQQHPDKAPKLMIYEVNKRPSGV PDRFSGSKSGNTASLTVSGLQAEDEADYYC SSYAGNNWFGVFGGGTKLTVL |
| SEQ ID NO: 160 (4A8 VL V97S) | QSALTQPPSASGSPGQSVTISCIGTSSDVGGY NYVSWYQQHPDKAPKLMIYEVNKRPSGVPD RFSGSKSGNTASLTVSGLQAEDEADYYCSSY AGNNNFGSFGGGTKLTVL | SEQ ID NO: 161 (4A8 VL V97D) | QSALTQPPSASGSPGQSVTISCIGTSSDVGG YNYVSWYQQHPDKAPKLMIYEVNKRPSGV PDRFSGSKSGNTASLTVSGLQAEDEADYYC SSYAGNNNFGDFGGGTKLTVL |
| Additional BKO-4A8 combinatorial variants | | | |
| SEQ ID NO: 162 4A8 VH Variant 102 M34Q_ A40P_ N56S_ R75K_ M96E | EVQLLESGGGLVQPGGSLRLSCAASGFTFSSS TQSWVRQPPGKGLEWVSAISGRGRSTYYADS VKGRFTISRDNSKNTLYLQMNSLRAEDTAVY YCAIQEGYWGQGILVTVSS | SEQ ID NO: 163 4A8 VH Variant 103 M34Q_ A40P_ R53S_ R55G_ N56S_ R75K | EVQLLESGGGLVQPGGSLRLSCAASGFTFS SSTQSWVRQPPGKGLEWVSAISGSGGSTYY ADSVKGRFTISRDNSKNTLYLQMNSLRAED TAVYYCAIQMGYWGQGILVTVSS |
| SEQ ID NO: 164 4A8 VH Variant 104 M34Q_ A40P_ R53S_ R55G_ N56S_ R75K_ M96K | EVQLLESGGGLVQPGGSLRLSCAASGFTFSSS TQSWVRQPPGKGLEWVSAISGSGGSTYYADS VKGRFTISRDNSKNTLYLQMNSLRAEDTAVY YCAIQKGYWGQGILVTVSS | SEQ ID NO: 165 4A8 VH Variant 105 M34Q_ A40P_ R53S_ R55G_ N56S_ R75K_ M96A | EVQLLESGGGLVQPGGSLRLSCAASGFTFS SSTQSWVRQPPGKGLEWVSAISGSGGSTYY ADSVKGRFTISRDNSKNTLYLQMNSLRAED AVYYCAIQAGYWGQGILVTVSS |
| SEQ ID NO: 166 4A8 VH Variant | EVQLLESGGGLVQPGGSLRLSCAASGFTFSSS TQSWVRQPPGKGLEWVSAISGSGGSTYYADS VKGRFTISRDNSKNTLYLQMNSLRAEDTAVY YCAIQEGYWGQGILVTVSS | | |

TABLE 19-continued

Sequences

| Sequence Identifier | Sequence | Sequence Identifier | Sequence |
|---|---|---|---|
| 106 | M34Q_A40P_R53S_R55G_N56S_R75K_M96E | | |

Consensus Sequences

| Sequence Identifier | Sequence | Sequence Identifier | Sequence |
|---|---|---|---|
| SEQ ID NO: 167 (4A8 Consensus VH) | EVQLLESGGGLVQPGGSLRLSCAASGFTFSS $X_1X_2X_3$SWVRQAPGKGLEWVSA$X_4$S$X_5X_6X_7$ R$X_8$TYYADSVKGRFTISRDNSRNTLYLQMNS LRAEDTAVYYCA$X_9$Q$X_{10}X_{11}X_{12}$WGQGILV TVSS Wherein: $X_1$ is S, Q, H, L, W, or Y; $X_2$ is T or A; and $X_3$ is M, Q, D, H, or W $X_4$ is I or H; $X_5$ is G or D; $X_6$ is R, S, or Q; $X_7$ is G or D; and $X_8$ is N or S $X_9$ is I or K, $X_{10}$ is M, A, Q, or K; $X_{11}$ is G or D; $X_{12}$ is Y, S, or K | SEQ ID NO: 168 (4A8 Consensus VL) | QSALTQPPSASGSPGQSVTISCIGTSSDVGG YNYVSWYQQHPDKAPKLMIY$X_{13}$V$X_{14}X_{15}$ $X_{16}$PSGVPDRFSGSKSGNTASLTVSGLQAED EADYYCSS$X_{17}$AG$X_{18}$N$X_{19}$FG$X_{20}$FGGGTK LTVL Wherein: $X_{13}$ is E or D; $X_{14}$ is N, D, or S; $X_{15}$ is K, A, D, or H; and $X_{16}$ is R or Q $X_{17}$ is Y or A; $X_{18}$ is N, A, S, K, L, W, or Y; $X_{19}$ is N, Q, D, H, K, L, or Y; and $X_{20}$ is V, A, or K |
| SEQ ID NO: 169 (Consensus VH CDR1) | S$X_1X_2X_3$S wherein: $X_1$ is S, Q, H, L, W, or Y; $X_2$ is T or A; and $X_3$ is M, Q, D, H, or W | SEQ ID NO: 170 (Consensus VH CDR2) | A$X_4$S$X_5X_6X_7$R$X_8$TYYADSVKG wherein: $X_4$ is I or H; $X_5$ is G or D; $X_6$ is R, S, or Q; $X_7$ is G or D; and $X_8$ is N or S |
| SEQ ID NO: 171 (Consensus VH CDR3) | Q$X_{10}X_{11}X_{12}$ wherein $X_{10}$ is M, A, Q, or K; $X_{11}$ is G or D; and $X_{12}$ is Y, S, or K | SEQ ID NO: 172 (Consensus VL CDR1) | IGTSSDVGGYNYVS |
| SEQ ID NO: 173 (Consensus VL CDR2) | $X_{13}$V$X_{14}X_{15}X_{16}$PS wherein: $X_{13}$ is E or D; $X_{14}$ is N, D, or S; $X_{15}$ is K, A, D, or H; and $X_{16}$ is R or Q | SEQ ID NO: 174 (Consensus VL CDR3) | SS$X_{17}$AG$X_{18}$N$X_{19}$FG$X_{20}$ wherein: $X_{17}$ is Y or A; $X_{18}$ is N, A, S, K, L, W, or Y; $X_{19}$ is N, Q, D, H, K, L, or Y; and $X_{20}$ is V, A, or K |

CDR Sequences

| Sequence Identifier | Sequence | Sequence Identifier | Sequence |
|---|---|---|---|
| SEQ ID NO: 175 (4A8 VHCDR1) | SSTMS | SEQ ID NO: 176 (4A8 S32Q VHCDR1) | SQTMS |
| SEQ ID NO: 177 (4A8 S32H VHCDR1) | SHTMS | SEQ ID NO: 178 (4A8 S32L VHCDR1) | SLTMS |
| SEQ ID NO: 179 (4A8 S32W VHCDR1) | SWTMS | SEQ ID NO: 180 (4A8 S32Y VHCDR1) | SYTMS |
| SEQ ID NO: 181 (4A8 T33A VHCDR1) | SSAMS | SEQ ID NO: 182 (4A8 M34Q VHCDR1) | SSTQS |
| SEQ ID NO: 183 (4A8 M34D VHCDR1) | SSTDS | SEQ ID NO: 184 (4A8 M34H VHCDR1) | SSTHS |

TABLE 19-continued

Sequences

| Sequence Identifier | Sequence | Sequence Identifier | Sequence |
| --- | --- | --- | --- |
| SEQ ID NO: 185 (4A8 M34W VHCDR1) | SSTWS | SEQ ID NO: 186 (4A8 VHCDR2) | AISGRGRNTYYADSVKG |
| SEQ ID NO: 187 4A8 I51H VHCDR2 | AHSGRGRNTYYADSVKG | SEQ ID NO: 188 4A8 G52aD VHCDR2 | AISDRGRNTYYADSVKG |
| SEQ ID NO: 189 4A8 R53S VHCDR2 | AISGSGRNTYYADSVKG | SEQ ID NO: 190 4A8 R53Q VHCDR2 | AISGQGRNTYYADSVKG |
| SEQ ID NO: 191 4A8 G54D VHCDR2 | AISGRDRNTYYADSVKG | SEQ ID NO: 192 4A8 N56S VHCDR2 | AISGRGRSTYYADSVKG |
| SEQ ID NO: 193 4A8 103, 104, 105 VHCDR2 | AISGSGGSTYYADSVKG | SEQ ID NO: 194 4A8 VHCDR3 | QMGY |
| SEQ ID NO: 195 4A8 M96A VHCDR3 | QAGY | SEQ ID NO: 196 4A8 M96Q VHCDR3 | QQGY |
| SEQ ID NO: 197 4A8 M96K VHCDR3 | QKGY | SEQ ID NO: 198 4A8 G101D VHCDR3 | QMDY |
| SEQ ID NO: 199 4A8 Y102S VHCDR3 | QMGS | SEQ ID NO: 200 4A8 Y102K VHCDR3 | QMGK |
| SEQ ID NO: 201 4A8 VLCDR1 | IGTSSDVGGYNYVS | SEQ ID NO: 202 4A8 VLCDR2 | EVNKRPS |
| SEQ ID NO: 203 4A8 E50D VLCDR2 | DVNKRPS | SEQ ID NO: 204 4A8 N52D VLCDR2 | EVDKRPS |
| SEQ ID NO: 205 4A8 N52A VLCDR2 | EVSKRPS | SEQ ID NO: 206 4A8 K53A VLCDR2 | EVNARPS |
| SEQ ID NO: 207 4A8 K53D VLCDR2 | EVNDRPS | SEQ ID NO: 208 4A8 K53H VLCDR2 | EVNHRPS |

TABLE 19-continued

Sequences

| Sequence Identifier | Sequence | Sequence Identifier | Sequence |
|---|---|---|---|
| SEQ ID NO: 209 4A8 R54Q VLCDR2 | EVNKQPS | SEQ ID NO: 210 4A8 VLCDR3 | SSYAGNNNFGV |
| SEQ ID NO: 211 4A8 Y91A VLCDR3 | SSAAGNNNFGV | SEQ ID NO: 212 4A8 N94A VLCDR3 | SSYAGANNFGV |
| SEQ ID NO: 213 4A8 N94S VLCDR3 | SSYAGSNNFGV | | |
| SEQ ID NO: 214 4A8 N94K VLCDR3 | SSYAGKNNFGV | SEQ ID NO: 215 4A8 N94L VLCDR3 | SSYAGLNNFGV |
| SEQ ID NO: 216 4A8 N94W VLCDR3 | SSYAGWNNFGV | SEQ ID NO: 217 4A8 N94Y VLCDR3 | SSYAGYNNFGV |
| SEQ ID NO: 218 4A8 N95aQ VLCDR3 | SSYAGNNQFGV | SEQ ID NO: 219 4A8 N95aD VLCDR3 | SSYAGNNDFGV |
| SEQ ID NO: 220 4A8 N95aH VLCDR3 | SSYAGNNHFGV | SEQ ID NO: 221 4A8 N95aK VLCDR3 | SSYAGNNKFGV |
| SEQ ID NO: 222 4A8 N95aL VLCDR3 | SSYAGNNLFGV | SEQ ID NO: 223 A48 N95aY VLCDR3 | SSYAGNNYFGV |
| SEQ ID NO: 224 4A8 V97A VLCDR3 | SSYAGNNNFGA | SEQ ID NO: 225 4A8 V97K VLCDR3 | SSYAGNNNFGK |

Consensus Sequences

| SEQ ID NO: 226 (4A8 Consensus VH) | EVQLLESGGGLVQPGGSLRLSCAASGFTFSSS TX$_{21}$SWVRQX$_{22}$PGKGLEWVSAISGX$_{23}$GX$_{24}$ X$_{25}$TYYADSVKGRFTISRDNSX$_{26}$NTLYLQMN SLRAEDTAVYYCAX$_{27}$QX$_{28}$GYWGQGILVTVSS Wherein: X$_{21}$ is M or Q; X$_{22}$ is A or P; X$_{23}$ is R or S; X$_{24}$ is R or G; and X$_{25}$ is N or S; X$_{26}$ is R or K; X$_{27}$ is I or K; X$_{28}$ is M, K, or A | SEQ ID NO: 227 (4A8 Consensus VL) | QSALTQPPSASGSPGQSVTISCIGTSSDVGG YNYVSWYQQHPX$_{29}$KAPKLMIYEVX$_{30}$KRPS GVPDRFSGSKSGNTASLTVSGLQAEDEADY YCSSYAGX$_{31}$NNFGVFGGGTKLTVL Wherein: X$_{29}$ is D or G; X$_{30}$ is N or S; X$_{31}$ is N or S |
| SEQ ID NO: 228 (Consensus VH CDR1) | SSTX$_{21}$S wherein: X$_{21}$ is M or Q | SEQ ID NO: 229 (Consensus VH CDR2) | AISGX$_{23}$GX$_{24}$X$_{25}$TYYADSVKG wherein: X$_{23}$ is R or S; X$_{24}$ is R or G; and X$_{25}$ is N or S |

TABLE 19-continued

Sequences

| Sequence Identifier | Sequence | Sequence Identifier | Sequence |
|---|---|---|---|
| SEQ ID NO: 230 (Consensus VH CDR3) | QX$_{28}$GY wherein: X$_{28}$ is M, K, or A | SEQ ID NO: 201 (Consensus VL CDR1) | IGTSSDVGGYNYVS |
| SEQ ID NO: 231 (Consensus VL CDR2) | EVX$_{30}$KRPS wherein: X$_{30}$ is N or S | SEQ ID NO: 232 (Consensus VL CDR3) | SSYAGX$_{31}$NNFGV wherein: X$_{31}$ is N or S |

Polynucleotide sequences

| | | | |
|---|---|---|---|
| BKO-4A8 VH SEQ ID NO: 233 | GAAGTGCAGCTGCTGGAATCTGGCGGAGGACTGG TGCAGCCTGGCGGCAGCCTGAGACTGTCTTGTGC CGCCAGCGGCTTCACCTTCAGCAGCAGCACAATG AGCTGGGTCCGACAGGCCCCTGGCAAGGGACTGG AATGGGTGTCCGCCATCAGCGGCAGAGGCCGAA CACCTACTACGCCGACAGCGTGAAGGGCCGGTTC ACCATCAGCCGGGACAACAGCAGAAACACCCTGT ACCTGCAGATGAACAGCCTGCGGGCCGAGGACAC CGCCGTGTACTACTGTGCCATCCAGATGGGCTAC TGGGGCCAGGGCATTCTCGTGACAGTGTCCTCA | 4A8 VH Variant 1 SEQ ID NO: 234 | GAAGTGCAGCTGCTGGAATCTGGCGGAGGACTGG GTGCAGCCTGGCGGCAGCCTGAGACTGTCTTGT GCCGCCAGCGGCTTCACCTTCAGCAGCAGCACA CAGAGCTGGGTCCGACAGGCCCCTGGCAAGGGA CTGGAATGGGTGTCCGCCATCAGCGGCAGAGGC CGGAGTACCTACTACGCCGACAGCGTGAAGGGC CGGTTCACCATCAGCCGGGACAACAGCAGAAAC ACCCTGTACCTGCAGATGAACAGCCTGCGGGCC GAGGACACCGCCGTGTACTACTGTGCCATCCAG ATGGGCTACTGGGGCCAGGGCATTCTCGTGACA GTGTCCTCA |
| 4A8 VH Variant 2 SEQ ID NO: 235 | GAAGTGCAGCTGCTGGAATCTGGCGGAGGACTGG TGCAGCCTGGCGGCAGCCTGAGACTGTCTTTGTGC CGCCAGCGGCTTCACCTTCAGCAGCAGCACACAG AGCTGGGTCCGACAGCCTCCTGGCAAGGGACTGG AATGGGTGTCCGCCATCAGCGGCAGAGGCCGGAG TACCTACTACGCCGACAGCGTGAAGGGCCGGTTC ACCATCAGCCGGGACAACAGCAGAAACACCCTGT ACCTGCAGATGAACAGCCTGCGGGCCGAGGACAC CGCCGTGTACTACTGTGCCATCCAGATGGGCTAC TGGGGCCAGGGCATTCTCGTGACAGTGTCCTCA | 4A8 VH Variant 3 SEQ ID NO: 236 | GAAGTGCAGCTGCTGGAATCTGGCGGAGGACTGG GTGCAGCCTGGCGGCAGCCTGAGACTGTCTTGT GCCGCCAGCGGCTTCACCTTCAGCAGCAGCACA CAGAGCTGGGTCCGACAGCCTCCTGGCAAGGGA CTGGAATGGGTGTCCGCCATCAGCGGCAGAGGC CGGAGTACCTACTACGCCGACAGCGTGAAGGGC CGGTTCACCATCAGCCGGGACAACAGCAGAAAAC ACCCTGTACCTGCAGATGAACAGCCTGCGGGCC GAGGACACCGCCGTGTACTACTGTGCCATCCAG ATGGGCTACTGGGGCCAGGGCATTCTCGTGACA GTGTCCTCA |
| 4A8 VH Variant 4 SEQ ID NO: 237 | GAAGTGCAGCTGCTGGAATCTGGCGGAGGACTGG TGCAGCCTGGCGGCAGCCTGAGACTGTCTTGTGC CGCCAGCGGCTTCACCTTCAGCAGCAGCACACAG AGCTGGGTCCGACAGCCTCCTGGCAAGGGACTGG AATGGGTGTCCGCCATCAGCGGCAGAGGCCGGAG TACCTACTACGCCGACAGCGTGAAGGGCCGGTTC ACCATCAGCCGGGACAACAGCAGAAACACCCTGT ACCTGCAGATGAACAGCCTGCGGGCCGAGGACAC CGCCGTGTACTACTGTGCCATCCAGAAGGGCTAC TGGGGCCAGGGCATTCTCGTGACAGTGTCCTCA | 4A8 VH Variant 5 SEQ ID NO: 238 | GAAGTGCAGCTGCTGGAATCTGGCGGAGGACTGG GTGCAGCCTGGCGGCAGCCTGAGACTGTCTTGT GCCGCCAGCGGCTTCACCTTCAGCAGCAGCACA CAGAGCTGGGTCCGACAGCCTCCTGGCAAGGGA CTGGAATGGGTGTCCGCCATCAGCGGCAGAGGC CGGAGTACCTACTACGCCGACAGCGTGAAGGGC CGGTTCACCATCAGCCGGGACAACAGCAAAAAC ACCCTGTACCTGCAGATGAACAGCCTGCGGGCC GAGGACACCGCCGTGTACTACTGTGCCATCCAG AAGGGCTACTGGGGCCAGGGCATTCTCGTGACA GTGTCCTCA |
| 4A8 VH Variant 6 SEQ ID NO: 239 | GAAGTGCAGCTGCTGGAATCTGGCGGAGGACTGG TGCAGCCTGGCGGCAGCCTGAGACTG TCTTGTGCCGCCAGCGGCTTCACCTTCAGCAGCA GCACACAGAGCTGGGTCCGACAGCCTCCTGGCAA GGGACTGGAATGGGTGTCCGCCATCAGCGGCAGA GGCCGGAGTACCTACTACGCCGACAGCGTGAAGG GCCGGTTCACCATCAGCCGGGACAACAGCAAAAA CACCCTGTACCTGCAGATGAACAGCCTGCGGGCC GAGGACACCGCCGTGTACTACTGTGCCAAGCAGA AAGGGCTACTGGGGCCAGGGCATTCTCGTGACAGT GTCCTCA | 4A8 VH Variant 7 SEQ ID NO: 240 | GAAGTGCAGCTGCTGGAATCTGGCGGAGGACTGG GTGCAGCCTGGCGGCAGCCTGAGACTG TCTTGTGCCGCCAGCGGCTTCACCTTCAGCAGC AGCACACAGAGCTGGGTCCGACAGCCTCCTGGC AAGGGACTGGAATGGGTGTCCGCCATCAGCGGC AGAGGCCGGAGTACCTACTACGCCGACAGCGTG AAGGGCCGGTTCACCATCAGCCGGGACAACAGC AGAAACACCCTGTACCTGCAGATGAACAGCCTG CGGGCCGAGGACACCGCCGTGTACTACTGTGCC AAGCAGAAGGGCTACTGGGGCCAGGGCATTCTC GTGACAGTGTCCTCA |
| 4A8 VH Variant 8 SEQ ID NO: 241 | GAAGTGCAGCTGCTGGAATCTGGCGGAGGACTGG TGCAGCCTGGCGGCAGCCTGAGACTGTCTTGTGC CGCCAGCGGCTTCACCTTCAGCAGCAGCACACAG AGCTGGGTCCGACAGGCCCCTGGCAAGGGACTGG AATGGGTGTCCGCCATCAGCGGCAGAGGCCGGAG TACCTACTACGCCGACAGCGTGAAGGGCCGGTTC ACCATCAGCCGGGACAACAGCAGAAACACCCTGT ACCTGCAGATGAACAGCCTGCGGGCCGAGGACAC CGCCGTGTACTACTGTGCCATCCAGAAGGGCTAC TGGGGCCAGGGCATTCTCGTGACAGTGTCCTCA | 4A8 VH Variant 9 SEQ ID NO: 242 | GAAGTGCAGCTGCTGGAATCTGGCGGAGGACTGG GTGCAGCCTGGCGGCAGCCTGAGACTGTCTTGT GCCGCCAGCGGCTTCACCTTCAGCAGCAGCACA CAGAGCTGGGTCCGACAGGCCCCTGGCAAGGGA CTGGAATGGGTGTCCGCCATCAGCGGCAGAGGC CGGAGTACCTACTACGCCGACAGCGTGAAGGGC CGGTTCACCATCAGCCGGGACAACAGCAAAAAC ACCCTGTACCTGCAGATGAACAGCCTGCGGGCC GAGGACACCGCCGTGTACTACTGTGCCATCCAG AAGGGCTACTGGGGCCAGGGCATTCTCGTGACA GTGTCCTCA |

TABLE 19-continued

Sequences

| Sequence Identifier | Sequence | Sequence Identifier | Sequence |
|---|---|---|---|
| 4A8 VH Variant 10 SEQ ID NO: 243 | GAAGTGCAGCTGCTGGAATCTGGCGGAGGACTGG TGCAGCCTGGCGGCAGCCTGAGACTGTCTTGTGC CGCCAGCGGCTTCACCTTCAGCAGCAGCACAATG AGCTGGGTCCGACAGGCCCCTGGCAAGGGACTGG AATGGGTGTCCGCCATCAGCGGCAGAGGCCGGAA CACCTACTACGCCGACAGCGTGAAGGGCCGGTTC ACCATCAGCCGGGACAACAGCAGAAACACCCTGT ACCTGCAGATGAACAGCCTGCGGGCCGAGGACAC CGCCGTGTACTACTGTGCCAAGCAGAAGGGCTAC TGGGGCCAGGGCATTCTCGTGACAGTGTCCTCA | 4A8 VH Variant 101 SEQ ID NO: 244 | GAAGTTCAGCTGCTTGAATCTGGCGGAGGACTGG GTTCAGCCTGGCGGATCTCTGAGACTGTCTTGT GCCGCCAGCGGCTTCACCTTTAGCAGCAGCACA CAGAGCTGGGTCCGACAGCCTCCTGGCAAGGA CTGGAATGGGTGTCCGCCATCTCTGGCAGAGGC AGAAGCACCTACTACGCCGACTCTGTGAAGGGC AGATTCACCATCAGCCGGGACAACAGCAAGAAC ACCCTGTACCTGCAGATGAACAGCCTGAGAGCC GAGGACACCGCCGTGTACTATTGTGCCATCCAG GCCGGCTATTGGGGCCAGGGAATACTCGTGACA GTGTCCTCA |
| 4A8 VH Variant 103 SEQ ID NO: 245 | GAAGTTCAGCTGCTTGAATCTGGCGGAGGACTGG TTCAGCCTGGCGGATCTCTGAGACTGTCTTGTGC CGCCAGCGGCTTCACCTTTAGCAGCAGCACACAG AGCTGGGTCCGACAGCCTCCTGGCAAGGGACTGG AATGGGTGTCCGCCATCTCTGGCAGCGGCGGCAG CACATATTACGCCGATTCTGTGAAGGGCAGATTC ACCATCAGCCGGGACAACAGCAAGAACACCCTGT ACCTGCAGATGAACAGCCTGAGAGCCGAGGACAC CGCCGTGTACTATTGCGCCATCCAGATGGGCTAT TGGGGCCAGGGAATCCTCGTGACAGTGTCCTCA | 4A8 VH Variant 104 SEQ ID NO: 246 | GAAGTTCAGCTGCTTGAATCTGGCGGAGGACTGG GTTCAGCCTGGCGGATCTCTGAGACTGTCTTGT GCCGCCAGCGGCTTCACCTTTAGCAGCAGCACA CAGAGCTGGGTCCGACAGCCTCCTGGCAAGGA CTGGAATGGGTGTCCGCCATCTCTGGCAGCGGC GGCACATATTACGCCGATTCTGTGAAGGGC AGATTCACCATCAGCCGGGACAACAGCAAGAAC ACCCTGTACCTGCAGATGAACAGCCTGAGAGCC GAGGACACCGCCGTGTACTATTGCGCCATCCAG AAAGGCTATTGGGGCCAGGGCATCCTCGTGACA GTGTCCTCA |
| 4A8 VH Variant 105 SEQ ID NO: 247 | GAAGTTCAGCTGCTTGAATCTGGCGGAGGACTGG TTCAGCCTGGCGGATCTCTGAGACTGTCTTGTGC CGCCAGCGGCTTCACCTTTAGCAGCAGCACACAG AGCTGGGTCCGACAGCCTCCTGGCAAGGGACTGG AATGGGTGTCCGCCATCTCTGGCAGCGGCGGCAG CACATATTACGCCGATTCTGTGAAGGGCAGATTC ACCATCAGCCGGGACAACAGCAAGAACACCCTGT ACCTGCAGATGAACAGCCTGAGAGCCGAGGACAC CGCCGTGTACTATTGTGCCATCCAGGCCGGCTAT TGGGGCCAGGGAATACTCGTGACAGTGTCCTCA | Human IgG1 SEQ ID NO: 248 | GCTAGCACCAAGGGACCCAGCGTGTTCCCCCTG GCCCCCAGCAGCAAGAGCACATCTGGCGGAACA GCGCCCTGGGCTGCCTGGTGAAAGACTACTTC CCCGAGCCCGTGACCGTGAGCTGGAACAGCGGA GCCCTGACCAGCGGCGTGCACACCTTTCCAGCC GTGCTGCAGAGCAGCGGCCTGTACAGCCTGAGC AGCGTGGTGACAGTGCCCTCTAGCAGCCTGGGC ACCCAGACCTACATCTGCAACGTGAACCACAAG CCCAGCAACACCAAGGTGGACAAAAAGGTGGAA CCCAAGAGCTGCGACAAGACCCACACCTGTCCC CCCTGCCCTGCCCCTGAACTGCTGGGCGGACCC TCCGTGTTCCTGTTCCCCCCAAAGCCCAAGGAC ACCCTGATGATCAGCCGGACCCCCGAAGTGACC TGCGTGGTGGTGGACGTGTCCCACGAGGACCCT GAAGTGAAGTTCAATTGGTACGTGGACGGCGTG GAAGTGCACAACGCCAAGACCAAGCCCAGAGAG GAACAGTACAACAGCACCTACCGGGTGGTGTCC GTGCTGACCGTGCTGCACCAGGACTGGCTGAAC GGCAAAGAGTACAAGTGCAAGGTGTCCAACAAG GCCCTGCCTGCTCCCATCGAGAAAACCATCAGC AAGGCCAAGGGCCAGCCCCGCGAGCCTCAGGTG TACACACTGCCCCCCAGCCGGGACGAGCTGACC AAGAACCAGGTGTCCCTGACCTGTCTGGTGAAA GGCTTCTACCCCAGCGATATCGCCGTGGAATGG GAGAGCAACGGCCAGCCCGAGAACAACTACAAG ACCACCCCCCCTGTGCTGGACAGCGACGGCTCA TTCTTCCTGTACAGCAAGCTGACCGTGGACAAG AGCCGGTGGCAGCAGGGCAACGTGTTCAGCTGC AGCGTGATGCACGAGGCCCTGCACAACCACTAC ACCCAGAAGTCCCTGAGCCTGAGCCCCGGC |
| Human IgG1* SEQ ID NO: 249 | GCTAGCACCAAGGGACCCAGCGTGTTCCCCCTGG CCCCCAGCAGCAAGAGCACATCTGGCGGAACAGC CGCCCTGGGCTGCCTGGTGAAAGACTACTTCCCC GAGCCCGTGACCGTGAGCTGGAACAGCGGAGCCC TGACCAGCGGCGTGCACACCTTTCCAGCCGTGCT GCAGAGCAGCGGCCTGTACAGCCTGAGCAGCGTG GTGACAGTGCCCTCTAGCAGCCTGGGCACCCAGA CCTACATCTGCAACGTGAACCACAAGCCCAGCAA CACCAAGGTGGACAAAAAGGTGGAACCCAAGAGC TGCGACAAGACCCACACCTGTCCCCCCTGCCCTG CCCCTGAACTGGCTGGCGCTCCCCCGTGTTCCT GTTCCCCCCAAAGCCCAAGGACACCCTGATGATC AGCCGGACCCCCGAAGTGACCTGCGTGGTGGTGG ACGTGTCCCACGAGGACCCTGAAGTGAAGTTCAA TTGGTACGTGGACGGCGTGGAAGTGCACAACGCC AAGACCAAGCCCAGAGAGGAACAGTACAACAGCA CCTACCGGGTGGTGTCCGTGCTGACCGTGCTGCA CCAGGACTGGCTGAACGGCAAAGAGTACAAGTGC | Human IgG4 SEQ ID NO: 250 | GCTAGCACCAAGGGCCCCAGCGTGTTCCCCCTG GCCCCTTGTAGCAGAAGCACCAGCGAGAGCACA GCCGCCCTGGGCTGCCTGGTGAAAGACTACTTC CCCGAGCCCGTGACCGTGTCCTGGAACAGCGGA GCCCTGACCAGCGGCGTGCACACCTTTCCAGCC GTGCTGCAGAGCAGCGGCCTGTACAGCCTGAGC AGCGTGGTGACAGTGCCCTCCAGCAGCCTGGGC ACCAAGACCTACACCTGTAACGTGGACCACAAG CCCAGCAACACCAAGGTGGACAAGCGGGTGGAA TCTAAGTACGGCCCACCCTGCCCCCCCTGCCCT GCCCCTGAATTTCTGGGCGGACCCTCCGTGTTC CTGTTCCCCCCAAAGCCCAAGGACACCCTGATG ATCAGCCGGACCCCCGAAGTGACCTGCGTGGTG GTGGACGTGTCCCAGGAAGATCCCGAGGTCCAG TTCAATTGGTACGTGGACGGCGTGGAAGTGCAC AACGCCAAGACCAAGCCCAGAGAGGAACAGTTC AACAGCACCTACCGGGTGGTGTCCGTGCTGACC GTGCTGCACCAGGACTGGCTGAACGGCAAAGAG |

TABLE 19-continued

Sequences

| Sequence Identifier | Sequence | Sequence Identifier | Sequence |
|---|---|---|---|
|  | AAGGTGTCCAACAAGGCCCTGCCTGCTCCCATCG AGAAAACCATCAGCAAGGCCAAGGGCCAGCCCCG CGAGCCTCAGGTGTACACACTGCCCCCCAGCCGG GACGAGCTGACCAAGAACCAGGTGTCCCTGACCT GTCTGGTGAAAGGCTTCTACCCCAGCGATATCGC CGTGGAATGGGAGAGCAACGGCCAGCCCGAGAAC AACTACAAGACCACCCCCCCTGTGCTGGACAGCG ACGGCTCATTCTTCCTGTACAGCAAGCTGACCGT GGACAAGAGCCGGTGGCAGCAGGGCAACGTGTTC AGCTGCAGCGTGATGCACGAGGCCCTGCACAACC ACTACACCCAGAAGTCCCTGAGCCTGAGCCCCGG C |  | TACAAGTGCAAAGTCTCCAACAAGGGCCTGCCC AGCTCCATCGAGAAAACCATCAGCAAGGCCAAG GGCCAGCCCCGCGAGCCTCAGGTGTACACACTG CCCCCAGCCAGGAAGAGATGACCAAGAACCAG GTGTCCCTGACCTGTCTGGTGAAAGGCTTCTAC CCCAGCGATATCGCCGTGGAATGGGAGAGCAAC GGCCAGCCCGAGAACAACTACAAGACCACCCCC CCTGTGCTGGACAGCGACGGCAGCTTCTTCCTG TACTCCCGGCTGACCGTGGACAAGAGCCGGTGG CAGGAAGGCAACGTCTTCAGCTGCAGCGTGATG CACGAGGCCCTGCACAACCACTACACCCAGAAG TCCCTGAGCCTGAGCCTGGGC |
| Human IgG4* SEQ ID NO: 251 | GCTAGCACCAAGGGCCCCAGCGTGTTCCCCCTGG CCCCTTGTAGCAGAAGCACCAGCGAGAGCACAGC CGCCCTGGGCTGCCTGGTGAAGACTACTTCCCC GAGCCCGTCACCGTGTCCTGGAACAGCGGAGCCC TGACCAGCGGCGTGCACACCTTTCCAGCCGTGCT GCAGAGCAGCGGCCTGTACAGCCTGAGCAGCGTG GTGACAGTGCCCTCCAGCAGCCTGGGCACCAAGA CCTACACCTGTAACGTGGACCACAAGCCCAGCAA CACCAAGGTGGACAAGCGGGTGGAATCTAAGTAC GGCCCACCCTGCCCCCCCTGCCCTGCCCCTGAAT TTCTGGGCGGACCCTCCGTGTTCCTGTTCCCCCC AAAGCCCAAGGACACCCTGTATATCACTCGGGAG CCCGAAGTGACCTGCGTGGTGGTGGACGTGTCCC AGGAAGATCCCGAGGTCCAGTTCAATTGGTACGT GGACGGCGTGGAAGTGCACAACGCCAAGACCAAG CCCAGAGAGGAACAGTTCAACAGCACCTACCGGG TGGTGTCCGTGCTGACCGTGCTGCACCAGGACTG GCTGAACGGCAAAGAGTACAAGTGCAAAGTCTCC AACAAGGGCCTGCCCAGCTCCATCGAGAAAACCA TCAGCAAGGCCAAGGGCCAGCCCCGCGAGCCTCA GGTGTACACACTGCCCCCCAGCCAGGAAGAGATG ACCAAGAACCAGGTGTCCCTGACCTGTCTGGTGA AAGGCTTCTACCCCAGCGATATCGCCGTGGAATG GGAGAGCAACGGCCAGCCCGAGAACAACTACAAG ACCACCCCCCCTGTGCTGGACAGCGACGGCAGCT TCTTCCTGTACTCCCGGCTGACCGTGGACAAGAG CCGGTGGCAGGAAGGCAACGTCTTCAGCTGCAGC GTGATGCACGAGGCCCTGCACAACCACTACACCC AGAAGTCCCTGAGCCTGAGCCTGGGC | Human IgG2* SEQ ID NO: 252 | GCTAGCACCAAGGGCCCCAGCGTGTTCCCTCTG GCCCCTTGTAGCAGAAGCACCAGCGAGTCTACA GCCGCCCTGGGCTGCCTCGTGAAGGACTACTTT CCCGAGCCCGTCACCGTGTCCTGGAACTCTGGG GCTCTGACAAGCGGCGTGCACACCTTTCCAGCC GTGCTGCAGAGCAGCGGCCTGTACTCTCTGAGC AGCGTCGTGACCGTGCCCAGCAGCAATTTCGGC ACCCAGACCTACACCTGTAACGTGGACCACAAG CCCAGCAACACCAAGGTGGACAAGACCGTGGAA CGGAAGTGCTGCGTGGAATGCCCCCCTTGTCCT GCCCCTCCAGTGGCTGGCCCTTCCGTGTTCCTG TTCCCCCCAAAGCCCAAGGACACCCTGATGATC AGCCGGACCCCCGAAGTGACCTGCGTGGTGGTG GATGTGTCCCACGAGGACCCCGAGGTGCAGTTC AATTGGTACGTGGACGGCGTGGAAGTGCACAAC GCCAAGACCAAGCCCAGAGAGGAACAGTTCAAC AGCACCTTCCGGGTGGTGTCCGTGCTGACCGTG GTGCATCAGGACTGGCTGAACGGCAAAGAGTAC AAGTGCAAGGTGTCCAACAAGGGCCTGCCCAGC TCCATCGAGAAAACCATCAGCAAGACCAAAGGC CAGCCCCGCGAGCCCCAGGTGTACACACTGCCT CCAAGCCGGGAAGAGATGACCAAGAATCAGGTG TCCCTGACCTGTCTGGTGAAAGGCTTCTACCCC TCCGATATCGCCGTGGAATGGGAGAGCAACGGC CAGCCCGAGAACAACTACAAGACCACCCCCCCC ATGCTGGACAGCGACGGCTCATTCTTCCTGTAC AGCAAGCTGACAGTGGACAAGTCCCGGTGGCAG CAGGGCAACGTGTTCAGCTGCAGCGTGATGCAC GAGGCCCTGCACAACCACTACACCCAGAAGTCC CTGAGCCTGAGCCCTGGC |
| BKO-4A8 VL SEQ ID NO: 253 | CAGTCTGCTCTGACACAGCCTCCTAGCGCCTCTG GCTCTCCTGGCCAGAGCGTGACCATCAGCTGTAT CGGCACCAGCAGCGACGTGGGCGGCTACAACTAC GTGTCCTGGTATCAGCAGCACCCCGACAAGGCCC CCAAGCTGATGATCTACGAAGTGAACAAGCGGCC CAGCGGCGTGCCCGATAGATTCAGCGGCAGCAAG AGCGGCAACACCGCCAGCCTCACAGTGTCTGGAC TGCAGGCCGAGGACGAGGCCGACTACTACTGTAG CAGCTACGCCGGCAACAACTTCGGCGTGTTC GGCGGAGGCACCAAGCTGACAGTCCTA | 4A8 VL variant b SEQ ID NO: 254 | CAGTCTGCTCTGACACAGCCTCCTAGCGCCTCT GGCTCTCCTGGCCAGAGCGTGACCATCAGCTGT ATCGGCACCAGCAGCGACGTGGGCGGCTACAAC TACGTGTCCTGGTATCAGCAGCACCCCGACAAG GCCCCCAAGCTGATGATCTACGAAGTGTCCAAG CGGCCCAGCGGCGTGCCCGATAGATTCAGCGGC AGCAAGAGCGGCAACACCGCCAGCCTCACAGTG TCTGGACTGCAGGCCGAGGACGAGGCCGACTAC TACTGTAGCAGCTACGCCGGCAGCAACAACTTC GGCGTGTTCGGCGGAGGCACCAAGCTGACAGTC CTA |
| 4A8 VL variant c SEQ ID NO: 255 | CAGTCTGCTCTGACACAGCCTCCTAGCGCCTCTG GCTCTCCTGGCCAGAGCGTGACCATCAGCTGTAT CGGCACCAGCAGCGACGTGGGCGGCTACAACTAC GTGTCCTGGTATCAGCAGCACCCCGgTAAGGCCC CCAAGCTGATGATCTACGAAGTGTCCAAGCGGCC CAGCGGCGTGCCCGATAGATTCAGCGGCAGCAAG AGCGGCAACACCGCCAGCCTCACAGTGTCTGGAC TGCAGGCCGAGGACGAGGCCGACTACTACTGTAG CAGCTACGCCGGCAgCAACAACTTCGGCGTGTTC GGCGGAGGCACCAAGCTGACAGTCCTA | lambda constant light chain SEQ ID NO: 256 | GGTCAGCCCAAGGCCGCTCCCAGCGTGACCCTG TTCCCCCCAAGCAGCGAGGAACTGCAGGCCAAC AAGGCCACCCTGGTGTGCCTGATCAGCGACTTC TACCCGGGGCCGTGACCGTGGCCTGGAAGGCC GATAGCAGCCCTGTGAAGGCCGGCGTGGAAACC ACCACCCCCTCCAAGCAGAGCAACAACAAATAC GCCGCCAGCAGCTACCTGTCCCTGACCCCCGAG CAGTGGAAGTCCCACCGGTCCTACAGCTGCCAG GTGACACACGAGGGCAGCACCGTGGAAAAGACC GTGGCCCCACCGAGTGCAGC |

What is claimed:

1. A method of treating airway neutrophilia or acute lung inflammation in a subject, the method comprising: administering to the subject a therapeutically effective amount of a human antibody molecule that immunospecifically binds to human CXCR2 and comprises a heavy chain CDR1 comprising the amino acid sequence of SEQ ID NO: 182, a heavy chain CDR2 comprising the amino acid sequence of SEQ ID NO: 192, a heavy chain CDR3 comprising the amino acid sequence of SEQ ID NO: 195, a light chain CDR1 comprising the amino acid sequence of SEQ ID NO: 201, a light chain CDR2 comprising the amino acid sequence of SEQ ID NO: 205, and a light chain CDR3 comprising the amino acid sequence of SEQ ID NO: 213 to thereby treat the airway neutrophilia or acute lung inflammation.

2. The method of claim 1, wherein the airway neutrophilia or acute lung inflammation or both are chronic obstructive pulmonary disease, severe neutrophilic asthma, or both.

3. The method of claim 1, wherein the human antibody molecule comprises a heavy chain variable region comprising the amino acid sequence of SEQ ID NO: 108 and a light chain variable region comprising the amino acid sequence of SEQ ID NO: 110.

4. The method of claim 1, wherein the human antibody molecule comprises a human IgG1 heavy chain constant region.

5. The method of claim 4, wherein the human IgG1 heavy chain constant region comprises the amino acid sequence of SEQ ID NO: 122 or 124.

6. The method of claim 1, wherein the human antibody molecule comprises a human IgG2 heavy chain constant region.

7. The method of claim 6, wherein the human IgG2 heavy chain constant region comprises the amino acid sequence of SEQ ID NO: 120.

8. The method of claim 1, wherein the human antibody molecule comprises a human IgG4 heavy chain constant region.

9. The method of claim 1, wherein the human antibody molecule is an Fab fragment, an F(ab)$_2$ fragment, or a single chain antibody.

10. A method of blocking chemotaxis migration of neutrophils into the lungs of a subject, the method comprising exposing neutrophils to a human antibody molecule that immunospecifically binds to human CXCR2 and comprises a heavy chain CDR1 comprising the amino acid sequence of SEQ ID NO: 182, a heavy chain CDR2 comprising the amino acid sequence of SEQ ID NO: 192, a heavy chain CDR3 comprising the amino acid sequence of SEQ ID NO: 195, a light chain CDR1 comprising the amino acid sequence of SEQ ID NO: 201, a light chain CDR2 comprising the amino acid sequence of SEQ ID NO: 205, and a light chain CDR3 comprising the amino acid sequence of SEQ ID NO: 213 to thereby block chemotaxis migration of the neutrophils into the lungs.

11. The method of claim 10, wherein the human antibody molecule comprises a heavy chain variable region comprising the amino acid sequence of SEQ ID NO: 108 and a light chain variable region comprising the amino acid sequence of SEQ ID NO: 110.

12. The method of claim 10, wherein the human antibody molecule comprises a human IgG1 heavy chain constant region.

13. The method of claim 12, wherein the human IgG1 heavy chain constant region comprises the amino acid sequence of SEQ ID NO: 122 or 124.

14. The method of claim 10, wherein the human antibody molecule comprises a human IgG2 heavy chain constant region.

15. The method of claim 14, wherein the human IgG2 heavy chain constant region comprises the amino acid sequence of SEQ ID NO: 120.

16. The method of claim 10, wherein the human antibody molecule comprises a human IgG4 heavy chain constant region.

17. The method of claim 10, wherein the human antibody molecule is an Fab fragment, an F(ab)2 fragment, or a single chain antibody.

18. A method of blocking CXCR2 mediated beta-arrestin signaling or CXCR2 mediated calcium flux in response to CXCL1 and/or CXCL5 in a cell expressing CXCR2 in vitro, the method comprising exposing the cell to a human antibody molecule that immunospecifically binds to human CXCR2 and comprises a heavy chain CDR1 comprising the amino acid sequence of SEQ ID NO: 182, a heavy chain CDR2 comprising the amino acid sequence of SEQ ID NO: 192, a heavy chain CDR3 comprising the amino acid sequence of SEQ ID NO: 195, a light chain CDR1 comprising the amino acid sequence of SEQ ID NO: 201, a light chain CDR2 comprising the amino acid sequence of SEQ ID NO: 205, and a light chain CDR3 comprising the amino acid sequence of SEQ ID NO: 213 to thereby block the CXCR2 mediated beta-arrestin signaling or CXCR2 mediated calcium flux.

19. The method of claim 18, wherein the human antibody molecule comprises a heavy chain variable region comprising the amino acid sequence of SEQ ID NO: 108 and a light chain variable region comprising the amino acid sequence of SEQ ID NO: 110.

20. The method of claim 18, wherein the human antibody molecule comprises a human IgG1 heavy chain constant region.

21. The method of claim 20, wherein the human IgG1 heavy chain constant region comprises the amino acid sequence of SEQ ID NO: 122 or 124.

22. The method of claim 18, wherein the antibody comprises a human IgG2 heavy chain constant region.

23. The method of claim 22, wherein the human IgG2 heavy chain constant region comprises the amino acid sequence of SEQ ID NO: 120.

24. The method of claim 18, wherein the antibody comprises a human IgG4 heavy chain constant region.

25. The method of claim 18, wherein the antibody molecule is an Fab fragment, an F(ab)$_2$ fragment, or a single chain antibody.

* * * * *

SEQUENCE LISTING

<160> NUMBER OF SEQ ID NOS: 256

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_1A1_VH

<400> SEQUENCE: 1

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Thr Ser
            20                  25                  30

Ser Tyr Tyr Trp Gly Trp Ile Arg Gln Pro Pro Gly Lys Gly Leu Glu
        35                  40                  45

Tyr Ile Gly Ser Ile Tyr Tyr Ser Gly Thr Thr Tyr Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Met Ser Ser Val Thr Ala Ala Asp Ser Ala Val Tyr Tyr
                85                  90                  95

Cys Ala Arg His Gly Arg Val Arg Glu Val Pro Pro Phe Asp Tyr Trp
            100                 105                 110

Gly Gln Gly Thr Leu Val Thr Val Ser Ser
        115                 120

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_1A1_VL

<400> SEQUENCE: 2

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Tyr Tyr Tyr Ala
            20                  25                  30

Ser Trp Tyr Gln Gln Lys Pro Gly Gln Ala Pro Val Leu Val Ile Tyr
        35                  40                  45

Asp Glu Asn Ser Arg Pro Ser Gly Ile Pro Asp Arg Phe Ser Gly Ser
    50                  55                  60

Ser Ser Gly Asn Thr Ala Ser Leu Ser Ile Thr Gly Thr Gln Ala Glu
65                  70                  75                  80

Asp Glu Ala Asp Tyr Tyr Cys Asn Ser Arg Asp Thr Ser Gly Asn His
                85                  90                  95

Trp Ala Phe Gly Gly Gly Thr Lys Leu Thr Val Leu
            100                 105

<210> SEQ ID NO 3
<211> LENGTH: 122
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: BKO_1B10_VH

<400> SEQUENCE: 3

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Thr Ser
            20                  25                  30

Ser Tyr Tyr Trp Gly Trp Ile Arg Gln Pro Pro Gly Lys Gly Leu Glu
        35                  40                  45

Tyr Ile Gly Ser Ile Tyr Tyr Ser Gly Thr Thr Tyr Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Gly Arg Val Arg Glu Val Pro Pro Phe Asp Tyr Trp
            100                 105                 110

Gly Gln Gly Thr Leu Val Thr Val Ser Ser
        115                 120

<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_1B10_VL

<400> SEQUENCE: 4

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Tyr Tyr Tyr Ala
            20                  25                  30

Ser Trp Tyr Gln Gln Lys Pro Gly Gln Ala Pro Val Leu Val Ile Tyr
        35                  40                  45

Asp Glu Asn Ser Arg Pro Ser Gly Ile Pro Asp Arg Phe Ser Gly Ser
    50                  55                  60

Ser Ser Gly Asn Thr Ala Ser Leu Arg Ile Thr Gly Thr Gln Ala Glu
65                  70                  75                  80

Asp Glu Ala Asp Tyr Tyr Cys Asn Ser Arg Asp Thr Ser Gly Asn His
                85                  90                  95

Trp Ala Phe Gly Gly Gly Thr Lys Leu Thr Val Leu
            100                 105

<210> SEQ ID NO 5
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_1D1_VH

<400> SEQUENCE: 5

Glu Val Gln Leu Leu Glu Ser Gly Gly Gly Leu Val Gln Pro Gly Gly

```
1               5                   10                  15
Ser Leu Arg Leu Ser Cys Ala Ala Ser Lys Leu Thr Phe Lys Asn Ser
            20                  25                  30

Ala Met Ser Trp Val Arg Gln Ala Pro Gly Lys Gly Leu Glu Trp Val
            35                  40                  45

Ser Ala Ile Thr Gly Ser Gly Gly Arg Thr Tyr Tyr Ala Asp Ser Val
            50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Ile Tyr Tyr Cys
            85                  90                  95

Ala Ile Gln Met Gly Tyr Trp Gly Gln Gly Ile Leu Val Thr Val Ser
            100                 105                 110

Ser
```

<210> SEQ ID NO 6
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_1D1_VL

<400> SEQUENCE: 6

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Glu Val Asn Lys Arg Pro Ser Gly Val Pro Ala Arg Phe
            50                  55                  60

Ser Gly Ser Lys Ser Gly Asn Thr Ala Ser Leu Thr Val Ser Gly Leu
65                      70                  75                  80

Gln Ala Glu Asp Glu Ala Asp Tyr Tyr Cys Ser Ser Tyr Ala Gly Ser
            85                  90                  95

Asn Asn Phe Gly Val Phe Gly Gly Gly Thr Lys Leu Thr Val Leu
            100                 105                 110
```

<210> SEQ ID NO 7
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_1H3_VH

<400> SEQUENCE: 7

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Arg Ser
            20                  25                  30

Ser Thr Ser Trp Val Arg Gln Thr Pro Gly Lys Gly Leu Glu Trp Val
            35                  40                  45

Ser Ala Ile Ser Gly Ser Gly Gly Arg Thr Tyr Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Ile Gln Leu Gly Tyr Trp Gly Gln Gly Ile Leu Val Thr Val Ser
                    100                 105                 110

Ser
```

```
<210> SEQ ID NO 8
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_1H3_VL

<400> SEQUENCE: 8

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                    20                  25                  30

Asn Tyr Val Ser Trp Tyr Gln Gln His Pro Gly Lys Ala Pro Lys Leu
                    35                  40                  45

Met Ile Tyr Asp Val Ser Asn Arg Pro Ser Gly Val Ser Asn Arg Phe
                    50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                     85                  90                  95

Ser Thr Trp Val Phe Gly Gly Gly Thr Lys Leu Thr Val Leu
                    100                 105                 110
```

```
<210> SEQ ID NO 9
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_2D8_VH

<400> SEQUENCE: 9

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Thr Phe Thr Ser Ser
                    20                  25                  30

Thr Met Ser Trp Val Arg Gln Ala Pro Gly Lys Gly Leu Glu Trp Val
                    35                  40                  45

Thr Ala Ile Ser Gly Arg Gly Gly Arg Thr Tyr Tyr Ala Asp Ser Val
                    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Ile Gln Leu Gly Asn Trp Gly Gln Gly Ile Leu Val Thr Val Ser
```

Ser

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_2D8_VL

<400> SEQUENCE: 10

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Val Ile Tyr Glu Val Asn Met Arg Pro Ser Gly Val Pro Ala Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asp Asn Phe Gly Val Phe Gly Gly Gly Thr Lys Leu Ser Val Leu
            100                 105                 110

<210> SEQ ID NO 11
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_3A9_VH

<400> SEQUENCE: 11

Gln Val Gln Val Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Leu Lys Arg Arg Ile Thr Ile Arg Pro Asp Thr Ser Arg Asn
65                  70                  75                  80

His Phe Ser Leu His Leu Ser Ser Val Thr Pro Glu Asp Thr Ala Val
                85                  90                  95

Tyr Tyr Cys Val Arg Ala Tyr Cys Gly Gly Gly Ser Cys Leu Asp Tyr
            100                 105                 110

Trp Gly Gln Gly Thr Leu Val Thr Val Ser Ser
        115                 120

<210> SEQ ID NO 12
<211> LENGTH: 110
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_3A9_L3_E03_VL

<400> SEQUENCE: 12

```
Gln Ser Ala Leu Thr Gln Pro Ala Ser Ala Ser Gly Ser Pro Gly Gln
1               5                   10                  15

Ser Ile Thr Ile Ser Cys Thr Gly Thr Ser Ser Asp Val Gly Asn Tyr
            20                  25                  30

Asn Arg Val Ser Trp Tyr Gln Gln His Pro Gly Lys Val Pro Lys Leu
        35                  40                  45

Met Ile Tyr Glu Gly Ser Lys Arg Pro Ser Gly Ile Ser Asn Arg Phe
    50                  55                  60

Ser Gly Ser Lys Ser Gly Asn Thr Ala Ser Leu Thr Ile Ser Gly Leu
65              70                  75                  80

Gln Pro Glu Asp Glu Ala Asp Tyr Phe Cys Cys Ser Tyr Ala Gly Ser
                85                  90                  95

Asn Thr Leu Val Phe Gly Gly Gly Thr Lys Leu Thr Val Leu
            100                 105                 110
```

<210> SEQ ID NO 13
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_3D6_VH

<400> SEQUENCE: 13

```
Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Lys Trp Val
        35                  40                  45

Ser Gly Ile Thr Trp Asn Ser Gly Asn Lys Arg Tyr Ala Asp Ser Val
    50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Leu Tyr Tyr Cys
                85                  90                  95

Ala Lys Asp Met Lys Gly Ser Gly Thr Tyr Phe Pro Ala Phe Asp Tyr
                100                 105                 110

Trp Gly Gln Gly Thr Leu Val Thr Val Ser Ser
        115                 120
```

<210> SEQ ID NO 14
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_3D6_L6_G06_VL (BKO_5H4_VL)

<400> SEQUENCE: 14

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105
```

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_3F4_VH

<400> SEQUENCE: 15

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Lys Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Val Gly Tyr Trp Gly Gln Gly Thr Leu Val Thr Val Ser
            100                 105                 110

Ser
```

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_3F4_L11_A11_VL

<400> SEQUENCE: 16

```
Gln Ser Ala Leu Thr Gln Pro Pro Ser Ala Ser Gly Ser Pro Gly Gln
1               5                   10                  15

Ser Val Thr Met Ser Cys Thr Gly Thr Ser Ser Asp Val Gly Gly Tyr
            20                  25                  30

Asn Tyr Val Thr Trp Tyr Gln Gln His Pro Gly Lys Ala Pro Lys Leu
        35                  40                  45
```

```
Met Ile Tyr Glu Val Ser Lys Arg Pro Ser Gly Val Pro Ala Arg Phe
        50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Pro
                 85                  90                  95

Asn Asn Phe Gly Val Phe Gly Gly Gly Thr Lys Leu Thr Val Leu
            100                 105                 110
```

<210> SEQ ID NO 17
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_4A8_VH

<400> SEQUENCE: 17

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Ser
                20                  25                  30

Thr Met Ser Trp Val Arg Gln Ala Pro Gly Lys Gly Leu Glu Trp Val
            35                  40                  45

Ser Ala Ile Ser Gly Arg Gly Arg Asn Thr Tyr Tyr Ala Asp Ser Val
        50                  55                  60

Lys Gly Arg Phe Thr Ile Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Gln Met Gly Tyr Trp Gly Gln Gly Ile Leu Val Thr Val Ser
            100                 105                 110

Ser
```

<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_4A8_VL

<400> SEQUENCE: 18

```
Gln Ser Ala Leu Thr Gln Pro Pro Ser Ala Ser Gly Ser Pro Gly Gln
 1               5                  10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
            35                  40                  45

Met Ile Tyr Glu Val Asn Lys Arg Pro Ser Gly Val Pro Asp Arg Phe
        50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Asn
                 85                  90                  95
```

Asn Asn Phe Gly Val Phe Gly Gly Gly Thr Lys Leu Thr Val Leu
            100                 105                 110

<210> SEQ ID NO 19
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_4F10_VH

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
            35                  40                  45

Gly Arg Phe Asn Pro Asn Asn Gly Gly Thr Asn Tyr Ala Gln Arg Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Pro Thr Ile Arg Leu Trp Phe Asp Asn Trp Phe Asp Ser
            100                 105                 110

Trp Gly Gln Gly Thr Leu Val Thr Val Ser Ser
            115                 120

<210> SEQ ID NO 20
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_4F10_VL

<400> SEQUENCE: 20

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Ile Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 21
<211> LENGTH: 122
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_5E8_H5_C05_VH

<400> SEQUENCE: 21
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

Ser Leu Arg Leu Ser Cys Ala Ala Ser Gly Phe Thr Phe Ser Ser Tyr
            20                  25                  30

Ala Met Ser Trp Val Arg Gln Ala Pro Gly Arg Gly Leu Glu Trp Val
        35                  40                  45

Ser Ala Ile Arg Gly Ser Gly Ala Gly Thr Tyr Tyr Ala Asp Ser Met
    50                  55                  60

Lys Gly Arg Phe Thr Ile Ser Arg Asp Asn Ser Lys Asp Thr Leu Tyr
65                  70                  75                  80

Leu Leu Met Asn Ser Leu Arg Ala Glu Asp Thr Ala Val Tyr Tyr Cys
                85                  90                  95

Ser Lys Leu Glu Ala Val Ser Gly Thr Gly Lys Tyr Phe Gln His Trp
            100                 105                 110

Gly Gln Gly Thr Leu Val Thr Val Ser Ser
        115                 120

```
<210> SEQ ID NO 22
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_5E8_L3_C03_VL

<400> SEQUENCE: 22
```

Ser Tyr Glu Leu Thr Gln Pro Pro Ser Val Ser Val Ser Pro Gly Gln
1               5                   10                  15

Thr Ala Asn Ile Thr Cys Ser Gly Asp Thr Leu Gly Asp Lys Phe Ala
            20                  25                  30

Cys Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
    50                  55                  60

Lys Ser Gly Ile Thr Ala Thr Leu Thr Ile Ser Gly Thr Gln Ala Met
65                  70                  75                  80

Asp Glu Ala Asp Phe Tyr Cys Gln Ala Trp Asn Ser Arg Gly Val Val
                85                  90                  95

Phe Gly Gly Gly Thr Arg Leu Thr Val Leu
            100                 105

```
<210> SEQ ID NO 23
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_5G11_VH

<400> SEQUENCE: 23
```

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Ala Ile Ser Gly Arg Gly Ser Arg Thr Tyr Tyr Ala Asp Ser Val
50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Asp Tyr Trp Gly Gln Gly Thr Leu Val Thr Val Ser Ser
            100                 105                 110

<210> SEQ ID NO 24
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_5G11_VL

<400> SEQUENCE: 24

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Phe Glu Val Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe Gly Val Phe Gly Gly Gly Thr Lys Leu Thr Val Leu
            100                 105                 110

<210> SEQ ID NO 25
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_5G6_VH

<400> SEQUENCE: 25

Gln Val Gln Leu Val Gln Ser Gly Ala Glu Val Thr Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Arg Phe Asn Pro Asn Asn Gly Gly Thr Asn Tyr Ala Gln Arg Phe

```
                    50                  55                  60
Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                     85                  90                  95

Ala Arg Gly Pro Thr Ile Arg Leu Trp Phe Asp Asn Trp Phe Asp Ser
                100                 105                 110

Trp Gly Gln Gly Thr Leu Val Thr Val Ser Ser
            115                 120
```

<210> SEQ ID NO 26
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_5G6_L12_E12_VL

<400> SEQUENCE: 26

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Ile Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Trp Val Phe Gly Gly Gly Thr Thr Leu Thr Val Leu
            100                 105                 110
```

<210> SEQ ID NO 27
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_6A1_H4_A04_VH

<400> SEQUENCE: 27

```
Gln Val Gln Leu Lys Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                20                  25                  30

Tyr Trp Thr Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
 50                  55                  60

Ser Arg Val Thr Met Ser Val Asp Thr Ser Lys Asn Gln Phe Ser Leu
 65                  70                  75                  80

Lys Leu Arg Ser Val Thr Ala Ala Asp Thr Ala Val Tyr Tyr Cys Ala
                 85                  90                  95
```

```
Arg Gly Glu Val Arg Gly Leu Ile Thr Leu Tyr Trp Tyr Phe Asp Val
            100                 105                 110

Trp Gly Arg Gly Ser Leu Val Thr Val Ser Ser
        115                 120

<210> SEQ ID NO 28
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_6A1_E10_VL

<400> SEQUENCE: 28

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105

<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_6A2_H1_B01_VH

<400> SEQUENCE: 29

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Asp Ile His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Gly Tyr Asn Tyr Gly Tyr Gly Tyr Trp Gly Gln
            100                 105                 110

Gly Thr Leu Val Thr Val Ser Ser
        115                 120

<210> SEQ ID NO 30
```

<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_6A2_L6_A06_VL

<400> SEQUENCE: 30

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 31
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_7C11_H6_B06_VH

<400> SEQUENCE: 31

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Arg Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Glu Val Arg Gly Val Phe Thr Leu Tyr Trp Tyr Phe Asp Val
            100                 105                 110

Trp Gly Arg Gly Thr Leu Val Thr Val Ser Ser
        115                 120

<210> SEQ ID NO 32
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_7C11_G01_VL

<400> SEQUENCE: 32

Ser Ser Glu Leu Thr Gln Gly Pro Ala Val Ser Val Ala Leu Gly Gln
1               5                   10                  15

Thr Val Arg Ile Thr Cys Gln Gly Asn Ser Leu Arg Phe Tyr Tyr Ala
            20                  25                  30

Ser Trp Tyr Gln Gln Arg Pro Gly Gln Ala Pro Ile Leu Val Ile Tyr
        35                  40                  45

Asp Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Tyr Tyr
                85                  90                  95

Met Ile Phe Gly Gly Gly Thr Lys Leu Thr Val Leu
            100                 105

<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_7G10_H1_B01_VH

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Ala Ile Ser Gly Arg Gly Ser Arg Thr Tyr Tyr Ala Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Asp Tyr Trp Gly Gln Gly Thr Leu Val Thr Val Ser Ser
            100                 105                 110

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_7G10_L6_E06_VL

<400> SEQUENCE: 34

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

```
Met Ile Phe Glu Val Ser Lys Arg Pro Ser Gly Val Pro Asp Arg Phe
            50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                 85                  90                  95

Asn Asn Phe Gly Val Phe Gly Gly Gly Thr Lys Leu Thr Val Leu
            100                 105                 110

<210> SEQ ID NO 35
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_7H8_H3_C03_VH

<400> SEQUENCE: 35

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Thr Phe Thr Ser Ser
             20                  25                  30

Thr Met Ser Trp Val Arg Gln Ala Pro Gly Lys Gly Leu Glu Trp Val
         35                  40                  45

Thr Ala Ile Ser Gly Arg Gly Gly Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Gln Leu Gly Asn Trp Gly Gln Gly Ile Leu Val Thr Val Ser
            100                 105                 110

Ser

<210> SEQ ID NO 36
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_7H8_L10_F10_VL

<400> SEQUENCE: 36

Gln Ser Ala Leu Thr Gln Pro Pro Ser Ala Ser Gly Ser Pro Gly Gln
 1               5                  10                  15

Ser Val Thr Ile Ser Cys Thr Gly Thr Ser Ser Asp Ile Gly Gly Tyr
             20                  25                  30

Asn Tyr Val Ser Trp Tyr Gln Gln His Pro Gly Lys Ala Pro Lys Leu
         35                  40                  45

Val Ile Tyr Glu Val Asn Met Arg Pro Ser Gly Val Pro Ala Arg Phe
     50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Asn
                 85                  90                  95
```

Asp Asn Phe Gly Val Phe Gly Gly Gly Thr Lys Leu Ser Val Leu
            100                 105                 110

<210> SEQ ID NO 37
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_8B6_VH

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ser Ala Ile Ser Asn Ser Gly Arg Ser Thr Tyr Tyr Ala Asp Ser Val
    50                  55                  60

Lys Gly Arg Phe Thr Ile Ser Arg Asp Ser Ser Lys Asn Thr Leu Tyr
65                  70                  75                  80

Leu Leu Met Asn Ser Leu Arg Ala Glu Asp Ser Ala Val Tyr Tyr Cys
                85                  90                  95

Ala Ile Lys Leu Gly Tyr Trp Gly Gln Gly Ser Leu Val Thr Val Ser
            100                 105                 110

Ser

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_8B6_VL

<400> SEQUENCE: 38

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Met Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asp Asn Phe Gly Val Phe Gly Gly Gly Thr Arg Leu Thr Val Leu
            100                 105                 110

<210> SEQ ID NO 39
<211> LENGTH: 122
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: BKO_8C4_VH

<400> SEQUENCE: 39

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Thr Ser
            20                  25                  30

Ser Tyr Tyr Trp Gly Trp Ile Arg Gln Pro Pro Gly Lys Gly Leu Glu
        35                  40                  45

Tyr Ile Gly Ser Ile Tyr Tyr Ser Gly Thr Thr Tyr Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Gly Arg Val Arg Glu Val Pro Pro Phe Asp Tyr Trp
            100                 105                 110

Gly Gln Gly Thr Leu Val Thr Val Ser Ser
        115                 120

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_8C4_VL

<400> SEQUENCE: 40

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Tyr Tyr Tyr Ala
            20                  25                  30

Ser Trp Tyr Gln Gln Lys Pro Gly Gln Ala Pro Val Leu Val Ile Tyr
        35                  40                  45

Asp Glu Asn Ser Arg Pro Ser Gly Ile Pro Asp Arg Phe Ser Gly Ser
    50                  55                  60

Ser Ser Gly Asn Thr Ala Ser Leu Arg Ile Thr Gly Thr Gln Ala Glu
65                  70                  75                  80

Asp Glu Ala Asp Tyr Tyr Cys Asn Ser Arg Asp Thr Ser Gly Asn His
                85                  90                  95

Trp Ala Phe Gly Gly Gly Thr Lys Leu Thr Val Leu
            100                 105

<210> SEQ ID NO 41
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_8G3_H4_D04_VH

<400> SEQUENCE: 41
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Thr Gly Ser Gly Gly Ser Thr Tyr Tyr Ala Asp Ser Val
50                  55                  60

Lys Gly Arg Phe Thr Ile Ser Arg Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Arg Leu Gly Tyr Trp Gly Gln Gly Ser Leu Val Thr Val Ser
            100                 105                 110

Ser
```

<210> SEQ ID NO 42
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_8G3_L1_G01_VL

<400> SEQUENCE: 42

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Val Pro Lys Leu
        35                  40                  45

Val Ile Tyr Glu Val Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe Gly Val Phe Gly Gly Gly Thr Lys Leu Thr Val Leu
            100                 105                 110
```

<210> SEQ ID NO 43
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_8H10_VH

<400> SEQUENCE: 43

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45
```

Gly Arg Ile Lys Pro Asp Ser Gly Gly Thr Asn Tyr Ala Gln Lys Phe
            50                  55                  60

Gln Gly Arg Val Thr Met Thr Arg Asp Thr Ser Ile Thr Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Ser Gly Trp Asp Tyr Trp Gly Gln Gly Thr Leu Val
            100                 105                 110

Thr Val Ser Ser
            115

<210> SEQ ID NO 44
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_8H10_VL

<400> SEQUENCE: 44

Gln Ser Ala Leu Thr Gln Pro Pro Ser Ala Ser Gly Ser Pro Gly Gln
1               5                   10                  15

Ser Val Thr Ile Ser Phe Thr Gly Thr Ser Arg Asp Val Gly Asp Tyr
                20                  25                  30

Asn Tyr Val Ser Trp Tyr Gln Gln His Pro Gly Lys Ala Pro Lys Leu
            35                  40                  45

Met Ile Tyr Glu Val Asn Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Thr Tyr Val Phe Gly Thr Gly Thr Lys Val Thr Val Leu
            100                 105                 110

<210> SEQ ID NO 45
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_8H8_H5_E05_VH

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Val Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Lys Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Val Tyr Tyr Cys
                85                  90                  95

```
Ala Ile Gln Val Gly Tyr Trp Gly Gln Gly Thr Leu Val Thr Val Ser
            100                 105                 110

Ser

<210> SEQ ID NO 46
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_8H8_L7_H08_VL

<400> SEQUENCE: 46

Gln Ser Ala Leu Thr Gln Pro Pro Ser Ala Ser Gly Ser Pro Gly Gln
1               5                   10                  15

Ser Val Thr Met Ser Cys Thr Gly Thr Ser Ser Asp Val Gly Gly Tyr
            20                  25                  30

Asn Tyr Val Thr Trp Tyr Gln Gln His Pro Gly Lys Ala Pro Lys Leu
        35                  40                  45

Val Ile Tyr Glu Val Ser Lys Arg Pro Ser Gly Val Pro Val Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Pro
                85                  90                  95

Asn Asn Phe Gly Ile Phe Gly Gly Gly Thr Lys Leu Thr Val Leu
            100                 105                 110

<210> SEQ ID NO 47
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_9A8_H3_F03_VH

<400> SEQUENCE: 47

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Ser Asn
            20                  25                  30

Thr Met Ser Trp Val Arg Gln Ala Pro Gly Lys Gly Leu Glu Trp Val
        35                  40                  45

Ser Ala Ile Ser Gly Ser Gly Arg Thr Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Ala Glu Asp Thr Ala Val Tyr Tyr Cys
                85                  90                  95

Ala Ile Gln Leu Gly Ser Trp Gly Gln Gly Ile Leu Val Thr Val Ser
            100                 105                 110

Ser

<210> SEQ ID NO 48
<211> LENGTH: 111
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_9A8_L1_H02_VL

<400> SEQUENCE: 48
```

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Glu Val Thr Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Val Phe Gly Gly Gly Thr Lys Leu Thr Val Leu
            100                 105                 110

```
<210> SEQ ID NO 49
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_9C3_H8_G08_VH

<400> SEQUENCE: 49
```

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Leu Gly Tyr Trp Gly Gln Gly Thr Leu Val Thr Val Ser
            100                 105                 110

Ser

```
<210> SEQ ID NO 50
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_9C3_L1_F01_VL

<400> SEQUENCE: 50
```

Gln Ser Ala Leu Thr Gln Pro Pro Ser Ala Ser Gly Ser Pro Gly Gln
1               5                   10                  15

Ser Val Ile Ile Ser Cys Thr Gly Thr Ser Ser Asp Val Gly Gly Tyr
                20                  25                  30

Asn Tyr Val Ser Trp Tyr Gln Gln His Pro Gly Lys Val Pro Lys Leu
            35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65              70                  75                  80

Gln Ala Glu Asp Glu Ala Asp Tyr Tyr Cys Thr Ser Tyr Ala Gly Ser
                85                  90                  95

Asn Asn Phe Gly Val Phe Gly Gly Gly Thr Lys Leu Thr Val Leu
            100                 105                 110

<210> SEQ ID NO 51
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_10G10_VH

<400> SEQUENCE: 51

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Arg Ser
                20                  25                  30

Ser Tyr Tyr Trp Gly Trp Ile Arg Gln Pro Pro Gly Lys Gly Leu Glu
            35                  40                  45

Trp Ile Gly Ser Phe Tyr Asn Ser Gly Asn Thr Tyr Tyr Lys Pro Ser
    50                  55                  60

Leu Lys Ser Arg Val Ala Ile Ser Val Asp Thr Pro Lys Asn Gln Phe
65              70                  75                  80

Ser Leu Lys Leu Ser Ser Val Thr Ala Ala Asp Thr Ala Val Tyr Tyr
                85                  90                  95

Cys Ala Arg Gly Tyr Ser Ser Gly Gly Phe Asp Pro Trp Gly Gln Gly
            100                 105                 110

Thr Leu Val Thr Val Ser Ser
        115

<210> SEQ ID NO 52
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO_10G10_VL

<400> SEQUENCE: 52

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Cys Gln Gln His Pro Gly Lys Ala Pro Lys Ile

```
                35                  40                  45
Met Ile Phe Asp Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Trp Val Phe Gly Gly Gly Thr Arg Leu Thr Val Leu
            100                 105                 110
```

<210> SEQ ID NO 53
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH S32Q

<400> SEQUENCE: 53

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Gln
             20                  25                  30

Thr Met Ser Trp Val Arg Gln Ala Pro Gly Lys Gly Leu Glu Trp Val
             35                  40                  45

Ser Ala Ile Ser Gly Arg Gly Arg Asn Thr Tyr Tyr Ala Asp Ser Val
     50                  55                  60

Lys Gly Arg Phe Thr Ile Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Gln Met Gly Tyr Trp Gly Gln Gly Ile Leu Val Thr Val Ser
            100                 105                 110

Ser
```

<210> SEQ ID NO 54
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH S32H

<400> SEQUENCE: 54

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
             20                  25                  30

Thr Met Ser Trp Val Arg Gln Ala Pro Gly Lys Gly Leu Glu Trp Val
             35                  40                  45

Ser Ala Ile Ser Gly Arg Gly Arg Asn Thr Tyr Tyr Ala Asp Ser Val
     50                  55                  60

Lys Gly Arg Phe Thr Ile Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
```

```
                            85                  90                  95

Ala Ile Gln Met Gly Tyr Trp Gly Gln Gly Ile Leu Val Thr Val Ser
                100                 105                 110

Ser

<210> SEQ ID NO 55
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH S32L

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Leu
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
                100                 105                 110

Ser

<210> SEQ ID NO 56
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH S32W

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Trp
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
                100                 105                 110

Ser
```

<210> SEQ ID NO 57
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: 4A8 VH S32Y

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 58
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH T33A

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 59
<211> LENGTH: 113
<212> TYPE: PRT
<213> ORGANISM: Artificial Sequence
<220> FEATURE:
<223> OTHER INFORMATION: Description of Artificial Sequence: Synthetic -continued

<220> FEATURE:
<223> OTHER INFORMATION: 4A8 VH M34Q

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Gln Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 60
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH M34D

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Asp Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 61
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH M34H

<400> SEQUENCE: 61

Glu Val Gln Leu Leu Glu Ser Gly Gly Gly Leu Val Gln Pro Gly Gly

```
                1               5                  10                 15
Ser Leu Arg Leu Ser Cys Ala Ala Ser Gly Phe Thr Phe Ser Ser Ser
            20                  25                 30

Thr His Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
        50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
            85                  90                  95

Ala Ile Gln Met Gly Tyr Trp Gly Gln Gly Ile Leu Val Thr Val Ser
            100                 105                110

Ser
```

<210> SEQ ID NO 62
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH M34W

<400> SEQUENCE: 62

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Trp Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
        50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
            85                  90                  95

Ala Ile Gln Met Gly Tyr Trp Gly Gln Gly Ile Leu Val Thr Val Ser
            100                 105                 110

Ser
```

<210> SEQ ID NO 63
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH I51H

<400> SEQUENCE: 63

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45
```

Ser Ala His Ser Gly Arg Gly Arg Asn Thr Tyr Tyr Ala Asp Ser Val
            50                  55                  60

Lys Gly Arg Phe Thr Ile Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Gln Met Gly Tyr Trp Gly Gln Gly Ile Leu Val Thr Val Ser
            100                 105                 110

Ser

<210> SEQ ID NO 64
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH G52aD

<400> SEQUENCE: 64

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
            35                  40                  45

Ser Ala Ile Ser Asp Arg Gly Arg Asn Thr Tyr Tyr Ala Asp Ser Val
            50                  55                  60

Lys Gly Arg Phe Thr Ile Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Gln Met Gly Tyr Trp Gly Gln Gly Ile Leu Val Thr Val Ser
            100                 105                 110

Ser

<210> SEQ ID NO 65
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH R53S

<400> SEQUENCE: 65

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
            35                  40                  45

Ser Ala Ile Ser Gly Ser Gly Arg Asn Thr Tyr Tyr Ala Asp Ser Val
            50                  55                  60

Lys Gly Arg Phe Thr Ile Ser Arg Asp Asn Ser Arg Asn Thr Leu Tyr
 65                  70                  75                  80

```
Leu Gln Met Asn Ser Leu Arg Ala Glu Asp Thr Ala Val Tyr Tyr Cys
            85                  90                  95

Ala Ile Gln Met Gly Tyr Trp Gly Gln Gly Ile Leu Val Thr Val Ser
            100                 105                 110

Ser

<210> SEQ ID NO 66
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH R53Q

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
            35                  40                  45

Ser Ala Ile Ser Gly Gln Gly Arg Asn Thr Tyr Tyr Ala Asp Ser Val
            50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
            85                  90                  95

Ala Ile Gln Met Gly Tyr Trp Gly Gln Gly Ile Leu Val Thr Val Ser
            100                 105                 110

Ser

<210> SEQ ID NO 67
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH G54D

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
            35                  40                  45

Ser Ala Ile Ser Gly Arg Asp Arg Asn Thr Tyr Tyr Ala Asp Ser Val
            50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
            85                  90                  95

Ala Ile Gln Met Gly Tyr Trp Gly Gln Gly Ile Leu Val Thr Val Ser
            100                 105                 110

Ser
```

<210> SEQ ID NO 68
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH N56S

<400> SEQUENCE: 68

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Ser Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser
```

<210> SEQ ID NO 69
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH I94K

<400> SEQUENCE: 69

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Met Gly Tyr Trp Gly Gln Gly Ile Leu Val Thr Val Ser
            100                 105                 110

Ser
```

<210> SEQ ID NO 70
<211> LENGTH: 113
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: 4A8 VH M96A

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Ala Gly Tyr Trp Gly Gln Gly Ile Leu Val Thr Val Ser
            100                 105                 110

Ser

<210> SEQ ID NO 71
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH M96Q

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Gln Gly Tyr Trp Gly Gln Gly Ile Leu Val Thr Val Ser
            100                 105                 110

Ser

<210> SEQ ID NO 72
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH M96K

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Lys Gly Tyr Trp Gly Gln Gly Ile Leu Val Thr Val Ser
            100                 105                 110

Ser
```

<210> SEQ ID NO 73
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH G101D

<400> SEQUENCE: 73

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Asp Tyr Trp Gly Gln Gly Ile Leu Val Thr Val Ser
            100                 105                 110

Ser
```

<210> SEQ ID NO 74
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Y102S

<400> SEQUENCE: 74

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
```

```
              35                  40                  45
Ser Ala Ile Ser Gly Arg Gly Arg Asn Thr Tyr Tyr Ala Asp Ser Val
         50                  55                  60
Lys Gly Arg Phe Thr Ile Ser Arg Asp Asn Ser Arg Asn Thr Leu Tyr
 65                  70                  75                  80
Leu Gln Met Asn Ser Leu Arg Ala Glu Asp Thr Ala Val Tyr Tyr Cys
                 85                  90                  95
Ala Ile Gln Met Gly Ser Trp Gly Gln Gly Ile Leu Val Thr Val Ser
                100                 105                 110
Ser
```

<210> SEQ ID NO 75
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Y102K

<400> SEQUENCE: 75

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Ser
             20                  25                  30
Thr Met Ser Trp Val Arg Gln Ala Pro Gly Lys Gly Leu Glu Trp Val
         35                  40                  45
Ser Ala Ile Ser Gly Arg Gly Arg Asn Thr Tyr Tyr Ala Asp Ser Val
     50                  55                  60
Lys Gly Arg Phe Thr Ile Ser Arg Asp Asn Ser Arg Asn Thr Leu Tyr
 65                  70                  75                  80
Leu Gln Met Asn Ser Leu Arg Ala Glu Asp Thr Ala Val Tyr Tyr Cys
                 85                  90                  95
Ala Ile Gln Met Gly Lys Trp Gly Gln Gly Ile Leu Val Thr Val Ser
                100                 105                 110
Ser
```

<210> SEQ ID NO 76
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL E50D

<400> SEQUENCE: 76

```
Gln Ser Ala Leu Thr Gln Pro Pro Ser Ala Ser Gly Ser Pro Gly Gln
 1               5                  10                  15
Ser Val Thr Ile Ser Cys Ile Gly Thr Ser Ser Asp Val Gly Gly Tyr
             20                  25                  30
Asn Tyr Val Ser Trp Tyr Gln Gln His Pro Asp Lys Ala Pro Lys Leu
         35                  40                  45
Met Ile Tyr Asp Val Asn Lys Arg Pro Ser Gly Val Pro Asp Arg Phe
     50                  55                  60
Ser Gly Ser Lys Ser Gly Asn Thr Ala Ser Leu Thr Val Ser Gly Leu
 65                  70                  75                  80
```

Gln Ala Glu Asp Glu Ala Asp Tyr Tyr Cys Ser Ser Tyr Ala Gly Asn
                85                  90                  95

Asn Asn Phe Gly Val Phe Gly Gly Gly Thr Lys Leu Thr Val Leu
            100                 105                 110

<210> SEQ ID NO 77
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N52D

<400> SEQUENCE: 77

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
            35                  40                  45

Met Ile Tyr Glu Val Asp Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Val Phe Gly Gly Gly Thr Lys Leu Thr Val Leu
            100                 105                 110

<210> SEQ ID NO 78
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N52S

<400> SEQUENCE: 78

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
            35                  40                  45

Met Ile Tyr Glu Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Val Phe Gly Gly Gly Thr Lys Leu Thr Val Leu
            100                 105                 110

<210> SEQ ID NO 79
<211> LENGTH: 111
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL K53A

<400> SEQUENCE: 79

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Ala Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Val Phe Gly Gly Gly Thr Lys Leu Thr Val Leu
            100                 105                 110

<210> SEQ ID NO 80
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL K53D

<400> SEQUENCE: 80

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Asp Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Val Phe Gly Gly Gly Thr Lys Leu Thr Val Leu
            100                 105                 110

<210> SEQ ID NO 81
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL K53H

<400> SEQUENCE: 81

Gln Ser Ala Leu Thr Gln Pro Pro Ser Ala Ser Gly Ser Pro Gly Gln
1               5                   10                  15

-continued

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn His Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Asn
                 85                  90                  95

Asn Asn Phe Gly Val Phe Gly Gly Gly Thr Lys Leu Thr Val Leu
             100                 105                 110

<210> SEQ ID NO 82
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL R54Q

<400> SEQUENCE: 82

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Gln Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Asn
                 85                  90                  95

Asn Asn Phe Gly Val Phe Gly Gly Gly Thr Lys Leu Thr Val Leu
             100                 105                 110

<210> SEQ ID NO 83
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL Y91A

<400> SEQUENCE: 83

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
 50                  55                  60

Ser Gly Ser Lys Ser Gly Asn Thr Ala Ser Leu Thr Val Ser Gly Leu 65                  70                  75                  80
Gln Ala Glu Asp Glu Ala Asp Tyr Tyr Cys Ser Ser Ala Ala Gly Asn
                85                  90                  95

Asn Asn Phe Gly Val Phe Gly Gly Gly Thr Lys Leu Thr Val Leu
                100                 105                 110

<210> SEQ ID NO 84
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N94A

<400> SEQUENCE: 84

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
            35                  40                  45

Met Ile Tyr Glu Val Asn Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ala
                85                  90                  95

Asn Asn Phe Gly Val Phe Gly Gly Gly Thr Lys Leu Thr Val Leu
                100                 105                 110

<210> SEQ ID NO 85
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N94S

<400> SEQUENCE: 85

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
            35                  40                  45

Met Ile Tyr Glu Val Asn Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe Gly Val Phe Gly Gly Gly Thr Lys Leu Thr Val Leu
                100                 105                 110

<210> SEQ ID NO 86
<211> LENGTH: 111

-continued

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N94K

<400> SEQUENCE: 86

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Lys
                85                  90                  95

Asn Asn Phe Gly Val Phe Gly Gly Gly Thr Lys Leu Thr Val Leu
            100                 105                 110

<210> SEQ ID NO 87
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N94L

<400> SEQUENCE: 87

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Leu
                85                  90                  95

Asn Asn Phe Gly Val Phe Gly Gly Gly Thr Lys Leu Thr Val Leu
            100                 105                 110

<210> SEQ ID NO 88
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N94W

<400> SEQUENCE: 88

Gln Ser Ala Leu Thr Gln Pro Pro Ser Ala Ser Gly Ser Pro Gly Gln
```

```
                1               5                  10                 15
Ser Val Thr Ile Ser Cys Ile Gly Thr Ser Ser Asp Val Gly Gly Tyr
                20                  25                 30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Trp
                85                  90                  95

Asn Asn Phe Gly Val Phe Gly Gly Gly Thr Lys Leu Thr Val Leu
                100                 105                 110

<210> SEQ ID NO 89
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N94Y

<400> SEQUENCE: 89

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Tyr
                85                  90                  95

Asn Asn Phe Gly Val Phe Gly Gly Gly Thr Lys Leu Thr Val Leu
                100                 105                 110

<210> SEQ ID NO 90
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N95aQ

<400> SEQUENCE: 90

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60
```

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Gln Phe Gly Val Phe Gly Gly Gly Thr Lys Leu Thr Val Leu
            100                 105                 110

<210> SEQ ID NO 91
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N95aD

<400> SEQUENCE: 91

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
            35                  40                  45

Met Ile Tyr Glu Val Asn Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asp Phe Gly Val Phe Gly Gly Gly Thr Lys Leu Thr Val Leu
            100                 105                 110

<210> SEQ ID NO 92
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N95aH

<400> SEQUENCE: 92

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
            35                  40                  45

Met Ile Tyr Glu Val Asn Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn His Phe Gly Val Phe Gly Gly Gly Thr Lys Leu Thr Val Leu
            100                 105                 110

<210> SEQ ID NO 93

```
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N95aK

<400> SEQUENCE: 93

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Lys Phe Gly Val Phe Gly Gly Gly Thr Lys Leu Thr Val Leu
            100                 105                 110

<210> SEQ ID NO 94
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N95aL

<400> SEQUENCE: 94

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Leu Phe Gly Val Phe Gly Gly Gly Thr Lys Leu Thr Val Leu
            100                 105                 110

<210> SEQ ID NO 95
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N95aY

<400> SEQUENCE: 95
```

-continued

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
            35                  40                  45

Met Ile Tyr Glu Val Asn Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Tyr Phe Gly Val Phe Gly Gly Gly Thr Lys Leu Thr Val Leu
            100                 105                 110

<210> SEQ ID NO 96
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: 4A8 VL V97A

<400> SEQUENCE: 96

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
            35                  40                  45

Met Ile Tyr Glu Val Asn Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Ala Phe Gly Gly Gly Thr Lys Leu Thr Val Leu
            100                 105                 110

<210> SEQ ID NO 97
<211> LENGTH: 111
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: 4A8 VL V97K

<400> SEQUENCE: 97

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
            35                  40                  45

Met Ile Tyr Glu Val Asn Lys Arg Pro Ser Gly Val Pro Asp Arg Phe
        50                  55                  60

-continued

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Lys Phe Gly Gly Gly Thr Lys Leu Thr Val Leu
            100                 105                 110

<210> SEQ ID NO 98
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 1 (M34Q_N56S)

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Gln Ser Trp Val Arg Gln Ala Pro Gly Lys Gly Leu Glu Trp Val
        35                  40                  45

Ser Ala Ile Ser Gly Arg Gly Arg Ser Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 99
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 2 (M34Q_A40P_N56S)

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Gln Ser Trp Val Arg Gln Pro Pro Gly Lys Gly Leu Glu Trp Val
        35                  40                  45

Ser Ala Ile Ser Gly Arg Gly Arg Ser Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 100
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 3 (M34Q_A40P_N56S_R75K)

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Gln Ser Trp Val Arg Gln Pro Pro Gly Lys Gly Leu Glu Trp Val
        35                  40                  45

Ser Ala Ile Ser Gly Arg Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 101
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 4 (M34Q_A40P_N56S_M96K)

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Gln Ser Trp Val Arg Gln Pro Pro Gly Lys Gly Leu Glu Trp Val
        35                  40                  45

Ser Ala Ile Ser Gly Arg Gly Arg Ser Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Lys Gly Tyr Trp Gly Gln Gly Ile Leu Val Thr Val Ser
            100                 105                 110

Ser

<210> SEQ ID NO 102
<211> LENGTH: 113
<212> TYPE: PRT

-continued

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 5 (M34Q_A40P_N56S_R75K_M96K)

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Gln Ser Trp Val Arg Gln Pro Pro Gly Lys Gly Leu Glu Trp Val
        35                  40                  45

Ser Ala Ile Ser Gly Arg Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Lys Gly Tyr Trp Gly Gln Gly Ile Leu Val Thr Val Ser
            100                 105                 110

Ser

<210> SEQ ID NO 103
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 6 (M34Q_A40P_N56S_R75K_I94K_
      M96K)

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Gln Ser Trp Val Arg Gln Pro Pro Gly Lys Gly Leu Glu Trp Val
        35                  40                  45

Ser Ala Ile Ser Gly Arg Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Lys Gly Tyr Trp Gly Gln Gly Ile Leu Val Thr Val Ser
            100                 105                 110

Ser

<210> SEQ ID NO 104
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 7 (M34Q_A40P_N56S_I94K_M96K)

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Gln Ser Trp Val Arg Gln Pro Pro Gly Lys Gly Leu Glu Trp Val
        35                  40                  45

Ser Ala Ile Ser Gly Arg Gly Arg Ser Thr Tyr Tyr Ala Asp Ser Val
50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Lys Gly Tyr Trp Gly Gln Gly Ile Leu Val Thr Val Ser
            100                 105                 110

Ser

<210> SEQ ID NO 105
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 8 (M34Q_N56S_M96K)

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Gln Ser Trp Val Arg Gln Ala Pro Gly Lys Gly Leu Glu Trp Val
        35                  40                  45

Ser Ala Ile Ser Gly Arg Gly Arg Ser Thr Tyr Tyr Ala Asp Ser Val
50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Lys Gly Tyr Trp Gly Gln Gly Ile Leu Val Thr Val Ser
            100                 105                 110

Ser

<210> SEQ ID NO 106
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 9 (M34Q_N56S_R75K_M96K)

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser

```
            20                  25                  30

Thr Gln Ser Trp Val Arg Gln Ala Pro Gly Lys Gly Leu Glu Trp Val
            35                  40                  45

Ser Ala Ile Ser Gly Arg Gly Arg Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Gln Lys Gly Tyr Trp Gly Gln Gly Ile Leu Val Thr Val Ser
            100                 105                 110

Ser

<210> SEQ ID NO 107
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 10 I94K_M96K

<400> SEQUENCE: 107

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
            35                  40                  45

Ser Ala Ile Ser Gly Arg Gly Arg Asn Thr Tyr Tyr Ala Asp Ser Val
        50                  55                  60

Lys Gly Arg Phe Thr Ile Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gln Lys Gly Tyr Trp Gly Gln Gly Ile Leu Val Thr Val Ser
            100                 105                 110

Ser

<210> SEQ ID NO 108
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 101 M34Q_A40P_N56S_R75K_M96A

<400> SEQUENCE: 108

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Ser
            20                  25                  30

Thr Gln Ser Trp Val Arg Gln Pro Pro Gly Lys Gly Leu Glu Trp Val
            35                  40                  45

Ser Ala Ile Ser Gly Arg Gly Arg Ser Thr Tyr Tyr Ala Asp Ser Val
        50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Gln Ala Gly Tyr Trp Gly Gln Gly Ile Leu Val Thr Val Ser
            100                 105                 110

Ser
```

<210> SEQ ID NO 109
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL variant b N52S_N94S

<400> SEQUENCE: 109

```
Gln Ser Ala Leu Thr Gln Pro Pro Ser Ala Ser Gly Ser Pro Gly Gln
 1               5                  10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Asp Lys Ala Pro Lys Leu
            35                  40                  45

Met Ile Tyr Glu Val Ser Lys Arg Pro Ser Gly Val Pro Asp Arg Phe
         50                 55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                 85                  90                  95

Asn Asn Phe Gly Val Phe Gly Gly Gly Thr Lys Leu Thr Val Leu
            100                 105                 110
```

<210> SEQ ID NO 110
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL variant c D41G_N52S_N94S

<400> SEQUENCE: 110

```
Gln Ser Ala Leu Thr Gln Pro Pro Ser Ala Ser Gly Ser Pro Gly Gln
 1               5                  10                  15

Ser Val Thr Ile Ser Cys Ile Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Lys Arg Pro Ser Gly Val Pro Asp Arg Phe
         50                 55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                 85                  90                  95

Asn Asn Phe Gly Val Phe Gly Gly Gly Thr Lys Leu Thr Val Leu
            100                 105                 110
```

<210> SEQ ID NO 111
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 4A8 VH M34Q_A40P_N56S_R75K_M96A

<400> SEQUENCE: 111
gaagttcagc tgcttgaatc tggcggagga ctggttcagc ctggcggatc tctgagactg     60
tcttgtgccg ccagcggctt cacctttagc agcagcacac agagctgggt ccgacagcct    120
cctggcaaag gactggaatg ggtgtccgcc atctctggca gaggcagaag cacctactac    180
gccgactctg tgaagggcag attcaccatc agccgggaca cagcaagaa caccctgtac    240 ctgcagatga acagcctgag agccgaggac accgccgtgt actattgtgc catccaggcc    300
ggctattggg gccagggaat actcgtgaca gtgtcctca                           339

<210> SEQ ID NO 112
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 4A8 VL D41G_N52S_N94S

<400> SEQUENCE: 112
cagtctgctc tgacacagcc tcctagcgcc tctggctctc ctggccagag cgtgaccatc     60
agctgtatcg gcaccagcag cgacgtgggc ggctacaact acgtgtcctg gtatcagcag    120
caccccggta aggcccccaa gctgatgatc tacgaagtgt ccaagcggcc agcggcgtg    180 cccgatagat tcagcggcag caagagcggc aacaccgcca gcctcacagt gtctggactg    240
caggccgagg acgaggccga ctactactgt agcagctacg ccggcagcaa caacttcggc    300
gtgttcggcg gaggcaccaa gctgacagtc cta                                333

<210> SEQ ID NO 113
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO-4A8-mIgG1 VH

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

```
Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser Ala Lys Thr Thr Pro Pro Ser Val Tyr Pro Leu Ala Pro Gly Ser
        115                 120                 125

Ala Ala Gln Thr Asn Ser Met Val Thr Leu Gly Cys Leu Val Lys Gly
    130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Pro Arg Pro Ser Glu Thr
            180                 185                 190

Val Thr Cys Asn Val Ala His Pro Ala Ser Ser Thr Lys Val Asp Lys
        195                 200                 205

Lys Ile Val Pro Arg Asp Cys Gly Cys Lys Pro Cys Ile Cys Thr Val
    210                 215                 220

Pro Glu Val Ser Ser Val Phe Ile Phe Pro Pro Lys Pro Lys Asp Val
225                 230                 235                 240

Leu Thr Ile Thr Leu Thr Pro Lys Val Thr Cys Val Val Val Ala Ile
                245                 250                 255

Ser Lys Asp Asp Pro Glu Val Gln Phe Ser Trp Phe Val Asp Asp Val
            260                 265                 270

Glu Val His Thr Ala Gln Thr Gln Pro Arg Glu Glu Gln Phe Asn Ser
        275                 280                 285

Thr Phe Arg Ser Val Ser Glu Leu Pro Ile Met His Gln Asp Trp Leu
    290                 295                 300

Asn Gly Lys Glu Phe Lys Cys Arg Val Asn Ser Ala Ala Phe Pro Ala
305                 310                 315                 320

Pro Ile Glu Lys Thr Ile Ser Lys Thr Lys Gly Arg Pro Lys Ala Pro
                325                 330                 335

Gln Val Tyr Thr Ile Pro Pro Pro Lys Glu Gln Met Ala Lys Asp Lys
            340                 345                 350

Val Ser Leu Thr Cys Met Ile Thr Asp Phe Phe Pro Glu Asp Ile Thr
        355                 360                 365

Val Glu Trp Gln Trp Asn Gly Gln Pro Ala Glu Asn Tyr Lys Asn Thr
    370                 375                 380

Gln Pro Ile Met Asn Thr Asn Gly Ser Tyr Phe Val Tyr Ser Lys Leu
385                 390                 395                 400

Asn Val Gln Lys Ser Asn Trp Glu Ala Gly Asn Thr Phe Thr Cys Ser
                405                 410                 415

Val Leu His Glu Gly Leu His Asn His His Thr Glu Lys Ser Leu Ser
            420                 425                 430

His Ser Pro Gly
        435

<210> SEQ ID NO 114
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO-4A8-mIgG1 VL
```

<400> SEQUENCE: 114

```
Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Val Phe Gly Gly Gly Thr Lys Leu Thr Val Leu Gly
            100                 105                 110

Gln Pro Lys Ser Ser Pro Ser Val Thr Leu Phe Pro Pro Ser Ser Glu
        115                 120                 125

Glu Leu Glu Thr Asn Lys Ala Thr Leu Val Cys Thr Ile Thr Asp Phe
130                 135                 140

Tyr Pro Gly Val Val Thr Val Asp Trp Lys Val Asp Gly Thr Pro Val
145                 150                 155                 160

Thr Gln Gly Met Glu Thr Thr Gln Pro Ser Lys Gln Ser Asn Asn Lys
                165                 170                 175

Tyr Met Ala Ser Ser Tyr Leu Thr Leu Thr Ala Arg Ala Trp Glu Arg
            180                 185                 190

His Ser Ser Tyr Ser Cys Gln Val Thr His Glu Gly His Thr Val Glu
        195                 200                 205

Lys Ser Leu Ser Arg Ala Asp Cys Ser
        210                 215
```

<210> SEQ ID NO 115
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO-4A8 IgG4

<400> SEQUENCE: 115

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110
```

```
Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Tyr Ile Thr Arg Glu Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly
            435

<210> SEQ ID NO 116
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG4

<400> SEQUENCE: 116

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 117
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO-4A8 IgG4

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30
```

Thr Met Ser Trp Val Arg Gln Ala Pro Gly Lys Gly Leu Glu Trp Val
 35                  40                  45

Ser Ala Ile Ser Gly Arg Gly Arg Asn Thr Tyr Tyr Ala Asp Ser Val
 50                  55                  60

Lys Gly Arg Phe Thr Ile Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Gln Met Gly Tyr Trp Gly Gln Gly Ile Leu Val Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
            195                 200                 205

Lys Arg Val Glu Ser Lys Tyr Gly Pro Pro Cys Pro Pro Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly
            435

```
<210> SEQ ID NO 118
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG4

<400> SEQUENCE: 118

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 119
<211> LENGTH: 438
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO-4A8 IgG2

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Asn Phe Gly Thr Gln
            180                 185                 190

Thr Tyr Thr Cys Asn Val Asp His Lys Pro Ser Asn Thr Lys Val Asp
        195                 200                 205

Lys Thr Val Glu Arg Lys Cys Cys Val Glu Cys Pro Pro Cys Pro Ala
    210                 215                 220

Pro Pro Val Ala Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Phe Arg Val Val Ser Val Leu Thr Val Val His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Thr Lys Gly Gln Pro Arg
                325                 330                 335

Glu Pro Gln Val Tyr Thr Leu Pro Pro Ser Arg Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys

```
            370                 375                 380
Thr Thr Pro Pro Met Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
                420                 425                 430

Leu Ser Leu Ser Pro Gly
            435

<210> SEQ ID NO 120
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG2

<400> SEQUENCE: 120

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
```

|   |   |   | 275 |   |   |   | 280 |   |   |   | 285 |   |   |
|---|---|---|---|---|---|---|---|---|---|---|---|---|---|

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
            325

<210> SEQ ID NO 121
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO-4A8 IgG1

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
210                 215                 220

Cys Pro Ala Pro Glu Leu Ala Gly Ala Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val

```
                290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
                340                 345                 350

Glu Leu Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly
                435                 440

<210> SEQ ID NO 122
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG1

<400> SEQUENCE: 122

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Ala Gly Ala Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
```

```
                195                 200                 205
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 123
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BKO-4A8 IgG1

<400> SEQUENCE: 123

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
```

```
            210                 215                 220
Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
                260                 265                 270

Trp Tyr Val Asp Gly Val Glu Val His Asn Ala Lys Thr Lys Pro Arg
                275                 280                 285

Glu Glu Gln Tyr Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
                340                 345                 350

Glu Leu Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly
                435                 440
```

<210> SEQ ID NO 124
<211> LENGTH: 329
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: IgG1

<400> SEQUENCE: 124

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 125
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human CXCR2

<400> SEQUENCE: 125

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Phe Val Val Ile Ile Tyr Ala Leu Val Phe Leu Leu Ser Leu Leu
    50                  55                  60

Gly Asn Ser Leu Val Met Leu Val Ile Leu Tyr Ser Arg Val Gly Arg
65                  70                  75                  80

Ser Val Thr Asp Val Tyr Leu Leu Asn Leu Ala Leu Ala Asp Leu Leu
                85                  90                  95

Phe Ala Leu Thr Leu Pro Ile Trp Ala Ala Ser Lys Val Asn Gly Trp
            100                 105                 110

Ile Phe Gly Thr Phe Leu Cys Lys Val Val Ser Leu Leu Lys Glu Val
        115                 120                 125

Asn Phe Tyr Ser Gly Ile Leu Leu Leu Ala Cys Ile Ser Val Asp Arg
```

```
        130                 135                 140
Tyr Leu Ala Ile Val His Ala Thr Arg Thr Leu Thr Gln Lys Arg Tyr
145                 150                 155                 160

Leu Val Lys Phe Ile Cys Leu Ser Ile Trp Gly Leu Ser Leu Leu Leu
                165                 170                 175

Ala Leu Pro Val Leu Leu Phe Arg Arg Thr Val Tyr Ser Ser Asn Val
                180                 185                 190

Ser Pro Ala Cys Tyr Glu Asp Met Gly Asn Asn Thr Ala Asn Trp Arg
                195                 200                 205

Met Leu Leu Arg Ile Leu Pro Gln Ser Phe Gly Phe Ile Val Pro Leu
                210                 215                 220

Leu Ile Met Leu Phe Cys Tyr Gly Phe Thr Leu Arg Thr Leu Phe Lys
225                 230                 235                 240

Ala His Met Gly Gln Lys His Arg Ala Met Arg Val Ile Phe Ala Val
                245                 250                 255

Val Leu Ile Phe Leu Leu Cys Trp Leu Pro Tyr Asn Leu Val Leu Leu
                260                 265                 270

Ala Asp Thr Leu Met Arg Thr Gln Val Ile Gln Glu Thr Cys Glu Arg
                275                 280                 285

Arg Asn His Ile Asp Arg Ala Leu Asp Ala Thr Glu Ile Leu Gly Ile
                290                 295                 300

Leu His Ser Cys Leu Asn Pro Leu Ile Tyr Ala Phe Ile Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
                340                 345                 350

Ser Gly His Thr Ser Thr Thr Leu
                355                 360

<210> SEQ ID NO 126
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Mouse CXCR2

<400> SEQUENCE: 126

Met Gly Glu Phe Lys Val Asp Lys Phe Asn Ile Glu Asp Phe Phe Ser
1               5                   10                  15

Gly Asp Leu Asp Ile Phe Asn Tyr Ser Ser Gly Met Pro Ser Ile Leu
                20                  25                  30

Pro Asp Ala Val Pro Cys His Ser Glu Asn Leu Glu Ile Asn Ser Tyr
                35                  40                  45

Ala Val Val Val Ile Tyr Val Leu Val Thr Leu Leu Ser Leu Val Gly
                50                  55                  60

Asn Ser Leu Val Met Leu Val Ile Leu Tyr Asn Arg Ser Thr Cys Ser
65                  70                  75                  80

Val Thr Asp Val Tyr Leu Leu Asn Leu Ala Ile Ala Asp Leu Phe Phe
                85                  90                  95

Ala Leu Thr Leu Pro Val Trp Ala Ala Ser Lys Val Asn Gly Trp Thr
                100                 105                 110

Phe Gly Ser Thr Leu Cys Lys Ile Phe Ser Tyr Val Lys Glu Val Thr
```

```
            115                 120                 125
Phe Tyr Ser Ser Val Leu Leu Leu Ala Cys Ile Ser Met Asp Arg Tyr
    130                 135                 140

Leu Ala Ile Val His Ala Thr Ser Thr Leu Ile Gln Lys Arg His Leu
145                 150                 155                 160

Val Lys Phe Val Cys Ile Ala Met Trp Leu Leu Ser Val Ile Leu Ala
                165                 170                 175

Leu Pro Ile Leu Ile Leu Arg Asn Pro Val Lys Val Asn Leu Ser Thr
            180                 185                 190

Leu Val Cys Tyr Glu Asp Val Gly Asn Asn Thr Ser Arg Leu Arg Val
            195                 200                 205

Val Leu Arg Ile Leu Pro Gln Thr Phe Gly Phe Leu Val Pro Leu Leu
    210                 215                 220

Ile Met Leu Phe Cys Tyr Gly Phe Thr Leu Arg Thr Leu Phe Lys Ala
225                 230                 235                 240

His Met Gly Gln Lys His Arg Ala Met Arg Val Ile Phe Ala Val Val
                245                 250                 255

Leu Val Phe Leu Leu Cys Trp Leu Pro Tyr Asn Leu Val Leu Phe Thr
            260                 265                 270

Asp Thr Leu Met Arg Thr Lys Leu Ile Lys Glu Thr Cys Glu Arg Arg
            275                 280                 285

Asp Asp Ile Asp Lys Ala Leu Asn Ala Thr Glu Ile Leu Gly Phe Leu
        290                 295                 300

His Ser Cys Leu Asn Pro Ile Ile Tyr Ala Phe Ile Gly Gln Lys Phe
305                 310                 315                 320

Arg His Gly Leu Leu Lys Ile Met Ala Thr Tyr Gly Leu Val Ser Lys
                325                 330                 335

Glu Phe Leu Ala Lys Glu Gly Arg Pro Ser Phe Val Ser Ser Ser Ser
            340                 345                 350

Ala Asn Thr Ser Thr Thr Leu
            355

<210> SEQ ID NO 127
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cynomolgus CXCR2

<400> SEQUENCE: 127

Met Gln Ser Phe Asn Phe Glu Asp Phe Trp Glu Asn Glu Asp Phe Ser
1               5                   10                  15

Asn Tyr Ser Tyr Ser Ser Asp Leu Pro Pro Ser Leu Pro Asp Val Ala
                20                  25                  30

Pro Cys Arg Pro Glu Ser Leu Glu Ile Asn Lys Tyr Phe Val Val Ile
            35                  40                  45

Ile Tyr Ala Leu Val Phe Leu Leu Ser Leu Leu Gly Asn Ser Leu Val
        50                  55                  60

Met Leu Val Ile Leu His Ser Arg Val Gly Arg Ser Ile Thr Asp Val
65                  70                  75                  80

Tyr Leu Leu Asn Leu Ala Met Ala Asp Leu Leu Phe Ala Leu Thr Leu
                85                  90                  95

Pro Ile Trp Ala Ala Ala Lys Val Asn Gly Trp Ile Phe Gly Thr Phe
```

```
                    100                 105                 110
Leu Cys Lys Val Val Ser Leu Leu Lys Glu Val Asn Phe Tyr Ser Gly
            115                 120                 125

Ile Leu Leu Leu Ala Cys Ile Ser Val Asp Arg Tyr Leu Ala Ile Val
        130                 135                 140

His Ala Thr Arg Thr Leu Thr Gln Lys Arg Tyr Leu Val Lys Phe Val
145                 150                 155                 160

Cys Leu Ser Ile Trp Ser Leu Ser Leu Leu Ala Leu Pro Val Leu
                165                 170                 175

Leu Phe Arg Arg Thr Val Tyr Leu Thr Tyr Ile Ser Pro Val Cys Tyr
                180                 185                 190

Glu Asp Met Gly Asn Asn Thr Ala Lys Trp Arg Met Val Leu Arg Ile
            195                 200                 205

Leu Pro Gln Thr Phe Gly Phe Ile Leu Pro Leu Ile Met Leu Phe
        210                 215                 220

Cys Tyr Gly Phe Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr His Leu Val Leu Leu Ala Asp Thr Leu Met
                260                 265                 270

Arg Thr Arg Leu Ile Asn Glu Thr Cys Gln Arg Arg Asn Asn Ile Asp
                275                 280                 285

Gln Ala Leu Asp Ala Thr Glu Ile Leu Gly Ile Leu His Ser Cys Leu
        290                 295                 300

Asn Pro Leu Ile Tyr Ala Phe Ile Gly Gln Lys Phe Arg His Gly Leu
305                 310                 315                 320

Leu Lys Ile Leu Ala Thr His Gly Leu Ile Ser Lys Asp Ser Leu Pro
                325                 330                 335

Lys Asp Ser Arg Pro Ser Phe Val Gly Ser Ser Ser Gly His Thr Ser
                340                 345                 350

Thr Thr Leu
        355

<210> SEQ ID NO 128
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: human CXCR3

<400> SEQUENCE: 128

Met Val Leu Glu Val Ser Asp His Gln Val Leu Asn Asp Ala Glu Val
1               5                   10                  15

Ala Ala Leu Leu Glu Asn Phe Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
        50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
```

-continued

```
                85                  90                  95
Val Ala Asp Thr Leu Leu Val Leu Thr Leu Pro Leu Trp Ala Val Asp
                100                 105                 110
Ala Ala Val Gln Trp Val Phe Gly Ser Gly Leu Cys Lys Val Ala Gly
                115                 120                 125
Ala Leu Phe Asn Ile Asn Phe Tyr Ala Gly Ala Leu Leu Leu Ala Cys
            130                 135                 140
Ile Ser Phe Asp Arg Tyr Leu Asn Ile Val His Ala Thr Gln Leu Tyr
145                 150                 155                 160
Arg Arg Gly Pro Pro Ala Arg Val Thr Leu Thr Cys Leu Ala Val Trp
                165                 170                 175
Gly Leu Cys Leu Leu Phe Ala Leu Pro Asp Phe Ile Phe Leu Ser Ala
                180                 185                 190
His His Asp Glu Arg Leu Asn Ala Thr His Cys Gln Tyr Asn Phe Pro
            195                 200                 205
Gln Val Gly Arg Thr Ala Leu Arg Val Leu Gln Leu Val Ala Gly Phe
        210                 215                 220
Leu Leu Pro Leu Leu Val Met Ala Tyr Cys Tyr Ala His Ile Leu Ala
225                 230                 235                 240
Val Leu Leu Val Ser Arg Gly Gln Arg Arg Leu Arg Ala Met Arg Leu
                245                 250                 255
Val Val Val Val Val Val Ala Phe Ala Leu Cys Trp Thr Pro Tyr His
                260                 265                 270
Leu Val Val Leu Val Asp Ile Leu Met Asp Leu Gly Ala Leu Ala Arg
            275                 280                 285
Asn Cys Gly Arg Glu Ser Arg Val Asp Val Ala Lys Ser Val Thr Ser
        290                 295                 300
Gly Leu Gly Tyr Met His Cys Cys Leu Asn Pro Leu Leu Tyr Ala Phe
305                 310                 315                 320
Val Gly Val Lys Phe Arg Glu Arg Met Trp Met Leu Leu Leu Arg Leu
                325                 330                 335
Gly Cys Pro Asn Gln Arg Gly Leu Gln Arg Gln Pro Ser Ser Ser Arg
                340                 345                 350
Arg Asp Ser Ser Trp Ser Glu Thr Ser Glu Ala Ser Tyr Ser Gly Leu
            355                 360                 365
```

<210> SEQ ID NO 129
<211> LENGTH: 352
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: human CXCR4

<400> SEQUENCE: 129

```
Met Glu Gly Ile Ser Ile Tyr Thr Ser Asp Asn Tyr Thr Glu Glu Met
1               5                   10                  15
Gly Ser Gly Asp Tyr Asp Ser Met Lys Glu Pro Cys Phe Arg Glu Glu
                20                  25                  30
Asn Ala Asn Phe Asn Lys Ile Phe Leu Pro Thr Ile Tyr Ser Ile Ile
            35                  40                  45
Phe Leu Thr Gly Ile Val Gly Asn Gly Leu Val Ile Leu Val Met Gly
        50                  55                  60
Tyr Gln Lys Lys Leu Arg Ser Met Thr Asp Lys Tyr Arg Leu His Leu
```

```
            65                  70                  75                  80
        Ser Val Ala Asp Leu Leu Phe Val Ile Thr Leu Pro Phe Trp Ala Val
                        85                  90                  95

Asp Ala Val Ala Asn Trp Tyr Phe Gly Asn Phe Leu Cys Lys Ala Val
                        100                 105                 110

His Val Ile Tyr Thr Val Asn Leu Tyr Ser Ser Val Leu Ile Leu Ala
                        115                 120                 125

Phe Ile Ser Leu Asp Arg Tyr Leu Ala Ile Val His Ala Thr Asn Ser
                    130                 135                 140

Gln Arg Pro Arg Lys Leu Leu Ala Glu Lys Val Val Tyr Val Gly Val
        145                 150                 155                 160

Trp Ile Pro Ala Leu Leu Leu Thr Ile Pro Asp Phe Ile Phe Ala Asn
                        165                 170                 175

Val Ser Glu Ala Asp Asp Arg Tyr Ile Cys Asp Arg Phe Tyr Pro Asn
                        180                 185                 190

Asp Leu Trp Val Val Phe Gln Phe Gln His Ile Met Val Gly Leu
                    195                 200                 205

Ile Leu Pro Gly Ile Val Ile Leu Ser Cys Tyr Cys Ile Ile Ile Ser
                210                 215                 220

Lys Leu Ser His Ser Lys Gly His Gln Lys Arg Lys Ala Leu Lys Thr
        225                 230                 235                 240

Thr Val Ile Leu Ile Leu Ala Phe Phe Ala Cys Trp Leu Pro Tyr Tyr
                        245                 250                 255

Ile Gly Ile Ser Ile Asp Ser Phe Ile Leu Leu Glu Ile Ile Lys Gln
                        260                 265                 270

Gly Cys Glu Phe Glu Asn Thr Val His Lys Trp Ile Ser Ile Thr Glu
                    275                 280                 285

Ala Leu Ala Phe Phe His Cys Cys Leu Asn Pro Ile Leu Tyr Ala Phe
                290                 295                 300

Leu Gly Ala Lys Phe Lys Thr Ser Ala Gln His Ala Leu Thr Ser Val
        305                 310                 315                 320

Ser Arg Gly Ser Ser Leu Lys Ile Leu Ser Lys Gly Lys Arg Gly Gly
                        325                 330                 335

His Ser Ser Val Ser Thr Glu Ser Glu Ser Ser Ser Phe His Ser Ser
                    340                 345                 350

<210> SEQ ID NO 130
<211> LENGTH: 372
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: human CXCR5

<400> SEQUENCE: 130

Met Asn Tyr Pro Leu Thr Leu Glu Met Asp Leu Glu Asn Leu Glu Asp
        1               5                   10                  15

Leu Phe Trp Glu Leu Asp Arg Leu Asp Asn Tyr Asn Asp Thr Ser Leu
                        20                  25                  30

Val Glu Asn His Leu Cys Pro Ala Thr Glu Gly Pro Leu Met Ala Ser
                        35                  40                  45

Phe Lys Ala Val Phe Val Pro Val Ala Tyr Ser Leu Ile Phe Leu Leu
                    50                  55                  60

Gly Val Ile Gly Asn Val Leu Val Leu Val Ile Leu Glu Arg His Arg
```

```
                65                  70                  75                  80
        Gln Thr Arg Ser Ser Thr Glu Thr Phe Leu Phe His Leu Ala Val Ala
                        85                  90                  95

Asp Leu Leu Leu Val Phe Ile Leu Pro Phe Ala Val Ala Glu Gly Ser
                        100                 105                 110

Val Gly Trp Val Leu Gly Thr Phe Leu Cys Lys Thr Val Ile Ala Leu
                        115                 120                 125

His Lys Val Asn Phe Tyr Cys Ser Ser Leu Leu Leu Ala Cys Ile Ala
                        130                 135                 140

Val Asp Arg Tyr Leu Ala Ile Val His Ala Val His Ala Tyr Arg His
        145                 150                 155                 160

Arg Arg Leu Leu Ser Ile His Ile Thr Cys Gly Thr Ile Trp Leu Val
                        165                 170                 175

Gly Phe Leu Leu Ala Leu Pro Glu Ile Leu Phe Ala Lys Val Ser Gln
                        180                 185                 190

Gly His His Asn Asn Ser Leu Pro Arg Cys Thr Phe Ser Gln Glu Asn
                        195                 200                 205

Gln Ala Glu Thr His Ala Trp Phe Thr Ser Arg Phe Leu Tyr His Val
                        210                 215                 220

Ala Gly Phe Leu Leu Pro Met Leu Val Met Gly Trp Cys Tyr Val Gly
        225                 230                 235                 240

Val Val His Arg Leu Arg Gln Ala Gln Arg Arg Pro Gln Arg Gln Lys
                        245                 250                 255

Ala Val Arg Val Ala Ile Leu Val Thr Ser Ile Phe Phe Leu Cys Trp
                        260                 265                 270

Ser Pro Tyr His Ile Val Ile Phe Leu Asp Thr Leu Ala Arg Leu Lys
                        275                 280                 285

Ala Val Asp Asn Thr Cys Lys Leu Asn Gly Ser Leu Pro Val Ala Ile
                        290                 295                 300

Thr Met Cys Glu Phe Leu Gly Leu Ala His Cys Cys Leu Asn Pro Met
        305                 310                 315                 320

Leu Tyr Thr Phe Ala Gly Val Lys Phe Arg Ser Asp Leu Ser Arg Leu
                        325                 330                 335

Leu Thr Lys Leu Gly Cys Thr Gly Pro Ala Ser Leu Cys Gln Leu Phe
                        340                 345                 350

Pro Ser Trp Arg Arg Ser Ser Leu Ser Glu Ser Glu Asn Ala Thr Ser
                        355                 360                 365

Leu Thr Thr Phe
                        370

<210> SEQ ID NO 131
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: human CXCR6

<400> SEQUENCE: 131

Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
                20                  25                  30

Phe Leu Pro Cys Met Tyr Leu Val Val Phe Val Cys Gly Leu Val Gly
```

```
            35                  40                  45
Asn Ser Leu Val Leu Val Ile Ser Ile Phe Tyr His Lys Leu Gln Ser
 50                  55                  60

Leu Thr Asp Val Phe Leu Val Asn Leu Pro Leu Ala Asp Leu Val Phe
 65                  70                  75                  80

Val Cys Thr Leu Pro Phe Trp Ala Tyr Ala Gly Ile His Glu Trp Val
                 85                  90                  95

Phe Gly Gln Val Met Cys Lys Ser Leu Leu Gly Ile Tyr Thr Ile Asn
                100                 105                 110

Phe Tyr Thr Ser Met Leu Ile Leu Thr Cys Ile Thr Val Asp Arg Phe
                115                 120                 125

Ile Val Val Val Lys Ala Thr Lys Ala Tyr Asn Gln Gln Ala Lys Arg
130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
                180                 185                 190

Ala Thr Gln Met Thr Leu Gly Phe Phe Leu Pro Leu Leu Thr Met Ile
                195                 200                 205

Val Cys Tyr Ser Val Ile Ile Lys Thr Leu Leu His Ala Gly Gly Phe
210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
                260                 265                 270

Thr Glu Ala Ile Ala Tyr Leu Arg Ala Cys Leu Asn Pro Val Leu Tyr
                275                 280                 285

Ala Phe Val Ser Leu Lys Phe Arg Lys Asn Phe Trp Lys Leu Val Lys
                290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
                340

<210> SEQ ID NO 132
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: human CXCR7

<400> SEQUENCE: 132

Met Asp Leu His Leu Phe Asp Tyr Ser Glu Pro Gly Asn Phe Ser Asp
  1               5                  10                  15

Ile Ser Trp Pro Cys Asn Ser Ser Asp Cys Ile Val Val Asp Thr Val
                 20                  25                  30

Met Cys Pro Asn Met Pro Asn Lys Ser Val Leu Leu Tyr Thr Leu Ser
```

35                  40                  45
Phe Ile Tyr Ile Phe Ile Phe Val Ile Gly Met Ile Ala Asn Ser Val
    50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                 85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Gly Ser Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360

<210> SEQ ID NO 133
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human CXCR1

<400> SEQUENCE: 133

Met Ser Asn Ile Thr Asp Pro Gln Met Trp Asp Phe Asp Asp Leu Asn
 1               5                  10                  15

Phe Thr Gly Met Pro Pro Ala Asp Glu Asp Tyr Ser Pro Cys Met Leu

```
                    20                  25                  30

Glu Thr Glu Thr Leu Asn Lys Tyr Val Val Ile Ile Ala Tyr Ala Leu
                35                  40                  45

Val Phe Leu Leu Ser Leu Leu Gly Asn Ser Leu Val Met Leu Val Ile
            50                  55                  60

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95

Ala Ser Lys Val Asn Gly Trp Ile Phe Gly Thr Phe Leu Cys Lys Val
            100                 105                 110

Val Ser Leu Leu Lys Glu Val Asn Phe Tyr Ser Gly Ile Leu Leu Leu
        115                 120                 125

Ala Cys Ile Ser Val Asp Arg Tyr Leu Ala Ile Val His Ala Thr Arg
    130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly
            180                 185                 190

Asn Asp Thr Ala Lys Trp Arg Met Val Leu Arg Ile Leu Pro His Thr
        195                 200                 205

Phe Gly Phe Ile Val Pro Leu Phe Val Met Leu Phe Cys Tyr Gly Phe
    210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
            260                 265                 270

Ile Gln Glu Ser Cys Glu Arg Arg Asn Asn Ile Gly Arg Ala Leu Asp
        275                 280                 285

Ala Thr Glu Ile Leu Gly Phe Leu His Ser Cys Leu Asn Pro Ile Ile
    290                 295                 300

Tyr Ala Phe Ile Gly Gln Asn Phe Arg His Gly Phe Leu Lys Ile Leu
305                 310                 315                 320

Ala Met His Gly Leu Val Ser Lys Glu Phe Leu Ala Arg His Arg Val
                325                 330                 335

Thr Ser Tyr Thr Ser Ser Ser Val Asn Val Ser Ser Asn Leu
            340                 345                 350

<210> SEQ ID NO 134
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Lambda light chain constant region

<400> SEQUENCE: 134

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
```

```
                    20                  25                  30
Phe Tyr Pro Gly Ala Val Thr Val Ala Trp Lys Ala Asp Ser Ser Pro
            35                  40                  45

Val Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 135
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Human Kappa light chain constant region

<400> SEQUENCE: 135

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 136
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH S32D

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asp
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80
```

-continued

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 137
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH S35Q

<400> SEQUENCE: 137

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Gln Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 138
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH S35D

<400> SEQUENCE: 138

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Asp Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 139
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH S35K

<400> SEQUENCE: 139

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Lys Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 140
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH A50S

<400> SEQUENCE: 140

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ser Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 141
<211> LENGTH: 113
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: 4A8 VH R55Q

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Gln Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 142
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH R55D

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Asp Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser

<210> SEQ ID NO 143
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH R55H

<400> SEQUENCE: 143

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly His Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Tyr Trp Gly Gln Gly Ile Leu Val Thr Val Ser
            100                 105                 110

Ser
```

<210> SEQ ID NO 144
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH M96S

<400> SEQUENCE: 144

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Ser Gly Tyr Trp Gly Gln Gly Ile Leu Val Thr Val Ser
            100                 105                 110

Ser
```

<210> SEQ ID NO 145
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH M96D

<400> SEQUENCE: 145

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
```

```
                35                  40                  45
Ser Ala Ile Ser Gly Arg Gly Arg Asn Thr Tyr Tyr Ala Asp Ser Val
        50                  55                  60
Lys Gly Arg Phe Thr Ile Ser Arg Asp Asn Ser Arg Asn Thr Leu Tyr
65                  70                  75                  80
Leu Gln Met Asn Ser Leu Arg Ala Glu Asp Thr Ala Val Tyr Tyr Cys
                85                  90                  95
Ala Ile Gln Asp Gly Tyr Trp Gly Gln Gly Ile Leu Val Thr Val Ser
            100                 105                 110
Ser
```

<210> SEQ ID NO 146
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH M96H

<400> SEQUENCE: 146

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Ser
            20                  25                  30
Thr Met Ser Trp Val Arg Gln Ala Pro Gly Lys Gly Leu Glu Trp Val
        35                  40                  45
Ser Ala Ile Ser Gly Arg Gly Arg Asn Thr Tyr Tyr Ala Asp Ser Val
        50                  55                  60
Lys Gly Arg Phe Thr Ile Ser Arg Asp Asn Ser Arg Asn Thr Leu Tyr
65                  70                  75                  80
Leu Gln Met Asn Ser Leu Arg Ala Glu Asp Thr Ala Val Tyr Tyr Cys
                85                  90                  95
Ala Ile Gln His Gly Tyr Trp Gly Gln Gly Ile Leu Val Thr Val Ser
            100                 105                 110
Ser
```

<210> SEQ ID NO 147
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH M96L

<400> SEQUENCE: 147

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Ser
            20                  25                  30
Thr Met Ser Trp Val Arg Gln Ala Pro Gly Lys Gly Leu Glu Trp Val
        35                  40                  45
Ser Ala Ile Ser Gly Arg Gly Arg Asn Thr Tyr Tyr Ala Asp Ser Val
        50                  55                  60
Lys Gly Arg Phe Thr Ile Ser Arg Asp Asn Ser Arg Asn Thr Leu Tyr
65                  70                  75                  80
```

Leu Gln Met Asn Ser Leu Arg Ala Glu Asp Thr Ala Val Tyr Tyr Cys
                85                  90                  95

Ala Ile Gln Leu Gly Tyr Trp Gly Gln Gly Ile Leu Val Thr Val Ser
            100                 105                 110

Ser

<210> SEQ ID NO 148
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH M96W

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Trp Gly Tyr Trp Gly Gln Gly Ile Leu Val Thr Val Ser
            100                 105                 110

Ser

<210> SEQ ID NO 149
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH M96Y

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Tyr Gly Tyr Trp Gly Gln Gly Ile Leu Val Thr Val Ser
            100                 105                 110

Ser

<210> SEQ ID NO 150
<211> LENGTH: 113
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: 4A8 VH Y102Q

<400> SEQUENCE: 150

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Gln Trp Gly Gln Gly Ile Leu Val Thr Val Ser
            100                 105                 110

Ser

<210> SEQ ID NO 151
<211> LENGTH: 113
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: 4A8 VH Y102D

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Met Ser Trp Val Arg Gln Ala Pro Gly Lys Gly Leu Glu Trp Val
        35                  40                  45

Ser Ala Ile Ser Gly Arg Gly Arg Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Met Gly Asp Trp Gly Gln Gly Ile Leu Val Thr Val Ser
            100                 105                 110

Ser

<210> SEQ ID NO 152
<211> LENGTH: 111
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: 4A8 VL V51D

<400> SEQUENCE: 152

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Asp Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Val Phe Gly Gly Gly Thr Lys Leu Thr Val Leu
            100                 105                 110

<210> SEQ ID NO 153
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL V51Y

<400> SEQUENCE: 153

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Tyr Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Val Phe Gly Gly Gly Thr Lys Leu Thr Val Leu
            100                 105                 110

<210> SEQ ID NO 154
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL R54D

<400> SEQUENCE: 154

Gln Ser Ala Leu Thr Gln Pro Pro Ser Ala Ser Gly Ser Pro Gly Gln
1               5                   10                  15
```

```
Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Asp Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Val Phe Gly Gly Gly Thr Lys Leu Thr Val Leu
            100                 105                 110
```

<210> SEQ ID NO 155
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL Y91S

<400> SEQUENCE: 155

```
Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Ser Ala Gly Asn
                85                  90                  95

Asn Asn Phe Gly Val Phe Gly Gly Gly Thr Lys Leu Thr Val Leu
            100                 105                 110
```

<210> SEQ ID NO 156
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL Y91H

<400> SEQUENCE: 156

```
Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80
```

Gln Ala Glu Asp Glu Ala Asp Tyr Tyr Cys Ser Ser His Ala Gly Asn
                85                  90                  95

Asn Asn Phe Gly Val Phe Gly Gly Gly Thr Lys Leu Thr Val Leu
            100                 105                 110

<210> SEQ ID NO 157
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N94H

<400> SEQUENCE: 157

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly His
                85                  90                  95

Asn Asn Phe Gly Val Phe Gly Gly Gly Thr Lys Leu Thr Val Leu
            100                 105                 110

<210> SEQ ID NO 158
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N95aS

<400> SEQUENCE: 158

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Ser Phe Gly Val Phe Gly Gly Gly Thr Lys Leu Thr Val Leu
            100                 105                 110

<210> SEQ ID NO 159
<211> LENGTH: 111
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL N95aW

<400> SEQUENCE: 159

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Trp Phe Gly Val Phe Gly Gly Gly Thr Lys Leu Thr Val Leu
            100                 105                 110

<210> SEQ ID NO 160
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL V97S

<400> SEQUENCE: 160

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Ser Phe Gly Gly Gly Thr Lys Leu Thr Val Leu
            100                 105                 110

<210> SEQ ID NO 161
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VL V97D

<400> SEQUENCE: 161

Gln Ser Ala Leu Thr Gln Pro Pro Ser Ala Ser Gly Ser Pro Gly Gln
1               5                   10                  15

```
Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Glu Val Asn Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Asn Asn Phe Gly Asp Phe Gly Gly Gly Thr Lys Leu Thr Val Leu
            100                 105                 110
```

<210> SEQ ID NO 162
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: 4A8 VH Variant 102 M34Q_A40P_N56S_R75K_M96E

<400> SEQUENCE: 162

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Gln Ser Trp Val Arg Gln Pro Pro Gly Lys Gly Leu Glu Trp Val
        35                  40                  45

Ser Ala Ile Ser Gly Arg Gly Arg Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gln Glu Gly Tyr Trp Gly Gln Gly Ile Leu Val Thr Val Ser
            100                 105                 110

Ser
```

<210> SEQ ID NO 163
<211> LENGTH: 113
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: 4A8 VH Variant 103 M34Q_A40P_R53S_R55G_N56S_
    R75K

<400> SEQUENCE: 163

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Thr Gln Ser Trp Val Arg Gln Pro Pro Gly Lys Gly Leu Glu Trp Val
        35                  40                  45

Ser Ala Ile Ser Gly Ser Gly Gly Ser Thr Tyr Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Ile Gln Met Gly Tyr Trp Gly Gln Gly Ile Leu Val Thr Val Ser
                100                 105                 110

Ser
```

<210> SEQ ID NO 164
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 104 M34Q_A40P_R53S_R55G_N56S_
      R75K_M96K

<400> SEQUENCE: 164

```
Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Ser Ser Ser
                    20                  25                  30

Thr Gln Ser Trp Val Arg Gln Pro Pro Gly Lys Gly Leu Glu Trp Val
                    35                  40                  45

Ser Ala Ile Ser Gly Ser Gly Gly Ser Thr Tyr Tyr Ala Asp Ser Val
                    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Ile Gln Lys Gly Tyr Trp Gly Gln Gly Ile Leu Val Thr Val Ser
                100                 105                 110

Ser
```

<210> SEQ ID NO 165
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 105 M34Q_A40P_R53S_R55G_N56S_
      R75K_M96A

<400> SEQUENCE: 165

```
Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Ser Ser Ser
                    20                  25                  30

Thr Gln Ser Trp Val Arg Gln Pro Pro Gly Lys Gly Leu Glu Trp Val
                    35                  40                  45

Ser Ala Ile Ser Gly Ser Gly Gly Ser Thr Tyr Tyr Ala Asp Ser Val
                    50                  55                  60

Lys Gly Arg Phe Thr Ile Ser Arg Asp Asn Ser Lys Asn Thr Leu Tyr
 65                  70                  75                  80
```

-continued

Leu Gln Met Asn Ser Leu Arg Ala Glu Asp Thr Ala Val Tyr Tyr Cys
                    85                  90                  95

Ala Ile Gln Ala Gly Tyr Trp Gly Gln Gly Ile Leu Val Thr Val Ser
            100                 105                 110

Ser

<210> SEQ ID NO 166
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 VH Variant 106 M34Q_A40P_R53S_R55G_N56S_
      R75K_M96E

<400> SEQUENCE: 166

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
                20                  25                  30

Thr Gln Ser Trp Val Arg Gln Pro Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Ile Gln Glu Gly Tyr Trp Gly Gln Gly Ile Leu Val Thr Val Ser
            100                 105                 110

Ser

<210> SEQ ID NO 167
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 Consensus VH
<220> FEATURE:
<221> NAME/KEY: MOD_RES
<222> LOCATION: (32)..(32)
<223> OTHER INFORMATION: S, Q, H, L, W or Y
<220> FEATURE:
<221> NAME/KEY: MOD_RES
<222> LOCATION: (33)..(33)
<223> OTHER INFORMATION: T or A
<220> FEATURE:
<221> NAME/KEY: MOD_RES
<222> LOCATION: (34)..(34)
<223> OTHER INFORMATION: M, Q, D, H or W
<220> FEATURE:
<221> NAME/KEY: MOD_RES
<222> LOCATION: (51)..(51)
<223> OTHER INFORMATION: I or H
<220> FEATURE:
<221> NAME/KEY: MOD_RES
<222> LOCATION: (53)..(53)
<223> OTHER INFORMATION: G or D
<220> FEATURE:
<221> NAME/KEY: MOD_RES
<222> LOCATION: (54)..(54)
<223> OTHER INFORMATION: R, S or Q

```
<220> FEATURE:
<221> NAME/KEY: MOD_RES
<222> LOCATION: (55)..(55)
<223> OTHER INFORMATION: G or D
<220> FEATURE:
<221> NAME/KEY: MOD_RES
<222> LOCATION: (57)..(57)
<223> OTHER INFORMATION: N or S
<220> FEATURE:
<221> NAME/KEY: MOD_RES
<222> LOCATION: (98)..(98)
<223> OTHER INFORMATION: I or K
<220> FEATURE:
<221> NAME/KEY: MOD_RES
<222> LOCATION: (100)..(100)
<223> OTHER INFORMATION: M, A, Q or K
<220> FEATURE:
<221> NAME/KEY: MOD_RES
<222> LOCATION: (101)..(101)
<223> OTHER INFORMATION: G or D
<220> FEATURE:
<221> NAME/KEY: MOD_RES
<222> LOCATION: (102)..(102)
<223> OTHER INFORMATION: Y, S or K

<400> SEQUENCE: 167

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Xaa
            20                  25                  30

Xaa Xaa Ser Trp Val Arg Gln Ala Pro Gly Lys Gly Leu Glu Trp Val
        35                  40                  45

Ser Ala Xaa Ser Xaa Xaa Xaa Arg Xaa Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Xaa Gln Xaa Xaa Xaa Trp Gly Gln Gly Ile Leu Val Thr Val Ser
            100                 105                 110

Ser

<210> SEQ ID NO 168
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 Consensus VL
<220> FEATURE:
<221> NAME/KEY: MOD_RES
<222> LOCATION: (52)..(52)
<223> OTHER INFORMATION: E or D
<220> FEATURE:
<221> NAME/KEY: MOD_RES
<222> LOCATION: (54)..(54)
<223> OTHER INFORMATION: N, D or S
<220> FEATURE:
<221> NAME/KEY: MOD_RES
<222> LOCATION: (55)..(55)
<223> OTHER INFORMATION: K, A, D or H
<220> FEATURE:
<221> NAME/KEY: MOD_RES
<222> LOCATION: (56)..(56)
<223> OTHER INFORMATION: R or Q
<220> FEATURE:
<221> NAME/KEY: MOD_RES
<222> LOCATION: (93)..(93)
```

```
<223> OTHER INFORMATION: Y or A
<220> FEATURE:
<221> NAME/KEY: MOD_RES
<222> LOCATION: (96)..(96)
<223> OTHER INFORMATION: N, A, S, K, L, W or Y
<220> FEATURE:
<221> NAME/KEY: MOD_RES
<222> LOCATION: (98)..(98)
<223> OTHER INFORMATION: N, Q, D, H, K, L or Y
<220> FEATURE:
<221> NAME/KEY: MOD_RES
<222> LOCATION: (101)..(101)
<223> OTHER INFORMATION: V, A or K

<400> SEQUENCE: 168

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Met Ile Tyr Xaa Val Xaa Xaa Xaa Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Xaa Ala Gly Xaa
                85                  90                  95

Asn Xaa Phe Gly Xaa Phe Gly Gly Gly Thr Lys Leu Thr Val Leu
            100                 105                 110

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus VH CDR1
<220> FEATURE:
<221> NAME/KEY: MOD_RES
<222> LOCATION: (2)..(2)
<223> OTHER INFORMATION: S, Q, H, L, W or Y
<220> FEATURE:
<221> NAME/KEY: MOD_RES
<222> LOCATION: (3)..(3)
<223> OTHER INFORMATION: T or A
<220> FEATURE:
<221> NAME/KEY: MOD_RES
<222> LOCATION: (4)..(4)
<223> OTHER INFORMATION: M, Q, D, H or W

<400> SEQUENCE: 169

Ser Xaa Xaa Xaa Ser
1               5

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus VH CDR2
<220> FEATURE:
<221> NAME/KEY: MOD_RES
<222> LOCATION: (2)..(2)
<223> OTHER INFORMATION: I or H
```

-continued

```
<220> FEATURE:
<221> NAME/KEY: MOD_RES
<222> LOCATION: (4)..(4)
<223> OTHER INFORMATION: G or D
<220> FEATURE:
<221> NAME/KEY: MOD_RES
<222> LOCATION: (5)..(5)
<223> OTHER INFORMATION: R, S or Q
<220> FEATURE:
<221> NAME/KEY: MOD_RES
<222> LOCATION: (6)..(6)
<223> OTHER INFORMATION: G or D
<220> FEATURE:
<221> NAME/KEY: MOD_RES
<222> LOCATION: (8)..(8)
<223> OTHER INFORMATION: N or S

<400> SEQUENCE: 170

Ala Xaa Ser Xaa Xaa Xaa Arg Xaa Thr Tyr Tyr Ala Asp Ser Val Lys
1               5                   10                  15

Gly

<210> SEQ ID NO 171
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus VH CDR3
<220> FEATURE:
<221> NAME/KEY: MOD_RES
<222> LOCATION: (2)..(2)
<223> OTHER INFORMATION: M, A, Q or K
<220> FEATURE:
<221> NAME/KEY: MOD_RES
<222> LOCATION: (3)..(3)
<223> OTHER INFORMATION: G or D
<220> FEATURE:
<221> NAME/KEY: MOD_RES
<222> LOCATION: (4)..(4)
<223> OTHER INFORMATION: Y, S or K

<400> SEQUENCE: 171

Gln Xaa Xaa Xaa
1

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus VL CDR1

<400> SEQUENCE: 172

Ile Gly Thr Ser Ser Asp Val Gly Gly Tyr Asn Tyr Val Ser
1               5                   10

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus VL CDR2
<220> FEATURE:
```

```
<221> NAME/KEY: MOD_RES
<222> LOCATION: (1)..(1)
<223> OTHER INFORMATION: E or D
<220> FEATURE:
<221> NAME/KEY: MOD_RES
<222> LOCATION: (3)..(3)
<223> OTHER INFORMATION: N, D or S
<220> FEATURE:
<221> NAME/KEY: MOD_RES
<222> LOCATION: (4)..(4)
<223> OTHER INFORMATION: K, A, D or H
<220> FEATURE:
<221> NAME/KEY: MOD_RES
<222> LOCATION: (5)..(5)
<223> OTHER INFORMATION: R or Q

<400> SEQUENCE: 173

Xaa Val Xaa Xaa Xaa Pro Ser
1               5

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus VL CDR3
<220> FEATURE:
<221> NAME/KEY: MOD_RES
<222> LOCATION: (3)..(3)
<223> OTHER INFORMATION: Y or A
<220> FEATURE:
<221> NAME/KEY: MOD_RES
<222> LOCATION: (6)..(6)
<223> OTHER INFORMATION: N, A, S, K, L, W or Y
<220> FEATURE:
<221> NAME/KEY: MOD_RES
<222> LOCATION: (8)..(8)
<223> OTHER INFORMATION: N, Q, D, H, K, L or Y
<220> FEATURE:
<221> NAME/KEY: MOD_RES
<222> LOCATION: (11)..(11)
<223> OTHER INFORMATION: V, A or K

<400> SEQUENCE: 174

Ser Ser Xaa Ala Gly Xaa Asn Xaa Phe Gly Xaa
1               5                   10

<210> SEQ ID NO 175
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 VHCDR1

<400> SEQUENCE: 175

Ser Ser Thr Met Ser
1               5

<210> SEQ ID NO 176
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 S32Q VHCDR1
```

<400> SEQUENCE: 176

Ser Gln Thr Met Ser
1               5

<210> SEQ ID NO 177
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 S32H VHCDR1

<400> SEQUENCE: 177

Ser His Thr Met Ser
1               5

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 S32L VHCDR1

<400> SEQUENCE: 178

Ser Leu Thr Met Ser
1               5

<210> SEQ ID NO 179
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 S32W VHCDR1

<400> SEQUENCE: 179

Ser Trp Thr Met Ser
1               5

<210> SEQ ID NO 180
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 S32Y VHCDR1

<400> SEQUENCE: 180

Ser Tyr Thr Met Ser
1               5

<210> SEQ ID NO 181
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: 4A8 T33A VHCDR1

<400> SEQUENCE: 181

Ser Ser Ala Met Ser
1               5

<210> SEQ ID NO 182
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 M34Q VHCDR1

<400> SEQUENCE: 182

Ser Ser Thr Gln Ser
1               5

<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 M34D VHCDR1

<400> SEQUENCE: 183

Ser Ser Thr Asp Ser
1               5

<210> SEQ ID NO 184
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 M34H VHCDR1

<400> SEQUENCE: 184

Ser Ser Thr His Ser
1               5

<210> SEQ ID NO 185
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 M34W VHCDR1

<400> SEQUENCE: 185

Ser Ser Thr Trp Ser
1               5

<210> SEQ ID NO 186
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: 4A8 VHCDR2

<400> SEQUENCE: 186

Ala Ile Ser Gly Arg Gly Arg Asn Thr Tyr Tyr Ala Asp Ser Val Lys
1               5                   10                  15

Gly

<210> SEQ ID NO 187
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 I51H VHCDR2

<400> SEQUENCE: 187

Ala His Ser Gly Arg Gly Arg Asn Thr Tyr Tyr Ala Asp Ser Val Lys
1               5                   10                  15

Gly

<210> SEQ ID NO 188
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 G52aD VHCDR2

<400> SEQUENCE: 188

Ala Ile Ser Asp Arg Gly Arg Asn Thr Tyr Tyr Ala Asp Ser Val Lys
1               5                   10                  15

Gly

<210> SEQ ID NO 189
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 R53S VHCDR2

<400> SEQUENCE: 189

Ala Ile Ser Gly Ser Gly Arg Asn Thr Tyr Tyr Ala Asp Ser Val Lys
1               5                   10                  15

Gly

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 R53Q VHCDR2

<400> SEQUENCE: 190

Ala Ile Ser Gly Gln Gly Arg Asn Thr Tyr Tyr Ala Asp Ser Val Lys
1               5                   10                  15
```

Gly

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 G54D VHCDR2

<400> SEQUENCE: 191

Ala Ile Ser Gly Arg Asp Arg Asn Thr Tyr Tyr Ala Asp Ser Val Lys
1               5                   10                  15

Gly

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N56S VHCDR2

<400> SEQUENCE: 192

Ala Ile Ser Gly Arg Gly Arg Ser Thr Tyr Tyr Ala Asp Ser Val Lys
1               5                   10                  15

Gly

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 103,104, 105 VHCDR2

<400> SEQUENCE: 193

Ala Ile Ser Gly Ser Gly Gly Ser Thr Tyr Tyr Ala Asp Ser Val Lys
1               5                   10                  15

Gly

<210> SEQ ID NO 194
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 VHCDR3

<400> SEQUENCE: 194

Gln Met Gly Tyr
1

<210> SEQ ID NO 195
<211> LENGTH: 4
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: 4A8 M96A VHCDR3

<400> SEQUENCE: 195

Gln Ala Gly Tyr
1

<210> SEQ ID NO 196
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 M96Q VHCDR3

<400> SEQUENCE: 196

Gln Gln Gly Tyr
1

<210> SEQ ID NO 197
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 M96K VHCDR3

<400> SEQUENCE: 197

Gln Lys Gly Tyr
1

<210> SEQ ID NO 198
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 G101D VHCDR3

<400> SEQUENCE: 198

Gln Met Asp Tyr
1

<210> SEQ ID NO 199
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 Y102S VHCDR3

<400> SEQUENCE: 199

Gln Met Gly Ser
1

<210> SEQ ID NO 200
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: 4A8 Y102K VHCDR3

<400> SEQUENCE: 200

Gln Met Gly Lys
1

<210> SEQ ID NO 201
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 VLCDR1 and Consensus VL CDR1

<400> SEQUENCE: 201

Ile Gly Thr Ser Ser Asp Val Gly Gly Tyr Asn Tyr Val Ser
1               5                   10

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 VLCDR2

<400> SEQUENCE: 202

Glu Val Asn Lys Arg Pro Ser
1               5

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 E50D VLCDR2

<400> SEQUENCE: 203

Asp Val Asn Lys Arg Pro Ser
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N52D VLCDR2

<400> SEQUENCE: 204

Glu Val Asp Lys Arg Pro Ser
1               5

<210> SEQ ID NO 205
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N52S VLCDR2

<400> SEQUENCE: 205

Glu Val Ser Lys Arg Pro Ser
1               5

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 K53A VLCDR2

<400> SEQUENCE: 206

Glu Val Asn Ala Arg Pro Ser
1               5

<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 K53D VLCDR2

<400> SEQUENCE: 207

Glu Val Asn Asp Arg Pro Ser
1               5

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 K53H VLCDR2

<400> SEQUENCE: 208

Glu Val Asn His Arg Pro Ser
1               5

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 R54Q VLCDR2

<400> SEQUENCE: 209

Glu Val Asn Lys Gln Pro Ser
1               5

<210> SEQ ID NO 210
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 VLCDR3

<400> SEQUENCE: 210

Ser Ser Tyr Ala Gly Asn Asn Asn Phe Gly Val
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 Y91A VLCDR3

<400> SEQUENCE: 211

Ser Ser Ala Ala Gly Asn Asn Asn Phe Gly Val
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N94A VLCDR3

<400> SEQUENCE: 212

Ser Ser Tyr Ala Gly Ala Asn Asn Phe Gly Val
1               5                   10

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N94S VLCDR3

<400> SEQUENCE: 213

Ser Ser Tyr Ala Gly Ser Asn Asn Phe Gly Val
1               5                   10

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N94K VLCDR3

<400> SEQUENCE: 214

Ser Ser Tyr Ala Gly Lys Asn Asn Phe Gly Val
1               5                   10

<210> SEQ ID NO 215
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N94L VLCDR3

<400> SEQUENCE: 215

Ser Ser Tyr Ala Gly Leu Asn Asn Phe Gly Val
1               5                   10

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N94W VLCDR3

<400> SEQUENCE: 216

Ser Ser Tyr Ala Gly Trp Asn Asn Phe Gly Val
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N94Y VLCDR3

<400> SEQUENCE: 217

Ser Ser Tyr Ala Gly Tyr Asn Asn Phe Gly Val
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N95aQ VLCDR3

<400> SEQUENCE: 218

Ser Ser Tyr Ala Gly Asn Asn Gln Phe Gly Val
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N95aD VLCDR3

<400> SEQUENCE: 219

Ser Ser Tyr Ala Gly Asn Asn Asp Phe Gly Val
1               5                   10
```

```
<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N95aH VLCDR3

<400> SEQUENCE: 220

Ser Ser Tyr Ala Gly Asn Asn His Phe Gly Val
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N95aK VLCDR3

<400> SEQUENCE: 221

Ser Ser Tyr Ala Gly Asn Asn Lys Phe Gly Val
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 N95aL VLCDR3

<400> SEQUENCE: 222

Ser Ser Tyr Ala Gly Asn Asn Leu Phe Gly Val
1               5                   10

<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: A48 N95aYVLCDR3

<400> SEQUENCE: 223

Ser Ser Tyr Ala Gly Asn Asn Tyr Phe Gly Val
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 V97A VLCDR3

<400> SEQUENCE: 224

Ser Ser Tyr Ala Gly Asn Asn Asn Phe Gly Ala
1               5                   10
```

<210> SEQ ID NO 225
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 4A8 V97K VLCDR3

<400> SEQUENCE: 225

Ser Ser Tyr Ala Gly Asn Asn Asn Phe Gly Lys
1               5                   10

<210> SEQ ID NO 226
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 Consensus VH
<220> FEATURE:
<221> NAME/KEY: MOD_RES
<222> LOCATION: (34)..(34)
<223> OTHER INFORMATION: M or Q
<220> FEATURE:
<221> NAME/KEY: MOD_RES
<222> LOCATION: (40)..(40)
<223> OTHER INFORMATION: A or P
<220> FEATURE:
<221> NAME/KEY: MOD_RES
<222> LOCATION: (54)..(54)
<223> OTHER INFORMATION: R or S
<220> FEATURE:
<221> NAME/KEY: MOD_RES
<222> LOCATION: (56)..(56)
<223> OTHER INFORMATION: R or G
<220> FEATURE:
<221> NAME/KEY: MOD_RES
<222> LOCATION: (57)..(57)
<223> OTHER INFORMATION: N or S
<220> FEATURE:
<221> NAME/KEY: MOD_RES
<222> LOCATION: (76)..(76)
<223> OTHER INFORMATION: R or K
<220> FEATURE:
<221> NAME/KEY: MOD_RES
<222> LOCATION: (98)..(98)
<223> OTHER INFORMATION: I or K
<220> FEATURE:
<221> NAME/KEY: MOD_RES
<222> LOCATION: (100)..(100)
<223> OTHER INFORMATION: M, K or A

<400> SEQUENCE: 226

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
                20                  25                  30

Thr Xaa Ser Trp Val Arg Gln Xaa Pro Gly Lys Gly Leu Glu Trp Val
            35                  40                  45

Ser Ala Ile Ser Gly Xaa Gly Xaa Xaa Thr Tyr Tyr Ala Asp Ser Val
        50                  55                  60

Lys Gly Arg Phe Thr Ile Ser Arg Asp Asn Ser Xaa Asn Thr Leu Tyr
65                  70                  75                  80

Leu Gln Met Asn Ser Leu Arg Ala Glu Asp Thr Ala Val Tyr Tyr Cys
                85                  90                  95

Ala Xaa Gln Xaa Gly Tyr Trp Gly Gln Gly Ile Leu Val Thr Val Ser
         100                 105                 110

Ser

<210> SEQ ID NO 227
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 4A8 Consensus VL
<220> FEATURE:
<221> NAME/KEY: MOD_RES
<222> LOCATION: (43)..(43)
<223> OTHER INFORMATION: D or G
<220> FEATURE:
<221> NAME/KEY: MOD_RES
<222> LOCATION: (54)..(54)
<223> OTHER INFORMATION: N or S
<220> FEATURE:
<221> NAME/KEY: MOD_RES
<222> LOCATION: (96)..(96)
<223> OTHER INFORMATION: N or S

<400> SEQUENCE: 227

Gln Ser Ala Leu Thr Gln Pro Pro Ser Ala Ser Gly Ser Pro Gly Gln
1               5                   10                  15

Ser Val Thr Ile Ser Cys Ile Gly Thr Ser Ser Asp Val Gly Gly Tyr
            20                  25                  30

Asn Tyr Val Ser Trp Tyr Gln Gln His Pro Xaa Lys Ala Pro Lys Leu
        35                  40                  45

Met Ile Tyr Glu Val Xaa Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Xaa
                85                  90                  95

Asn Asn Phe Gly Val Phe Gly Gly Gly Thr Lys Leu Thr Val Leu
            100                 105                 110

<210> SEQ ID NO 228
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus VH CDR1
<220> FEATURE:
<221> NAME/KEY: MOD_RES
<222> LOCATION: (4)..(4)
<223> OTHER INFORMATION: M or Q

<400> SEQUENCE: 228

Ser Ser Thr Xaa Ser
1               5

<210> SEQ ID NO 229
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: Consensus VH CDR2
<220> FEATURE:
<221> NAME/KEY: MOD_RES
<222> LOCATION: (5)..(5)
<223> OTHER INFORMATION: R or S
<220> FEATURE:
<221> NAME/KEY: MOD_RES
<222> LOCATION: (7)..(7)
<223> OTHER INFORMATION: R or G
<220> FEATURE:
<221> NAME/KEY: MOD_RES
<222> LOCATION: (8)..(8)
<223> OTHER INFORMATION: N or S

<400> SEQUENCE: 229

Ala Ile Ser Gly Xaa Gly Xaa Xaa Thr Tyr Tyr Ala Asp Ser Val Lys
1               5                   10                  15
Gly

<210> SEQ ID NO 230
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus VH CDR3
<220> FEATURE:
<221> NAME/KEY: MOD_RES
<222> LOCATION: (2)..(2)
<223> OTHER INFORMATION: M, K or A

<400> SEQUENCE: 230

Gln Xaa Gly Tyr
1

<210> SEQ ID NO 231
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus VL CDR2
<220> FEATURE:
<221> NAME/KEY: MOD_RES
<222> LOCATION: (3)..(3)
<223> OTHER INFORMATION: N or S

<400> SEQUENCE: 231

Glu Val Xaa Lys Arg Pro Ser
1               5

<210> SEQ ID NO 232
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Consensus VL CDR3
<220> FEATURE:
<221> NAME/KEY: MOD_RES
<222> LOCATION: (6)..(6)
<223> OTHER INFORMATION: N or S

<400> SEQUENCE: 232
```

Ser Ser Tyr Ala Gly Xaa Asn Asn Phe Gly Val
1               5                   10

<210> SEQ ID NO 233
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: BKO-4A8 VH

<400> SEQUENCE: 233

```
gaagtgcagc tgctggaatc tggcggagga ctggtgcagc ctggcggcag cctgagactg    60
tcttgtgccg ccagcggctt caccttcagc agcagcacaa tgagctgggt ccgacaggcc   120
cctggcaagg gactggaatg ggtgtccgcc atcagcggca gaggccggaa cacctactac   180
gccgacagcg tgaagggccg gttcaccatc agccgggaca acagcagaaa caccctgtac   240
ctgcagatga acagcctgcg ggccgaggac accgccgtgt actactgtgc catccagatg   300
ggctactggg gccagggcat tctcgtgaca gtgtcctca                          339
```

<210> SEQ ID NO 234
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 1

<400> SEQUENCE: 234

```
gaagtgcagc tgctggaatc tggcggagga ctggtgcagc ctggcggcag cctgagactg    60
tcttgtgccg ccagcggctt caccttcagc agcagcacac agagctgggt ccgacaggcc   120
cctggcaagg gactggaatg ggtgtccgcc atcagcggca gaggccggag tacctactac   180
gccgacagcg tgaagggccg gttcaccatc agccgggaca acagcagaaa caccctgtac   240
ctgcagatga acagcctgcg ggccgaggac accgccgtgt actactgtgc catccagatg   300
ggctactggg gccagggcat tctcgtgaca gtgtcctca                          339
```

<210> SEQ ID NO 235
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 2

<400> SEQUENCE: 235

```
gaagtgcagc tgctggaatc tggcggagga ctggtgcagc ctggcggcag cctgagactg    60
tcttgtgccg ccagcggctt caccttcagc agcagcacac agagctgggt ccgacagcct   120
cctggcaagg gactggaatg ggtgtccgcc atcagcggca gaggccggag tacctactac   180
gccgacagcg tgaagggccg gttcaccatc agccgggaca acagcagaaa caccctgtac   240
```
ctgcagatga acagcctgcg ggccgaggac accgccgtgt actactgtgc catccagatg    300
ggctactggg gccagggcat tctcgtgaca gtgtcctca                            339

<210> SEQ ID NO 236
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 3

<400> SEQUENCE: 236
gaagtgcagc tgctggaatc tggcggagga ctggtgcagc tggcggcag cctgagactg     60 tcttgtgccg ccagcggctt caccttcagc agcagcacac agagctgggt ccgacagcct   120
cctggcaagg gactggaatg ggtgtccgcc atcagcggca gaggccggag tacctactac   180
gccgacagcg tgaagggccg gttcaccatc agccgggaca acagcaaaaa cacccctgtac  240 ctgcagatga acagcctgcg ggccgaggac accgccgtgt actactgtgc catccagatg   300
ggctactggg gccagggcat tctcgtgaca gtgtcctca                            339

<210> SEQ ID NO 237
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 4

<400> SEQUENCE: 237
gaagtgcagc tgctggaatc tggcggagga ctggtgcagc tggcggcag cctgagactg     60 tcttgtgccg ccagcggctt caccttcagc agcagcacac agagctgggt ccgacagcct   120
cctggcaagg gactggaatg ggtgtccgcc atcagcggca gaggccggag tacctactac   180
gccgacagcg tgaagggccg gttcaccatc agccgggaca acagcagaaa cacccctgtac  240 ctgcagatga acagcctgcg ggccgaggac accgccgtgt actactgtgc catccagaag   300
ggctactggg gccagggcat tctcgtgaca gtgtcctca                            339

<210> SEQ ID NO 238
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 5

<400> SEQUENCE: 238
gaagtgcagc tgctggaatc tggcggagga ctggtgcagc tggcggcag cctgagactg     60 tcttgtgccg ccagcggctt caccttcagc agcagcacac agagctgggt ccgacagcct   120
cctggcaagg gactggaatg ggtgtccgcc atcagcggca gaggccggag tacctactac   180

```
gccgacagcg tgaagggccg gttcaccatc agccgggaca acagcaaaaa cacccctgtac    240 ctgcagatga acagcctgcg ggccgaggac accgccgtgt actactgtgc catccagaag    300
ggctactggg gccagggcat tctcgtgaca gtgtcctca                           339
```

<210> SEQ ID NO 239
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 6

<400> SEQUENCE: 239

```
gaagtgcagc tgctggaatc tggcggagga ctggtgcagc ctggcggcag cctgagactg    60
tcttgtgccg ccagcggctt caccttcagc agcagcacac agagctgggt ccgacagcct    120
cctggcaagg gactggaatg ggtgtccgcc atcagcggca gggccggag tacctactac    180 gccgacagcg tgaagggccg gttcaccatc agccgggaca acagcaaaaa cacccctgtac    240 ctgcagatga acagcctgcg ggccgaggac accgccgtgt actactgtgc caagcagaag    300
ggctactggg gccagggcat tctcgtgaca gtgtcctca                           339
```

<210> SEQ ID NO 240
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 7

<400> SEQUENCE: 240

```
gaagtgcagc tgctggaatc tggcggagga ctggtgcagc ctggcggcag cctgagactg    60
tcttgtgccg ccagcggctt caccttcagc agcagcacac agagctgggt ccgacagcct    120
cctggcaagg gactggaatg ggtgtccgcc atcagcggca gaggccggag tacctactac    180
gccgacagcg tgaagggccg gttcaccatc agccgggaca acagcagaaaa cacccctgtac    240 ctgcagatga acagcctgcg ggccgaggac accgccgtgt actactgtgc caagcagaag    300
ggctactggg gccagggcat tctcgtgaca gtgtcctca                           339
```

<210> SEQ ID NO 241
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 8

<400> SEQUENCE: 241

```
gaagtgcagc tgctggaatc tggcggagga ctggtgcagc ctggcggcag cctgagactg    60
tcttgtgccg ccagcggctt caccttcagc agcagcacac agagctgggt ccgacaggcc    120
```

```
cctggcaagg gactggaatg ggtgtccgcc atcagcggca gaggccggag tacctactac      180
gccgacagcg tgaagggccg gttcaccatc agccgggaca acagcagaaa cacccctgtac    240 ctgcagatga acagcctgcg ggccgaggac accgccgtgt actactgtgc catccagaag     300
ggctactggg gccagggcat tctcgtgaca gtgtcctca                              339
```

<210> SEQ ID NO 242
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 9

<400> SEQUENCE: 242

```
gaagtgcagc tgctggaatc tggcggagga ctggtgcagc ctggcggcag cctgagactg      60
tcttgtgccg ccagcggctt caccttcagc agcagcacac agagctgggt ccgacaggcc     120
cctggcaagg gactggaatg ggtgtccgcc atcagcggca gaggccggag tacctactac     180
gccgacagcg tgaagggccg gttcaccatc agccgggaca acagcaaaaa cacccctgtac   240 ctgcagatga acagcctgcg ggccgaggac accgccgtgt actactgtgc catccagaag    300
ggctactggg gccagggcat tctcgtgaca gtgtcctca                             339
```

<210> SEQ ID NO 243
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 10

<400> SEQUENCE: 243

```
gaagtgcagc tgctggaatc tggcggagga ctggtgcagc ctggcggcag cctgagactg      60
tcttgtgccg ccagcggctt caccttcagc agcagcacaa tgagctgggt ccgacaggcc     120
cctggcaagg gactggaatg ggtgtccgcc atcagcggca gaggccggaa cacctactac     180
gccgacagcg tgaagggccg gttcaccatc agccgggaca acagcagaaa cacccctgtac   240 ctgcagatga acagcctgcg ggccgaggac accgccgtgt actactgtgc caagcagaag    300
ggctactggg gccagggcat tctcgtgaca gtgtcctca                             339
```

<210> SEQ ID NO 244
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 101

<400> SEQUENCE: 244

```
gaagttcagc tgcttgaatc tggcggagga ctggttcagc ctggcggatc tctgagactg      60
```

```
tcttgtgccg ccagcggctt cacctttagc agcagcacac agagctgggt ccgacagcct      120
cctggcaaag gactggaatg ggtgtccgcc atctctggca gaggcagaag cacctactac      180
gccgactctg tgaagggcag attcaccatc agccgggaca acagcaagaa caccctgtac      240
ctgcagatga acagcctgag agccgaggac accgccgtgt actattgtgc catccaggcc      300
ggctattggg gccagggaat actcgtgaca gtgtcctca                            339
```

```
<210> SEQ ID NO 245
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 103

<400> SEQUENCE: 245
```

```
gaagttcagc tgcttgaatc tggcggagga ctggttcagc ctggcggatc tctgagactg       60
tcttgtgccg ccagcggctt cacctttagc agcagcacac agagctgggt ccgacagcct      120
cctggcaaag gactggaatg ggtgtccgcc atctctggca gcggcggcag cacatattac      180
gccgattctg tgaagggcag attcaccatc agccgggaca acagcaagaa caccctgtac      240
ctgcagatga acagcctgag agccgaggac accgccgtgt actattgcgc catccagatg      300
ggctattggg gccagggaat cctcgtgaca gtgtcctca                            339
```

```
<210> SEQ ID NO 246
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 104

<400> SEQUENCE: 246
```

```
gaagttcagc tgcttgaatc tggcggagga ctggttcagc ctggcggatc tctgagactg       60
tcttgtgccg ccagcggctt cacctttagc agcagcacac agagctgggt ccgacagcct      120
cctggcaaag gactggaatg ggtgtccgcc atctctggca gcggcggcag cacatattac      180
gccgattctg tgaagggcag attcaccatc agccgggaca acagcaagaa caccctgtac      240
ctgcagatga acagcctgag agccgaggac accgccgtgt actattgcgc catccagaaa      300
ggctattggg gccagggcat cctcgtgaca gtgtcctca                            339
```

```
<210> SEQ ID NO 247
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VH Variant 105

<400> SEQUENCE: 247
```

```
gaagttcagc tgcttgaatc tggcggagga ctggttcagc ctggcggatc tctgagactg    60
tcttgtgccg ccagcggctt cacctttagc agcagcacac agagctgggt ccgacagcct   120
cctggcaaag gactgaatg ggtgtccgcc atctctggca gcggcggcag cacatattac   180
gccgattctg tgaagggcag attcaccatc agccgggaca cagcaagaa cacccctgtac   240 ctgcagatga acagcctgag agccgaggac accgccgtgt actattgtgc catccaggcc   300
ggctattggg gccagggaat actcgtgaca gtgtcctca                           339
```

<210> SEQ ID NO 248
<211> LENGTH: 987
<212> TYPE: DNA
<213> ORGANISM: Homo sapiens
<220> FEATURE:
<223> OTHER INFORMATION: Human IgG1

<400> SEQUENCE: 248

```
gctagcacca agggaccccag cgtgttcccc ctggcccca gcagcaagag cacatctggc    60
ggaacagccg ccctgggctg cctggtgaaa gactacttcc ccgagcccgt gaccgtgagc   120
tggaacagcg gagccctgac cagcggcgtg cacacctttc cagccgtgct gcagagcagc   180
ggcctgtaca gcctgagcag cgtggtgaca gtgccctcta gcagcctggg cacccagacc   240
tacatctgca acgtgaacca caagcccagc aacaccaagg tggacaaaaa ggtggaaccc   300
aagagctgcg acaagaccca cacctgtccc ccctgccctg ccctgaact gctgggcgga   360 ccctccgtgt tcctgttccc cccaaagccc aaggacaccc tgatgatcag ccggaccccc   420
gaagtgacct gcgtggtggt ggacgtgtcc cacgaggacc ctgaagtgaa gttcaattgg   480
tacgtggacg gcgtggaagt gcacaacgcc aagaccaagc cagagagga cagtacaac   540 agcacctacc gggtggtgtc cgtgctgacc gtgctgcacc aggactggct gaacggcaaa   600
gagtacaagt gcaaggtgtc caacaaggcc ctgcctgctc ccatcgagaa aaccatcagc   660
aaggccaagg gccagccccg cgagcctcag gtgtacacac tgcccccag ccgggacgag   720 ctgaccaaga accaggtgtc cctgacctgt ctggtgaaag gcttctaccc cagcgatatc   780
gccgtggaat gggagagcaa cggccagccc gagaacaact acaagaccac ccccctgtg   840 ctggacagcg acggctcatt cttcctgtac agcaagctga ccgtggacaa gagccggtgg   900
cagcagggca acgtgttcag ctgcagcgtg atgcacgagg ccctgcacaa ccactacacc   960
cagaagtccc tgagcctgag ccccggc                                       987
```

<210> SEQ ID NO 249
<211> LENGTH: 987
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: Human IgG1

<400> SEQUENCE: 249

```
gctagcacca agggacccag cgtgttcccc ctggcccca gcagcaagag cacatctggc    60
ggaacagccg ccctgggctg cctggtgaaa gactacttcc ccgagcccgt gaccgtgagc   120
tggaacagcg gagccctgac cagcggcgtg cacacctttc cagccgtgct gcagagcagc   180
ggcctgtaca gcctgagcag cgtggtgaca gtgccctcta gcagcctggg cacccagacc   240
```

```
tacatctgca acgtgaacca caagcccagc aacaccaagg tggacaaaaa ggtggaaccc    300
aagagctgcg acaagaccca cacctgtccc cctgccctg ccctgaact ggctggcgct     360 ccctccgtgt tcctgttccc cccaaagccc aaggacaccc tgatgatcag ccggacccc     420 gaagtgacct gcgtggtggt ggacgtgtcc cacgaggacc ctgaagtgaa gttcaattgg   480
tacgtggacg gcgtggaagt gcacaacgcc aagaccaagc ccagagagga acagtacaac   540
agcacctacc gggtggtgtc cgtgctgacc gtgctgcacc aggactggct gaacggcaaa   600
gagtacaagt gcaaggtgtc caacaaggcc ctgcctgctc ccatcgagaa aaccatcagc   660
aaggccaagg gccagccccg cgagcctcag gtgtacacac tgccccccag ccgggacgag   720
ctgaccaaga accaggtgtc cctgacctgt ctggtgaaag cttctaccc cagcgatatc    780 gccgtggaat gggagagcaa cggccagccc gagaacaact acaagaccac cccccctgtg   840
ctggacagcg acggctcatt cttcctgtac agcaagctga ccgtggacaa gagccggtgg   900
cagcagggca acgtgttcag ctgcagcgtg atgcacgagg ccctgcacaa ccactacacc   960
cagaagtccc tgagcctgag ccccggc                                      987
```

<210> SEQ ID NO 250
<211> LENGTH: 978
<212> TYPE: DNA
<213> ORGANISM: Homo sapiens
<220> FEATURE:
<223> OTHER INFORMATION: Human IgG4

<400> SEQUENCE: 250

```
gctagcacca agggcccag cgtgttccc ctggccccctt gtagcagaag caccagcgag     60
agcacagccg ccctgggctg cctggtgaaa gactacttcc ccgagcccgt caccgtgtcc   120
tggaacagcg gagccctgac cagcggcgtg cacacctttc cagccgtgct gcagagcagc   180
ggcctgtaca gcctgagcag cgtggtgaca gtgccctcca gcagcctggg caccaagacc   240
tacacctgta acgtggacca caagcccagc aacaccaagg tggacaagcg ggtggaatct   300
aagtacggcc cacctgccc cctgccct gcccctgaat ttctgggcgg accctccgtg      360
ttcctgttcc cccaaagcc aaggacacc ctgatgatca gccggacccc cgaagtgacc    420
tgcgtggtgg tggacgtgtc ccaggaagat cccgaggtcc agttcaattg gtacgtggac   480
ggcgtggaag tgcacaacgc caagaccaag cccagagagg aacagttcaa cagcacctac   540
cgggtggtgt ccgtgctgac cgtgctgcac caggactggc tgaacggcaa agagtacaag   600
tgcaaagtct ccaacaaggg cctgcccagc tccatcgaga aaaccatcag caaggccaag   660
ggccagcccc gcgagcctca ggtgtacaca ctgccccca gccaggaaga gatgaccaag   720
aaccaggtgt ccctgacctg tctggtgaaa ggcttctacc ccagcgatat cgccgtggaa   780
tgggagagca acggccagcc cgagaacaac tacaagacca ccccccctgt gctggacagc   840
gacggcagct tcttcctgta ctcccggct accgtggaca gagccggtg gcaggaaggc     900 aacgtcttca gctgcagcgt gatgcacgag gccctgcaca accactacac ccagaagtcc   960
ctgagcctga gcctgggc                                                 978
```

<210> SEQ ID NO 251
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide

```
<220> FEATURE:
<223> OTHER INFORMATION: Completely synthesized
<220> FEATURE:
<223> OTHER INFORMATION: Human IgG4

<400> SEQUENCE: 251
gctagcacca agggcccag cgtgttcccc ctggccccct gtagcagaag caccagcgag      60
agcacagccg ccctgggctg cctggtgaaa gactacttcc ccgagcccgt caccgtgtcc    120
tggaacagcg gagccctgac cagcggcgtg cacacctttc cagccgtgct gcagagcagc    180
ggcctgtaca gcctgagcag cgtggtgaca gtgccctcca gcagcctggg caccaagacc    240
tacacctgta acgtggacca caagcccagc aacaccaagg tggacaagcg ggtggaatct    300
aagtacggcc accctgccc cctgccct gcccctgaat ttctgggcgg accctccgtg    360
ttcctgttcc cccaaagcc aaggacacc ctgtatatca ctcggagcc cgaagtgacc      420
tgcgtggtgg tggacgtgtc ccaggaagat cccgaggtcc agttcaattg gtacgtggac    480
ggcgtggaag tgcacaacgc caagaccaag cccagagagg aacagttcaa cagcacctac    540
cgggtggtgt ccgtgctgac cgtgctgcac caggactggc tgaacggcaa agagtacaag    600
tgcaaagtct ccaacaaggg cctgccagc tccatcgaga aaaccatcag caaggccaag    660
ggccagcccc gcgagcctca ggtgtacaca ctgccccca gccaggaaga gatgaccaag    720
aaccaggtgt ccctgacctg tctggtgaaa ggcttctacc ccagcgatat cgccgtggaa    780
tgggagagca acggccagcc cgagaacaac tacaagacca cccccctgt gctggacagc    840
gacggcagct tcttcctgta ctcccggct accgtggaca gagccggtg gcaggaaggc    900
aacgtcttca gctgcagcgt gatgcacgag gccctgcaca accactacac ccagaagtcc    960
ctgagcctga gcctgggc                                                 978

<210> SEQ ID NO 252
<211> LENGTH: 975
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: Human IgG2

<400> SEQUENCE: 252
gctagcacca agggcccag cgtgttccct ctggccccct gtagcagaag caccagcgag      60
tctacagccg ccctgggctg cctcgtgaag gactactttc ccgagcccgt caccgtgtcc    120
tggaactctg gcgctctgac aagcggcgtg cacacctttc cagccgtgct gcagagcagc    180
ggcctgtact ctctgagcag cgtcgtgacc gtgcccagca gcaatttcgg cacccagacc    240
tacacctgta acgtggacca caagcccagc aacaccaagg tggacaagac cgtggaacgg    300
aagtgctgcg tggaatgccc cccttgtcct gcccctccag tggctggccc ttccgtgttc    360
ctgttcccc caaagcccaa ggacaccctg atgatcagcc gacccccga agtgacctgc    420
gtggtggtgg atgtgtccca cgaggacccc gaggtgcagt tcaattggta cgtggacggc    480
gtggaagtgc acaacgccaa gaccaagccc agagaggaac agttcaacag cacctccgg    540
gtggtgtccg tgctgaccgt ggtgcatcag gactggctga acggcaaaga gtacaagtgc    600
aaggtgtcca acaagggcct gcccagctcc atcgagaaaa ccatcagcaa gaccaaaggc    660
cagccccgcg agccccaggt gtacacactg cctccaagcc gggaagagat gaccaagaat    720
```

-continued

```
caggtgtccc tgacctgtct cgtgaaaggc ttctaccccct ccgatatcgc cgtggaatgg    780
gagagcaacg gccagcccga gaacaactac aagaccaccc cccccatgct ggacagcgac    840
ggctcattct tcctgtacag caagctgaca gtggacaagt cccggtggca gcagggcaac    900
gtgttcagct gcagcgtgat gcacgaggcc ctgcacaacc actacaccca gaagtccctg    960
agcctgagcc ctggc                                                     975
```

```
<210> SEQ ID NO 253
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: BKO-4A8 VL

<400> SEQUENCE: 253
cagtctgctc tgacacagcc tcctagcgcc tctggctctc ctggccagag cgtgaccatc     60
agctgtatcg gcaccagcag cgacgtgggc ggctacaact acgtgtcctg gtatcagcag    120
caccccgaca aggcccccaa gctgatgatc tacgaagtga acaagcggcc cagcggcgtg    180
cccgatagat tcagcggcag caagagcggc aacaccgcca gcctcacagt gtctggactg    240
caggccgagg acgaggccga ctactactgt agcagctacg ccggcaacaa caacttcggc    300
gtgttcggcg gaggcaccaa gctgacagtc cta                                 333
```

```
<210> SEQ ID NO 254
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VL variant b

<400> SEQUENCE: 254
cagtctgctc tgacacagcc tcctagcgcc tctggctctc ctggccagag cgtgaccatc     60
agctgtatcg gcaccagcag cgacgtgggc ggctacaact acgtgtcctg gtatcagcag    120
caccccgaca aggcccccaa gctgatgatc tacgaagtgt ccaagcggcc cagcggcgtg    180
cccgatagat tcagcggcag caagagcggc aacaccgcca gcctcacagt gtctggactg    240
caggccgagg acgaggccga ctactactgt agcagctacg ccggcagcaa caacttcggc    300
gtgttcggcg gaggcaccaa gctgacagtc cta                                 333
```

```
<210> SEQ ID NO 255
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Completely synthesized
<220> FEATURE:
<223> OTHER INFORMATION: 4A8 VL variant c

<400> SEQUENCE: 255
```

```
cagtctgctc tgacacagcc tcctagcgcc tctggctctc ctggccagag cgtgaccatc      60
agctgtatcg gcaccagcag cgacgtgggc ggctacaact acgtgtcctg gtatcagcag     120 cacccggta aggcccccaa gctgatgatc tacgaagtgt ccaagcggcc cagcggcgtg      180
cccgatagat tcagcggcag caagagcggc aacaccgcca gcctcacagt gtctggactg     240
caggccgagg acgaggccga ctactactgt agcagctacg ccggcagcaa caacttcggc    300
gtgttcggcg gaggcaccaa gctgacagtc cta                                  333

<210> SEQ ID NO 256
<211> LENGTH: 318
<212> TYPE: DNA
<213> ORGANISM: Homo sapiens
<220> FEATURE:
<223> OTHER INFORMATION: lambda constant light chain

<400> SEQUENCE: 256
ggtcagccca aggccgctcc cagcgtgacc ctgttccccc caagcagcga ggaactgcag      60
gccaacaagg ccaccctggt gtgcctgatc agcgacttct accctggggc cgtgaccgtg    120
gcctggaagg ccgatagcag ccctgtgaag gccggcgtgg aaaccaccac ccctccaag    180 cagagcaaca acaaatacgc cgccagcagc tacctgtccc tgaccccccga gcagtggaag     240 tcccaccggt cctacagctg ccaggtgaca cacgagggca gcaccgtgga aaagaccgtg    300
gcccccaccg agtgcagc                                                   318
```